US008629141B2

(12) United States Patent
Wang et al.

(10) Patent No.: US 8,629,141 B2
(45) Date of Patent: Jan. 14, 2014

(54) SPIRO-OXINDOLE MDM2 ANTAGONISTS

(75) Inventors: Shaomeng Wang, Saline, MI (US); Wei Sun, Ann Arbor, MI (US); Angelo Aguilar, Ann Arbor, MI (US); Carlos Garcia-Echeverria, Paris (FR)

(73) Assignees: The Regents of the University of Michigan, Ann Arbor, MI (US); Sanofi, Paris (FR)

( * ) Notice: Subject to any disclaimer, the term of this patent is extended or adjusted under 35 U.S.C. 154(b) by 0 days.

(21) Appl. No.: 13/469,928

(22) Filed: May 11, 2012

(65) Prior Publication Data

US 2012/0289494 A1 Nov. 15, 2012

Related U.S. Application Data

(60) Provisional application No. 61/484,986, filed on May 11, 2011.

(51) Int. Cl.
*A61K 31/4015* (2006.01)
*C07D 209/96* (2006.01)
*C07D 273/04* (2006.01)
*C07D 401/14* (2006.01)

(52) U.S. Cl.
USPC .......... 514/232.8; 514/278; 514/409; 544/70; 546/18; 548/486

(58) Field of Classification Search
USPC ....................................... 548/486
See application file for complete search history.

(56) References Cited

U.S. PATENT DOCUMENTS

| | | |
|---|---|---|
| 3,219,661 A | 11/1965 | Shavel, Jr. et al. |
| 6,617,346 B1 | 9/2003 | Kong et al. |
| 6,734,302 B2 | 5/2004 | Kong et al. |
| 6,916,833 B2 | 7/2005 | Kim et al. |
| 7,060,713 B2 | 6/2006 | Kim et al. |
| 7,083,983 B2 | 8/2006 | Lane et al. |
| 7,125,659 B1 | 10/2006 | Kiyoi et al. |
| 7,132,421 B2 | 11/2006 | Fotouhi et al. |
| 7,425,638 B2 | 9/2008 | Haley et al. |
| 7,495,007 B2 | 2/2009 | Chen et al. |
| 7,553,833 B2 | 6/2009 | Liu et al. |
| 7,576,082 B2 | 8/2009 | Luk et al. |
| 7,625,895 B2 | 12/2009 | Dominique et al. |
| 7,638,548 B2 | 12/2009 | Liu et al. |
| 7,723,372 B2 | 5/2010 | Liu |
| 7,737,174 B2 | 6/2010 | Wang et al. |
| 7,759,383 B2 | 7/2010 | Wang et al. |
| 7,776,875 B2 | 8/2010 | Chen et al. |
| 7,834,179 B2 | 11/2010 | Liu et al. |
| 7,928,233 B2 | 4/2011 | Chen et al. |
| 8,053,475 B2 | 11/2011 | Klein |
| 8,058,269 B2 | 11/2011 | Chen et al. |
| 8,076,482 B2 | 12/2011 | Chen et al. |
| 8,088,815 B2 | 1/2012 | Bartkovitz et al. |
| 8,134,001 B2 | 3/2012 | Ding et al. |
| 2002/0039790 A1 | 4/2002 | Keplinger et al. |
| 2002/0132977 A1 | 9/2002 | Yuan et al. |
| 2004/0171035 A1 | 9/2004 | Huang et al. |
| 2005/0137137 A1 | 6/2005 | Lane et al. |
| 2005/0227932 A1 | 10/2005 | Lu et al. |
| 2005/0288287 A1 | 12/2005 | Fotouhi et al. |
| 2006/0211718 A1 | 9/2006 | Weissman et al. |
| 2006/0211757 A1 | 9/2006 | Wang et al. |
| 2006/0241017 A1 | 10/2006 | Chandran |
| 2006/0287244 A1 | 12/2006 | Chandran |
| 2007/0249564 A1 | 10/2007 | Erion et al. |
| 2008/0039472 A1 | 2/2008 | Lacrampe et al. |
| 2008/0125430 A1* | 5/2008 | Wang et al. ................. 514/235.2 |
| 2008/0171723 A1 | 7/2008 | Khan |
| 2008/0261917 A1 | 10/2008 | Willems et al. |
| 2008/0280769 A1 | 11/2008 | Doemling |
| 2009/0030181 A1 | 1/2009 | Han et al. |
| 2009/0143364 A1 | 6/2009 | Fotouhi et al. |
| 2009/0149493 A1 | 6/2009 | Lacrampe et al. |
| 2009/0227542 A1 | 9/2009 | Khan |
| 2009/0312310 A1 | 12/2009 | Kawato et al. |
| 2010/0048593 A1 | 2/2010 | Weissman et al. |
| 2010/0216770 A1 | 8/2010 | Storck et al. |
| 2011/0112052 A1 | 5/2011 | Wang et al. |
| 2011/0201635 A1 | 8/2011 | Liu et al. |
| 2011/0251252 A1 | 10/2011 | Wang et al. |
| 2011/0269809 A1 | 11/2011 | Chu et al. |
| 2012/0046306 A1 | 2/2012 | Bartkovitz et al. |
| 2012/0071499 A1 | 3/2012 | Chu et al. |
| 2012/0122947 A1 | 5/2012 | Wang et al. |
| 2012/0289494 A1 | 11/2012 | Wang et al. |

FOREIGN PATENT DOCUMENTS

| | | |
|---|---|---|
| CN | 1410401 A | 4/2003 |
| EP | 2 298 778 A1 | 3/2011 |
| GB | 1056537 | 1/1967 |
| JP | 40-23184 | 10/1965 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Alper, P. B. et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38:3186-3189, Wiley-VCH Verlag GmbH (1999).
Azmi, A.S. et al., "MDM2 inhibitor MI-319 in combination with cisplatin is an effective treatment for pancreatic cancer independent of p53 function," *Eur. J. Cancer* 46:1122-1131, Elsevier Ltd. (2010).
Ban, Y. and Oishi, T., "The Synthesis of 3-Spiro-oxindole Derivatives. I. Syntheses of 1-Methyl-2', 3', 10',10'α-tetrahydrospiro[indoline-3,1'(5'H)-pyrrolo[1,2-b]-isoquinoline]-2-one and its Homologs," *Chem. Pharm. Bull.* 4:441-445, Pharmaceutical Society of Japan (1963).

(Continued)

*Primary Examiner* — Shawquia Young
(74) *Attorney, Agent, or Firm* — Casimir Jones SC

(57) ABSTRACT

Provided herein are compounds, compositions, and methods in the field of medicinal chemistry. The compounds and compositions provided herein relate to spiro-oxindoles which function as antagonists of the interaction between p53 and MDM2, and their use as therapeutics for the treatment of cancer and other diseases.

19 Claims, 6 Drawing Sheets

(56) References Cited

FOREIGN PATENT DOCUMENTS

| JP | 44-4986 | 2/1969 |
|---|---|---|
| RU | 2 084 449 C1 | 7/1997 |
| RU | 2186776 C2 | 10/2002 |
| WO | WO 98/00409 A1 | 1/1998 |
| WO | WO 99/12904 A1 | 3/1999 |
| WO | WO 03/051360 A1 | 6/2003 |
| WO | WO 2005/046575 A2 | 5/2005 |
| WO | WO 2005/110992 A1 | 11/2005 |
| WO | WO 2006/125784 A1 | 11/2006 |
| WO | WO 2008/106507 A2 | 9/2008 |
| WO | WO 2008/119741 A2 | 10/2008 |
| WO | WO 2008/125487 A1 | 10/2008 |
| WO | WO 2009/156735 A2 | 12/2009 |
| WO | WO 2011/067185 A1 | 6/2011 |
| WO | WO 2011/106650 A2 | 9/2011 |

OTHER PUBLICATIONS

Barakat, K. et al., "Ensemble-based virtual screening reveals dual-inhibitors for the p53-MDM2/MDMX interactions," *Journal of Molecular Graphics & Modelling* 28:555-568, Elsevier Inc. (2010).

Baxter, E.W. and Reitz, A.B, "Reductive aminations of carbonyl compounds with borohydride and borane reducing agents. Organic reactions" (Hoboken, NJ, United States, 59, (2002) (online); Found from database ASC on STN, CA: 149-5759820 (2010).

Canner, J.A. et al., "MI-63: A novel small-molecule inhibitor targets MDM2 and induces apoptosis in embryonal and alveolar rhabdomyosarcoma cells with wild-type p53," *Br. J. Cancer* 101:774-781, Cancer Research UK (2009).

Chène, P., "Inhibiting the p53-MDM2 Interaction: An Important Target for Cancer Therapy," *Nature Reviews: Cancer* 3:102-109, Nature Publishing Group, London, UK (2003).

Cochard, F. et al., "Synthesis of Substituted 1,2,3,4-Tetrahydro-1-thiacarbazole and Spiro[pyrrolidinone-3,3'-indolinones] through a Common Intermediate Obtained by Condensation of Indolin-2-one, (Aryl)aldehydes, and Meldrum's Acid," *Eur. J. Org. Chem.* 20:3481-3490, Wiley-VCH Verlag GmbH (2002).

Cossy, J. et al., "A Convenient Route to Spiropyrrolidinyl-Oxindole Alkaloids via C-3 Substituted Ene-Pyrrolidine Carbamate Radical Cyclization," *Tetrahedron Letters* 39:2331-2332, Elsevier Science Ltd. (1998).

Cui, C-B et al., "Isolation, Structure Determination and Biological Activities of Novel Mammalian Cell Cycle Inhibitors, Spirotryprostatins A & B, Tryprostatins A & B and Related New Diketopiperazine Derivatives Produced by a Fungus, *Aspergillus fumigatus*," *Symposium on the Chemistry of Natural Products* 38:49-54 (1996).

Ding, K. et al., "Structure-Based Design of Spiro-oxindoles as Potent, Specific Small-Molecule Inhibitors of the MDM2-p53 Interaction," *J. Med. Chem.* 49:3432-3435, American Chemical Society (2006).

Ding, K. et al., "Structure-Based Design of Potent Non-Peptide MDM2 Inhibitors," *J. Am. Chem. Soc.* 127:10130-10131, American Chemical Society (2005).

Ding, K. et al., "Synthesis of spirooxindoles via asymmetric 1,3-dipolar cycloaddition," *Tetrahedron Letters* 46:5949-5951, Elsevier Ltd. (2005).

Döé de Maindreville, M. and Lévy, J., "Synthèses en série indolique. VII. Synthèse et transformation chimiques de l'enchaînement tétracyclique commun aux alcaloïdes à chromophore ester anilinoacrylique," *Bulletin de la Société Chimique de France* 5-6:179-184, Societe Francaise De Chimie (1981).

Dörnyei, G. et al., "Intramolecular Mannich Reaction of 2-Oxotryptamine and Homologues with Oxo Reagents Yielding Spiro Compounds. Part II," *Collect. Czech Chem. Commun.* 67:1669-1680, Nakladatelstvi Ceskoslovenski Akademie Ved. (2002).

Edmondson, S. et al., "Total Synthesis of Spirotryprostatin A, Leading to the Discovery of Some Biologically Promising Analogs," *J. Am. Chem. Soc.* 121:2147-2155, American Chemical Society (1999).

García-Echeverría, C. et al., "Discovery of Potent Antagonists of the Interaction between Human Double Minute 2 and Tumor Suppressor p53," *J. Med. Chem.* 43:3205-3208, American Chemical Society (2000).

Giese, B. et al., Radical cyclization reactions, Organic reactions (Hoboken, NJ, United States), 48 (1996) (online); Found from database ASC on STN, CA: 149:5550940 (2010).

Grigg, R. et al., "Spiro-oxindoles via bimetallic [Pd(0)/Ag(I)] catalytic intramolecular Heck-1,3-dipolar cycloaddition cascade reactions," *Tetrahedron Letters* 43:2605-2608, Elsevier Science Ltd. (2002).

Harley-Mason, J. and Ingleby, R.F.J., "Hydroxytryptamines, Part IV. Synthesis and Reactions of 2-3'-Oxindolylethylamines," *J. Chem. Soc.* 3639-3642, Chemical Society of Great Britain, London, UK (1958).

Incze, M. et al., "Intramolecular Mannich Reaction of 2-Oxotryptamines with Acetone Yielding Spiro[indole-3,3'-pyrrolidin]-2-ones," *Collect. Czech Chem. Commun.* 64:408-416, Institute of Organic Chemistry and Biochemistry, Academy of Sciences of the Czech Republic, Prague (1999).

Jones, R.J. et al., "Inhibition of the p53 E3 Ligase HDM-2 Induces Apoptosis and DNA Damage-Independent p53 Phosphorylation in Mantle Cell Lymphoma," *Clin. Cancer Res.* 14:5416-5425, American Association of Cancer Research (2008).

Kabankin, A.S., et al., "Analysis of Structure—Hepatoprotective Activity Relationship for Indole Derivatives." *Chemical and Pharmaceutical Magazine*, 39:24-28 (2005).

Kuroda, M. et al., "Cytotoxic Alkaloids from the Barks of *Ochrosia elliptica*," *Natural Medicines* 53:272 (1999).

Kussie, P.H. et al., "Structure of the MDM2 Oncoprotein Bound to the p53 Tumor Suppressor Transactivation Domain," *Science* 274:948-953, American Association for the Advancement of Science (1996).

Leclercq, J., et al., "Screening of Cytotoxic Activities of *Strychnos* Alkaloids (Methods and Results)," *J. Ethnopharmacology* 15:305-316, Elsevier Scientific Publishers Ireland Ltd. (1986).

Lizos, D. et al., "A novel and economical route to (±)-horsfiline using an aryl iodoazide tandem radical cyclisation strategy," *Chem. Commun.* 2732-2733, The Royal Society of Chemistry (2001).

Lizos, D.E. and Murphy, J.A., "Concise synthesis of (±)-horsfiline and (±)- coerulescine by tandem cyclisation of iodoaryl alkenyl azides," *Org. Biomol. Chem.* 1:117-122, The Royal Society of Chemistry (2003).

Lu, Y. et al., "Discovery of a Nanomolar Inhibitor of the Human Murine Double Minute 2 (MDM2)-p53 Interaction through an Integrated, Virtual Database Screening Strategy," *J. Med. Chem.* 49:3759-3762, American Chemical Society (2006).

Marti, C. and Carreira, E.M., "Construction of Spiro[pyrrolidine-3,3'-oxindoles]—Recent Applications to the Synthesis of Oxindole Alkaloids." *Eur. J. Org. Chem.* 2209-2219, Wiley-VCH Verlag GmbH & Co. (2003).

Miyake, F.Y. et al., "Preparation and Synthetic Applications of 2-Halotryptophan Methyl Esters: Synthesis of Spirotryprostatin B," *Angew. Chem. Int. Ed.* 43:5357-5360, Wiley-VCH Verlag GmbH & Co. (2004).

Mohammad, R.M. et al., "An MDM2 antagonist (MI-319) restores p53 functions and increases the life span of orally treated follicular lymphoma bearing animals," *Mol. Canc.* 8:115, BioMed Central (2009).

Muhammad, I., "Investigation of Uña De Gato I. 7-Deoxyloganic acid and $^{15}$N NMR spectropscopic studies on pentacyclic oxindole alkaloids from *Uncaria tomentosa*," *Phytochemistry* 57:781-785, Elsevier Science Ltd. (2001).

Nikolovska-Coleska, Z. et al., "Development and optimization of a binding assay for the XIAP BIR3 domain using fluorescence polarization," *Analytical Biochemistry* 332:261-273, Elsevier Inc. (2004).

Onishi T. et al., "Concise, asymmetric total synthesis of spirotryprostatin A," *Tetrahedron* 60:9503-9515, Elsevier Ltd. (2004).

Onishi, T. et al., "Concise, Asymmetric Total Synthesis of Spirotryprostatin A," *Org. Lett.* 5:3135-3137, American Chemical Society (2003).

Pellegrini, C. et al., "Synthesis of the Oxindole Alkaloid (−)-Horsfiline," *Tetrahedron: Asymmetry* 5:1979-1992, Elsevier Science Ltd. (1994).

(56) References Cited

OTHER PUBLICATIONS

Pellegrini, C. et al., "Total Synthesis of (+)-Elacomine and (−)-Isoelacomine, Two Hitherto Unnamed Oxindole Alkaloids from *Elaeagnus commutata*," *Helv. Chim. Acta* 79:151-168, Schweizerische Chemische Gessellschaft, Basel (1996).

Rothweiler, U. et al., "Isoquinolin-1-one Inhibitors of the MDM2-p53 Interaction," *ChemMedChem* 3:1118-1128, Wiley-VCH Verlag GmbH & Co. (2008).

Saddler, C. et al., "Comprehensive biomarker and genomic analysis identifies p53 status as the major determinant of response to MDM2 inhibitors in chronic lymphocytic leukemia," *Blood* 111:1584-1593, The American Society of Hematology (2008).

Samudio, I.J. et al., "Activation of p53 signaling by MI-63 induces apoptosis in acute myeloid leukemia cells," *Leukemia & Lymphoma* 51:911-919, Informa Healthcare USA, Inc. (2010).

Schubert, M.A. and Müller-Goymann, C.C. "Solvent injection as a new approach for manufacturing lipid nanoparticles—evaluation of the method and process parameters," *European Journal of Pharmaceutics and Biopharmaceutics* 55:125-131, Elsevier Science B.V. (2003).

Sebahar, P.R. and Williams, R.M., "The Synthesis of Spirooxindole Pyrrolidines Via an Asymmetric Azomethine Ylide [1,3]-Dipolar Cycloaddition Reaction," *Heterocycles* 58:563-575, Elsevier Science (2002).

Sebahar, P.R. et al., "Asymmetric, stereocontrolled total synthesis of (+) and (−)-spirotryprostatin B via a diastereoselective azomethine ylide [1,3]-dipolar cycloaddition reaction," *Tetrahedron* 58:6311-6322, Elsevier Science Ltd. (2002).

Sebahar, P.R. and Williams, R.M., "The Asymmetric Total Synthesis of (+)- and (−)-Spirotryprostatin B," *J. Am. Chem. Soc.* 122:5666-5667, American Chemical Society (2000).

Shangary, S. et al., "Reactivation of p53 by a specific MDM2 antagonist (MI-43) leads to p21-mediated cell cycle arrest and selective cell death in colon cancer," *Mol. Cancer Ther.* 7:1533-1542, American Association for Cancer Research (2008).

Shangary, S. et al., "Temporal activation of p53 by a specific MDM2 inhibitor is selectively toxic to tumors and leads to complete tumor growth inhibition," *Proc. Nat. Acad. Sci. (USA)* 105:3933-3938, The National Academy of Sciences of the USA (2008).

Sharma, P. et al., "Alkaloids of *Amsonia brevifolia*," *Phytochemistry* 27:3649-3652, Pergamon Press (1988).

Somei, M. et al., "Preparation and a Novel Rearrangement Reaction of 1,2,3,4-tetrahydro-9-hydroxy-β-carboline, and Their Applications for the Total Synthesis of (±)-Coerulescine," *Heterocycles* 53:7-10, Elsevier Science (2000).

Sun, S.H. et al., "A small molecule that disrupts Mdm2-p53 binding activates p53, induces apoptosis and sensitizes lung cancer cells to chemotherapy," *Cancer Biology & Therapy* 7:845-852, Landes Bioscience (2008).

Usui, T. et al., "Tryprostatin A, a specific and novel inhibitor of microtubule assembly," *Biochem. J.* 333:543-548, The Biochemical Society, London (1998).

van Tamelen, E.E. et al., "Spiro[Pyrrolidine-3 : 3'-Oxindole and -2'-*Pseudo*-Indoxyl]," *Chemistry & Industry* 1145-1146, Society of Chemical Industry, London (1956).

Vassilev, L.T. et al., "In Vivo Activation of the p53 Pathway by Small-Molecule Antagonists of MDM2," *Science* 303:844-848, American Association for the Advancement of Science (2004).

Vogelstein, B. et al., "Surfing the p53 network," *Nature* 408:307-310, Nature Publishing Group (2000).

Wade, M. et al., "BH3 activation blocks Hdmx suppression of apoptosis and cooperates with Nutlin to induce cell death," *Cell Cycle* 7:1973-1982, Landes Bioscience (2008).

Wang, H. and Ganesan, A., "A Biomimetic Total Synthesis of (−)-Spirotryprostatin B and Related Studies," *J. Org. Chem.* 65:4685-4693, The American Chemical Society (2000).

Wu, K-M and Farrelly, J.G, "Regulatory perspectives of Type II prodrug development and time-dependent toxicity management: Nonclinical Pharm/Tox analysis and the role of comparative toxicology" *Toxicology* 236: 1-6, Elsevier Ireland Ltd. (2007).

Wu, X. et al., "The p53-mdm-2 autoregulatory feedback loop," *Genes & Development* 7:1126-1132, Cold Spring Harbor Laboratory Press (1993).

Yu, S. et al., "Potent and Orally Active Small-Molecule Inhibitors of the MDM2—p53 Interaction," *J. Med. Chem.* 52:7970-7973, American Chemical Society (2009).

Antonchick, A.P. et al., "Highly enantioselective synthesis and cellular evaluation of spirooxindoles inspired by natural products," *Nature Chemistry* 2:735-740, Macmillan Publishers Limited (Sep. 2010; published online Jul. 11, 2010).

Chen, X.-H. et al., "Organocatalytic Synthesis of Spiro[pyrrolidin-3,3'-oxindoles] with High Enantiopurity and Structural Diversity," *J. Am. Chem. Soc.* 131:13819-13825, American Chemical Society (2009).

Dudkina, A.S. and Lindsley, C.W., "Small Molecule Protein-Protein Inhibitors for the p53-MDM2 Interaction," *Current Topics in Medicinal Chemistry* 7:952-960, Bentham Science Publishers Ltd. (2007).

Galliford, C.V. and Scheidt, K.A., "Pyrrolidinyl-Spirooxindole Natural Products as Inspirations for the Development of Potential Therapeutic Agents," *Angew. Chem. Int. Ed.* 46:8748-8758, Wiley-VCH Verlag GmbH & Co. KGaA, Weinheim (2007).

Jansen, A.B.A. and Richards, C.G., "A Synthesis of Some Spiro [Indoline-3,3'-Pyrrolidines]," *Tetrahedron* 21:1327-1331, Pergamon Press Ltd. (1965).

Kang, T.-H. et al., "Pteropodine and isopteropodine positively modulate the function of rat muscarinic $M_1$ and 5-$HT_2$ receptors expressed in *Xenopus* oocyte," *Eur. J. Pharmacol.* 444:39-45, Elsevier Science B.V. (2002).

Lo, M. M.-C. et al., "A Library of Spirooxindoles Based on a Stereoselective Three-Component Coupling Reaction," *J. Am. Chem. Soc.* 126:16077-16086, American Chemical Society (2004).

Seaton, J.C. et al., "The Structure and Stereoisomerism of Three Mitragyna Alkaloids," *Can. J. Chem.* 38:1035-1042, NRC Research Press, Ottawa (1960).

Seto, M. et al., "The Synthesis of 3-Spirooxindole Derivatives. IX. The Reactions of 2-Hydroxytryptamine with Hemiacetals," *Chem. Pharm. Bull.* 24:1393-1397, Pharmaceutical Society of Japan, Tokyo (1976).

Trost, B.M. and Brennan, M.K., "Asymmetric Syntheses of Oxindole and Indole Spirocyclic Alkaloid Natural Products," *Synthesis* 18:3003-3025, Thieme Stuttgart, New York (2009).

Van Tamelen, E.E. et al., "Total Synthesis of Rhyncophyllol and *dl*-Isorhyncophyllol," *J. Am. Chem. Soc.* 91:7333-7341, American Chemical Society (1969).

Von Nussbaum, F. and Danishefsky, S.J., "A Rapid Total Synthesis of Spirotryprostatin B: Proof of Its Relative and Absolute Stereochemistry," *Angew. Chem. Int. Ed.* 39:2175-2178, Wiley-VCH Verlag GmbH, Weinheim (2000).

Wenkert, E. et al., "3-Hydroxymethyleneoxindole and its Derivatives," *J. Am. Chem. Soc.* 81:3763-3768, American Chemical Society (1959).

\* cited by examiner

SPIRO-OXINDOLE MDM2 ANTAGONISTS

CROSS REFERENCE TO RELATED APPLICATIONS

This application claims priority to U.S. Provisional Patent Application No. 61/484,986, filed May 11, 2011, the contents of which are incorporated by reference in its entirety.

STATEMENT REGARDING FEDERALLY SPONSORED RESEARCH OR DEVELOPMENT

This invention was made with government support under CA121279 awarded by the National Institutes of Health. The government has certain rights in the invention

BACKGROUND

The aggressive cancer cell phenotype is the result of a variety of genetic and epigenetic alterations leading to deregulation of intracellular signaling pathways (Ponder, Nature 411:336 (2001)). Cancer cells typically fail to execute an apoptotic program, and lack of appropriate apoptosis due to defects in the normal apoptosis machinery is considered a hallmark of cancer (Lowe et al., Carcinogenesis 21:485 (2000)). The inability of cancer cells to execute an apoptotic program due to defects in the normal apoptotic machinery is often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., Carcinogenesis 21:485 (2000); Nicholson, Nature 407:810 (2000)). Accordingly, current and future efforts towards designing and developing new molecular target-specific anti-cancer therapies to improve survival and quality of life of cancer patients must include strategies that specifically target cancer cell resistance to apoptosis.

The p53 tumor suppressor plays a central role in controlling cell cycle progression, senescence, and apoptosis (Vogelstein et al., Nature 408:307 (2000); Goberdhan, Cancer Cell 7:505 (2005)). MDM2 and p53 are part of an auto-regulatory feed-back loop (Wu et al., Genes Dev. 7:1126 (1993)). MDM2 is transcriptionally activated by p53 and MDM2, in turn, inhibits p53 activity by at least three mechanisms (Wu et al., Genes Dev. 7:1126 (1993). First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

Although high-affinity peptide-based inhibitors of MDM2 have been successfully designed in the past (Garcia-Echeverria et al., Med. Chem. 43:3205 (2000)), these inhibitors are not suitable therapeutic molecules because of their poor cell permeability and in vivo bioavailability. Despite intensive efforts by the pharmaceutical industry, high throughput screening strategies have had very limited success in identifying potent, non-peptide small molecule inhibitors. Accordingly, there is a need for non-peptide, drug-like, small molecule inhibitors of the p53-MDM2 interaction. The structural basis of the interaction p53 and MDM2 has been established by x-ray crystallography (Kussie et al., Science 274:948 (1996)). Spiro-oxindole-based antagonists of the p53-MDM2 interaction are described in U.S. Pat. Nos. 7,759,383 B2 and 7,737,174 B2, U.S. Patent Appl. Pub. No. 2011/0112052 A2, and U.S. application Ser. No. 13/294,315.

SUMMARY OF THE INVENTION

In one aspect, the present disclosure provides spiro-oxindoles having Formula I:

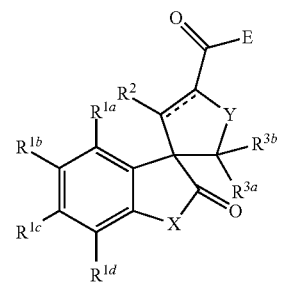

wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^{3b}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl; or $R^{3a}$ and $R^{3b}$ taken together form a 3- to 9-membered optionally substituted cycloalkyl or a 3- to 9-membered optionally substituted heterocyclo;

E is selected from the group consisting of —$OR^{26a}$ and —$NR^{26b}R^{26c}$;

$R^{26a}$ is selected from the group consisting of hydrogen, optionally substituted alkyl, optionally substituted cycloalkyl, and optionally substituted aryl;

$R^{26b}$ is $R^4$;

$R^{26c}$ is selected from the group consisting of hydrogen, optionally substituted alkyl, optionally substituted cycloalkyl, optionally substituted heterocyclo, optionally substituted aryl, optionally substituted heteroaryl, aralkyl, —$SO_2R^{5b}$, and $R^5$; or $R^{26b}$ and $R^{26c}$ taken together form a 4- to 9-membered optionally substituted heterocyclo;

wherein $R^4$ and $R^5$ has the meanings as described below in connection with Formula II;

$R^{5b}$ is selected from the group consisting of optionally substituted alkyl, optionally substituted cycloalkyl, optionally substituted heterocyclo, optionally substituted aryl, and optionally substituted heteroaryl;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ⚌ represents a single or a double bond, or a pharmaceutically acceptable salt, solvate, or prodrug thereof.

In another aspect, the present disclosure provides spiro-oxindoles having Formula II:

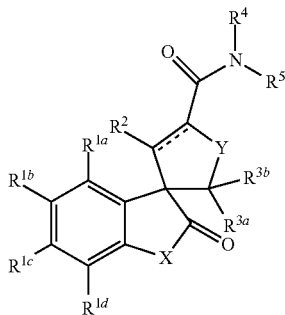

II wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^{3b}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl; or $R^{3a}$ and $R^{3b}$ taken together form a 3- to 9-membered optionally substituted cycloalkyl;

$R^4$ is selected from the group consisting of hydrogen and optionally substituted $C_1$-$C_6$ alkyl;

$R^5$ is selected from the group consisting of

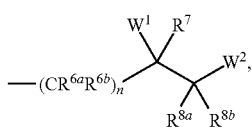

R5-1

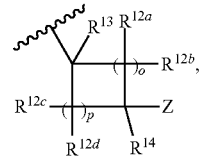

R5-2

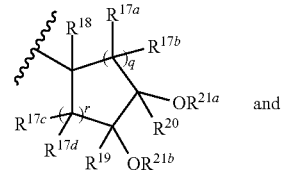

R5-3 and

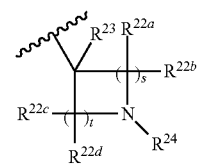

R5-4 wherein:

each $R^{6a}$ and $R^{6b}$ is independently selected from the group consisting of hydrogen and optionally substituted $C_1$-$C_6$ alkyl;

$R^7$ is selected from the group consisting of hydrogen, optionally substituted $C_1$-$C_6$ alkyl, and optionally substituted cycloalkyl;

$R^{8a}$ and $R^{8b}$ are each independently selected from the group consisting of hydrogen, optionally substituted $C_1$-$C_6$ alkyl, and optionally substituted cycloalkyl; or $R^{8a}$ and $R^{8b}$ taken together with the carbon that they are attached form a 3- to 8-membered optionally substituted cycloalkyl;

$W^1$ is selected from the group consisting of —$OR^{9a}$ and —$NR^{9b}R^{9c}$;

$R^{9a}$ is hydrogen;

$R^{9b}$ is selected from the group consisting of hydrogen, optionally substituted alkyl, optionally substituted cycloalkyl, optionally substituted aryl, optionally substituted heteroaryl, —$SO_2R^{9d}$, and —$CONR^{9e}R^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$W^2$ is selected from the group consisting of —$OR^{10}$ and —$NR^{11a}R^{11b}$;

with the proviso that when $W^1$ is —$OR^{9a}$ and $W^2$ is —$OR^{10}$ then at least one of $R^7$, $R^{8a}$, and $R^{8b}$ is other than hydrogen;

$R^{10}$ is hydrogen; or one of $R^{9a}$ and $R^{10}$ is hydrogen and the other is a metabolically cleavable group;

$R^{11a}$ is selected from the group consisting of hydrogen, optionally substituted alkyl, optionally substituted cycloalkyl, optionally substituted aryl, optionally substituted heteroaryl, —SO$_2$R$^{11c}$, and —CONR$^{11d}$R$^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

n is 1, 2, 3, 4, or 5;

each $R^{12a}$, $R^{12b}$, $R^{12c}$ and $R^{12d}$ is independently selected from the group consisting of hydrogen and optionally substituted $C_1$-$C_6$ alkyl;

$R^{13}$ is selected from the group consisting of hydrogen and optionally substituted $C_1$-$C_6$ alkyl;

$R^{14}$ is selected from the group consisting of hydrogen, optionally substituted $C_1$-$C_6$ alkyl, and optionally substituted cycloalkyl;

Z is selected from the group consisting of —OR$^{15}$ and —NR$^{16a}$R$^{16b}$; or Z and $R^{14}$ taken together form a carbonyl, i.e., a C=O, group.

$R^{15}$ is selected from the group consisting of hydrogen and metabolically cleavable group;

$R^{16a}$ is selected from the group consisting of —SO$_2$R$^{16c}$ and —CONR$^{16d}$R$^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

o is 1, 2, or 3;

p is 0, 1, 2, or 3;

each $R^{17a}$, $R^{17b}$, $R^{17c}$ and $R^{17d}$ is independently selected from the group consisting of hydrogen and optionally substituted $C_1$-$C_6$ alkyl;

$R^{18}$ is selected from the group consisting of hydrogen and optionally substituted $C_1$-$C_6$ alkyl;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

q is 0, 1, 2, or 3;

r is 1, 2, or 3;

each $R^{22a}$, $R^{22b}$, $R^{22c}$, and $R^{22d}$ is independently selected from the group consisting of hydrogen and optionally substituted $C_1$-$C_6$ alkyl;

$R^{23}$ is selected from the group consisting of hydrogen and optionally substituted $C_1$-$C_6$ alkyl;

$R^{24}$ is selected from the group consisting of —SO$_2$R$^{24a}$ and —CONR$^{24b}$ $R^{24a}$ is selected from the group consisting of optionally substituted alkyl, optionally substituted cycloalkyl, optionally substituted aryl, and optionally substituted heteroaryl;

$R^{24b}$ and $R^{24c}$ are each independently selected from the group consisting of hydrogen, optionally substituted cycloalkyl, optionally substituted aryl, and optionally substituted heteroaryl; or $R^{24b}$ and $R^{24c}$ taken together with the nitrogen atom to which they are attached form a 4- to 8-membered heterocyclo;

s and t are each independently 1, 2, or 3;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ⚌ represents a single or a double bond, or a pharmaceutically acceptable salt, solvate, or prodrug thereof.

In another aspect, the present disclosure provides compounds having Formula I that inhibit the interaction between p53 or p53-related proteins and MDM2 or MDM2-related proteins.

In another aspect, the present disclosure provides methods to induce senescence, cell cycle arrest and/or apoptosis in cells containing functional p53 or p53-related proteins, comprising contacting the cell with a compound of Formula I, or a pharmaceutically acceptable salt, solvate, or prodrug thereof, In another aspect, the present disclosure provides methods of treating, ameliorating, or preventing a hyperproliferative disease, e.g., cancer, e.g., adrenal cortical cancer, advanced cancer, anal cancer, aplastic anemia, bile duct cancer, bladder cancer, bone cancer, bone metastasis, brain/CNS tumors in adults, brain/CNS tumors in children, breast cancer, breast cancer in men, cancer in children, cancer of unknown primary, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, leukemia—acute lymphocytic (ALL) in adults, leukemia—acute myeloid (AML), leukemia—chronic lymphocytic (CLL), leukemia—chronic myeloid (CML), leukemia—chronic myelomonocytic (CMML), leukemia in children, liver cancer, lung cancer—non-small cell, lung cancer—small cell, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, non-Hodgkin lymphoma in children, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer—basal and squamous cell, skin cancer—melanoma, small intestine cancer, stomach cancer, testicular cancer, thymus cancer, thyroid cancer, uterine sarcoma, vaginal cancer, vulvar cancer, Waldenstrom macroglobulinemia, or Wilms Tumor, in a patient comprising administering to the patient a compound of Formula I, or a pharmaceutically acceptable salt, solvate, or prodrug thereof.

In another aspect, the present disclosure provides methods of treating, ameliorating, or preventing a hyperproliferative disease, e.g., cancer, in a patient comprising administering to the patient a compound of Formula I, or a pharmaceutically acceptable salt, solvate, or prodrug thereof, in combination with one or more additional therapeutic agents, e.g., one or more additional anticancer agents.

In another aspect, the present disclosure provides pharmaceutical compositions comprising a compound of Formula I, or a pharmaceutically acceptable salt, solvate, or prodrug thereof, for treating, ameliorating, or preventing a hyperproliferative disease, e.g., cancer, in a patient.

In another aspect, the present disclosure provides kits comprising a compound of Formula I, or a pharmaceutically acceptable salt, solvate, or prodrug thereof, for treating, ameliorating, or preventing a hyperproliferative disease, e.g., cancer, in a patient.

DETAILED DESCRIPTION OF THE INVENTION

Figure 1:
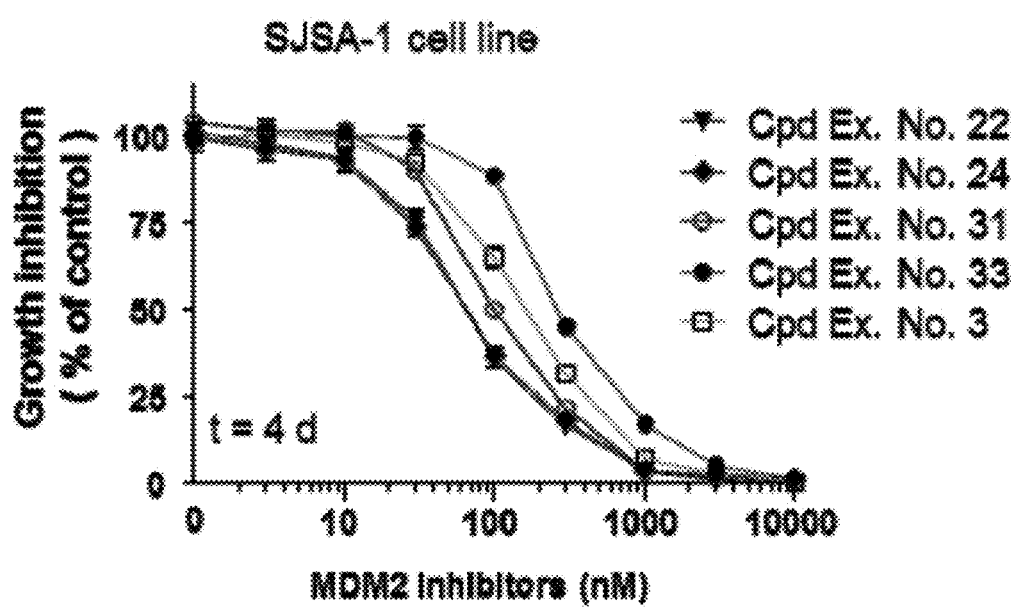
FIG. 1 is a line graph showing cell growth inhibition of MDM2 inhibitors in the SJSA-1 cell line as determined using the WST-based assay. SJSA-1 cells were treated with each compound for 4 days.

Provided herein are compounds having Formulae I-XXVIII. These compounds inhibit the interaction between p53 or p53-related proteins and MDM2 or MDM2-related proteins. By inhibiting the negative effect of MDM2 or MDM2-related proteins on p53 or p53-related proteins, these compounds sensitize cells to inducers of apoptosis and/or cell cycle arrest. In one embodiment, compounds having Formulae I-XXVIII induce apoptosis and/or cell cycle arrest. Therefore, also provided herein are methods of sensitizing cells to inducers of apoptosis and/or cell cycle arrest and to methods of inducing apoptosis and/or cell cycle arrest in cells. In one embodiment, the methods comprise contacting the cells with one or more compounds having Formulae I-XXVIII alone or in combination with additional agent(s), e.g., an inducer of apoptosis or a cell cycle disrupter.

Also provided herein are methods of treating, ameliorating, or preventing disorders in an patient, comprising administering to the patient one or more compounds having Formulae I-XXVIII alone or in combination with additional agent(s), e.g., an inducer of apoptosis. Such disorders include those characterized by a dysregulation of apoptosis and those characterized by the proliferation of cells expressing functional p53 or p53-related proteins. In another embodiment, methods of protecting normal (e.g., non-hyperproliferative) cells in an animal from the toxic side effects of chemotherapeutic agents and treatments are provided. This method comprises administering to the animal one or more compounds having Formulae I-XXVIII.

Also provided herein are compounds having any one of Formulae I-XXVIII for use in the manufacture of a medicament for treating a hyperproliferative disease such as cancer.

Also provided herein are compounds having any one of Formulae I-XXVIII, or a pharmaceutical composition comprising a compound having any one of Formulae I-XXVIII, for use in treating a hyperproliferative disease such as cancer.

Definitions

The term "anticancer agent" as used herein, refers to any therapeutic agent (e.g., chemotherapeutic compound and/or molecular therapeutic compound), antisense therapy, radiation therapy, or surgical intervention, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate, see, e.g., US 2007/0249564 A1.

The term "metabolically cleavable group" as used herein, refers to groups which can be cleaved from the parent molecule by metabolic processes and be substituted with hydrogen. Certain compounds containing metabolically cleavable groups may be prodrugs, i.e., they are pharmacologically inactive. Certain other compounds containing metabolically cleavable groups may be antagonists of the interaction between p53 and MDM2. In such cases, these compounds may have more, less, or equivalent activity of the parent molecule. Examples of metabolically cleavable groups include those derived from amino acids (see, e.g., US 2006/0241017 A1; US 2006/0287244 A1; and WO 2005/046575 A2) or phosphorus-containing compounds (see, e.g., U.S. 2007/0249564 A1) as illustrated in Scheme 1.

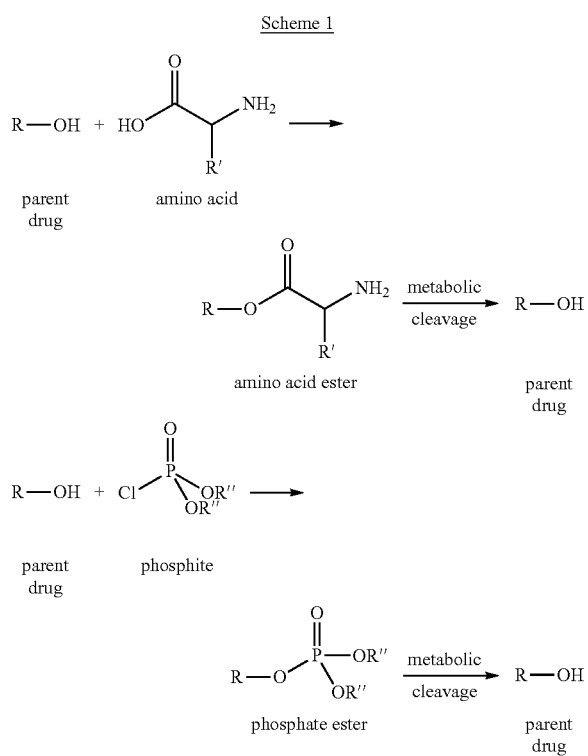

The term "pharmaceutically acceptable salt" as used herein, refers to any salt (e.g., obtained by reaction with an acid or a base) of a compound provided herein that is physiologically tolerated in the target animal (e.g., a mammal). Salts of the compounds of provided herein may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds provided herein and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds provided herein compounded with a suitable cation such as $Na^+$, $NH_4^+$, and $NW_4^+$ (wherein W is a $C_{1-4}$ alkyl group), and the like. For therapeutic use, salts of the compounds provided herein are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound provided herein with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "monovalent pharmaceutically acceptable cation" as used herein refers to inorganic cations such as, but not limited to, alkaline metal ions, e.g., $Na^+$ and $K^+$, as well as organic cations such as, but not limited to, ammonium and substituted ammonium ions, e.g., $NH_4^+$, $NHMe_3^+$, $NH_2Me_2^+$, $NHMe_3^+$ and $NMe_4^+$.

The term "divalent pharmaceutically acceptable cation" as used herein refers to inorganic cations such as, but not limited to, alkaline earth metal cations, e.g., $Ca^{2+}$ and $Mg^{2+}$.

Examples of monovalent and divalent pharmaceutically acceptable cations are discussed, e.g., in Berge et al. *J. Pharm. Sci.*, 66:1-19 (1997).

The term "therapeutically effective amount," as used herein, refers to that amount of the therapeutic agent (including the compounds and compositions of matter provided herein) sufficient to result in amelioration of one or more symptoms of a disorder, or prevent advancement of a disorder, or cause regression of the disorder. For example, with respect to the treatment of cancer, in one embodiment, a therapeutically effective amount can refer to the amount of a therapeutic agent that decreases the rate of tumor growth, decreases tumor mass, decreases the number of metastases, increases time to tumor progression, increase tumor cell apoptosis, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first therapeutic agent (e.g., a compound provided herein), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second therapeutic agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "functional p53," as used herein, refers to wild-type p53 expressed at normal, high, or low levels and mutant or allelic variants of p53 that retain(s) at least about 5% of the activity of wild-type p53, e.g., at least about 10%, about 20%, about 30%, about 40%, about 50%, or more of wild-type activity.

The term "p53-related protein," as used herein, refers to proteins that have at least 25% sequence homology with p53, have tumor suppressor activity, and are inhibited by interaction with MDM2 or MDM2-related proteins. Examples of p53-related proteins include, but are not limited to, p63 and p73.

The term "MDM2-related protein," as used herein, refers to proteins that have at least 25% sequence homology with MDM2, and interact with and inhibit p53 or p53-related proteins. Examples of MDM2-related proteins include, but are not limited to, MDMX.

The term "senescence" as used herein, refers to the phenomenon whereby non-cancerous diploid cells lose the ability to divide, and characterized in part by telomeric dysfunction or shortening.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas, leukemias and the like. A neoplasm is said to be benign if it does not undergo invasion or metastasis and malignant if it does either of these. A "metastatic" cell means that the cell can invade neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without treatment with one or more compounds provided herein.

The term "apoptosis-modulating agents," as used herein, refers to agents which are involved in modulating (e.g., inhibiting, decreasing, increasing, promoting) apoptosis. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptosis-modulating agents include, but are not limited to, TNFα, Fas ligand, antibodies to Fas/CD95 and other TNF family receptors, TRAIL (also known as Apo2 Ligand or Apo2L/TRAIL), antibodies to TRAIL-R1 or TRAIL-R2, Bcl-2, p53, BAX, BAD, Akt, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Apoptosis-modulating agents include those which are inducers of apoptosis, such as TNF or a TNF-related ligand, particularly a TRAMP ligand, a Fas/CD95 ligand, a TNFR-1 ligand, or TRAIL.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

The terms "pulsatile administration," "pulsatile dose administration" or "pulsatile dosing" as used herein, refer to intermittent (i.e., not continuous) administration of compounds having Formulae I-XXVIII, or pharmaceutically acceptable salts, solvates, or prodrugs thereof, to a patient. Pulsatile dose administration regimens useful in the present disclosure encompass any discontinuous administration regimen that provides a therapeutically effective amount of compounds having Formulae I-XXVIII, or pharmaceutically acceptable salts, solvates, or prodrugs thereof, to a patient in need thereof. Pulsatile dosing regimens can use equivalent, lower, or higher doses of compounds having Formulae I-XXVIII than would be used in continuous dosing regimens. Advantages of pulsatile dose administration of compounds having Formulae I-XXVIII, or pharmaceutically acceptable salts, solvates, or prodrugs thereof, include, but are not limited to, improved safety, decreased toxicity, increased exposure, increased efficacy, and increased patient compliance. These advantages may be realized when compounds having Formulae I-XXVIII, or pharmaceutically acceptable salts, solvates, or prodrugs thereof, are administered as a single agent or are administered in combination with one or more additional anticancer agents. On the day that compounds having Formulae I-XXVIII, or pharmaceutically acceptable salts, solvates, or prodrugs thereof, are scheduled to be administered to the patient, administration can occur in a single or in divided doses, e.g., once-a-day, twice-a-day, three times a day, four times a day or more. In one embodiment, compounds having Formulae I-XXVIII, or pharmaceutically acceptable salts, solvates, or prodrugs thereof, are administered once (QD) or twice (BID) on the day it is schedule to be administered The term "alkyl" as used herein by itself or part of another group refers to a straight-chain or branched saturated aliphatic hydrocarbon having from one to eighteen carbons or the number of carbons designated (e.g., $C_1$-$C_{18}$ means 1 to 18 carbons). In one embodiment, the alkyl is a $C_1$-$C_{10}$ alkyl. In another embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl. In another embodiment, the alkyl is a $C_2$-$C_{10}$ alkyl. In another embodiment, the alkyl is a $C_3$-$C_{10}$ alkyl. In another embodiment, the alkyl is a $C_3$-$C_6$ alkyl. Exemplary alkyl groups include methyl, ethyl, n-propyl, isopropyl, n-butyl, sec-butyl, isobutyl, tert-butyl, n-pentyl, isopentyl, neopentyl, n-hexyl, isohexyl, n-heptyl, 4,4-dimethylpentyl, n-octyl, 2,2,4-trimethylpentyl, nonyl, decyl and the like.

The term "optionally substituted alkyl" as used herein by itself or part of another group means that the alkyl as defined above is either unsubstituted or substituted with one, two or three substituents independently selected from hydroxy (i.e., —OH), nitro (i.e., —$NO_2$), cyano (i.e., —CN), amino, optionally substituted cycloalkyl, optionally substituted heteroaryl, optionally substituted heterocyclo, alkoxy, aryloxy, aralkyloxy, alkylthio, carboxamido, sulfonamido, —$CO_2R^c$, —$COR^c$, —$SO_2R^d$, —$N(R^e)COR^f$, —$N(R^e)SO_2R^g$ or —$N(R^e)C$=$N(R^h)$-amino, wherein $R^c$ is hydrogen, optionally substituted alkyl, optionally substituted aryl, or optionally substituted heteroaryl; $R^d$ is optionally substituted alkyl, optionally substituted aryl, or optionally substituted heteroaryl; $R^e$ is hydrogen, optionally substituted alkyl, optionally substituted aryl, or optionally substituted heteroaryl; $R^f$ is hydrogen, optionally substituted alkyl, optionally substituted aryl, or optionally substituted heteroaryl; $R^g$ is optionally substituted alkyl, optionally substituted aryl, or optionally substituted heteroaryl; and $R^h$ is hydrogen, —CN, optionally substituted alkyl, optionally substituted aryl, or optionally substituted heteroaryl. In one embodiment, the optionally substituted alkyl is substituted with two substituents. In another embodiment, the optionally substituted alkyl is substituted with one substituent. In another embodiment, the substituents are selected from hydroxyl (i.e., a hydroxyalkyl, e.g., a monohydroxyalkyl or dihydroxyalkyl), optionally substituted cycloalkyl (i.e., a (cycloalkyl)alkyl), optionally substituted heterocyclo (i.e., a (heterocyclo)alkyl), —$CO_2H$, or amino (i.e., an aminoalkyl). Exemplary optionally substituted alkyl groups include —$CH_2OCH_3$, —$CH_2CH_2NH_2$, —$CH_2CH_2NH(CH_3)$, —$CH_2CH_2CN$, —$CH_2CO_2H$, —$CH_2CONH_2$, —$CH_2SO_2CH_3$, —$CH_2CH_2SO_2CH_3$, —$C(CH_3)_2CO_2H$, hydroxymethyl, hydroxyethyl, hydroxypropyl, and the like.

The term "alkylenyl" as used herein by itself or part of another group refers to a divalent alkyl radical containing one, two, three, four, or more joined methylene groups. Exemplary alkylenyl groups include —($CH_2$)—, —($CH_2$)$_2$—, —($CH_2$)$_3$—, —($CH_2$)$_4$—, and the like.

The term "optionally substituted alkylenyl" as used herein by itself or part of another group means the alkylenyl as defined above is either unsubstituted or substituted with one, two, three, or four substituents independently selected from the group consisting of optionally substituted $C_1$-$C_6$ alkyl, optionally substituted cycloalkyl, optionally substituted aryl, and optionally substituted heteroaryl. In one embodiment, the optionally substituted $C_1$-$C_6$ alkyl is methyl. In one embodiment, the optionally substituted aryl is a phenyl optionally substituted with one or two halo groups. Exemplary optionally substituted alkylenyl groups include —$CH(CH_3)$—, —$C(CH_3)_2$—, —$CH_2CH(CH_3)$—, —$CH_2CH(CH_3)CH_2$—, —$CH_2CH(Ph)CH_2$—, —$CH(CH_3)CH(CH_3)$—, and the like.

The term "haloalkyl" as used herein by itself or part of another group refers to an alkyl as defined above having one to six halo substituents. In one embodiment, the haloalkyl has one, two or three halo substituents. Exemplary haloalkyl groups include trifluoromethyl, —$CH_2CH_2F$ and the like.

The term "monohydroxyalkyl" as used herein by itself or part of another group refers to an alkyl as defined above having exactly one hydroxy substituent. Exemplary hydroxyalkyl groups include hydroxymethyl, hydroxyethyl, hydroxypropyl, and the like.

The term "dihydroxyalkyl" as used herein by itself or part of another group refers to alkyl as defined above having exactly two hydroxyl substituents. Exemplary dihydroxyalkyl groups include —$CH_2CH_2CCH_3(OH)CH_2OH$, —$CH_2CH_2CH(OH)CH(CH_3)OH$, —$CH_2(OH)CH_2OH$, —$CH_2CH(CH_2OH)_2$, —$CH_2CH_2CH(OH)C(CH_3)_2OH$, —$CH_2CH_2CCH_3(OH)CH(CH_3)OH$, and the like, including stereoisomers thereof.

The term "hydroxycycloalkyl" as used herein by itself or part of another group refers to an optionally substituted cycloalkyl as defined below having a least one, e.g., one or two hydroxy substituents. Exemplary hydroxycycloalkyl groups include:

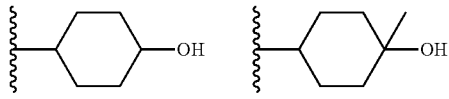

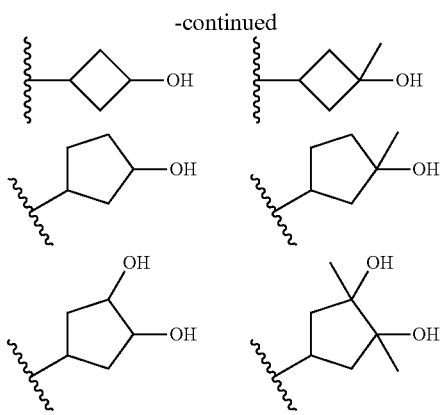

and the like, including stereoisomers thereof.

The term "optionally substituted (cycloalkyl)alkyl" as used herein by itself or part of another group refers to an optionally substituted alkyl as defined above having an optionally substituted cycloalkyl (as defined below) substituent. Exemplary optionally substituted (cycloalkyl)alkyl groups include:

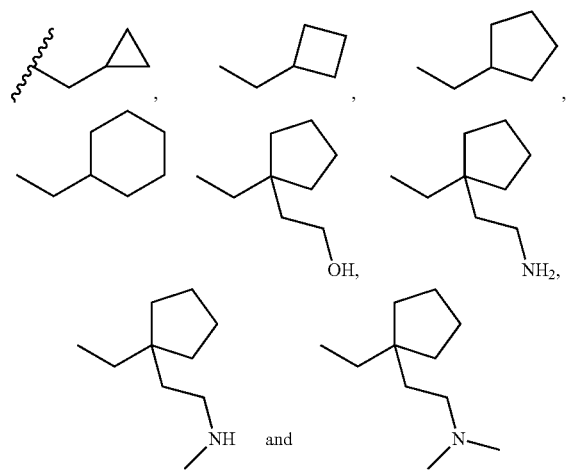

and the like, including stereoisomers thereof.

The term "(heterocyclo)alkyl" as used herein by itself or part of another group refers to an alkyl as defined above having an optionally substituted heterocyclo (as defined below) substituent.

The term "aralkyl" as used herein by itself or part of another group refers to an optionally substituted alkyl as defined above having one, two or three optionally substituted aryl substituents. In one embodiment, the aralkyl has two optionally substituted aryl substituents. In another embodiment, the aralkyl has one optionally substituted aryl substituent. In another embodiment, the aralkyl is an aryl($C_1$-$C_4$ alkyl). In another embodiment, the aryl($C_1$-$C_4$ alkyl) has two optionally substituted aryl substituents. In another embodiment, the aryl($C_1$-$C_4$ alkyl) has one optionally substituted aryl substituent. Exemplary aralkyl groups include, for example, benzyl, phenylethyl, (4-fluorophenyl)ethyl, phenylpropyl, diphenylmethyl (i.e., $Ph_2CH$—), diphenylethyl ($Ph_2CHCH_2$—) and the like.

The term "cycloalkyl" as used herein by itself or part of another group refers to saturated and partially unsaturated (containing one or two double bonds) cyclic hydrocarbon groups containing one to three rings having from three to twelve carbon atoms (i.e., $C_3$-$C_{12}$ cycloalkyl) or the number of carbons designated. In one embodiment, the cycloalkyl has one ring. In another embodiment, the cycloalkyl is a $C_3$-$C_6$ cycloalkyl. Exemplary cycloalkyl groups include cyclopropyl, cyclobutyl, cyclopentyl, cyclohexyl, cycloheptyl, cyclooctyl, norbornyl, decalin, adamantyl and the like.

The term "optionally substituted cycloalkyl" as used herein by itself or part of another group means the cycloalkyl as defined above is either unsubstituted or substituted with one, two or three substituents independently selected from halo, nitro, cyano, hydroxy, amino, optionally substituted alkyl, haloalkyl, hydroxyalkyl, aminoalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido, sulfonamido, —$CO_2R^c$, —$COR^c$, —$SO_2R^d$, —$N(R^e)COR^f$, —$N(R^e)SO_2R^g$ or —$N(R^e)C$=$N(R^h)$-amino, wherein $R^c$, $R^d$, $R^e$, $R^f$, $R^g$, and $R^h$ are as defined above in connection with optionally substituted alkyl. The term "optionally substituted cycloalkyl" also means the cycloalkyl as defined above may be fused to an optionally substituted aryl. In one embodiment, the optionally substituted cycloalkyl is substituted with two substituents. In another embodiment, the optionally substituted cycloalkyl is substituted with one substituent. In another embodiment, the substituents are selected from hydroxy (i.e., a hydroxycycloalkyl, e.g., a monohydroxycycloalkyl or dihydroxycycloalkyl) or —$CO_2H$. Exemplary optionally substituted cycloalkyl groups include:

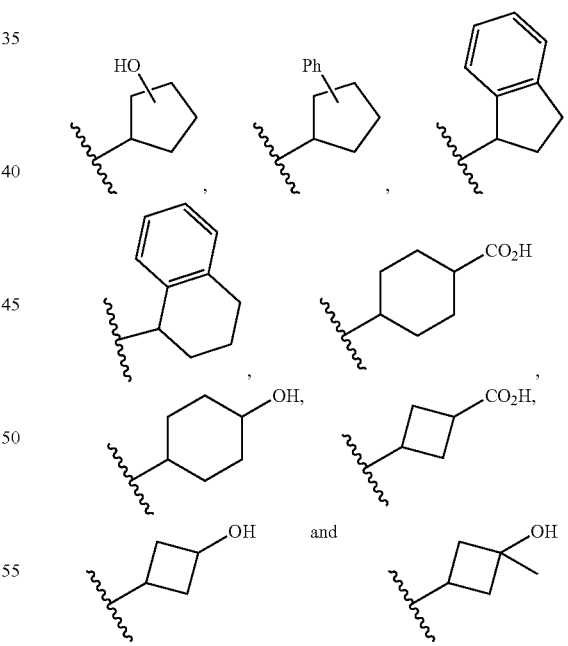

and the like.

The term "alkenyl" as used herein by itself or part of another group refers to an alkyl group as defined above containing one, two or three carbon-to-carbon double bonds. In one embodiment, the alkenyl has one carbon-to-carbon double bond. Exemplary alkenyl groups include —CH=$CH_2$, —$CH_2$CH=$CH_2$, —$CH_2CH_2$CH=$CH_2$, —$CH_2CH_2$CH=$CHCH_3$ and the like.

The term "optionally substituted alkenyl" as used herein by itself or part of another group means the alkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Exemplary optionally substituted alkenyl groups include —CH=CHPh, —CH$_2$CH=CHPh and the like.

The term "cycloalkenyl" as used herein by itself or part of another group refers to a cycloalkyl group as defined above containing one, two or three carbon-to-carbon double bonds. In one embodiment, the cycloalkenyl has one carbon-to-carbon double bond. Exemplary cycloalkenyl groups include cyclopentene, cyclohexene and the like.

The term "optionally substituted cycloalkenyl" as used herein by itself or part of another group means the cycloalkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido.

The term "alkynyl" as used herein by itself or part of another group refers to an alkyl group as defined above containing one to three carbon-to-carbon triple bonds. In one embodiment, the alkynyl has one carbon-to-carbon triple bond. Exemplary alkynyl groups include —C≡CH, —C≡CCH$_3$, —CH$_2$C≡CH, —CH$_2$CH$_2$C≡CH and —CH$_2$CH$_2$C≡CCH$_3$.

The term "optionally substituted alkynyl" as used herein by itself or part of another group means the alkynyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Exemplary optionally substituted alkenyl groups include —C≡CPh, —CH$_2$C≡CPh and the like.

The term "aryl" as used herein by itself or part of another group refers to monocyclic and bicyclic aromatic ring systems having from six to fourteen carbon atoms (i.e., C$_6$-C$_{14}$ aryl) such as phenyl (abbreviated as Ph), 1-naphthyl and 2-naphthyl and the like.

The term "optionally substituted aryl" as used herein by itself or part of another group means the aryl as defined above is either unsubstituted or substituted with one to five substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido, sulfonamido, —CONHSO$_2$Me, —CO$_2$R$^c$, —COR$^c$, —SO$_2$R$^d$, —N(R$^e$)COR$^f$, —N(R$^e$)SO$_2$R$^g$ or —N(R$^e$)C=N(R$^h$)-amino, wherein R$^c$, R$^d$, R$^e$, R$^f$, R$^g$, and R$^h$ are as defined above in connection with optionally substituted alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl, 2-fluoro-3-chlorophenyl, 3-chloro-4-fluorophenyl, 4-CO$_2$H-phenyl and the like. The term optionally substituted aryl is meant to include groups having fused optionally substituted cycloalkyl and fused optionally substituted heterocyclo rings. Examples include

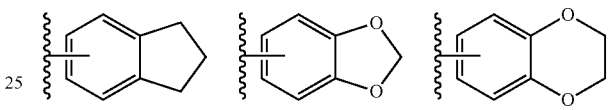

and the like.

The term "heteroaryl" as used herein by itself or part of another group refers to monocyclic and bicyclic aromatic ring systems having from five to fourteen ring atoms (i.e., 5- to 14-membered heteroaryl) and one, two, three, or four heteroatoms independently selected from the group consisting of oxygen, nitrogen and sulfur. In one embodiment, the heteroaryl has three heteroatoms. In one embodiment, the heteroaryl has two heteroatoms. In one embodiment, the heteroaryl has one heteroatom. In one embodiment, the heteroaryl is a 5-membered heteroaryl. In another embodiment, the heteroaryl is a 6-membered heteroaryl. In another embodiment, the heteroaryl is a 6-membered heteroaryl having one or two nitrogen atoms. Exemplary heteroaryl groups include 1-pyrrolyl, 2-pyrrolyl, 3-pyrrolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, purinyl, 2-benzimidazolyl, 4-benzimidazolyl, 5-benzimidazolyl, 2-benzthiazolyl, 4-benzthiazolyl, 5-benzthiazolyl, 5-indolyl, 3-indazolyl, 4-indazolyl, 5-indazolyl, 1-isoquinolyl, 5-isoquinolyl, 2-quinoxalinyl, 5-quinoxalinyl, 2-quinolyl 3-quinolyl, 6-quinolyl and the like. The term heteroaryl is meant to include possible N-oxides. Exemplary N-oxides include pyridyl N-oxide and the like.

The term "optionally substituted heteroaryl" as used herein by itself or part of another group means the heteroaryl as defined above is either unsubstituted or substituted with one to four substituents, typically one or two substituents, independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido, sulfonamido, —CO$_2$R$^c$, —COR$^c$, —SO$_2$R$^d$, —N(R$^e$)COR$^f$, —N(R$^e$)SO$_2$R$^g$ or —N(R$^e$)C=N(R$^h$)-amino, wherein R$^c$, R$^d$, R$^e$, R$^f$, R$^g$, and R$^h$ are as defined above in connection with optionally substituted alkyl. In one embodiment, the optionally substituted heteroaryl has one substituent. In another embodiment, the substituent is an optionally substituted aryl, aralkyl, or optionally substituted alkyl. In another embodiment, the substituent is an optionally substituted phenyl. Any available carbon or nitrogen atom may be substituted. Exemplary optionally substituted heteroaryl groups include

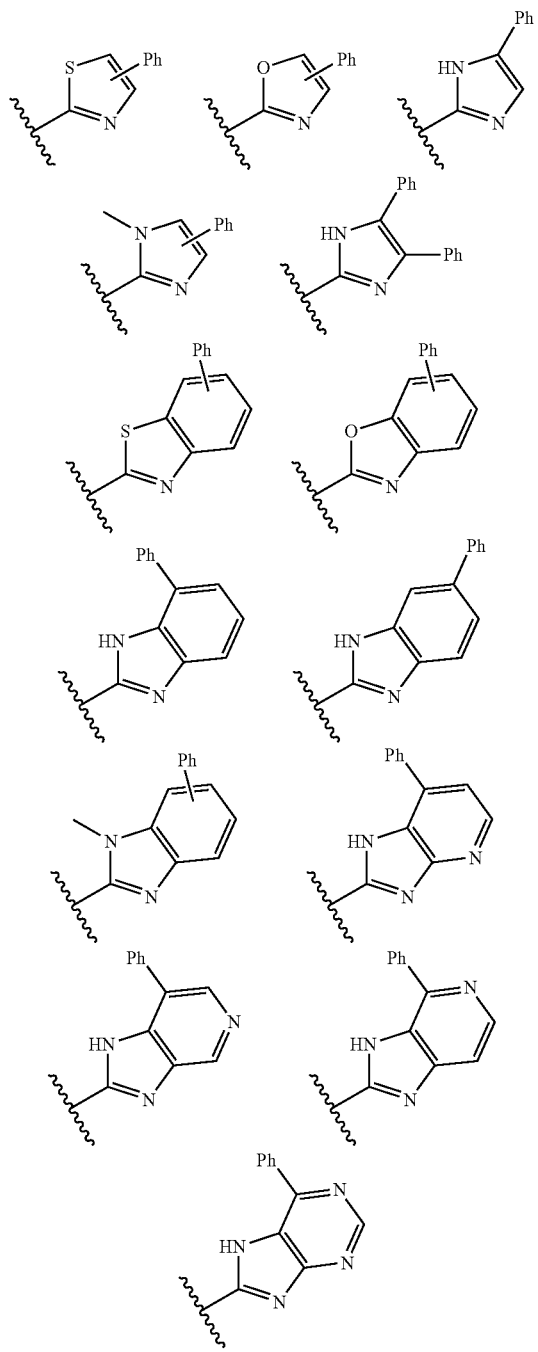

and the like.

The term "heterocyclo" as used herein by itself or part of another group refers to saturated and partially unsaturated (containing one or two double bonds) cyclic groups containing one to three rings having from three to fourteen ring members (i.e., 3- to 14-membered heterocyclo) and at least one oxygen, sulfur, including sulfoxide and sulfone, and/or nitrogen atom. In one embodiment, the heterocyclo group is chosen from a 5- or 6-membered cyclic group containing one ring and one or two oxygen and/or nitrogen atoms. In one embodiment, the heterocyclo group is a 6-membered cyclic group containing one ring and one sulfur atom, including sulfoxide and sulfone. The heterocyclo can be optionally linked to the rest of the molecule through a carbon or nitrogen atom. Exemplary heterocyclo groups include:

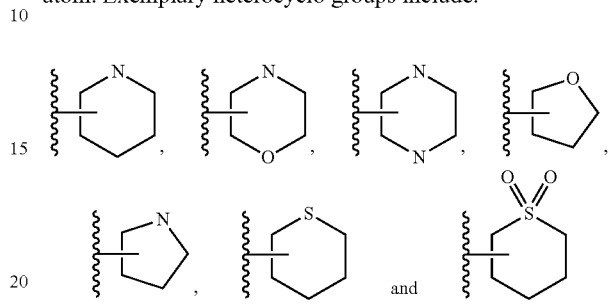

and the like.

The term "optionally substituted heterocyclo" as used herein by itself or part of another group means the heterocyclo as defined above is either unsubstituted or substituted with one to four substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido, sulfonamido, —CO$_2$R$^c$, —COR$^c$, —SO$_2$R$^d$, —N(R$^e$)COR$^f$, —N(R$^e$)SO$_2$R$^g$ or —N(R$^e$)C=N(R$^h$)-amino, wherein R$^c$, R$^d$, R$^e$, R$^f$, R$^g$, and R$^h$ are as defined above in connection with optionally substituted alkyl. Substitution may occur on any available carbon or nitrogen atom. Exemplary substituted heterocyclo groups include

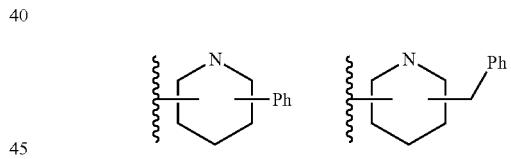

and the like. An optionally substituted heterocyclo may be fused to an aryl group to provide an optionally substituted aryl as described above.

The term "alkoxy" as used herein by itself or part of another group refers to a haloalkyl, optionally substituted alkyl, optionally substituted cycloalkyl, optionally substituted alkenyl or optionally substituted alkynyl attached to a terminal oxygen atom. Exemplary alkoxy groups include methoxy, tert-butoxy, —OCH$_2$CH=CH$_2$, —OCH$_2$CH$_2$OH, —OC(CH$_3$)$_2$CO$_2$H, and the like.

The term "aryloxy" as used herein by itself or part of another group refers to an optionally substituted aryl attached to a terminal oxygen atom. Exemplary aryloxy groups include phenoxy and the like.

The term "aralkyloxy" as used herein by itself or part of another group refers to an aralkyl attached to a terminal oxygen atom. Exemplary aralkyloxy groups include benzyloxy and the like.

The term "alkylthio" as used herein by itself or part of another group refers to a haloalkyl, aralkyl, optionally substituted alkyl, optionally substituted cycloalkyl, optionally substituted alkenyl or optionally substituted alkynyl attached to a terminal sulfur atom. Exemplary alkyl groups include —SCH₃ and the like.

The term "halo" or "halogen" as used herein by itself or part of another group refers to fluoro, chloro, bromo or iodo. In one embodiment, the halo is fluoro or chloro.

The term "amino" as used herein by itself or part of another group refers to a radical of formula —NR$^a$R$^b$ wherein R$^a$ and R$^b$ are independently hydrogen, haloalkyl, aralkyl, optionally substituted alkyl, optionally substituted cycloalkyl, optionally substituted heterocyclo, optionally substituted aryl or optionally substituted heteroaryl; or R$^a$ and R$^b$ taken together with the nitrogen atom to which they are attached form a four to seven membered optionally substituted heterocyclo. Exemplary amino groups include —NH₂, —N(H)CH₃, —N(CH₃)₂, —N(H)CH₂CH₃, —N(CH₂CH₃), —N(H)CH₂Ph and the like.

The term "carboxamido" as used herein by itself or part of another group refers to a radical of formula —CO-amino. Exemplary carboxamido groups include —CONH₂, —CON(H)CH₃, —CON(H)Ph, —CON(H)CH₂CH₂Ph, —CON(CH₃)₂, CON(H)CHPh₂ and the like.

The term "sulfonamido" as used herein by itself or part of another group refers to a radical of formula —SO₂-amino. Exemplary sulfonamido groups include —SO₂NH₂, —SO₂N(H)CH₃, —SO₂N(H)Ph and the like.

The term "about," as used herein, includes the recited number ±10%. Thus, "about 10" means 9 to 11.

Certain of the compounds of the present disclosure may exist as stereoisomers, i.e., isomers that differ only in the spatial arrangement of atoms, including optical isomers and conformational isomers (or conformers). The disclosure includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

The term "substantially free of" as used herein means that the compound comprises less than about 25% of other stereoisomers, e.g., diastereomers and/or enantiomers, as established using conventional analytical methods routinely used by those of skill in the art. In one embodiment, the amount of other stereoisomers is less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5%.

Stereoisomerically enriched compounds that contain about 95% or more of a desired stereoisomer, for example, about 96% or more, about 97% or more, about 98% or more, or about 99% or more are referred to herein as "substantially pure stereoisomers."

Stereoisomerically enriched compounds that contain about 99% or more of a desired stereoisomer are referred to herein as "pure" stereoisomers. The purity of any stereoisomerically enriched compound can be determined using conventional analytical methods such as, for example, normal phase HPLC, reverse phase HPLC, chiral HPLC, and $^1$H and $^{13}$C NMR.

Compounds

In one embodiment, compounds of Formula I are provided:

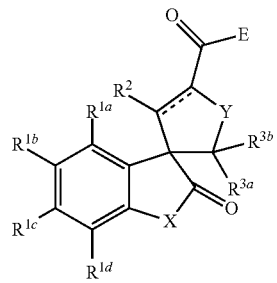

I wherein:

R$^{1a}$, R$^{1b}$, R$^{1c}$, and R$^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

R$^2$ is selected from the group consisting of optionally substituted aryl and optionally substituted heteroaryl;

R$^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

R$^{3b}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl; or R$^{3a}$ and R$^{3b}$ taken together form a 3- to 9-membered optionally substituted cycloalkyl or a 3- to 9-membered optionally substituted heterocyclo;

E is selected from the group consisting of —OR$^{26a}$ and —NR$^{26b}$R$^{26c}$;

R$^{26a}$ is selected from the group consisting of hydrogen, optionally substituted alkyl, optionally substituted cycloalkyl, and optionally substituted aryl;

R$^{26b}$ is R4;

R$^{26c}$ is selected from the group consisting of hydrogen, optionally substituted alkyl, optionally substituted cycloalkyl, optionally substituted heterocyclo, optionally substituted aryl, optionally substituted heteroaryl, aralkyl, —SO₂R$^{5b}$, and R$^5$;

wherein R$^4$ and R$^5$ have the meanings as described below for Formula II;

or R$^{26b}$ and R$^{26c}$ taken together form a 4- to 9-membered optionally substituted heterocyclo;

R$^{5b}$ is selected from the group consisting of optionally substituted alkyl, optionally substituted cycloalkyl, optionally substituted heterocyclo, optionally substituted aryl, and optionally substituted heteroaryl;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ---  represents a single or a double bond, or a pharmaceutically acceptable salt, solvate, or prodrug thereof.

In another embodiment, compounds of Formula I are provided, wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^{3b}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl; or $R^{3a}$ and $R^{3b}$ taken together form a 3- to 9-membered optionally substituted cycloalkyl or a 3- to 9-membered optionally substituted heterocyclo;

E is selected from the group consisting of —$OR^{26a}$ and —$NR^{26b}R^{26c}$;

$R^{26a}$ is selected from the group consisting of hydrogen, optionally substituted alkyl, optionally substituted cycloalkyl, and optionally substituted aryl;

$R^{26b}$ is selected from the group consisting of hydrogen and optionally substituted alkyl;

$R^{26c}$ is selected from the group consisting of hydrogen, optionally substituted alkyl, optionally substituted cycloalkyl, optionally substituted heterocyclo, optionally substituted aryl, optionally substituted heteroaryl, aralkyl, and —$SO_2R^{5b}$;

or $R^{26b}$ and $R^{26c}$ taken together form a 4- to 9-membered optionally substituted heterocyclo;

$R^{5b}$ is selected from the group consisting of optionally substituted alkyl, optionally substituted cycloalkyl, optionally substituted heterocyclo, optionally substituted aryl, and optionally substituted heteroaryl;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ---  represents a single or a double bond, or a pharmaceutically acceptable salt, solvate, or prodrug thereof In another embodiment, compounds of Formula I are provided, wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^{3a}$ and $R^{3b}$ taken together form a 3- to 9-membered optionally substituted cycloalkyl or a 3- to 9-membered optionally substituted heterocyclo;

E is selected from the group consisting of —$OR^{26a}$ and —$NR^{26b}R^{26c}$;

$R^{26a}$ is selected from the group consisting of hydrogen, optionally substituted alkyl, optionally substituted cycloalkyl, and optionally substituted aryl;

$R^{26b}$ is selected from the group consisting of hydrogen and optionally substituted alkyl;

$R^{26c}$ is selected from the group consisting of hydrogen, optionally substituted alkyl, optionally substituted cycloalkyl, optionally substituted heterocyclo, optionally substituted aryl, optionally substituted heteroaryl, aralkyl, and —$SO_2R^{5b}$;

wherein $R^4$ and $R^5$ have the meanings as described below for Formula II;

or $R^{26b}$ and $R^{26c}$ taken together form a 4- to 9-membered optionally substituted heterocyclo;

$R^{5b}$ is selected from the group consisting of optionally substituted alkyl, optionally substituted cycloalkyl, optionally substituted heterocyclo, optionally substituted aryl, and optionally substituted heteroaryl;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ---  represents a single or a double bond, or a pharmaceutically acceptable salt, solvate, or prodrug thereof.

In another embodiment, compounds of Formula II are provided:

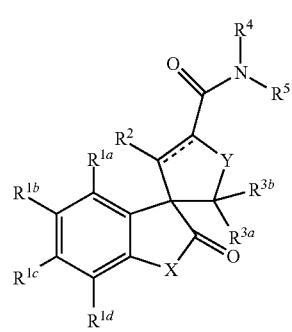

wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^{3b}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl; or $R^{3a}$ and $R^{3b}$ taken together form a 3- to 9-membered optionally substituted cycloalkyl;

$R^4$ is selected from the group consisting of hydrogen and optionally substituted alkyl;

$R^5$ is selected from the group consisting of:

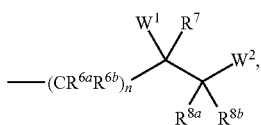

R5-1

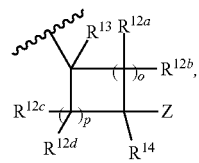

R5-2

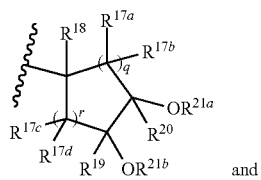

and

R5-3

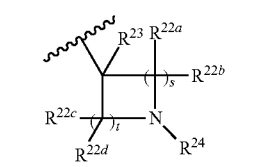

R5-4 wherein:

each $R^{6a}$ and $R^{6b}$ is independently selected from the group consisting of hydrogen and optionally substituted $C_1$-$C_6$ alkyl;

$R^7$ is selected from the group consisting of hydrogen, optionally substituted $C_1$-$C_6$ alkyl, and optionally substituted cycloalkyl;

$R^{8a}$ and $R^{8b}$ are each independently selected from the group consisting of hydrogen, optionally substituted $C_1$-$C_6$ alkyl, and optionally substituted cycloalkyl; or $R^{8a}$ and $R^{8b}$ taken together with the carbon that they are attached form a 3- to 8-membered optionally substituted cycloalkyl;

$W^1$ is selected from the group consisting of —$OR^{9a}$ and —$NR^{9b}R^{9b}$;

$R^{9a}$ is hydrogen;

$R^{9b}$ is selected from the group consisting of hydrogen, optionally substituted alkyl, optionally substituted cycloalkyl, optionally substituted aryl, optionally substituted heteroaryl, —$SO_2R^{9d}$, and —$CONR^{9e}R^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$W^2$ is selected from the group consisting of —$OR^{10}$ and —$NR^{11a}R^{11b}$;

with the proviso that when $W^1$ is —$OR^{9a}$ and $W^2$ is —$OR^{10}$ then at least one of $R^7$, $R^{8a}$, and $R^{8b}$ is other than hydrogen;

$R^{10}$ is hydrogen; or one of $R^{9a}$ and $R^{10}$ is hydrogen and the other is a metabolically cleavable group;

$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ together with the nitrogen atom to which they are attached form a 4- to 8-membered optionally substituted heterocyclo;

n is 1, 2, 3, 4, or 5;

each $R^{12a}$, $R^{12b}$, $R^{12c}$, and $R^{11d}$ is independently selected from the group consisting of hydrogen and optionally substituted $C_1$-$C_6$ alkyl;

$R^{13}$ is selected from the group consisting of hydrogen and optionally substituted $C_1$-$C_6$ alkyl;

$R^{14}$ is selected from the group consisting of hydrogen, optionally substituted $C_1$-$C_6$ alkyl, and optionally substituted cycloalkyl;

Z is selected from the group consisting of —$OR^{15}$ and —$NR^{16a}R^{16b}$; or Z and $R^{14}$ taken together form a carbonyl, i.e., a C=O, group.

$R^{15}$ is selected from the group consisting of hydrogen and metabolically cleavable group;

$R^{16a}$ is selected from the group consisting of —$SO_2R^{16c}$ and —$CONR^{16d}R^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

o is 1, 2, or 3;

p is 0, 1, 2, or 3;

each $R^{17a}$, $R^{17b}$, $R^{17c}$ and $R^{17d}$ is independently selected from the group consisting of hydrogen and optionally substituted $C_1$-$C_6$ alkyl;

$R^{18}$ is selected from the group consisting of hydrogen and optionally substituted $C_1$-$C_6$ alkyl;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

q is 0, 1, 2, or 3;

r is 1, 2, or 3;

each $R^{22a}$, $R^{22b}$, $R^{22c}$, and $R^{22d}$ is independently selected from the group consisting of hydrogen and optionally substituted $C_1$-$C_6$ alkyl;

$R^{23}$ is selected from the group consisting of hydrogen and optionally substituted $C_1$-$C_6$ alkyl;

$R^{24}$ is selected from the group consisting of —$SO_2R^{24a}$ and —$CONR^{24b}$ $R^{24a}$ is selected from the group consisting of optionally substituted alkyl, optionally substituted cycloalkyl, optionally substituted aryl, and optionally substituted heteroaryl;

$R^{24b}$ and $R^{24c}$ are each independently selected from the group consisting of hydrogen, optionally substituted cycloalkyl, optionally substituted aryl, and optionally substituted heteroaryl; or $R^{24b}$ and $R^{24c}$ taken together with the nitrogen atom to which they are attached form a 4- to 8-membered heterocyclo;

s and t are each independently 1, 2, or 3;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ⚌ represents a single or a double bond, or a pharmaceutically acceptable salt, solvate, or prodrug thereof.

In another embodiment, the compound of Formula I or II is provided as a mixture of stereoisomers, e.g., a mixture of diastereomers and/or enantiomers, e.g., a racemic mixture. In another embodiment, the compound of Formula I or II is provided as a single stereoisomer.

In another embodiment, compounds of Formula III are provided:

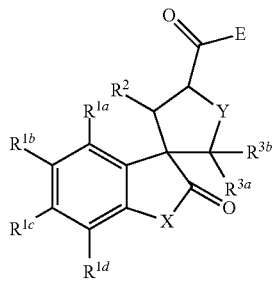

III wherein $R^{1a}$, $R^{1b}$, $R^{1c}$, $R^{1d}$, $R^2$, $R^{3a}$, $R^{3b}$, E, X, and Y have the meanings as described above for Formula I, or a pharmaceutically acceptable salt, solvate, or prodrug thereof.

In another embodiment, compounds of Formula III are provided wherein E is $NR^4R^5$, and $R^{1a}$, $R^{1b}$, $R^{1c}$, $R^{1d}$, $R^2$, $R^{3a}$, $R^{3b}$, $R^4$, $R^5$, X, and Y have the meanings as described above for Formula II, or a pharmaceutically acceptable salt, solvate, or prodrug thereof.

In another embodiment, compounds of Formula IV are provided:

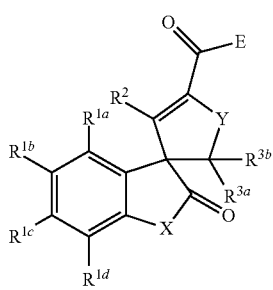

IV wherein $R^{1a}$, $R^{1b}$, $R^{1c}$, $R^{1d}$, $R^2$, $R^{3a}$, $R^{3b}$, E, X, and Y have the meanings as described above for Formula I, or tautomer thereof, or a pharmaceutically acceptable salt, solvate, or prodrug thereof.

In another embodiment, compounds of Formula IV are provided wherein E is —$NR^4R^5$, and $R^{1a}$, $R^{1b}$, $R^{1c}$, $R^{1d}$, $R^2$, $R^{3a}$, $R^{3b}$, $R^4$, $R^5$, X, and Y have the meanings as described above for Formula II, or tautomer thereof, or a pharmaceutically acceptable salt, solvate, or prodrug thereof.

In another embodiment, compounds of Formula V are provided:

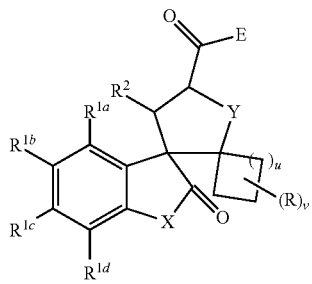

V i.e., $R^{3a}$ and $R^{3b}$ of Formula I are taken together form a 3- to 9-membered optionally substituted cycloalkyl, wherein $R^{1a}$, $R^{1b}$, $R^{1c}$, $R^{1d}$, $R^2$, E, X, and Y have the meanings as described above for Formula I, u is 0, 1, 2, 3, 4, 5, or 6, v is 0, 1, 2, 3, or 4, and each R is independently halo, nitro, cyano, hydroxy, amino, optionally substituted alkyl, haloalkyl, hydroxyalkyl, aminoalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido, or a pharmaceutically acceptable salt, solvate, or prodrug thereof.

In another embodiment, compounds of Formula V are provided wherein E is $NR^4R^5$, and $R^{1a}$, $R^{1b}$, $R^{1c}$, $R^{1d}$, $R^2$, $R^4$, $R^5$, X, and Y have the meanings as described above for Formula II, u is 0, 1, 2, 3, 4, 5, or 6, v is 0, 1, 2, 3, or 4, and each R is independently halo, nitro, cyano, hydroxy, amino, optionally substituted alkyl, haloalkyl, hydroxyalkyl, aminoalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido, or a pharmaceutically acceptable salt, solvate, or prodrug thereof.

In another embodiment, compounds of Formula V are provided wherein u is 1, 2, 3, 4, 5, or 6, each R is independently $(C_1-C_4)$alkyl and v is 0, 1, or 2, or a pharmaceutically acceptable salt, solvate, or prodrug thereof.

In another embodiment compounds of Formula V are provided wherein v is 0 and u is 0, 1, 2, 3, 4, 5, or 6, i.e., $R^{3a}$ and $R^{3b}$ of Formula I are taken together form a 3- to 9-membered unsubstituted cycloalkyl.

In another embodiment of Formula V are provided wherein v is 0 and u is 2, 3, or 4, i.e., $R^{3a}$ and $R^{3b}$ of Formula I are taken together form a 5-, 6-, or 7-membered unsubstituted cycloalkyl.

In another embodiment, compounds of any one of Formulae VI-XXI are provided:

VI
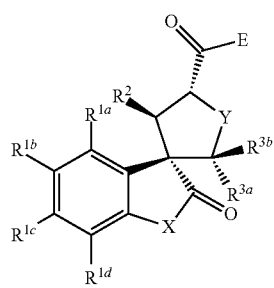

VII
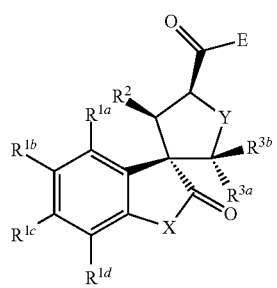

VIII
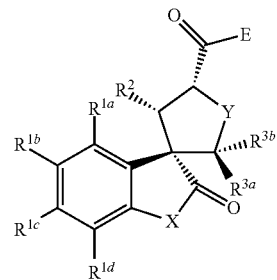

IX
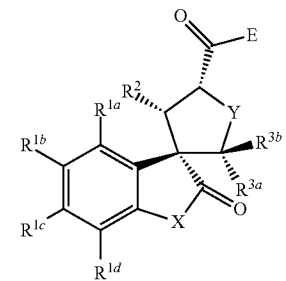

X
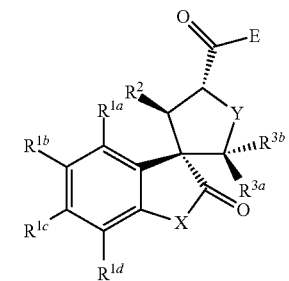

XI
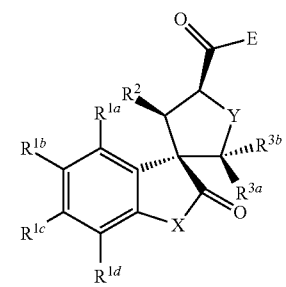

XII
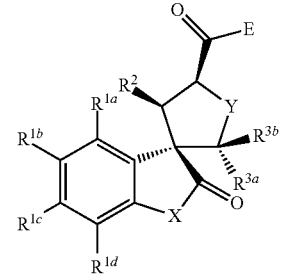

XIII

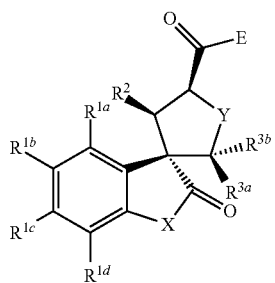

XIV

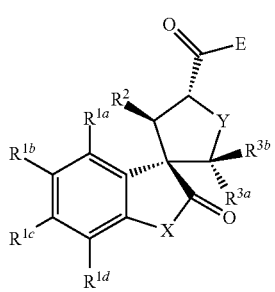

XV

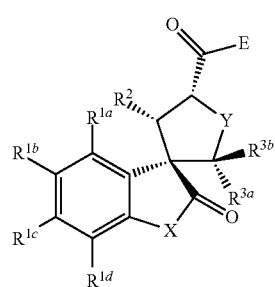

XVI

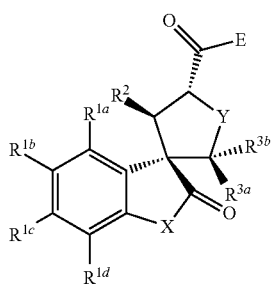

XVII

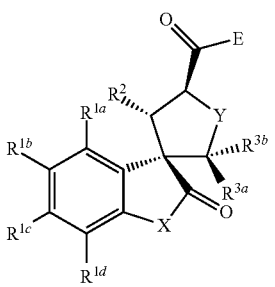

XVIII

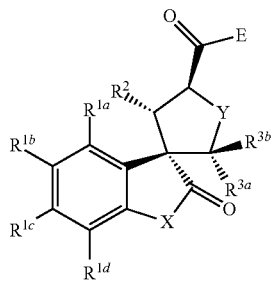

XIX

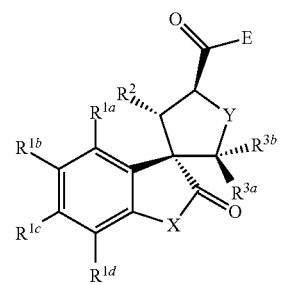

XX

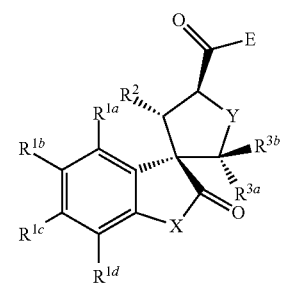

XXI

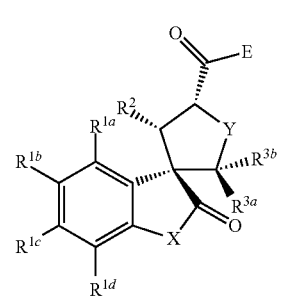

wherein $R^{1a}$, $R^{1b}$, $R^{1c}$, $R^{1d}$, $R^2$, $R^{3a}$, $R^{3b}$, E, X, and Y have the meanings as described above for Formula I, or a pharmaceutically acceptable salt, solvate, or prodrug thereof.

In another embodiment, compounds of any one of Formulae VI-XXI are provided, wherein E is $NR^4R^5$, and $R^{1a}$, $R^{1b}$, $R^{1c}$, $R^{1d}$, $R^2$, $R^{3a}$, $R^{3b}$, $R^4$, $R^5$, X, and Y have the meanings as described above for Formula II, or a pharmaceutically acceptable salt, solvate, or prodrug thereof.

In another embodiment, compounds of any one of Formulae VI-XXI are provided substantially free of one or more other stereoisomers. In another embodiment, compounds of any one of Formulae VI-XXI are substantially pure stereoisomers. In another embodiment, compounds of any one of Formulae VI-XXI are pure stereoisomers.

In another embodiment, compounds of any one of Formulae I-XXI, or a pharmaceutically acceptable salt, solvate, or prodrug thereof, are provided wherein:

a) $R^{1a}$, $R^{1b}$, $R^{1c}$, and $R^{1d}$ are independently selected from the group consisting of hydrogen, fluoro, and chloro;

b) $R^{1a}$ and $R^{1d}$ are hydrogen; $R^{1b}$ is selected from the group consisting of hydrogen and fluoro; and $R^{1c}$ is selected from the group consisting of fluoro and chloro;

c) $R^2$ is optionally substituted phenyl;

d) $R^{3a}$ is selected from the group consisting of halo, optionally substituted alkyl, optionally substituted (cycloalkyl)alkyl, and optionally substituted cycloalkyl;

e) $R^{3b}$ is selected from the group consisting of halo, optionally substituted alkyl, optionally substituted (cycloalkyl)alkyl, and optionally substituted cycloalkyl;

f) $R^{3a}$ and $R^{3b}$ taken together form an optionally substituted 3- to 9-membered cycloalkyl;

g) E is —$NR^4R^5$ and $R^4$ is hydrogen;

h) X is NH;

i) X is O;

j) X is S;

k) Y is O;

l) Y is S;

m) Y is NH; or n) X and Y are NH;

or any combination thereof.

In another embodiment, compounds of any one of Formulae I-XXI, or a pharmaceutically acceptable salt, solvate, or prodrug thereof are provided, wherein E is —$NR^4R^5$, $R^5$ is R5-1; $R^{6a}$ and $R^{6b}$ are hydrogen; $R^2$ is $C_1$-$C_4$ alkyl; $R^{8a}$ and $R^{8b}$ are hydrogen; W is —$OR^{10}$, $R^9$ and $R^{10}$ are hydrogen; and n is 2.

In another embodiment, compounds of any one of Formulae I-XXI, or a pharmaceutically acceptable salt, solvate, or prodrug thereof are provided, wherein E is —$NR^4R^5$; $R^5$ is R5-1; $R^{6a}$ and $R^{6b}$ are hydrogen; $R^7$ is $C_1$-$C_4$ alkyl; $R^{8a}$ and $R^{8b}$ are hydrogen; W is —$NR^{11a}R^{11b}$, $R^9$ is hydrogen; and n is 2.

In another embodiment, compounds of any one of Formulae I-XXI, or a pharmaceutically acceptable salt, solvate, or prodrug thereof are provided, wherein E is —$NR^4R^5$; $R^5$ is R5-1; $R^{6a}$ and $R^{6b}$ are hydrogen; $R^7$ is $C_1$-$C_4$ alkyl; $R^{8a}$ and $R^{8b}$ are hydrogen; W is —$OR^{10}$, one of $R^9$ and $R^{10}$ is hydrogen and the other is a metabolically cleavable group; and n is 2.

In another embodiment, compounds of any one of Formulae I-XXI, or a pharmaceutically acceptable salt, solvate, or prodrug thereof are provided, wherein E is —$NR^4R^5$; $R^5$ is R5-2; $R^{12a}$, $R^{12b}$, $R^{12c}$, and $R^{12d}$ are each hydrogen; $R^{13}$ is hydrogen; Z is —$OR^{15}$ and $R^{15}$ is hydrogen; o is 1 or 2; and p is 1 or 2.

In another embodiment, of any one of Formulae I-XXI, or a pharmaceutically acceptable salt, solvate, or prodrug thereof are provided, wherein E is —$NR^4R^5$; $R^5$ is R5-2; $R^{12a}$, $R^{12b}$, $R^{12c}$, and $R^{12d}$ are each hydrogen; $R^{13}$ is hydrogen; Z is —$NR^{16a}R^{16b}$; o is 1 or 2; and p is 1 or 2.

In another embodiment, compounds of any one of Formulae I-XXI, or a pharmaceutically acceptable salt, solvate, or prodrug thereof are provided, wherein E is —$NR^4R^5$; $R^5$ is R5-2; $R^{12a}$, $R^{12b}$, $R^{12c}$, and $R^{12d}$ are each hydrogen; $R^{13}$ is hydrogen; Z is —$OR^{15}$ and $R^{15}$ a metabolically cleavable group; o is 1 or 2; and p is 1 or 2.

In another embodiment, compounds of any one of Formulae I-XXI, or a pharmaceutically acceptable salt, solvate, or prodrug thereof are provided, wherein E is —$NR^4R^5$; $R^5$ is R5-3; $R^{17a}$, $R^{17b}$, $R^{17c}$, and $R^{17d}$ are each hydrogen; $R^{18}$, $R^{19}$, and $R^{20}$ are hydrogen; $R^{21a}$ and $R^{21b}$ are hydrogen; and q and r are 1.

In another embodiment, compounds of any one of Formulae I-XXI, or a pharmaceutically acceptable salt, solvate, or prodrug thereof are provided, wherein E is —$NR^4R^5$; $R^5$ is R5-3; $R^{17a}$, $R^{17b}$, $R^{17c}$, and $R^{17d}$ are each hydrogen; $R^{18}$, $R^{19}$, and $R^{20}$ are hydrogen; one of $R^{21a}$ and $R^{21b}$ is hydrogen and the other is a metabolically cleavable group; and q and r are 1.

In another embodiment, compounds of any one of Formulae I-XXI, or a pharmaceutically acceptable salt, solvate, or prodrug thereof are provided, wherein $R^2$ is an optionally substituted aryl having the Formula R3-1:

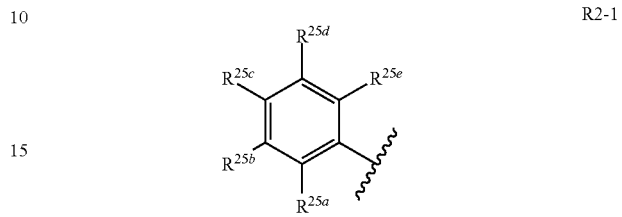

R2-1 and $R^{25a}$, $R^{25b}$, $R^{25c}$, $R^{25d}$, and $R^{25e}$ are each independently selected from the group consisting of hydrogen, halogen, hydroxy, nitro, amino, cyano, alkoxy, optionally substituted alkyl, haloalkyl, optionally substituted aryl, and optionally substituted heteroaryl. In one embodiment, $R^{25a}$ is selected from the group consisting of hydrogen and fluoro; $R^{25b}$ is chloro; $R^{25c}$ is selected from the group consisting of hydrogen and fluoro; and $R^{25d}$ and $R^{25e}$ are hydrogen.

In another embodiment, compounds of any one of Formulae I-XXI, or a pharmaceutically acceptable salt, solvate, or prodrug thereof are provided, wherein $R^2$ is an optionally substituted pyridyl.

In another embodiment, compounds of any one of Formulae or a pharmaceutically acceptable salt, solvate, or prodrug thereof are provided, wherein E is —$NR^4R^5$, $R^4$ is hydrogen, and $R^5$ is selected from the group consisting of:

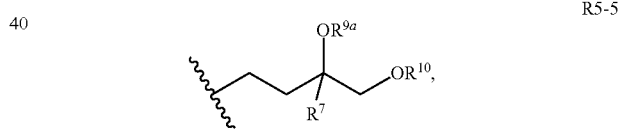

R5-5

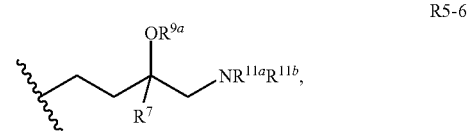

R5-6

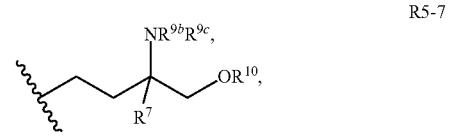

R5-7

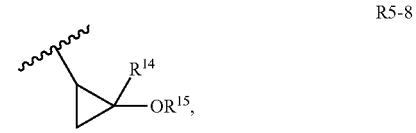

R5-8

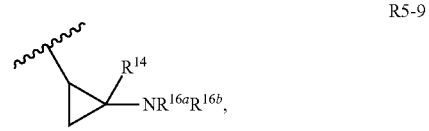

R5-9

R5-10 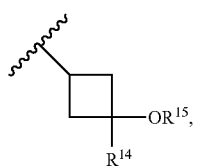

R5-11 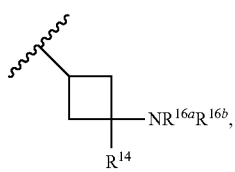

R5-12 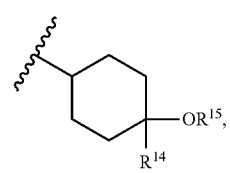

R5-13 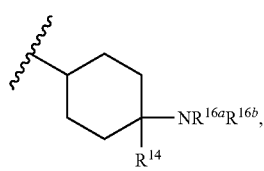

R5-14 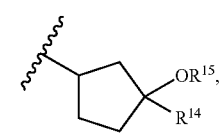

R5-15 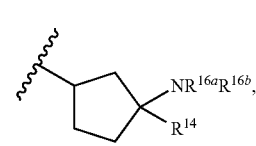

R5-16 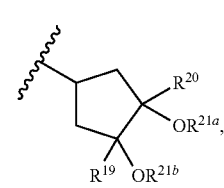

R5-17 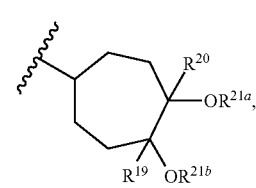

R5-18 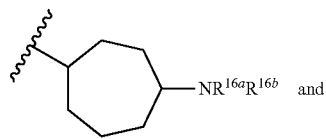 and

R5-19 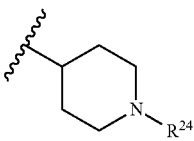

including stereoisomers, e.g., enantiomers, thereof, wherein:

$R^7$ is optionally substituted $C_1$-$C_4$ alkyl;

$R^{9d}$ and $R^{10}$ are each hydrogen; or one of $R^{9d}$ and $R^{10}$ is hydrogen and the other is a metabolically cleavable group;

$R^{9b}$ is selected from the group consisting of hydrogen, optionally substituted alkyl, optionally substituted cycloalkyl, optionally substituted aryl, optionally substituted heteroaryl, —$SO_2R^{9d}$, and —$CONR^{9e}R^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11d}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

$R^{14}$ is selected from the group consisting of hydrogen, $C_1$-$C_4$ alkyl, or $C_3$-$C_6$ cycloalkyl;

$R^{15}$ is hydrogen or a metabolically cleavable group;

$R^{16a}$ is selected from the group consisting of —$SO_2R^{16c}$ and —$CONR^{16d}R^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

$R^{24}$ is selected from the group consisting of —$SO_2R^{24a}$ and —$CONR^{24b}R^{24c}$;

$R^{24a}$ is selected from the group consisting of optionally substituted alkyl, optionally substituted cycloalkyl, optionally substituted aryl, and optionally substituted heteroaryl; and $R^{24b}$ and $R^{24c}$ are each independently selected from the group consisting of hydrogen, optionally substituted cycloalkyl, optionally substituted aryl, and optionally substituted heteroaryl, or $R^{24b}$ and $R^{24c}$ taken together with the nitrogen atom to which they are attached form a 4- to 8-membered heterocyclo.

In another embodiment, compounds of any one of Formulae I-XXI, or a pharmaceutically acceptable salt, solvate, or prodrug thereof are provided, wherein E is —$NR^4R^5$, $R^4$ is hydrogen, and $R^5$ is selected from the group consisting of R5-5, R5-6, R5-10, R5-11, R5-12, R5-13, and R5-14.

In another embodiment, compounds of any one of Formulae I-XXI, or a pharmaceutically acceptable salt, solvate, or prodrug thereof are provided, wherein E is —$NR^4R^5$, $R^4$ is hydrogen, and $R^5$ is selected from the group consisting of R5-10 and R5-12 and $R^{14}$ is hydrogen or methyl and $R^{15}$ is hydrogen.

In another embodiment, compounds of any one of Formulae I-XXI, or a pharmaceutically acceptable salt, solvate, or prodrug thereof are provided, wherein E is —$NR^4R^5$, $R^4$ is hydrogen, and $R^5$ is selected from the group consisting of:

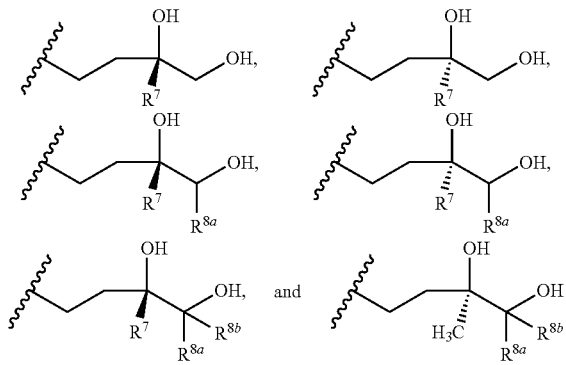

wherein:

$R^7$ is selected from the group consisting of methyl, ethyl, propyl, isopropyl, and cyclopropyl; and $R^{8a}$ and $R^{8b}$ are each independently selected from the group consisting of hydrogen, methyl, ethyl, propyl, isopropyl, and cyclopropyl.

In another embodiment, compounds of any one of Formulae I-XXI, or a pharmaceutically acceptable salt, solvate, or prodrug thereof are provided, wherein E is —$NR^4R^5$, $R^4$ is hydrogen, and $R^5$ is selected from the group consisting of:

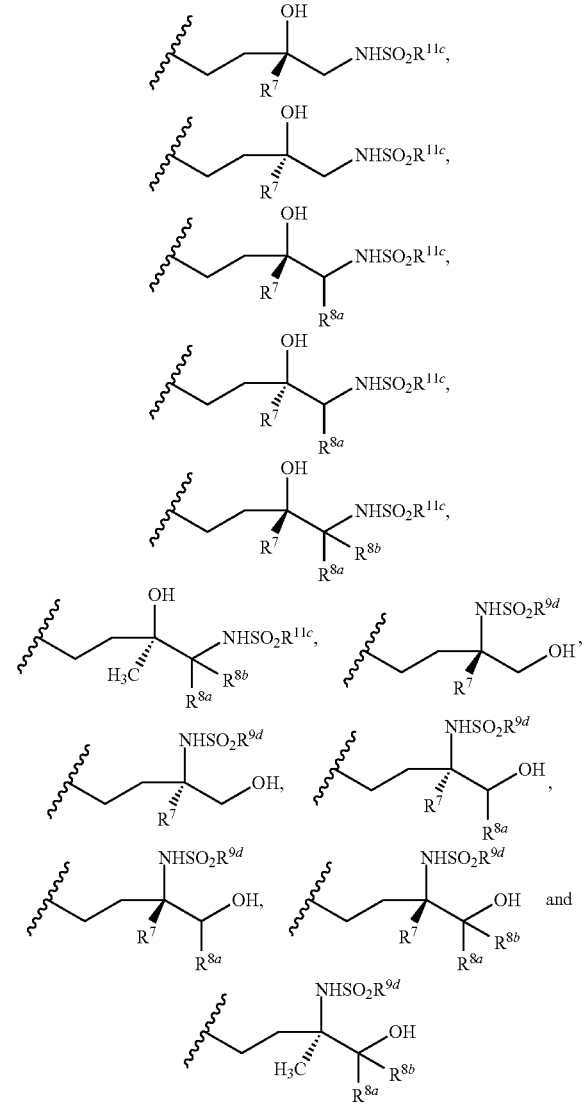

wherein:

$R^7$ is selected from the group consisting of methyl, ethyl, propyl, isopropyl, and cyclopropyl;

$R^{8a}$ and $R^{8b}$ are each independently is selected from the group consisting of hydrogen, methyl, ethyl, propyl, isopropyl, and cyclopropyl;

$R^{9d}$ is selected from the group consisting of methyl, trifluoromethyl, ethyl, propyl, isopropyl, and cyclopropyl; and $R^{11c}$ is selected from the group consisting of methyl, trifluoromethyl, ethyl, propyl, isopropyl, and cyclopropyl.

In another embodiment, compounds of any one of Formulae I-XXI, or a pharmaceutically acceptable salt, solvate, or prodrug thereof are provided, wherein E is —$NR^4R^5$, $R^4$ is hydrogen, and $R^5$ is selected from the group consisting of:

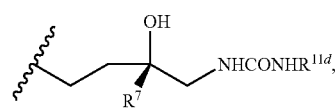

-continued

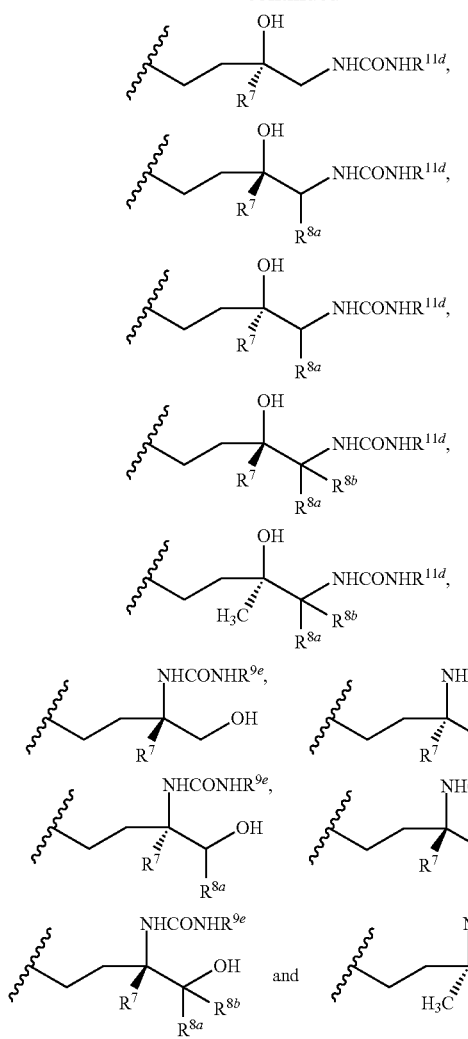

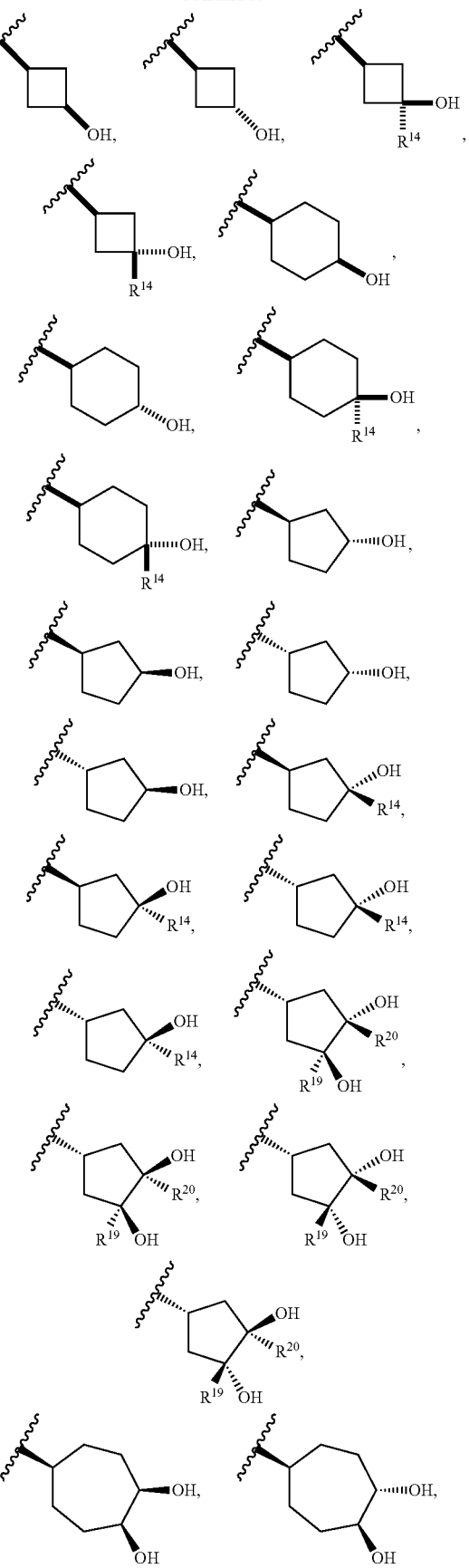

wherein:

$R^7$ is selected from the group consisting of methyl, ethyl, propyl, isopropyl, and cyclopropyl;

$R^{8a}$ and $R^{8b}$ are each independently is selected from the group consisting of hydrogen, methyl, ethyl, propyl, isopropyl, and cyclopropyl;

$R^{9e}$ is selected from the group consisting of methyl, trifluoromethyl, ethyl, propyl, isopropyl, and cyclopropyl; and $R^{11d}$ is selected from the group consisting of methyl, trifluoromethyl, ethyl, propyl, isopropyl, and cyclopropyl.

In another embodiment, compounds of any one of Formulae I-XXI, or a pharmaceutically acceptable salt, solvate, or prodrug thereof are provided, wherein E is —NR$^4$R$^5$, R$^4$ is hydrogen, and R$^5$ is selected from the group consisting of:

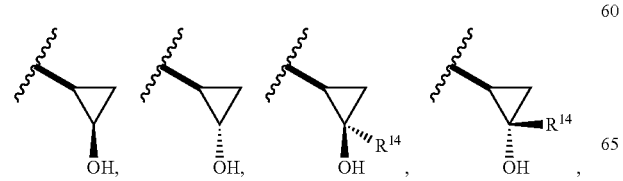

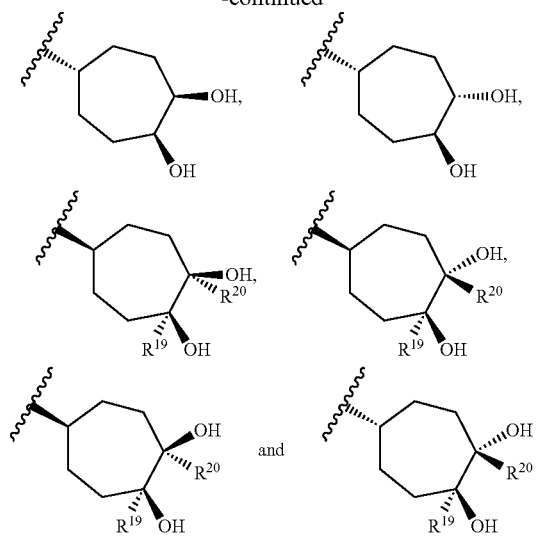

wherein:

R[14] is selected from the group consisting of methyl, ethyl, propyl, isopropyl, and cyclopropyl; and R[19] and R[20] are each independently is selected from the group consisting of hydrogen, methyl, ethyl, propyl, isopropyl, and cyclopropyl.

In another embodiment, compounds of any one of Formulae I-XXI, or a pharmaceutically acceptable salt, solvate, or prodrug thereof are provided, wherein E is —NR[4]R[5], R[4] is hydrogen, and R[5] is selected from the group consisting of:

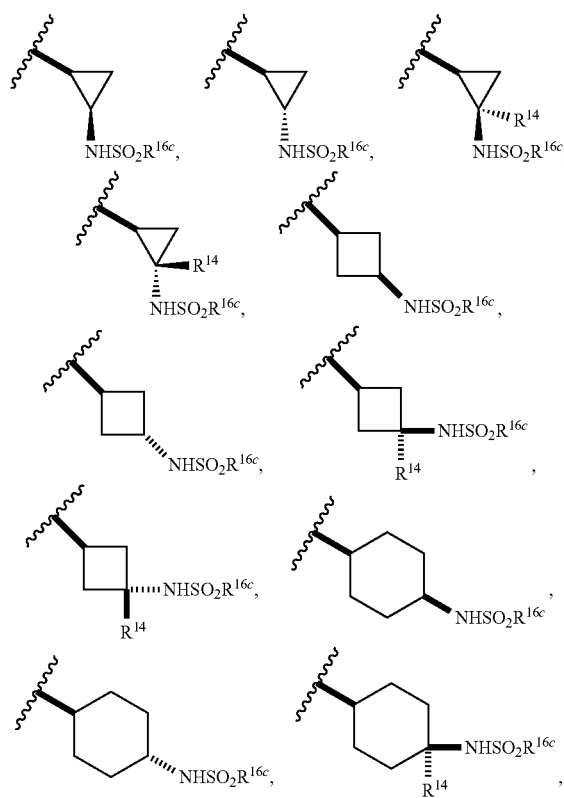

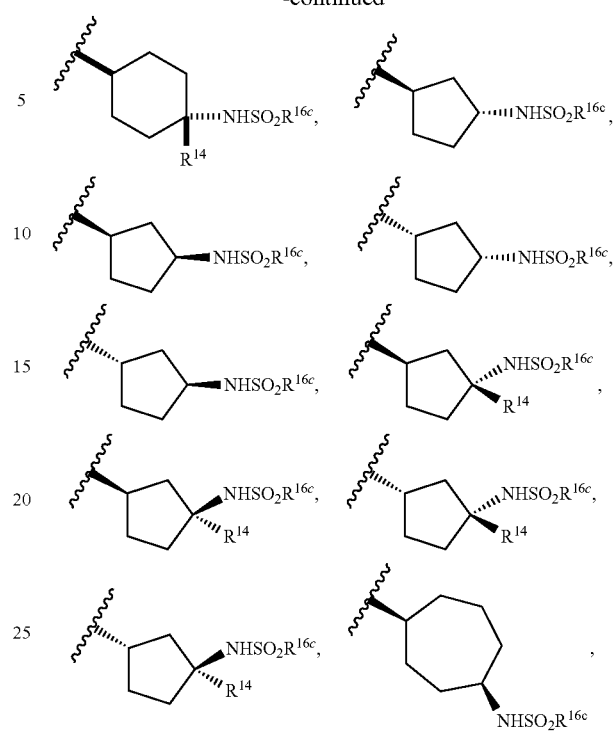

wherein:

R[14] is selected from the group consisting of methyl, ethyl, propyl, isopropyl, and cyclopropyl; and R[16c] is selected from the group consisting of methyl, trifluoromethyl, ethyl, propyl, isopropyl, and cyclopropyl.

In another embodiment, compounds of any one of Formulae I-XXI, or a pharmaceutically acceptable salt, solvate, or prodrug thereof are provided, wherein E is —NR[4]R[5], R[4] is hydrogen, and R[5] is selected from the group consisting of:

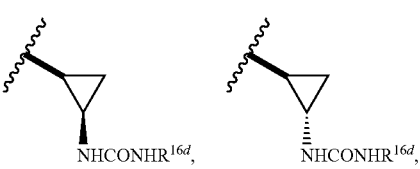

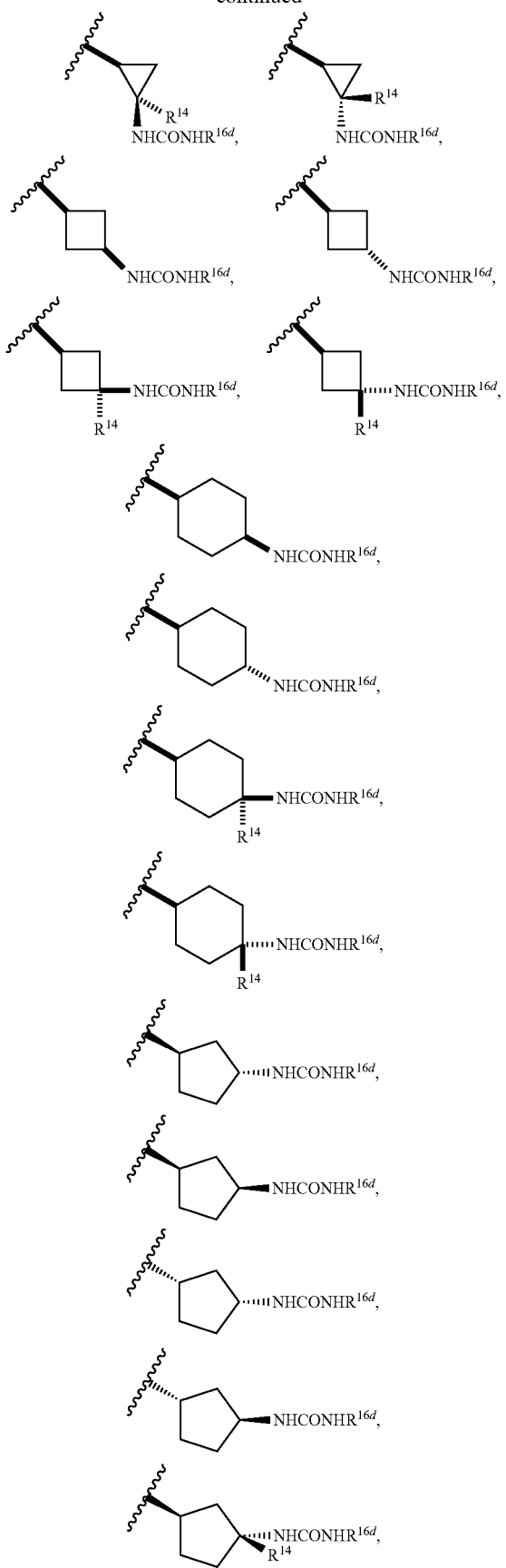
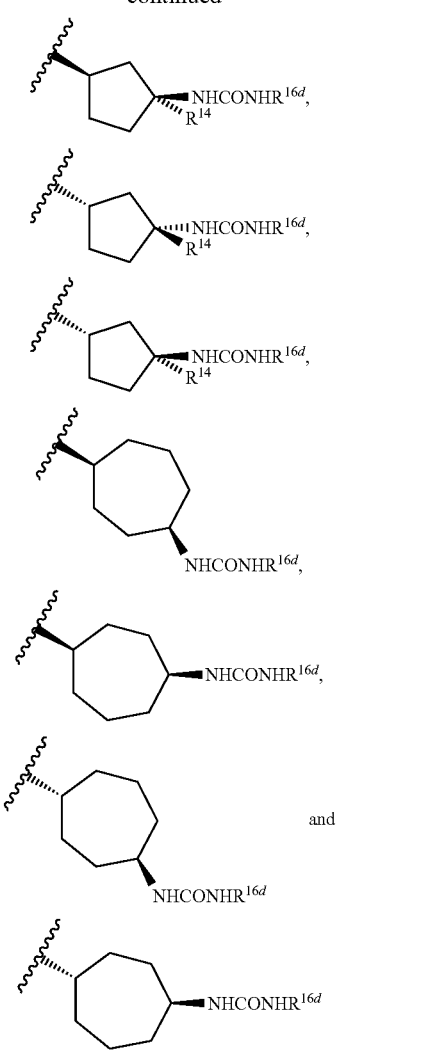

wherein:

$R^{14}$ is selected from the group consisting of methyl, ethyl, propyl, isopropyl, and cyclopropyl; and $R^{16d}$ is selected from the group consisting of methyl, trifluoromethyl, ethyl, propyl, isopropyl, and cyclopropyl.

In another embodiment, compounds of any one of Formulae I-XXI, or a pharmaceutically acceptable salt, solvate, or prodrug thereof are provided, wherein E is —NR$^4$R$^5$, R$^4$ is hydrogen, and R$^5$ is selected from the group consisting of:

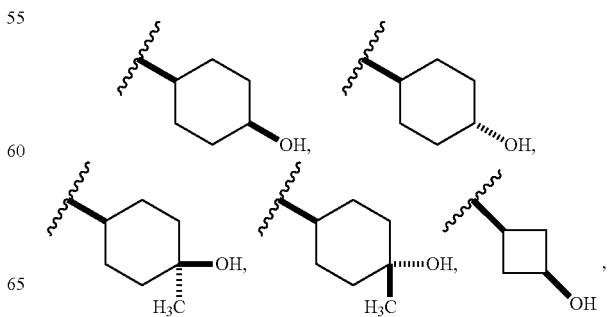

-continued

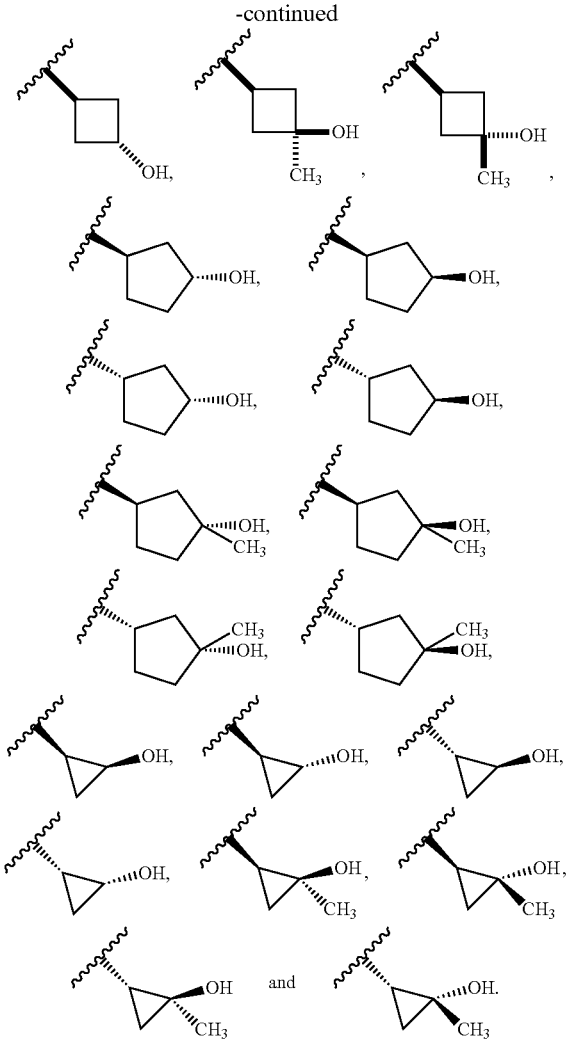

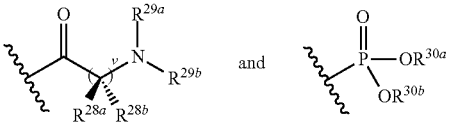

wherein:
each $R^{28a}$ and $R^{28b}$ is independently selected from the group consisting of hydrogen, optionally substituted alkyl, and aralkyl;
$R^{29a}$ and $R^{29b}$ are each selected from the group consisting of hydrogen and optionally substituted alkyl;
v is 1, 2, 3, or 4; and
$R^{30a}$ and $R^{30b}$ are each selected from the group consisting of hydrogen, optionally substituted alkyl, aralkyl, optionally substituted aryl, and monovalent pharmaceutically acceptable cation; or
taken together $R^{30a}$ and $R^{30b}$ represent a divalent pharmaceutically acceptable cation or an optionally substituted alkylenyl.

In another embodiment, the metabolically cleavable group at $R^{15}$ is the residue of a natural or unnatural amino acid. In another embodiment, the metabolically cleavable group at $R^{15}$ is the residue of glycine, isoleucine alanine, leucine, asparagine, lysine, aspartic acid, methionine, cysteine, phenylalanine, glutamic acid, threonine, glutamine, tryptophan, valine, proline, serine, tyrosine, arginine, and histidine.

In another embodiment, compounds of any one of Formulae I-XXI, or a pharmaceutically acceptable salt, solvate, or prodrug thereof are provided wherein X is NH and Y is NH.

In another embodiment, compounds of any one of Formulae I-XXI, or a pharmaceutically acceptable salt, solvate, or prodrug thereof are provided wherein X is O and Y is NH.

In another embodiment, compounds of any one of Formulae I-XXI, or a pharmaceutically acceptable salt, solvate, or prodrug thereof, are provided wherein X is S and Y is NH.

In another embodiment, compounds of any one of Formulae I-IV or VI-XXI, or a pharmaceutically acceptable salt, solvate, or prodrug thereof, are provided, wherein $R^{3a}$ and $R^{3b}$ are the same or different $C_1$-$C_{10}$ alkyl.

In another embodiment, compounds of any one of Formulae I-IV or VI-XXI, or a pharmaceutically acceptable salt, solvate, or prodrug thereof, are provided, wherein $R^{3a}$ and $R^{3b}$ are the same or different $C_2$-$C_{10}$ alkyl.

In another embodiment, compounds of any one of Formulae I-IV or VI-XXI, or a pharmaceutically acceptable salt, solvate, or prodrug thereof, are provided, wherein $R^{3a}$ and $R^{3b}$ are the same or different $C_1$-$C_6$ alkyl, e.g., methyl, ethyl, n-propyl, isopropyl, n-butyl, sec-butyl, isobutyl, tert-butyl, n-pentyl, isopentyl, neopentyl, n-hexyl, isohexyl.

In another embodiment, compounds of any one of Formulae I-IV or VI-XXI, or a pharmaceutically acceptable salt, solvate, or prodrug thereof, are provided, wherein $R^{3a}$ and $R^{3b}$ are the same or different $C_2$-$C_6$ alkyl.

In another embodiment, compounds of any one of Formulae I-IV or VI-XXI, or a pharmaceutically acceptable salt, solvate, or prodrug thereof, are provided, wherein $R^{3a}$ and $R^{3b}$ are the same or different $C_1$-$C_4$ alkyl.

In another embodiment, compounds of any one of Formulae I-IV or VI-XXI, or a pharmaceutically acceptable salt, solvate, or prodrug thereof, are provided, wherein $R^{3a}$ and $R^{3b}$ are the same or different $C_2$-$C_4$ alkyl.

In another embodiment, compounds of any one of Formulae I-IV or VI-XXI, or a pharmaceutically acceptable salt, In another embodiment, compounds of any one of Formulae I-XXI, or a pharmaceutically acceptable salt, solvate, or prodrug thereof are provided wherein E is —$NR^4R^5$, $R^4$ is hydrogen, and $R^5$ is selected from the group consisting of:

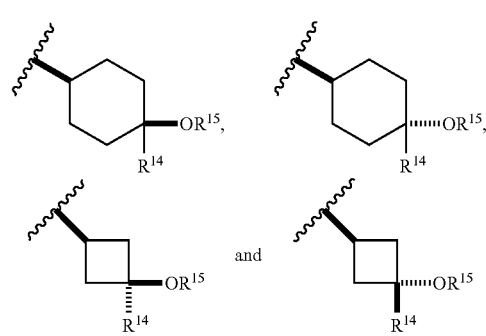

wherein:
$R^{14}$ is selected from the group consisting of hydrogen and $C_1$-$C_4$ alkyl; and
$R^{15}$ is hydrogen or a metabolically cleavable group.

In one embodiment, the metabolically cleavable group at $R^{15}$ is selected from the group consisting of:

solvate, or prodrug thereof, are provided, wherein $R^{3a}$ and $R^{3b}$ are the same or different $C_1$-$C_3$ alkyl.

In another embodiment, compounds of any one of Formulae I-IV or VI-XXI, or a pharmaceutically acceptable salt, solvate, or prodrug thereof are provided, wherein $R^{3a}$ and $R^{3b}$ are the same or different halo.

In another embodiment, compounds of any one of Formulae I-IV or VI-XXI, or a pharmaceutically acceptable salt, solvate, or prodrug thereof are provided, wherein $R^{3a}$ and $R^{3b}$ are the same or different, and are selected from the group consisting of methyl, ethyl, propyl, isopropyl, butyl, and neopentyl.

In another embodiment, compounds of any one of Formulae I-IV or VI-XXI, or a pharmaceutically acceptable salt, solvate, or prodrug thereof are provided, wherein $R^{3a}$ and $R^{3b}$ are the same or different, and are selected from the group consisting of ethyl, propyl, isopropyl, butyl, and neopentyl.

In another embodiment, compounds of any one of Formulae I-IV or VI-XXI, or a pharmaceutically acceptable salt, solvate, or prodrug thereof are provided, wherein $R^{3a}$ and $R^{3b}$ are fluoro.

In another embodiment, compounds of any one of Formulae I-IV or VI-XXI, or a pharmaceutically acceptable salt, solvate, or prodrug thereof are provided, wherein $R^{3a}$ and $R^{3b}$ are the same, e.g., $R^{3a}$ is methyl and $R^{3b}$ is methyl, $R^{3a}$ is ethyl and $R^{3b}$ is ethyl, $R^{3a}$ is propyl and $R^{3b}$ is propyl, etc. If $R^{3a}$ and $R^{3b}$ are the same, the carbon atom to which $R^{3a}$ and $R^{3b}$ are attached is not an asymmetric center. Under these circumstances, Formula VI and X; Formula VII and XIII; Formula VIII and IX; Formula XI and XII; Formula XIV and XVI; Formula XV and XXI; Formula XVII and XX; and Formula XVIII and XIX represent equivalent isomers.

In another embodiment, compounds of any one of Formulae I-IV or VI-XXI, or a pharmaceutically acceptable salt, solvate, or prodrug thereof are provided, wherein $R^{3a}$ and $R^{3b}$ are different, e.g., $R^{3a}$ is methyl and $R^{3b}$ is ethyl, $R^{3a}$ is methyl and $R^{3b}$ is neopentyl, $R^{3a}$ is ethyl and $R^{3b}$ is propyl, etc.

In another embodiment, compounds of any one of Formulae I-IV or VI-XXI, or a pharmaceutically acceptable salt, solvate, or prodrug thereof are provided, wherein $R^{3a}$ and $R^{3b}$ are taken together to form an optionally substituted cyclopropyl, cyclobutyl, cyclopentyl, cyclohexyl, or cycloheptyl ring. In one embodiment, the optional substituent is a ($C_1$-$C_4$) alkyl. In another embodiment, the cyclopropyl, cyclobutyl, cyclopentyl, cyclohexyl, or cycloheptyl ring is unsubstituted.

In another embodiment, compounds of any one of Formulae I-XXI, or a pharmaceutically acceptable salt, solvate, or prodrug thereof are provided, wherein $R^{1a}$ and $R^{1d}$ are hydrogen, $R^{1b}$ and $R^{1c}$ are each independently selected from the group consisting of hydrogen, chloro, and fluoro, and $R^2$ is R2-1 wherein $R^{25a}$, $R^{25b}$, $R^{25c}$, $R^{25d}$, and $R^{25e}$ are each independently selected from the group consisting of hydrogen, chloro, and fluoro.

In another embodiment, compounds having any one of Formulae VI-XXI, or a pharmaceutically acceptable salt, solvate, or prodrug thereof are provided, wherein:

E is $NR^4R^5$;

$R^{1a}$, $R^{1b}$, $R^{1c}$, and $R^{1d}$ are each independently selected from the group consisting of hydrogen, fluoro, and chloro;

$R^2$ is:

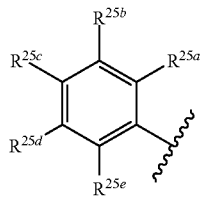

wherein:

$R^{25a}$, $R^{25b}$, $R^{25c}$, $R^{25d}$, and $R^{25e}$ are each independently selected from the group consisting of hydrogen, fluoro, and chloro;

$R^{3a}$ is $C_1$-$C_6$ alkyl;

$R^{3b}$ is $C_1$-$C_4$ alkyl; or $R^{3a}$ and $R^{3b}$ are taken together to form an optionally substituted 3- to 7-membered cycloalkyl;

$R^4$ is selected from the group consisting of hydrogen and optionally substituted $C_1$-$C_4$ alkyl;

$R^5$ is selected from the group consisting of:

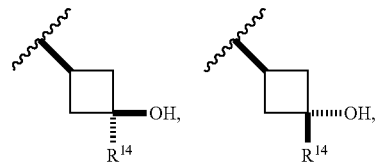

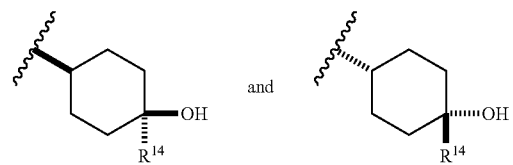

wherein:

$R^{14}$ is selected from the group consisting of hydrogen and optionally substituted $C_1$-$C_4$ alkyl;

X is selected from the group consisting of O, S, and NR';

Y is selected from the group consisting of O, S, and NR";

R' is selected from the group consisting of hydrogen and optionally substituted $C_1$-$C_4$ alkyl; and R" is selected from the group consisting of hydrogen and optionally substituted $C_1$-$C_4$ alkyl, wherein the compounds are substantially free of one or more other stereoisomers.

In another embodiment, compounds having any one of Formulae VI-XXI, or a pharmaceutically acceptable salt, solvate, or prodrug thereof are provided, wherein:

E is $NR^4R^5$;

$R^{1a}$ is hydrogen;

$R^{1b}$, $R^{1c}$, and $R^{1d}$ are each independently selected from the group consisting of hydrogen, fluoro, and chloro;

$R^2$ is:

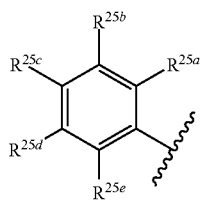

wherein:

$R^{25a}$, $R^{25b}$, $R^{25c}$, $R^{25d}$, and $R^{25e}$ are each independently selected from the group consisting of hydrogen, fluoro, and chloro;

$R^{3a}$ and $R^{3b}$ are methyl;

or $R^{3a}$ and $R^{3b}$ taken together form a cyclopentyl, cyclohexyl, or cycloheptyl ring;

$R^4$ is hydrogen;

$R^5$ is selected from the group consisting of:

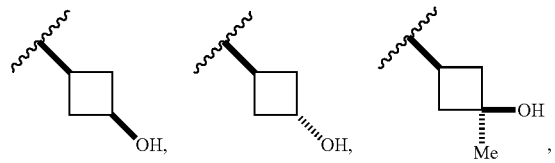

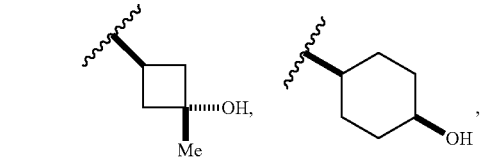

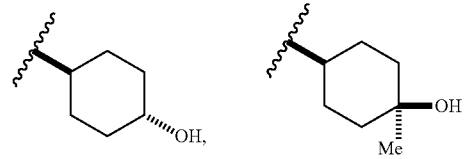

and

X and Y are NH, wherein the compounds are substantially free of one or more other stereoisomers.

In another embodiment, compounds having any one of Formulae VI-XXI, or a pharmaceutically acceptable salt, solvate, or prodrug thereof, are provided, wherein E is $NR^4R^5$, $R^4$ is hydrogen, and $R^5$ is selected from the group consisting of:

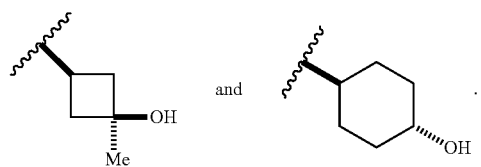 [SMILES: *[C@H]1C[C@@](C)(O)C1 ; *[C@H]1CC[C@H](O)CC1]

wherein the compound is substantially free of one or more other stereoisomers.

In another embodiment, compounds having Formula VI, or a pharmaceutically acceptable salt, solvate, or prodrug thereof, are provided, wherein the compounds are substantially pure stereoisomers.

In another embodiment, compounds having Formula XVIII, or a pharmaceutically acceptable salt, solvate, or prodrug thereof, are provided, wherein the compounds are substantially pure stereoisomers.

In another embodiment, compounds having Formula XVI, or a pharmaceutically acceptable salt, solvate, or prodrug thereof, are provided, wherein the compounds are substantially pure stereoisomers.

In another embodiment, compounds having Formula XVI, or a pharmaceutically acceptable salt, solvate, or prodrug thereof, are provided, wherein:

E is $NR^4R^5$;

$R^4$ is hydrogen;

X and Y are NH;

$R^{3a}$ and $R^{3b}$ are methyl or ethyl, or $R^{3a}$ and $R^{3b}$ taken together form a cyclopropyl, cyclobutyl, cyclopentyl, cyclohexyl, or cycloheptyl ring, each optionally substituted by one of more $C_1$-$C_4$ alkyl groups; and $R^5$ is selected from the group consisting of:

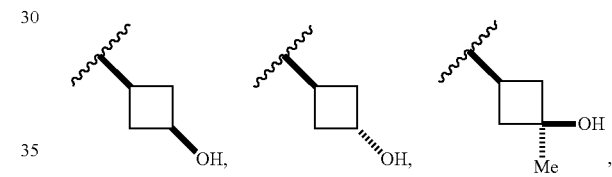

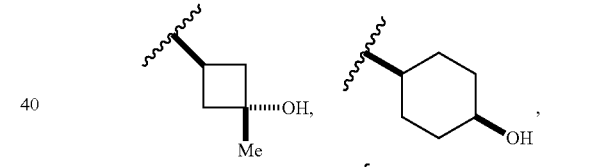

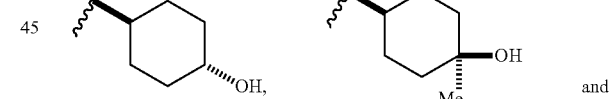

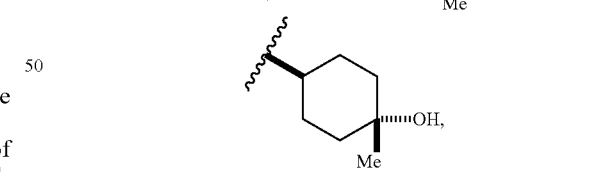

wherein the compounds are substantially pure stereoisomers.

In another embodiment, compounds of any one of Formulae VI-XXI are provided, wherein E is —$OR^{26a}$ and $R^{1a}$, $R^{1b}$, $R^{1c}$, $R^{1d}$, $R^2$, $R^{3a}$, $R^{3b}$, $R^{26a}$, X, and Y have the meanings as described above for Formula I, or a pharmaceutically acceptable salt, solvate, or prodrug thereof. In another embodiment, $R^{26a}$ is hydrogen.

In another embodiment, compounds of any one of Formulae VI-XXI are provided, wherein E is —$OR^{26a}$; $R^{1a}$, $R^{1b}$, $R^{1c}$, $R^{1d}$, $R^2$, $R^{26a}$, X, and Y have the meanings as described above for Formula I; and $R^{3a}$ and $R^{3b}$ taken together form a 4- to 7-membered optionally substituted cycloalkyl or 4- to 7-membered optionally substituted heterocyclo, or a pharmaceutically acceptable salt, solvate, or prodrug thereof. In another embodiment, $R^{26a}$ is hydrogen. In another embodiment, $R^{3a}$ and $R^{3b}$ taken together form a cyclobutyl, cyclopentyl, cyclohexyl, cycloheptyl, or optionally substituted piperidinyl group.

In another embodiment, compounds of any one of Formulae VI-XXI are provided, wherein E is —NR$^{26b}$R$^{26c}$; $R^{1a}$, $R^{1b}$, $R^{1c}$, $R^{1d}$, $R^2$, $R^{26b}$, $R^{26c}$, X, and Y and Y have the meanings as described above for Formula I, or a pharmaceutically acceptable salt, solvate, or prodrug thereof.

In another embodiment, compounds of any one of Formulae VI-XXI are provided, wherein E is —NR$^{26b}$, R$^{26c}$; $R^{1a}$, $R^{1b}$, $R^{1c}$, $R^{1d}$, $R^2$, $R^{26b}$, $R^{26c}$, X, and Y have the meanings as described above for Formula I; and $R^{3a}$ and $R^{3b}$ taken together form a 4- to 7-membered optionally substituted cycloalkyl or 4- to 7-membered optionally substituted heterocyclo, or a pharmaceutically acceptable salt, solvate, or prodrug thereof.

In another embodiment, compounds of any one of Formulae VI-XXI are provided, wherein E is —NR$^{26b}$, R$^{26c}$; $R^{1a}$, $R^{1b}$, $R^{1c}$, $R^{1d}$, $R^2$, $R^{26b}$, $R^{26c}$, X, and Y have the meanings as described above for Formula I; and $R^{3a}$ and $R^{3b}$ taken together form a 4- to 7-membered optionally substituted cycloalkyl, or a pharmaceutically acceptable salt, solvate, or prodrug thereof.

In another embodiment, compounds of any one of Formulae VI-XXI are provided, wherein E is —NR$^{26b}$R$^{26c}$, and $R^{1a}$, $R^{1b}$, $R^{1c}$, $R^{1d}$, $R^2$, $R^{26b}$, $R^{26c}$, X, and Y have the meanings as described above for Formula I, and $R^{3a}$ and $R^{3b}$ taken together form a cyclobutyl, cyclopentyl, cyclohexyl, or cycloheptyl, or a pharmaceutically acceptable salt, solvate, or prodrug thereof.

In another embodiment, compounds of any one of Formulae VI-XXI are provided, wherein E is —NR$^{26b}$R$^{26c}$, and $R^{1a}$, $R^{1b}$, $R^{1c}$, $R^{1d}$, $R^2$, $R^{26b}$, $R^{26c}$, X, and Y have the meanings as described above for Formula I, and $R^{3a}$ and $R^{3b}$ taken together form a 4- to 7-membered optionally substituted heterocyclo, or a pharmaceutically acceptable salt, solvate, or prodrug thereof.

In another embodiment, compounds of any one of Formula VI-XXI are provided, wherein E is —NR$^{26b}$R$^{26c}$, and $R^{1a}$, $R^{1b}$, $R^{1c}$, $R^{1d}$, $R^2$, $R^{26b}$, $R^{26c}$, X, and Y have the meanings as described above for Formula I, and $R^{3a}$ and $R^{3b}$ taken together form a tetrahydropyranyl or optionally substituted piperidinyl, or a pharmaceutically acceptable salt, solvate, or prodrug thereof.

In another embodiment, compounds of any one of Formulae VI-XXI are provided, wherein E is —NR$^{26b}$R$^{26c}$, and $R^{1a}$, $R^{1b}$, $R^{1c}$, $R^{1d}$, $R^2$, $R^{26b}$, $R^{26c}$, X, and Y have the meanings as described above for Formula I, $R^{26b}$ is hydrogen, and $R^{26c}$ is optionally substituted cycloalkyl. In another embodiment, $R^{26c}$ is hydroxycycloalkyl. In another embodiment, $R^{26c}$ is cycloalkyl substituted with —CO$_2$H.

In another embodiment, compounds of any one of Formulae VI-XXI are provided, wherein E is —NR$^{26b}$R$^{26c}$, and $R^{1a}$, $R^{1b}$, $R^{1c}$, $R^{1d}$, $R^2$, $R^{26b}$, $R^{26c}$, X, and Y have the meanings as described above for Formula I, $R^{26b}$ is hydrogen, and $R^{26c}$ is optionally substituted aryl. In another embodiment $R^{26c}$ is phenyl substituted with —CO$_2$H.

In another embodiment, compounds of Formula XXII are provided:

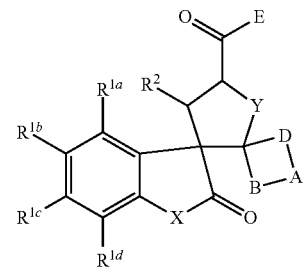

wherein:
$R^{1a}$, $R^{1b}$, $R^{1c}$, $R^{1d}$, $R^2$, E, X, and Y have the meanings as described above for Formula I;

A is selected from the group consisting of CR$^{27a}$R$^{27b}$, O, S, SO, SO$_2$, and NR$^{28}$;

$R^{27a}$ is selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, sulfonamido, and —CO$_2$R$^{31}$;

$R^{27b}$ is selected from the group consisting of hydrogen and optionally substituted alkyl; or $R^{27a}$ and $R^{27b}$ taken together form a 3- to 6-membered optionally substituted cycloalkyl or 3- to 6-membered optionally substituted heterocyclo;

$R^{28}$ is selected from the group consisting of hydrogen, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, carboxamido, sulfonamido, amino, —CO$_2$R$^{32a}$, —COR$^{32a}$, —SO$_2$R$^{32b}$, —N(R$^{32c}$)COR$^{32d}$, —N(R$^{32c}$)SO$_2$R$^{32e}$ and —N(R$^{32c}$)C=N(R$^{32d}$)-amino;

$R^{32a}$ is selected from the group consisting of hydrogen, optionally substituted alkyl, optionally substituted aryl, and optionally substituted heteroaryl;

$R^{32b}$ is selected from the group consisting of optionally substituted alkyl, optionally substituted aryl, and optionally substituted heteroaryl;

$R^{32c}$ is selected from the group consisting of hydrogen, optionally substituted alkyl, optionally substituted aryl, and optionally substituted heteroaryl;

$R^{32d}$ is selected from the group consisting of hydrogen, optionally substituted alkyl, optionally substituted aryl, and optionally substituted heteroaryl;

$R^{32e}$ is selected from the group consisting of optionally substituted alkyl, optionally substituted aryl, and optionally substituted heteroaryl; and $R^{32f}$ is selected from the group consisting of hydrogen, —CN, optionally substituted alkyl, optionally substituted aryl, and optionally substituted heteroaryl;

B is —(CR$^{29a}$R$^{29b}$)$_w$—;

D is —(CR$^{30a}$R$^{30b}$)$_x$—;

each $R^{29a}$, $R^{29b}$, $R^{30a}$, and $R^{30b}$ is independently selected from the group consisting of hydrogen, halo, nitro, cyano, hydroxy, amino, optionally substituted alkyl, haloalkyl, hydroxyalkyl, aminoalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido and sulfonamido;

$R^{31}$ is selected from the group consisting of hydrogen, optionally substituted alkyl, and optionally substituted aryl;

w is 0, 1, 2, 3, 4, 5, 6, 7, or 8; and x is 0, 1, 2, 3, 4, 5, 6, 7, or 8;

with the proviso that the sum of w plus x is 1, 2, 3, 4, 5, 6, 7 or 8, or a pharmaceutically acceptable salt, solvate, or prodrug thereof.

In another embodiment, compounds of Formula XXII are provided as a single stereoisomer, or a pharmaceutically acceptable salt, solvate, or prodrug thereof.

In another embodiment, compounds of Formula XXII are provided wherein w is 1, 2, or 3, x is 1, 2, or 3, and each $R^{29a}$, $R^{29b}$, $R^{30a}$, and $R^{30b}$ is independently hydrogen or $(C_1$-$C_4)$ alkyl, or a pharmaceutically acceptable salt, solvate, or prodrug thereof.

In another embodiment, compounds of Formula XXII are provided wherein w is 1, 2, or 3, x is 1, 2, or 3, each $R^{29a}$, $R^{29b}$, $R^{30a}$, and $R^{30b}$ is independently hydrogen or $(C_1$-$C_4)$alkyl, and A is $CR^{27a}R^{27b}$, or a pharmaceutically acceptable salt, solvate, or prodrug thereof.

In another embodiment, compounds of Formula XXII are provided wherein w is 1, 2, or 3, x is 1, 2, or 3, each $R^{29a}$, $R^{29b}$, $R^{30a}$, and $R^{30b}$ is independently hydrogen or $(C_1$-$C_4)$alkyl, A is $CR^{27a}R^{27b}$, and $R^{27a}$ and $R^{27b}$ are independently selected from the group consisting of hydrogen and alkyl, or a pharmaceutically acceptable salt, solvate, or prodrug thereof.

In another embodiment, compounds of Formula XXII are provided wherein w is 1, 2, or 3, x is 1, 2, or 3, each $R^{29a}$, $R^{29b}$, $R^{30a}$, and $R^{30b}$ is independently hydrogen or $(C_1$-$C_4)$alkyl, A is $CR^{27a}R^{27b}$, and $R^{27a}$ and $R^{27b}$ are hydrogen, or a pharmaceutically acceptable salt, solvate, or prodrug thereof.

In another embodiment, compounds of Formula XXII are provided wherein w is 1, 2, or 3, x is 1, 2, or 3, each $R^{29a}$, $R^{29b}$, $R^{30a}$, and $R^{30b}$ is independently hydrogen or $(C_1$-$C_4)$alkyl, and A is O, or a pharmaceutically acceptable salt, solvate, or prodrug thereof.

In another embodiment, compounds of Formula XXII are provided wherein w is 1, 2, or 3, x is 1, 2, or 3, each $R^{29a}$, $R^{29b}$, $R^{30a}$, and $R^{30b}$ is independently hydrogen or $(C_1$-$C_4)$ alkyl, and A is $SO_2$, or a pharmaceutically acceptable salt, solvate, or prodrug thereof.

In another embodiment, compounds of Formula XXII are provided wherein w is 1, 2, or 3, x is 1, 2, or 3, each $R^{29a}$, $R^{29b}$, $R^{30a}$, and $R^{30b}$ is independently hydrogen or $(C_1$-$C_4)$alkyl, and A is $NR^{28}$, or a pharmaceutically acceptable salt, solvate, or prodrug thereof.

In another embodiment, compounds of Formula XXII are provided wherein w is 1, 2, or 3, x is 1, 2, or 3, $R^{29a}$, $R^{29b}$, $R^{30a}$, and $R^{30b}$ are hydrogen, and A is $NR^{28}$, or a pharmaceutically acceptable salt, solvate, or prodrug thereof.

In another embodiment, compounds of Formula XXII are provided wherein w is 1, 2, or 3, x is 1, 2, or 3, $R^{29a}$, $R^{29b}$, $R^{30a}$, and $R^{30b}$ are hydrogen, A is $NR^{28}$, and $R^{28}$ is selected from the group consisting of hydrogen, optionally substituted alkyl, carboxamido, sulfonamido, amino, —$CO_2R^{32a}$, —$COR^{32a}$, —$SO_2R^{32b}$, —$N(R^{32c})COR^{32d}$, —$N(R^{32c})SO_2R^{32e}$ and —$N(R^{32c})C$=$N(R^{32f})$-amino, or a pharmaceutically acceptable salt, solvate, or prodrug thereof.

In another embodiment, compounds of Formula XXII are provided wherein w and x are 1, each $R^{29a}$, $R^{29b}$, $R^{30a}$, and $R^{30b}$ is hydrogen, A is $NR^{28}$, and $R^{28}$ is selected from the group consisting of hydrogen, optionally substituted alkyl, carboxamido, sulfonamido, —$CO_2R^{32a}$, —$COR^{32a}$, —$SO_2R^{32b}$, —$N(R^{32c})COR^{32d}$, —$N(R^{32e})SO_2R^{32e}$ and —$N(R^{32c})C$=$N(R^{32})$-amino, or a pharmaceutically acceptable salt, solvate, or prodrug thereof.

In another embodiment, compounds of Formula XXII are provided wherein w and x are 2, each $R^{29a}$, $R^{29b}$, $R^{30a}$, and $R^{30b}$ is hydrogen, A is $NR^{28}$, and $R^{28}$ is selected from the group consisting of hydrogen, optionally substituted alkyl, carboxamido, sulfonamido, —$CO_2R^{32a}$, —$COR^{32a}$, —$SO_2R^{32b}$, $N(R^{32c})COR^{32d}$, —$N(R^{32c})SO_2R^{32e}$ and —$N(R^{32c})C$=$N(R^{32f})$-amino, or a pharmaceutically acceptable salt, solvate, or prodrug thereof.

In another embodiment, compounds of Formula XXII are provided wherein w and x are 3, each $R^{29a}$, $R^{29b}$, $R^{30a}$, and $R^{30b}$ is hydrogen, A is $NR^{28}$, and $R^{28}$ is selected from the group consisting of hydrogen, optionally substituted alkyl, carboxamido, sulfonamide, —$CO_2R^{32a}$, —$COR^{32a}$, —$SO_2R^{32b}$, —$N(R^{32c})COR^{32d}$, —$N(R^{32c})SO_2R^{32e}$ and —$N(R^{32c})C$=$N(R^{32f})$-amino, or a pharmaceutically acceptable salt, solvate, or prodrug thereof.

In another embodiment, compounds of Formula XXII are provided wherein E is —$OR^{26a}$, or a pharmaceutically acceptable salt, solvate, or prodrug thereof.

In another embodiment, compounds of Formula XXII are provided wherein E is —$NR^{26b}R^{26c}$, or a pharmaceutically acceptable salt, solvate, or prodrug thereof.

In another embodiment, compounds of Formula XXIII are provided:

XXIII wherein $R^{1a}$, $R^{1b}$, $R^{1c}$, $R^{1d}$, $R^2$, E, X, and Y have the meanings as described above for Formula I, A has the meaning as described above for Formula XXII, and z is 0, 1, or 2, or a pharmaceutically acceptable salt, solvate, or prodrug thereof.

In another embodiment, compounds of Formula XXIV are provided:

XXIV wherein $R^{1a}$, $R^{1b}$, $R^{1c}$, $R^{1d}$, $R^2$, E, X, and Y have the meanings as described above for Formula I, A has the meaning as described above for Formula XXII, and z has the meaning as described above for Formula XXIII, or a pharmaceutically acceptable salt, solvate, or prodrug thereof.

In another embodiment, compounds of Formula XXV are provided:

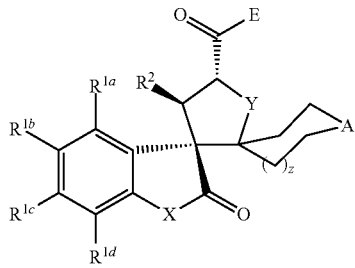

wherein $R^{1a}$, $R^{1b}$, $R^{1c}$, $R^{1d}$, $R^2$, E, X, and Y have the meanings as described above for Formula I, A has the meaning as described above for Formula XXII, and z has the meaning as described above for Formula XXIII, or a pharmaceutically acceptable salt, solvate, or prodrug thereof.

In another embodiment, compounds of any one of Formulae XXIII-XXV are provided, wherein E is —$OR^{26a}$ and $R^{26a}$ is hydrogen, or a pharmaceutically acceptable salt, solvate, or prodrug thereof.

In another embodiment, compounds of any one of Formulae XXIII-XXV are provided, wherein E is —$NR^{26b}R^{26c}$, $R^{26b}$ is hydrogen, and $R^{26c}$ is selected from the group consisting of optionally substituted alkyl, optionally substituted cycloalkyl, optionally substituted aryl, optionally substituted heteroaryl, and aralkyl, or a pharmaceutically acceptable salt, solvate, or prodrug thereof. In another embodiment, $R^{26c}$ is a hydroxyalkyl, e.g., a monohydroxyalkyl or dihydroxyalkyl. In another embodiment, $R^{26c}$ is an optionally substituted (cycloalkyl)alkyl. In another embodiment, $R^{26c}$ is a (heterocyclo)alkyl. In another embodiment, $R^{26c}$ is optionally substituted cycloalkyl. In another embodiment, $R^{26c}$ is optionally substituted phenyl.

In another embodiment, compounds of any one of Formulae XXIII-XXV are provided wherein A is $CR^{27a}R^{27b}$, O, or $NR^{28}$, or a pharmaceutically acceptable salt, solvate, or prodrug thereof.

In another embodiment, compounds of any one of Formulae XXIII-XXV are provided wherein A is $CHR^{27a}$, or a pharmaceutically acceptable salt, solvate, or prodrug thereof.

In another embodiment, compounds of any one of Formulae XXIII-XXV are provided wherein A is $CHR^{27a}$ and $R^{27a}$ is selected from the group consisting of hydrogen, hydroxy, amino, alkoxy, optionally substituted alkyl, haloalkyl, substituted heteroaryl, carboxamido, sulfonamido, and —$CO_2H$, or a pharmaceutically acceptable salt, solvate, or prodrug thereof.

In another embodiment, compounds of any one of Formulae XXIII-XXV are provided wherein A is $CH_2$ or $NR^{28}$, or a pharmaceutically acceptable salt, solvate, or prodrug thereof.

In another embodiment, compounds of any one of Formulae XXIII-XXV are provided wherein A is $CH_2$, or a pharmaceutically acceptable salt, solvate, or prodrug thereof.

In another embodiment, compounds of any one of Formulae XXIII-XXV are provided wherein A is $NR^{28}$, or a pharmaceutically acceptable salt, solvate, or prodrug thereof.

In another embodiment, compounds of any one of Formulae XXIII-XXV are provided wherein A is $CH_2$ and z is 1, or a pharmaceutically acceptable salt, solvate, or prodrug thereof.

In another embodiment, compounds of any one of Formulae XXIII-XXV are provided wherein A is $CH_2$, z is 1, E is —$NR^{26b}R^{26c}$, $R^{26b}$ is hydrogen, and $R^{26c}$ is selected from the group consisting of optionally substituted alkyl, optionally substituted cycloalkyl, optionally substituted aryl, optionally substituted heteroaryl, and aralkyl, or a pharmaceutically acceptable salt, solvate, or prodrug thereof. In another embodiment, $R^{26c}$ is optionally substituted cycloalkyl, e.g., a hydroxycycloalkyl, or a pharmaceutically acceptable salt, solvate, or prodrug thereof. In another embodiment, $R^{26c}$ is optionally substituted aryl, or a pharmaceutically acceptable salt, solvate, or prodrug thereof. In another embodiment, $R^{26c}$ is optionally substituted heteroaryl, or a pharmaceutically acceptable salt, solvate, or prodrug thereof.

In another embodiment, compounds of Formula XXVI are provided:

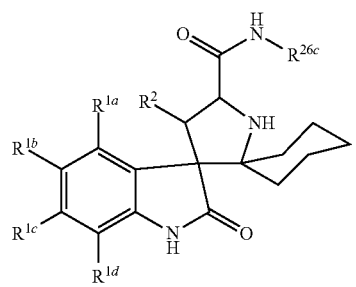

wherein $R^{1a}$, $R^{1b}$, $R^{1c}$, $R^{1d}$, $R^2$, and $R^{26c}$ have the meanings as described above for Formula I, or a pharmaceutically acceptable salt, solvate, or prodrug thereof.

In another embodiment, compounds of Formula XXVII are provided:

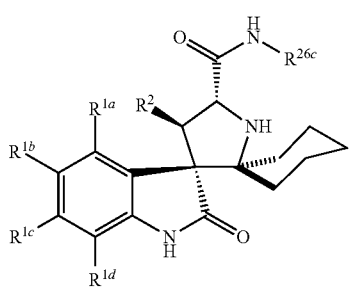

wherein $R^{1a}$, $R^{1b}$, $R^{1c}$, $R^{1d}$, $R^2$, and $R^{26c}$ have the meanings as described above for Formula I, or a pharmaceutically acceptable salt, solvate, or prodrug thereof.

In another embodiment, compounds of Formula XXVIII are provided:

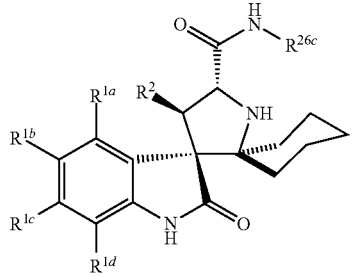

XXVIII wherein $R^{1a}$, $R^{1b}$, $R^{1c}$, $R^{1d}$, $R^2$, and $R^{26c}$ have the meanings as described above for Formula I, or a pharmaceutically acceptable salt, solvate, or prodrug thereof.

In another embodiment, compounds of any one of Formulae XXVI-XXVIII, or a pharmaceutically acceptable salt, solvate, or prodrug thereof are provided, wherein:

$R^{1a}$, $R^{1b}$, $R^{1c}$, and $R^{1d}$ are independently selected from the group consisting of hydrogen, fluoro, and chloro;

$R^2$ is optionally substituted phenyl; and $R^{26c}$ is selected from the group consisting of optionally substituted ($C_1$-$C_4$) alkyl, optionally substituted ($C_4$-$C_8$) cycloalkyl, optionally substituted phenyl, optionally substituted heteroaryl, and aralkyl;

or a pharmaceutically acceptable salt, solvate, or prodrug thereof.

In another embodiment, compounds of any one of Formulae I or III-XXVIII, or a pharmaceutically acceptable salt, solvate, or prodrug thereof are provided, wherein $R^{26c}$ is optionally substituted alkyl. In another embodiment, $R^{26c}$ is hydroxyalkyl. In another embodiment, $R^{26c}$ is dihydroxyalkyl. In another embodiment, $R^{26c}$ is (heterocyclo)alkyl.

In another embodiment, compounds of any one of Formulae I or III-XXVIII, or a pharmaceutically acceptable salt, solvate, or prodrug thereof are provided, wherein $R^{26c}$ is optionally substituted cycloalkyl. In another embodiment, $R^{26c}$ is hydroxycycloalkyl. In another embodiment, $R^{26}$ is cycloalkyl substituted with —CO$_2$H.

In another embodiment, compounds of any one of Formulae I or III-XXVIII, or a pharmaceutically acceptable salt, solvate, or prodrug thereof are provided, wherein $R^{26c}$ is selected from the group consisting of:

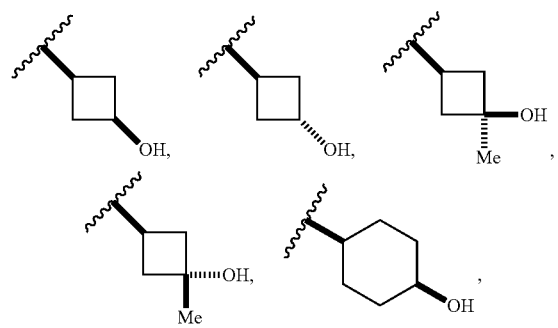

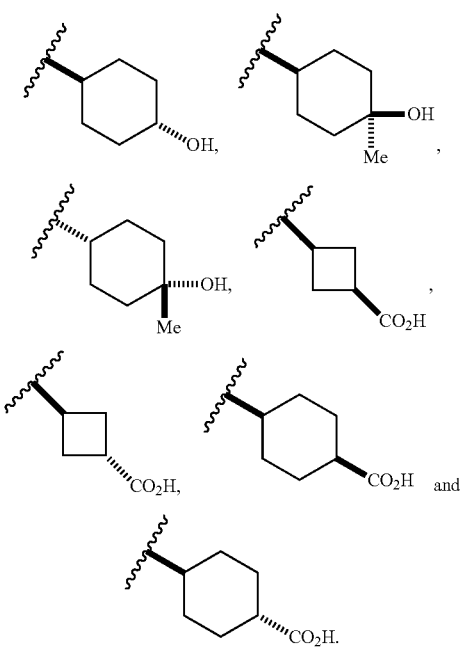

In another embodiment, compounds of any one of Formulae I or III-XXVIII, or a pharmaceutically acceptable salt, solvate, or prodrug thereof are provided, wherein $R^{26c}$ is optionally substituted aryl. In another embodiment, $R^{26c}$ is optionally substituted phenyl. In another embodiment, $R^{26c}$ is phenyl substituted with one or two of the following groups: halo, cyano, hydroxy, alkyl, haloalkyl, alkoxy, carboxamido, sulfonamido, —CONHSO$_2$Me, —CO$_2$R$^c$, —COR$^c$, —SO$_2$R$^d$, —N(R$^e$)COR$^f$, —N(R$^e$)SO$_2$R$^g$ or —N(R$^e$)C═N (R$^h$)-amino, wherein R$^c$, R$^d$, R$^e$, R$^f$, R$^g$, and R$^h$ are as defined above in connection with optionally substituted alkyl. In another embodiment, $R^{26c}$ is phenyl substituted with one or two of the following groups: halo, cyano, alkyl, haloalkyl, alkoxy, carboxamido, sulfonamido, —CO$_2$R$^c$, or —SO$_2$R$^d$, wherein R$^c$ and R$^d$ are as defined above in connection with optionally substituted alkyl. In another embodiment, $R^{26c}$ is phenyl substituted with —CO$_2$H.

In another embodiment, compounds of any one of Formulae I or III-XXVIII, or a pharmaceutically acceptable salt, solvate, or prodrug thereof are provided, wherein $R^{26c}$ is selected from the group consisting of:

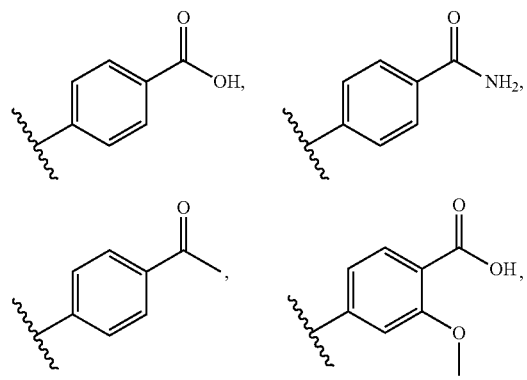

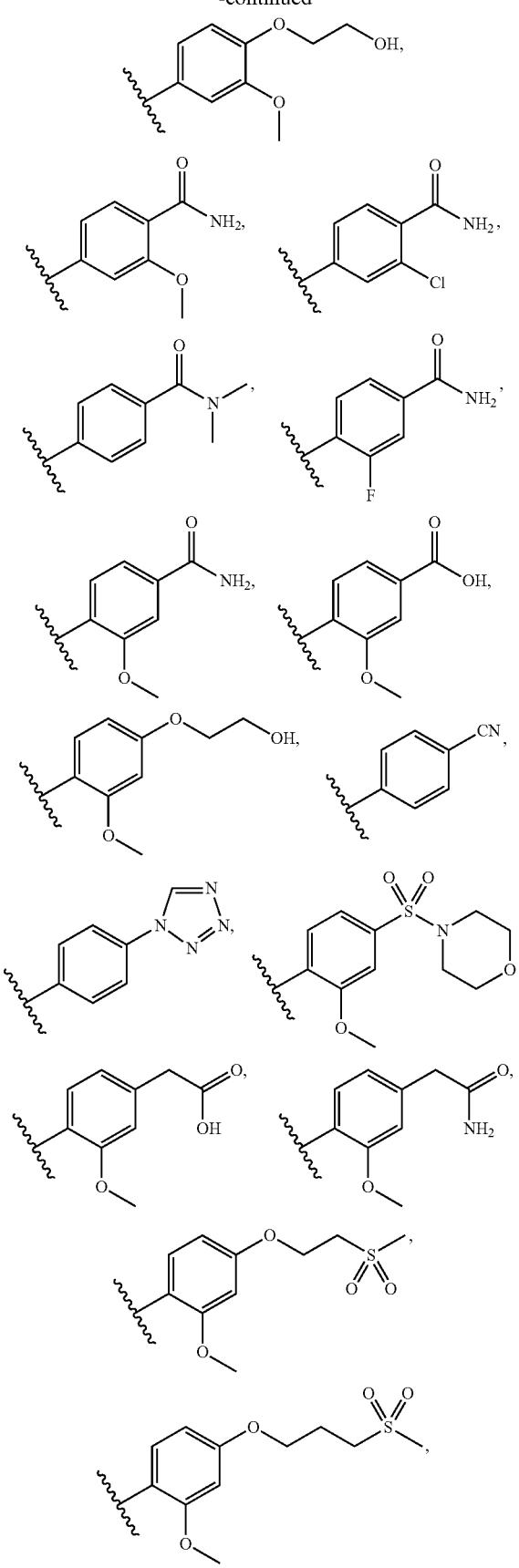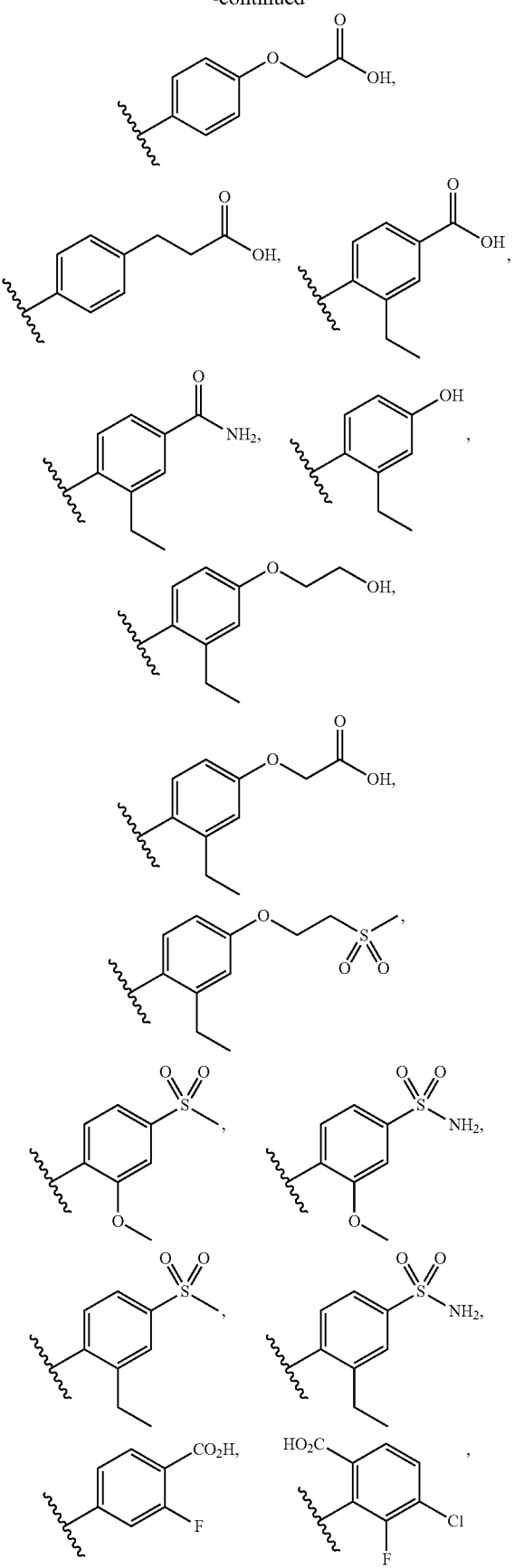

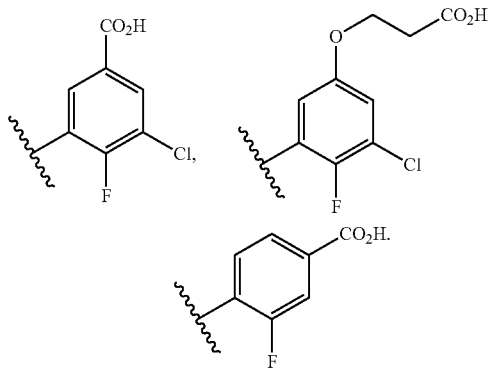

In another embodiment, compounds of any one of Formulae I or III-XXVIII, or a pharmaceutically acceptable salt, solvate, or prodrug thereof are provided, wherein $R^{26c}$ is optionally substituted heteroaryl. In another embodiment, the optionally substituted heteroaryl is an optionally substituted furyl, thienyl, pyridyl, pyrimidyl, benzimidazolyl, benzthiazolyl, or indolyl, In another embodiment, $R^{26c}$ is heteroaryl substituted with one or two of the following groups: halo, cyano, hydroxy, alkyl, haloalkyl, alkoxy, carboxamido, sulfonamide, —CONHSO$_2$Me, —CO$_2$R$^c$, —COR$^c$, —SO$_2$R$^d$, —N(R$^e$)COR$^f$, —N(R$^e$)SO$_2$R$^g$ or —N(R$^e$)C=N(R$^h$)-amino, wherein R$^c$, R$^d$, R$^e$, R$^f$, R$^g$, and R$^h$ are as defined above in connection with optionally substituted alkyl. In another embodiment, $R^{26c}$ is heteroaryl substituted with one or two of the following groups: halo, cyano, alkyl, haloalkyl, alkoxy, carboxamido, sulfonamido, —CO$_2$R$^c$, or —SO$_2$R$^d$, wherein R$^c$ and R$^d$ are as defined above in connection with optionally substituted alkyl. In another embodiment, $R^{26c}$ is heteroaryl substituted with —CO$_2$H.

In another embodiment, compounds of any one of Formulae I or III-XXVIII, or a pharmaceutically acceptable salt, solvate, or prodrug thereof are provided, wherein $R^{26c}$ is selected from the group consisting of:

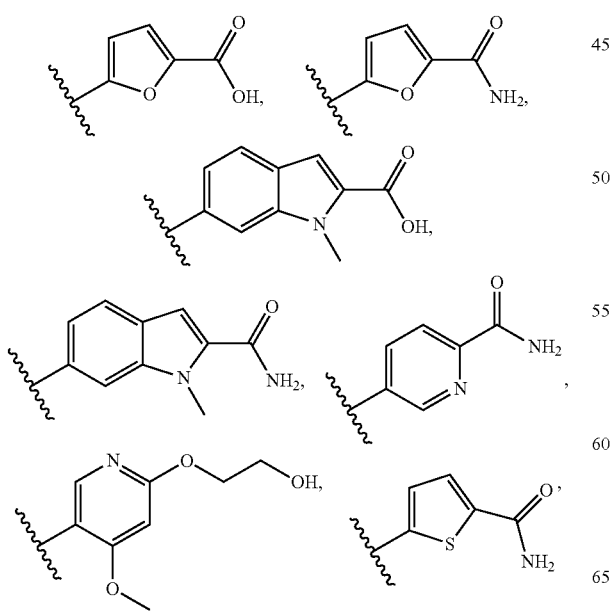

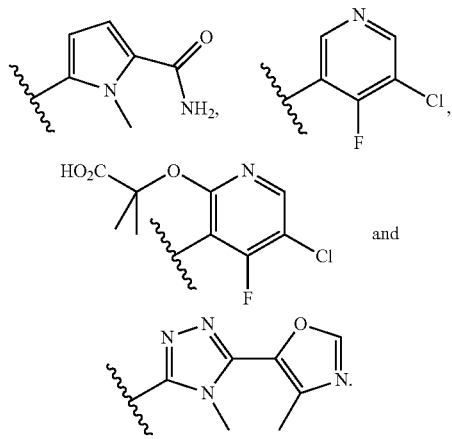

In another embodiment, compounds of any one of Formulae I or III-XXVIII, or a pharmaceutically acceptable salt, solvate, or prodrug thereof are provided, wherein $R^{26c}$ is aralkyl.

In another embodiment, compounds of any one of Formulae I or III-XXVIII, or a pharmaceutically acceptable salt, solvate, or prodrug thereof are provided, wherein $R^{26c}$ is selected from the group consisting of:

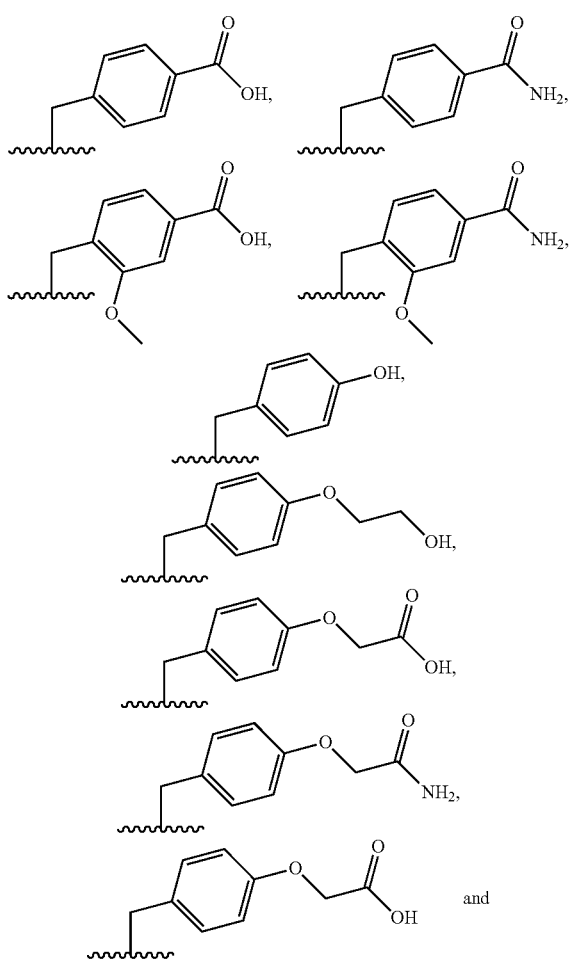

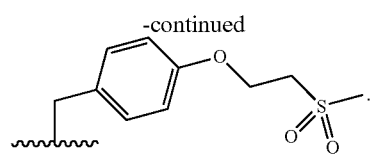

In another embodiment, compounds of any one of Formulae I or III-XXVIII are provided, wherein $R^{26c}$ is selected from the group consisting of:

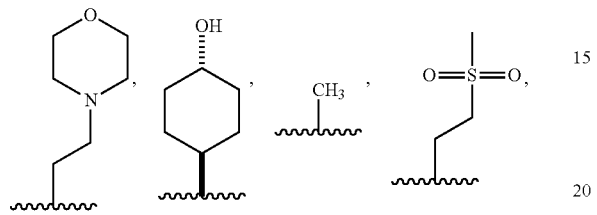

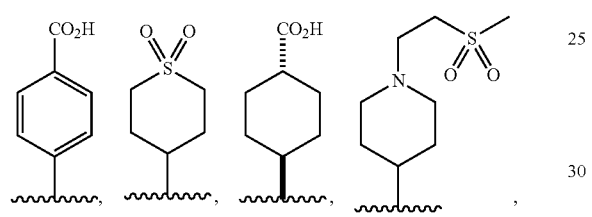

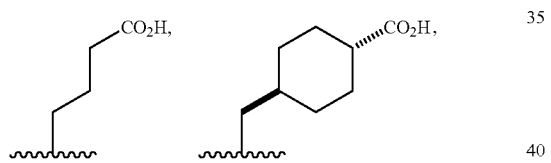

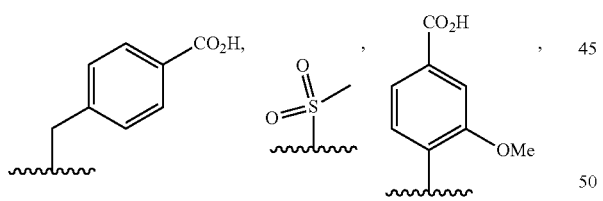

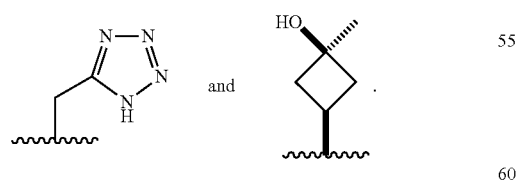

In another embodiment, compounds of Formulae XXVII or XXVIII are provided substantially free of one or more other stereoisomers. In another embodiment, compounds of any one of Formulae XXVII or XXVIII are substantially pure stereoisomers. In another embodiment, compounds of any one of Formulae XXVII or XXVIII are pure stereoisomers.

In another embodiment, compounds of Formula I are provided having the structure:

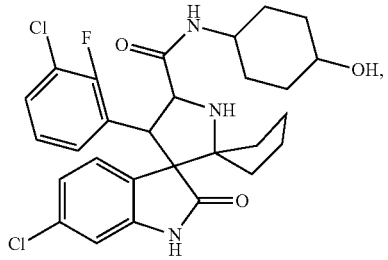

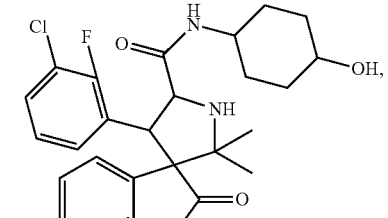

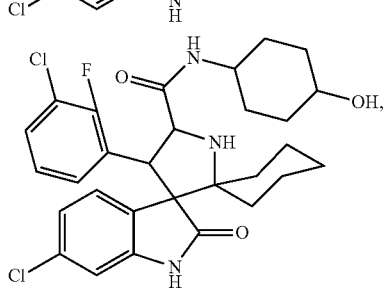

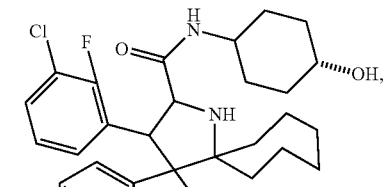

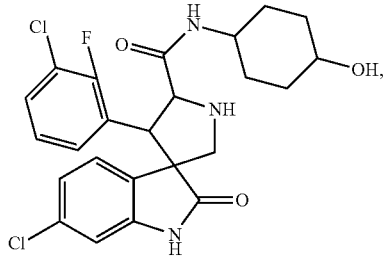

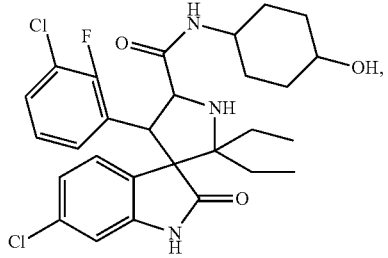

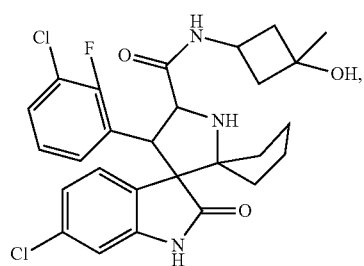
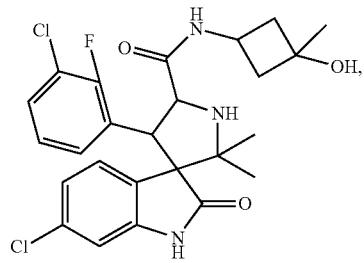
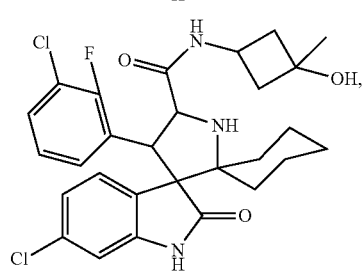
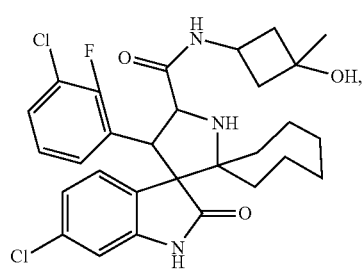
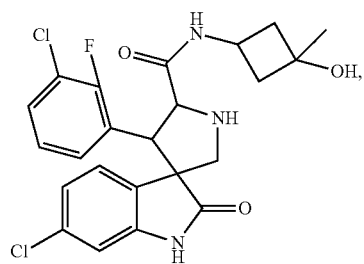
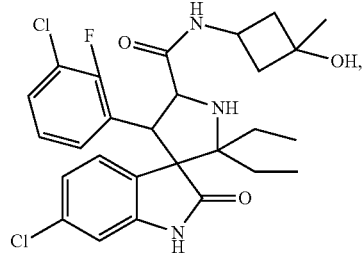
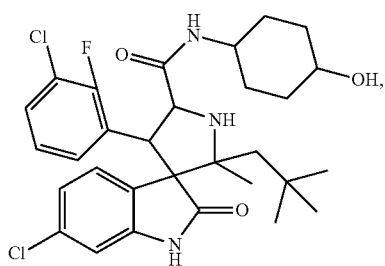
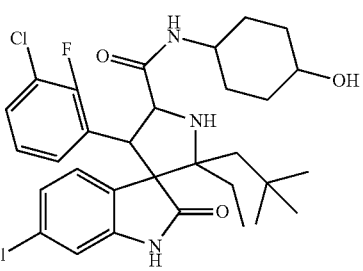
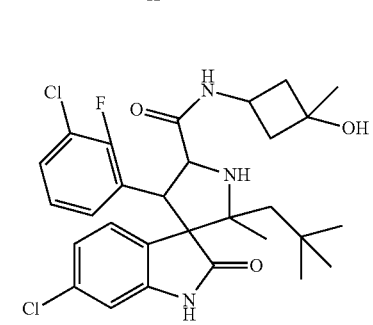
or
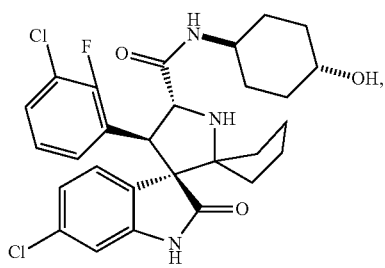
or stereoisomers thereof, or pharmaceutically acceptable salts, solvates, or prodrugs thereof.
In another embodiment, compounds of Formula I are provided having the structure:
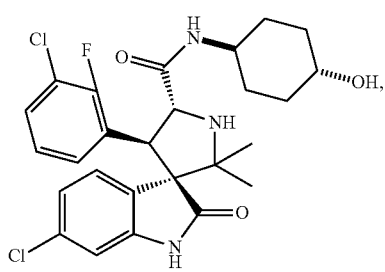

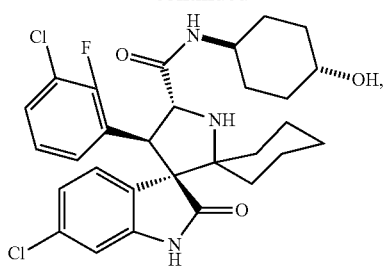
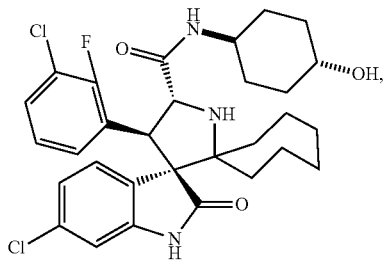
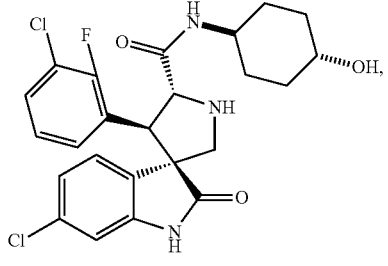
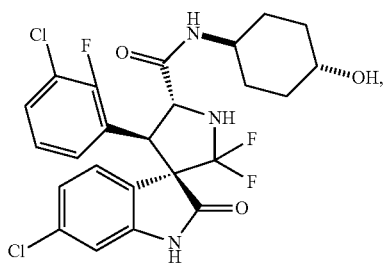
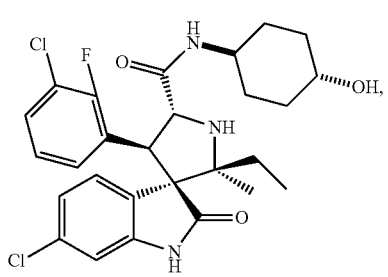
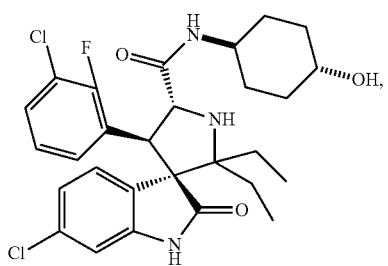
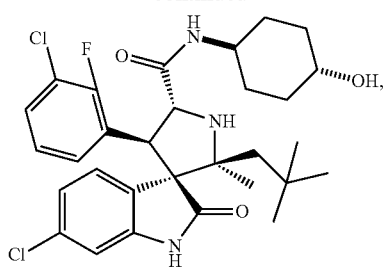
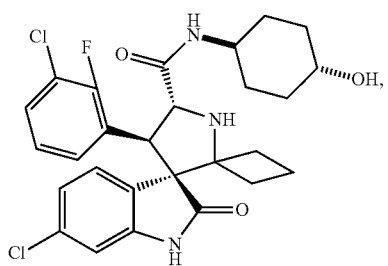
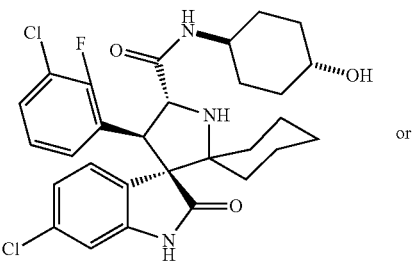
or
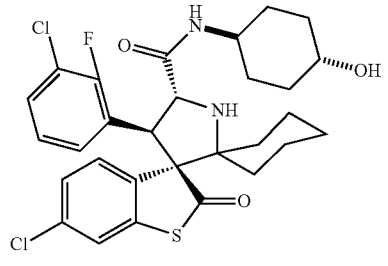
or pharmaceutically acceptable salts, solvates, or prodrugs thereof.
In another embodiment, compounds of Formula I are provided having the structure:
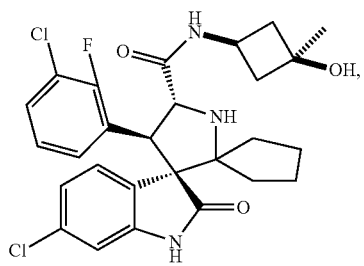

69
-continued
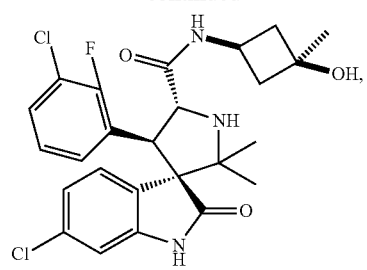
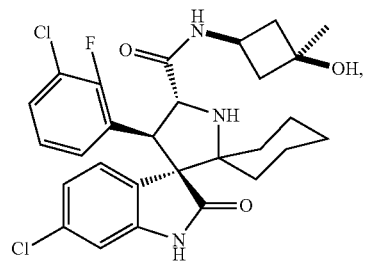
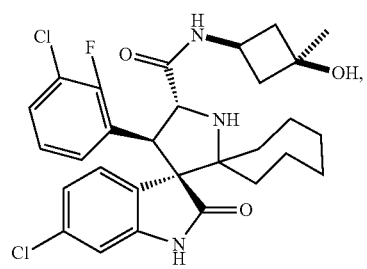
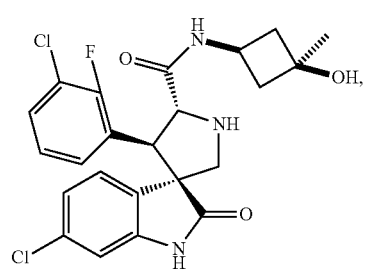
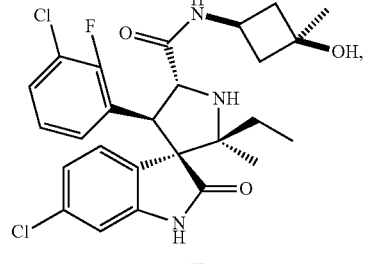
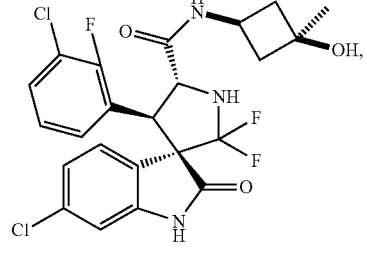
70
-continued
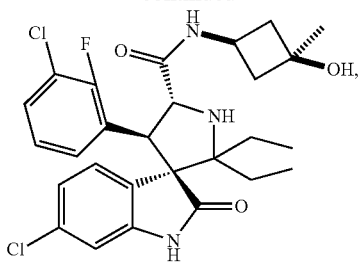
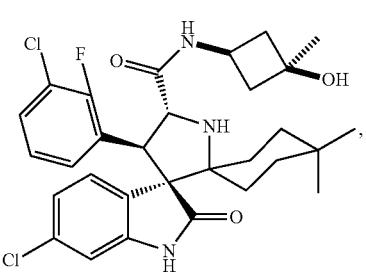
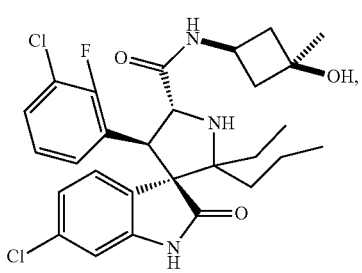
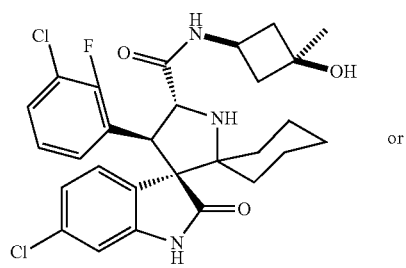 or
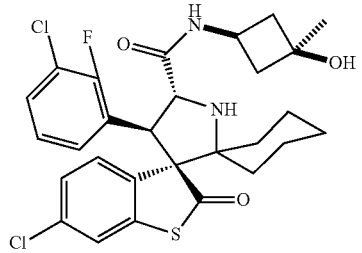
or pharmaceutically acceptable salts, solvates, or prodrugs thereof.

In another embodiment, compounds of Formula I are provided having the structure:
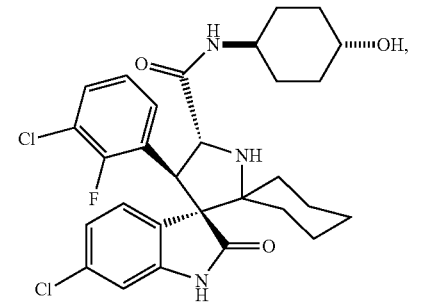
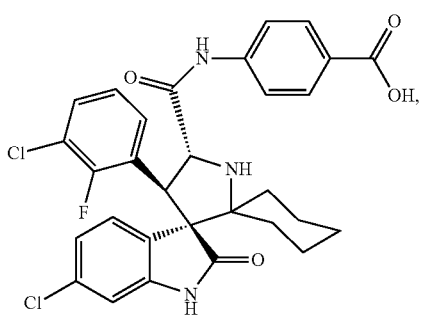
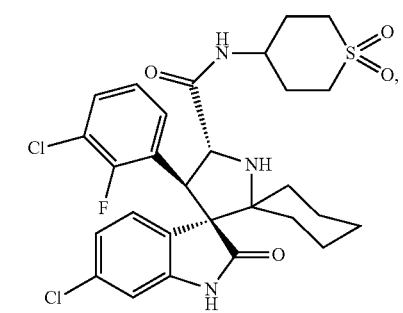
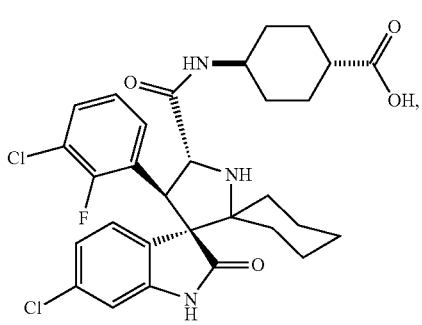
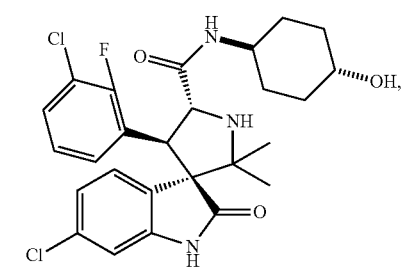
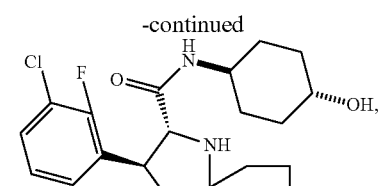
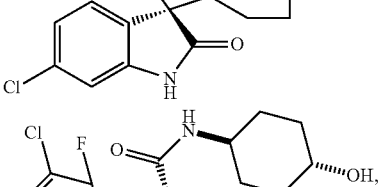
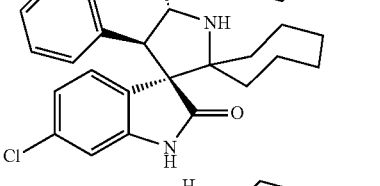
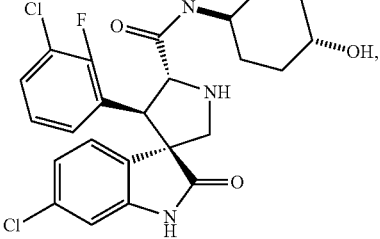
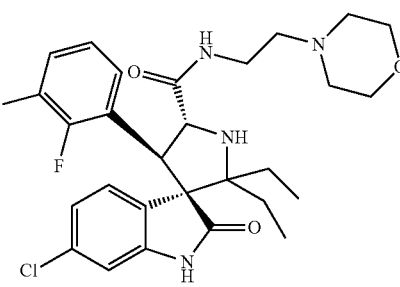
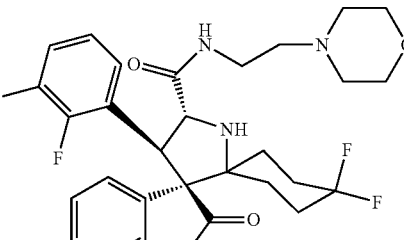
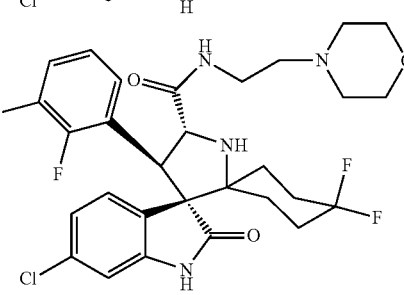

73
-continued
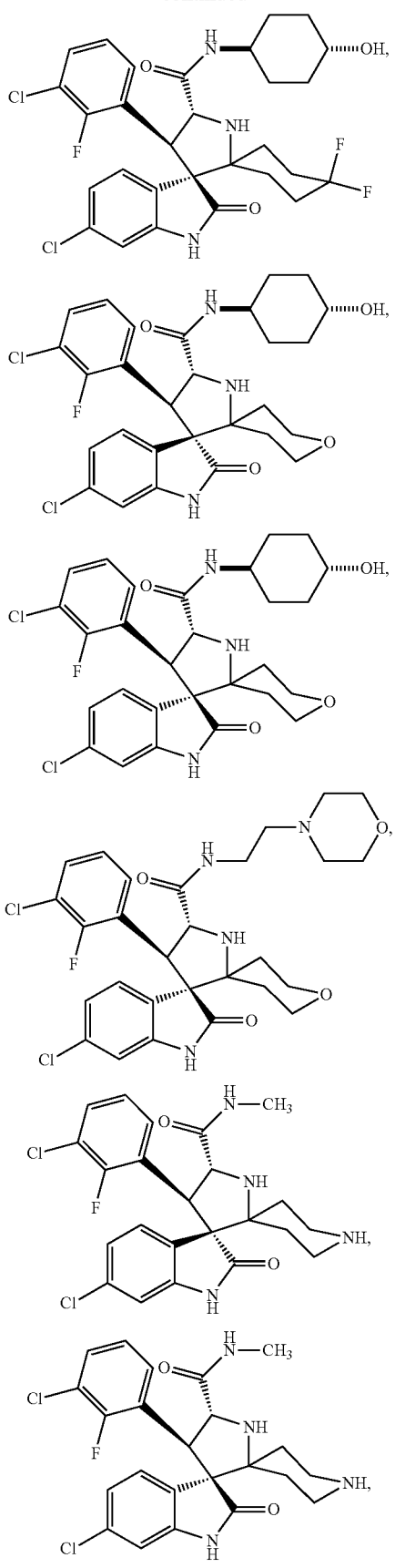
74
-continued
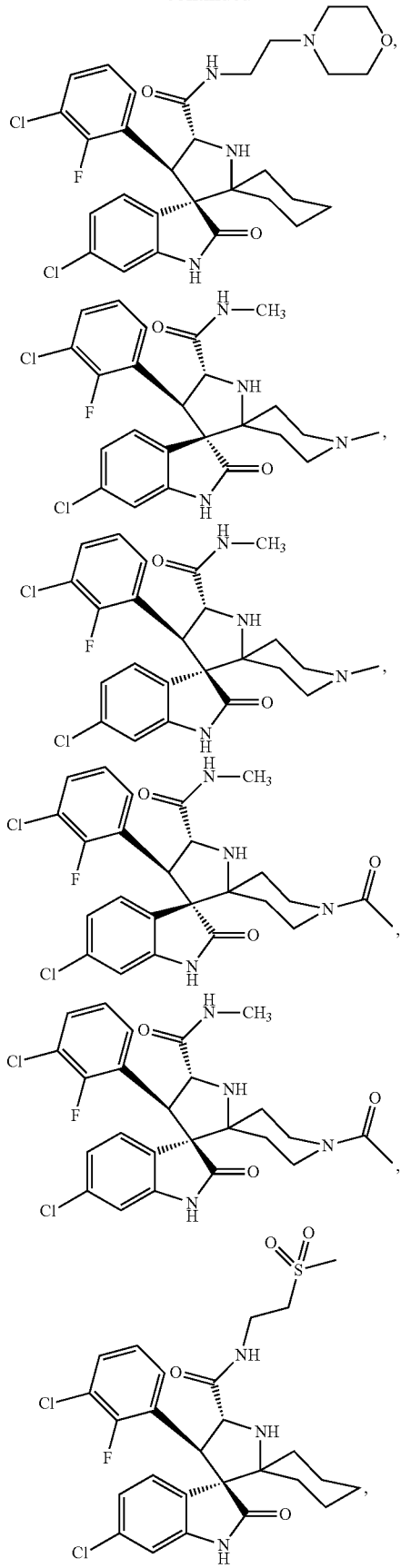

75
-continued
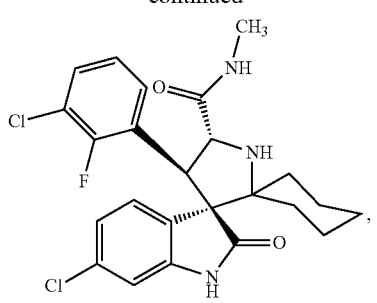
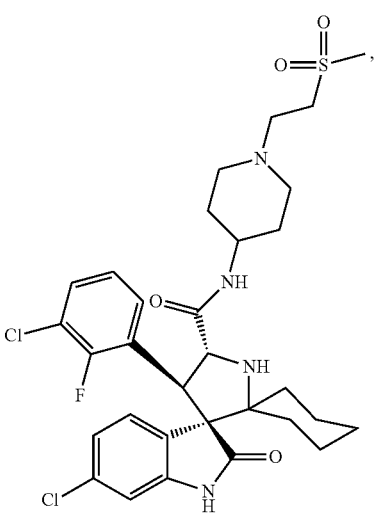
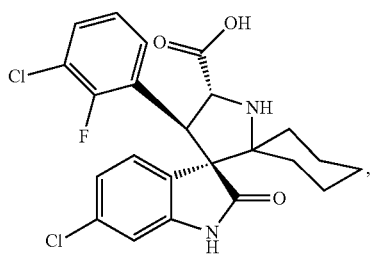
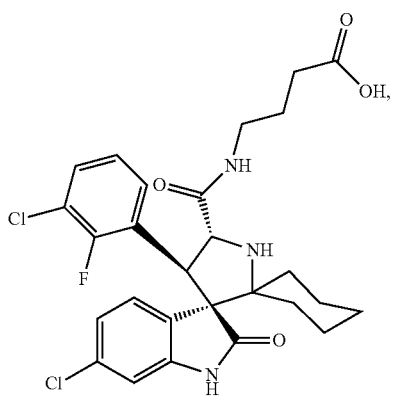
76
-continued
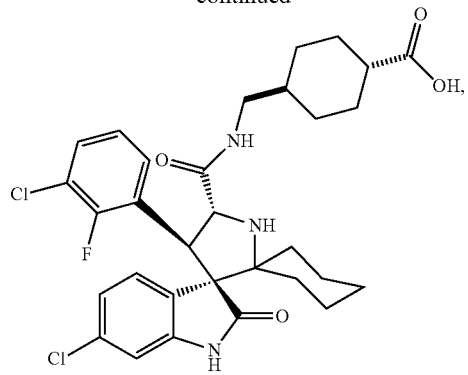
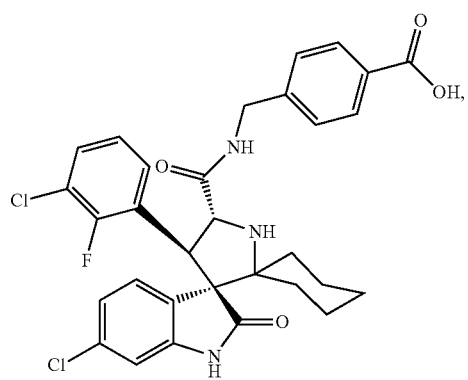
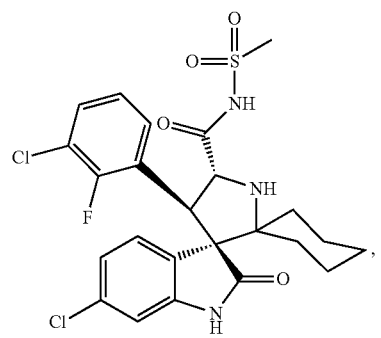
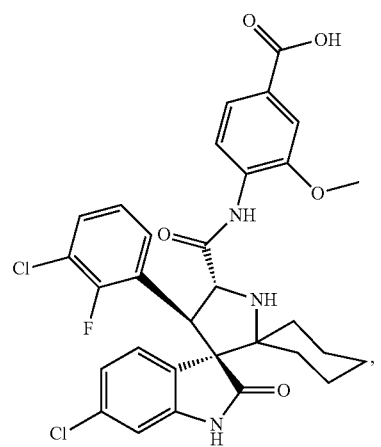

77
-continued
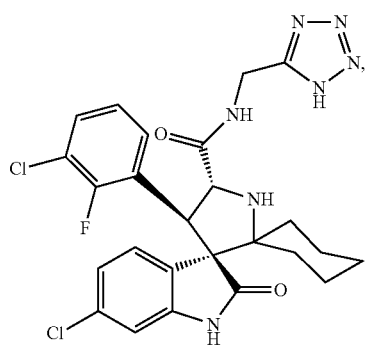
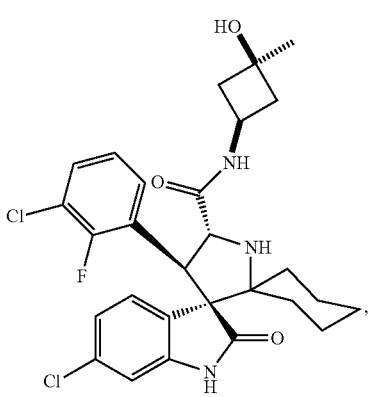
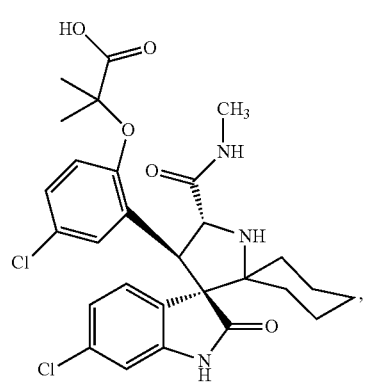
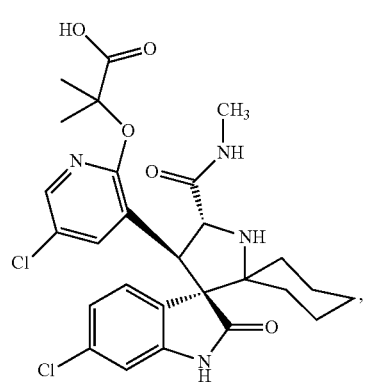
78
-continued
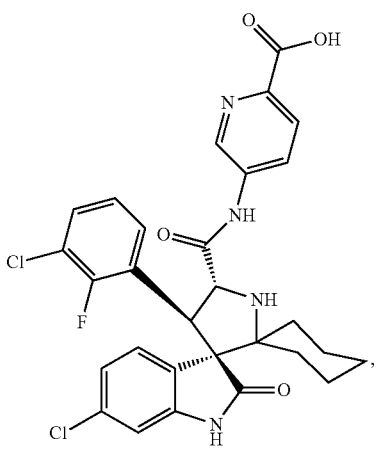
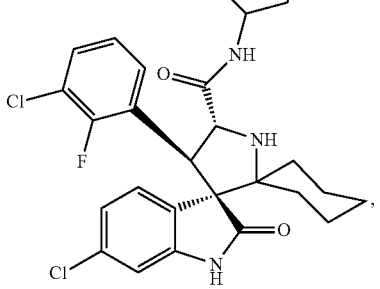
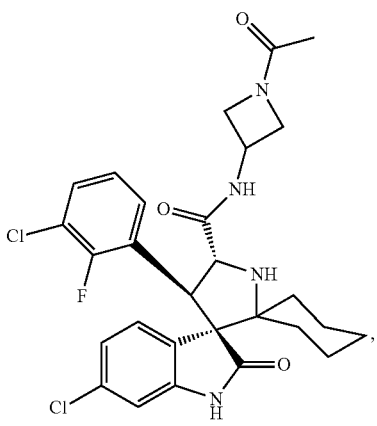

79
-continued
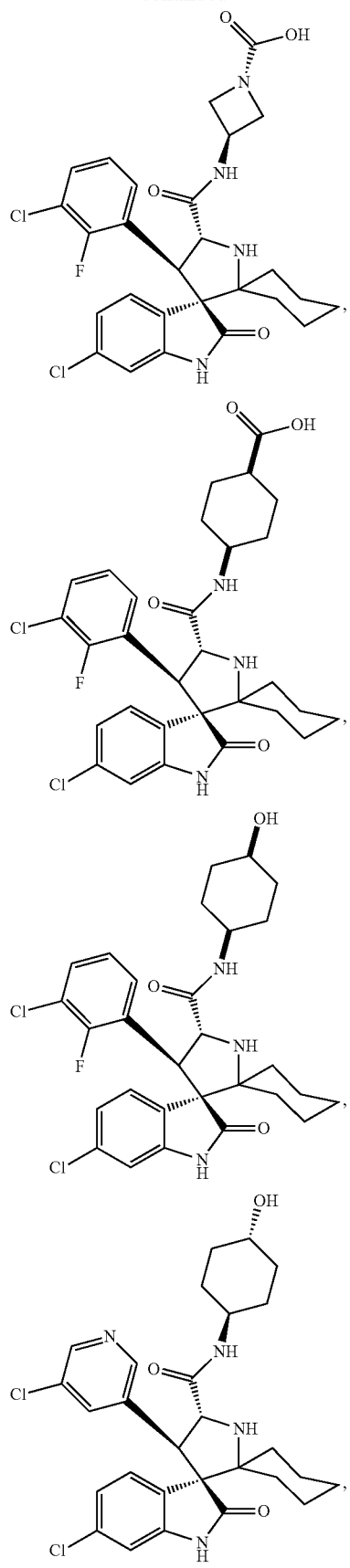
80
-continued
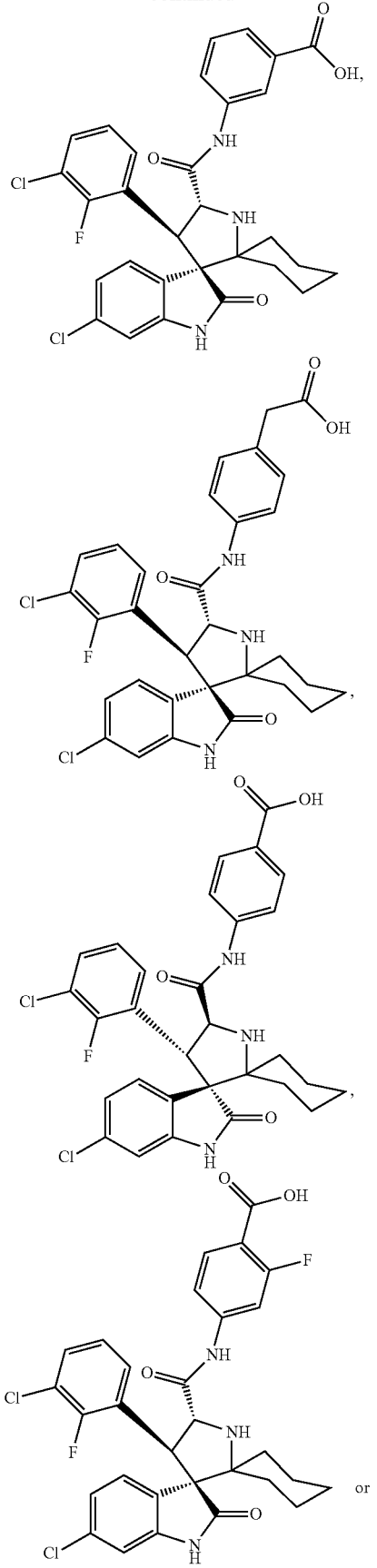

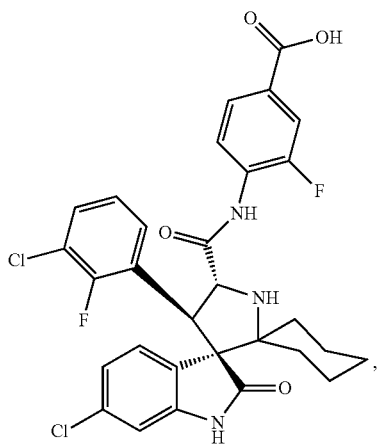

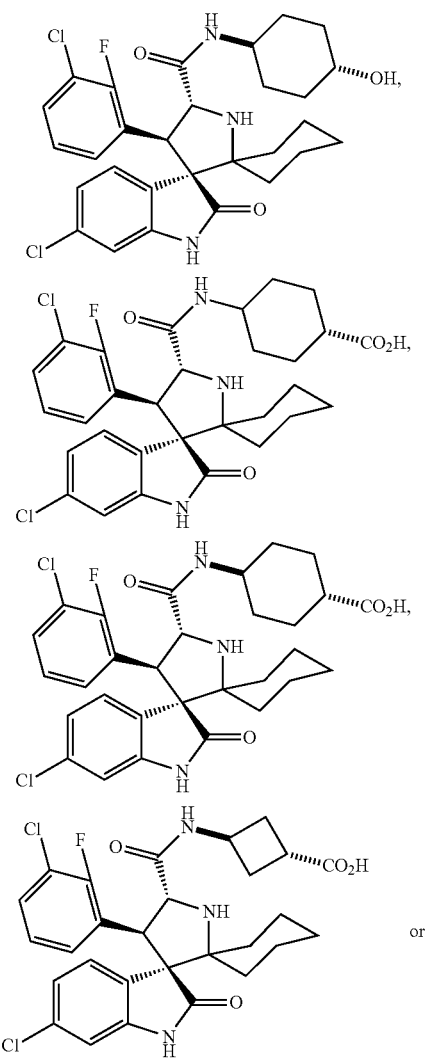

or pharmaceutically acceptable salts, solvates, or prodrugs thereof.

In another embodiment, compounds of Formula I are provided having the structure:

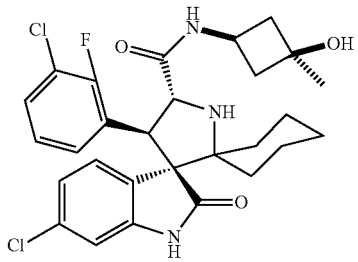

or pharmaceutically acceptable salts, solvates, or prodrugs thereof.

In another embodiment, the disclosure provides a method of preparing a compound having Formula XVI:

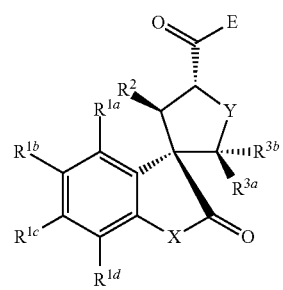

wherein $R^{1a}$, $R^{1b}$, $R^{1c}$, $R^{1d}$, $R^2$, $R^{3a}$, $R^{3b}$, and E have the meanings as described above for Formula I, and X and Y are NH. In another embodiment, E is —$OR^{26a}$. In another embodiment, E is —$NR^{26b}R^{26c}$. In another embodiment, $R^{26b}$ is hydrogen, and $R^{26c}$ is selected from the group consisting of optionally substituted alkyl, optionally substituted cycloalkyl, optionally substituted aryl, and optionally substituted heteroaryl. In another embodiment, $R^{3a}$ and $R^{3b}$ are taken together form an unsubstituted 4- to 8-membered cycloalkyl.

In another embodiment, the method of preparing a compound having Formula XVI comprises allowing a compound having Formula VI:

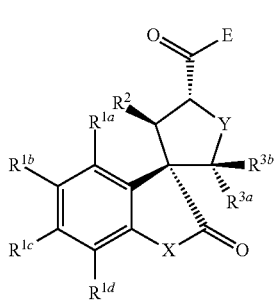

to isomerize to a compound having Formula XVI.

In another embodiment, the method of preparing a compound having Formula XVI comprises dissolving a compound having Formula VI in a solvent or a mixture of solvents.

In another embodiment, the method of preparing a compound having Formula XVI comprises:

a) dissolving a compound having Formula VI in a solvent or a mixture of solvents; and b) allowing the compound having Formula VI to isomerize to a compound having Formula XVI.

In another embodiment, the method of preparing a compound having Formula XVI comprises:

a) allowing the compound having Formula VI to isomerize to a compound having Formula XVI; and b) isolating the compound having Formula XVI substantially free from the compound having Formula VI, and one or more other stereoisomers.

In another embodiment, the method of preparing a compound having Formula XVI comprises:

a) dissolving a compound having Formula VI in a solvent or a mixture of solvents;

b) allowing the compound having Formula VI to isomerize to a compound having Formula XVI; and c) isolating the compound having Formula XVI substantially free from the compound having Formula VI, and one or more other stereoisomers.

In another embodiment, the solvent is selected from the group consisting of acetonitrile, methanol, ethyl acetate, and water, or a mixture thereof.

In another embodiment, the isomerization is carried out at a pH of less than 7, e.g., at a pH of about 6, about 5, about 4, about 3, about 2, or about 1. In one embodiment, the isomerization is carried out at a pH of about 7. In one embodiment, the isomerization is carried out at a pH of greater than 7, e.g., at a pH of about 8, about 9, about 10, about 11, about 12, or about 13.

In another embodiment, the isomerization is carried out in the presence of an acid, e.g., trifluoroacetic acid or acetic acid.

In one embodiment, the isomerization is carried out in the presence of a base, e.g., $NaHCO_3$.

In another embodiment, isomerization is carried out at a temperature of about 20° C. to about 100° C., e.g., at a temperature of about 20° C. to about 70° C., e.g., at a temperature of about 45° C. to about 65° C. In one embodiment the isomerization is carried out at about room temperature, e.g., at about 20° C. In one embodiment the isomerization is carried out above room temperature, e.g., at about 25° C., at about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

In another embodiment, the isomerization is carried about for a period of time between about 0.5 hours and about 2 weeks, e.g., for about 1 hour, about 3 hours, about 6 hours, about 12 hours, about 1 day, about 2 days, about 3 days, about 4 days, about 5 days, about 6 days, or about 1 week. The period of time needed for isomerization to occur may depend on a variety of factors including the chemical structure of Formula VI, the solvent(s), the temperature, and/or the pH.

In certain aspects, the disclosure provides the following particular embodiments:

I. A compound having Formula II:

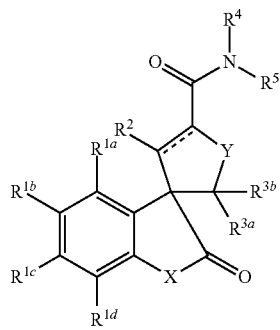

II wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl; or $R^{3a}$ and $R^{3b}$ taken together form a 3- to 9-membered optionally substituted cycloalkyl;

$R^4$ is selected from the group consisting of hydrogen and optionally substituted $C_1$-$C_6$ alkyl;

$R^5$ is selected from the group consisting of:

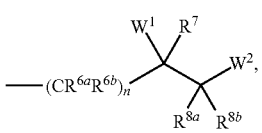

R5-1

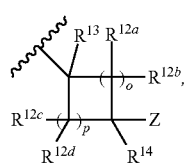

R5-2

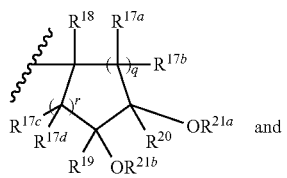

R5-3

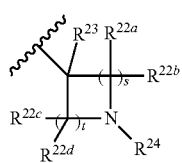

wherein:

each $R^{6a}$ and $R^{6b}$ is independently selected from the group consisting of hydrogen and optionally substituted $C_1$-$C_6$ alkyl;

$R^7$ is selected from the group consisting of hydrogen, optionally substituted $C_1$-$C_6$ alkyl, and optionally substituted cycloalkyl;

$R^{8a}$ and $R^{8b}$ are each independently selected from the group consisting of hydrogen, optionally substituted $C_1$-$C_6$ alkyl, and optionally substituted cycloalkyl; or $R^{8a}$ and $R^{8b}$ taken together with the carbon that they are attached form a 3- to 8-membered optionally substituted cycloalkyl;

$W^1$ is selected from the group consisting of —$OR^{9a}$ and —$NR^{9b}R^{9c}$;

$R^{9a}$ is hydrogen;

$R^{9b}$ is selected from the group consisting of hydrogen, optionally substituted alkyl, optionally substituted cycloalkyl, optionally substituted aryl, optionally substituted heteroaryl, —$SO_2R^{9d}$, and —$CONR^{9e}R^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$W^2$ is selected from the group consisting of —$OR^{10}$ and —$NR^{11a}R^{11b}$;

with the proviso that when $W^1$ is —$OR^{9a}$ and $W^2$ is —$OR^{10}$ then at least one of $R^7$, $R^{8a}$, and $R^{8b}$ is other than hydrogen;

$R^{10}$ is hydrogen; or one of $R^{9a}$ and $R^{10}$ is hydrogen and the other is a metabolically cleavable group;

$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

n is 1, 2, 3, 4, or 5;

each $R^{12a}$, $R^{12b}$, $R^{12c}$, and $R^{12d}$ is independently selected from the group consisting of hydrogen and optionally substituted $C_1$-$C_6$ alkyl;

$R^{13}$ is selected from the group consisting of hydrogen and optionally substituted $C_1$-$C_6$ alkyl;

$R^{14}$ is selected from the group consisting of hydrogen, optionally substituted $C_1$-$C_6$ alkyl, and optionally substituted cycloalkyl;

Z is selected from the group consisting of —$OR^{15}$ and —$NR^{16a}R^{16b}$; or Z and $R^{14}$ taken together form a carbonyl, i.e., a C=O, group.

$R^{15}$ is selected from the group consisting of hydrogen and metabolically cleavable group;

$R^{16a}$ is selected from the group consisting of —$SO_2R^{16c}$ and —$CONR^{16d}R^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

o is 1, 2, or 3;

p is 0, 1, 2, or 3;

each $R^{17a}$, $R^{17b}$, $R^{17c}$ and $R^{17d}$ is independently selected from the group consisting of hydrogen and optionally substituted $C_1$-$C_6$ alkyl;

$R^{18}$ is selected from the group consisting of hydrogen and optionally substituted $C_1$-$C_6$ alkyl;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

q is 0, 1, 2, or 3;

r is 1, 2, or 3;

each $R^{22a}$, $R^{22b}$, $R^{22c}$, and $R^{22d}$ is independently selected from the group consisting of hydrogen and optionally substituted $C_1$-$C_6$ alkyl;

$R^{23}$ is selected from the group consisting of hydrogen and optionally substituted $C_1$-$C_6$ alkyl;

$R^{24}$ is selected from the group consisting of —$SO_2R^{24a}$ and —$CONR^{24b}R^{24c}$;

$R^{24a}$ is selected from the group consisting of optionally substituted alkyl, optionally substituted cycloalkyl, optionally substituted aryl, and optionally substituted heteroaryl;

$R^{24b}$ and $R^{24c}$ are each independently selected from the group consisting of hydrogen, optionally substituted cycloalkyl, optionally substituted aryl, and optionally substituted heteroaryl; or $R^{24b}$ and $R^{24c}$ taken together with the nitrogen atom to which they are attached form a 4- to 8-membered heterocyclo;

s and t are each independently 1, 2, or 3;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ⸗ represents a single or a double bond, or a pharmaceutically acceptable salt, solvate, or prodrug thereof.

II. The compound of particular embodiment I having the formula:

<chemical structure> or a pharmaceutically acceptable salt, solvate, or prodrug thereof.

III. The compound of particular embodiment II having formula:

<chemical structure> or a pharmaceutically acceptable salt, solvate, or prodrug thereof.

IV. The compound of any one of particular embodiments I-III, wherein:

$R^{1a}$, $R^{1b}$, $R^{1c}$, and $R^{1d}$ are each independently selected from the group consisting of hydrogen, fluoro, and chloro;

$R^2$ is optionally substituted aryl;

$R^{3a}$ is halo or $C_1$-$C_{10}$ alkyl;

$R^{3b}$ is halo or $C_1$-$C_{10}$ alkyl; or $R^{3a}$ and $R^{3b}$ taken together form a 3- to 9-membered optionally substituted cycloalkyl;

$R^4$ is hydrogen; and

X and Y are NH, or a pharmaceutically acceptable salt, solvate, or prodrug thereof.

V. The compound of particular embodiment IV, wherein:

$R^{1a}$ and $R^{1d}$ are each hydrogen;

$R^{1b}$ is selected from the group consisting of hydrogen and fluoro; and $R^{1c}$ is selected from the group consisting of fluoro and chloro, or a pharmaceutically acceptable salt, solvate, or prodrug thereof.

VI. The compound of any one of particular embodiments I-V, wherein $R^2$ is an optionally substituted aryl having Formula R2-1:

<chemical structure R2-1> wherein $R^{25a}$, $R^{25b}$, $R^{25c}$, $R^{25d}$, and $R^{25e}$ are each independently selected from the group consisting of hydrogen, halogen, hydroxy, nitro, amino, cyano, alkoxy, alkyl, or haloalkyl, or a pharmaceutically acceptable salt, solvate, or prodrug thereof.

VII. The compound of particular embodiment VI, wherein:

$R^{25a}$ is selected from the group consisting of hydrogen and fluoro;

$R^{25b}$ is chloro;

$R^{25c}$ is selected from the group consisting of hydrogen and fluoro; and $R^{25d}$ and $R^{25e}$ are each hydrogen, or a pharmaceutically acceptable salt, solvate, or prodrug thereof.

VIII. The compound of any one of particular embodiment I-VII, wherein $R^5$ is selected from the group consisting of:

<chemical structures R5-5, R5-6, R5-7, R5-8, R5-9>

-continued

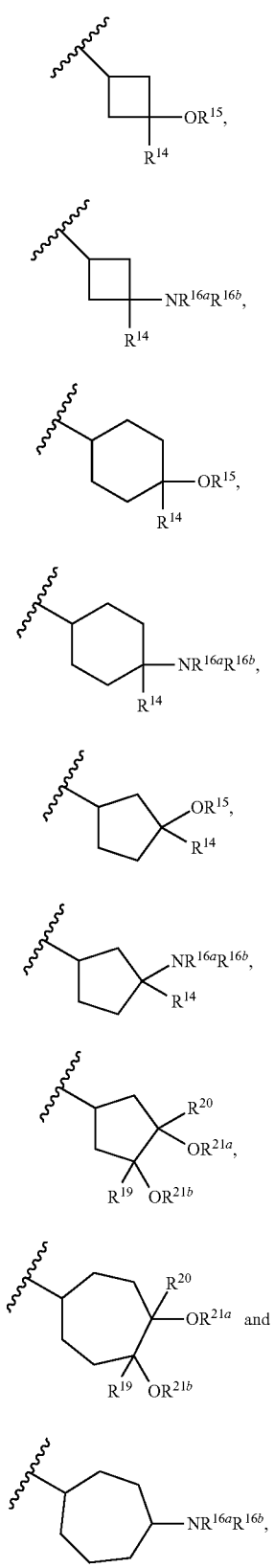

or a pharmaceutically acceptable salt, solvate, or prodrug thereof.

IX. The compound of particular embodiment VIII, wherein $R^5$ is selected from the group consisting of:

R5-10

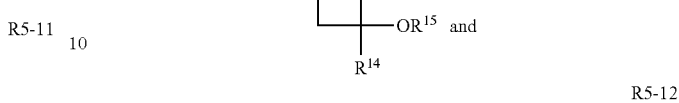

R5-12 wherein:

$R^{14}$ is hydrogen or $C_1$-$C_4$ alkyl; and $R^{15}$ is hydrogen, or a pharmaceutically acceptable salt, solvate, or prodrug thereof.

X. The compound of any one of particular embodiments I-IX, wherein $R^{3a}$ and $R^{3b}$ are each independently $C_1$-$C_6$ alkyl, or a pharmaceutically acceptable salt, solvate, or prodrug thereof.

XI. The compound of any one of particular embodiments I-IX, wherein $R^{3a}$ and $R^{3b}$ are taken together to form an optionally substituted cyclopropyl, cyclobutyl, cyclopentyl, cyclohexyl, or cycloheptyl ring, or a pharmaceutically acceptable salt, solvate, or prodrug thereof.

XII. The compound of any one of particular embodiments I-XI, wherein $R^5$ is selected from the group consisting of:

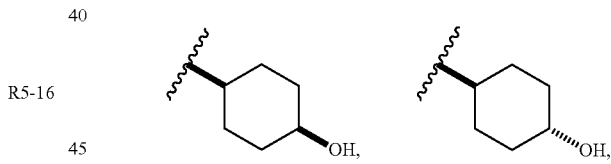

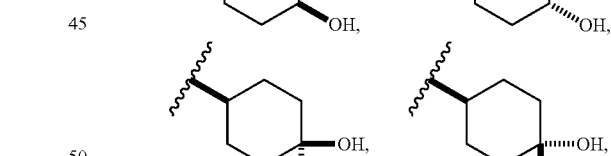

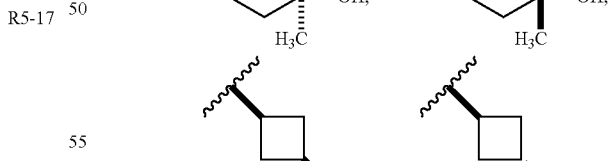

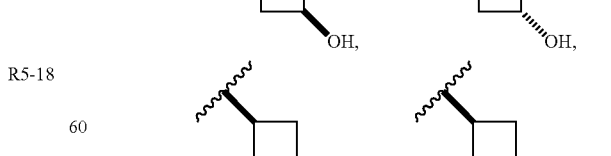

or a pharmaceutically acceptable salt, solvate, or prodrug thereof.

XIII. A compound selected from the group consisting of:

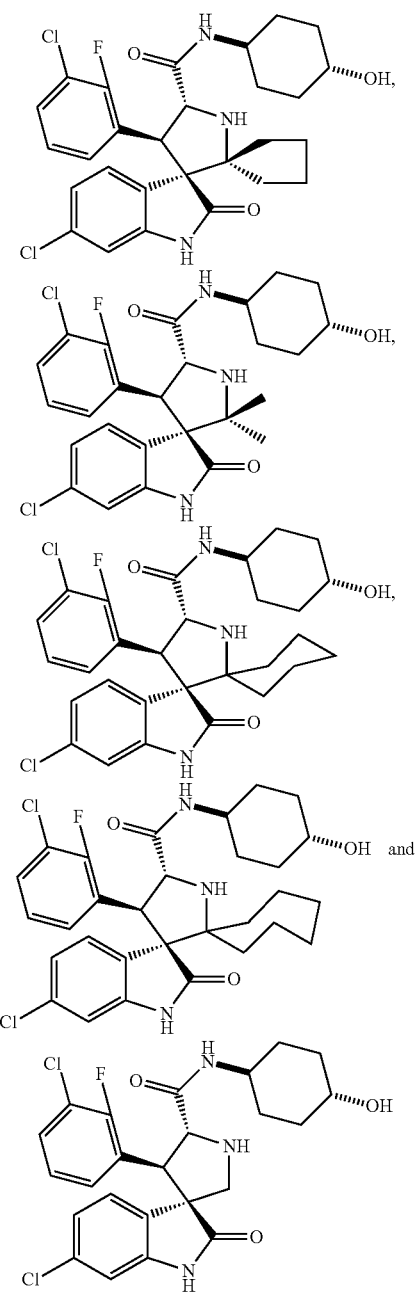

or a pharmaceutically acceptable salt, solvate, or prodrug thereof.

XIV. A pharmaceutical composition comprising the compound of any one of particular embodiments I-VIII, or a pharmaceutically acceptable salt, solvate, or prodrug thereof, and a pharmaceutically acceptable carrier.

XV. A method of treating a patient comprising administering to the patient a therapeutically effective amount of the compound of any one of particular embodiments I-VIII, or a pharmaceutically acceptable salt, solvate, or prodrug thereof, wherein the patient has a hyperproliferative disease.

XVI. A method of treating a patient comprising administering to the patient a therapeutically effective amount of the pharmaceutical composition of particular embodiment XIV, wherein the patient has a hyperproliferative disease.

XVII. The method of particular embodiments XV or XVI, wherein the hyperproliferative disease is cancer.

XVIII. The method of particular embodiments XV or XVI, wherein cells of the hyperproliferative disease express functional p53.

XIX. The method of particular embodiment XVII, further comprising administering to the patient one or more anticancer agents.

XX. The method of particular embodiment XIX, wherein the anticancer agent is a chemotherapeutic agent.

XXI. The method of particular embodiment XIX, wherein the anticancer agent is radiation therapy.

XXII. A method of treating a patient, wherein the patient has a hyperproliferative disorder and is being treated with an anticancer agent, comprising administering to the patient a compound of any one of particular embodiments I-XIII, or a pharmaceutically acceptable salt, solvate, or prodrug thereof.

XXIII. The method of particular embodiment XXII, wherein the patient is experiencing side-effects of the anticancer agent treatment selected from the group consisting of mucositis, stomatitis, xerostoma, alopecia, and gastrointestinal disorder.

XXIV. The method of particular embodiment XXII, wherein cells of the hyperproliferative disorder express functional p53.

XXV. A kit comprising a compound of any one of particular embodiments I-XIII, or a pharmaceutically acceptable salt, solvate, or prodrug thereof, and instructions for administering the compound to a patient having a hyperproliferative disease.

XXVI. The kit of particular embodiment XXV, wherein the hyperproliferative disease is cancer.

XXVII. The kit of particular embodiment XXVI, further comprising one or more anticancer agents.

XXVIII. The kit of particular embodiment XXVII, wherein the instructions direct co-administration of the compound together with the one or more anticancer agents.

XXIX. A compound having Formula I:

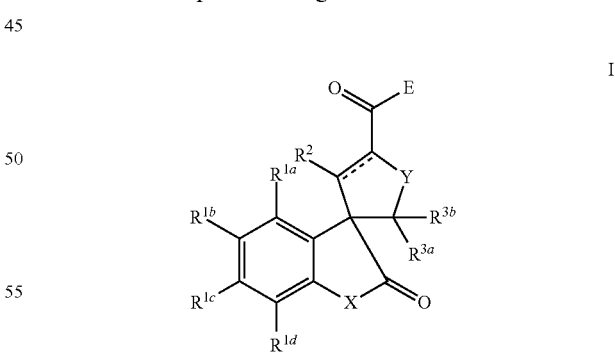

wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl and optionally substituted heteroaryl;

$R^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^{3a}$ is selected from the group consisting of halo, optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl; or $R^{3a}$ and $R^{3b}$ taken together form a 3- to 9-membered optionally substituted cycloalkyl or a 3- to 9-membered optionally substituted heterocyclo;

E is selected from the group consisting of —$OR^{26a}$ and —$NR^{26b}R^{26c}$;

$R^{26a}$ is selected from the group consisting of hydrogen, optionally substituted alkyl, optionally substituted cycloalkyl, and optionally substituted aryl;

$R^{26b}$ is selected from the group consisting of hydrogen and optionally substituted $C_1$-$C_6$ alkyl;

$R^{26c}$ is selected from the group consisting of hydrogen, optionally substituted alkyl, optionally substituted cycloalkyl, optionally substituted heterocyclo, optionally substituted aryl, optionally substituted heteroaryl, aralkyl, and —$SO_2R^{5b}$; or $R^{26b}$ and $R^{26c}$ taken together form a 4- to 9-membered optionally substituted heterocyclo;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, and optionally substituted cycloalkyl; and ⚌ represents a single or a double bond, or a pharmaceutically acceptable salt thereof.

XXX. The compound of particular embodiment XXIX having Formula III:

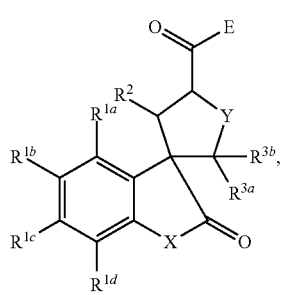

or a pharmaceutically acceptable salt thereof.

XXXI. The compound of particular embodiment XXX having Formula VI:

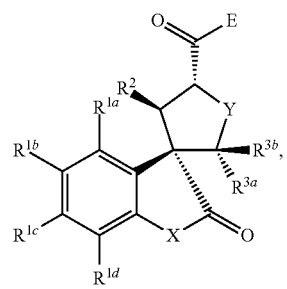

or a pharmaceutically acceptable salt thereof.

XXXII. The compound of particular embodiment XXX having Formula XVI:

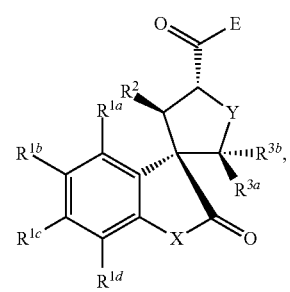

or a pharmaceutically acceptable salt thereof.

XXXIII. The compound of any one of particular embodiments XXIX-XXXII, wherein:
E is —$NR^{26b}R^{26c}$;
$R^2$ is optionally substituted aryl;
$R^{3a}$ is halo or $C_1$-$C_{10}$ alkyl;
$R^{3b}$ is halo or $C_1$-$C_{10}$ alkyl; or
$R^{3a}$ and $R^{3b}$ taken together form a 3- to 9-membered optionally substituted cycloalkyl or a 3- to 9-membered optionally substituted heterocyclo;
$R^{26b}$ is hydrogen; and
X and Y are NH,
or a pharmaceutically acceptable salt thereof.

XXXIV. The compound of any one of particular embodiments XXIX-XXXIII, wherein $R^{3a}$ and $R^{3b}$ are each independently $C_1$-$C_{10}$ alkyl.

XXXV. The compound of any one of particular embodiments XXIX-XXXIII, wherein $R^{3a}$ and $R^{3b}$ taken together form a 4- to 8-membered optionally substituted cycloalkyl or a 4- to 8-membered optionally substituted heterocyclo, or a pharmaceutically acceptable salt thereof.

XXXVI. The compound of particular embodiment XXXV, wherein $R^{3a}$ and $R^{3b}$ taken together form a 6-membered optionally substituted heterocyclo, or a pharmaceutically acceptable salt thereof.

XXXVII. The compound of particular embodiment XXXVI, wherein $R^{3a}$ and $R^{3b}$ taken together form an optionally substituted piperidine or a tetrahydropyran.

XXXVIII. The compound of particular embodiment XXXV, wherein $R^{3a}$ and $R^{3b}$ taken together form a 4- to 8-membered optionally substituted cycloalkyl, or a pharmaceutically acceptable salt thereof.

XXXIX. The compound of particular embodiment XXX-VIII, wherein $R^{3a}$ and $R^{3b}$ are taken together to form an unsubstituted cyclobutyl, cyclopentyl, cyclohexyl, or cycloheptyl ring, or a pharmaceutically acceptable salt thereof.

XL. The compound of any one of particular embodiments XXIX-XXXIX, wherein:

$R^{1a}$ and $R^{1d}$ are each hydrogen;

$R^{1b}$ is selected from the group consisting of hydrogen and fluoro; and $R^{1c}$ is selected from the group consisting of fluoro and chloro;

or a pharmaceutically acceptable salt thereof.

XLI. The compound of any one of particular embodiments XXIX-XL, wherein $R^2$ is optionally substituted aryl having Formula R2-1:

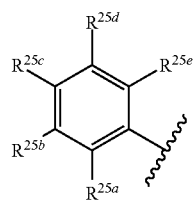

R2-1 wherein $R^{25a}$, $R^{25b}$, $R^{25c}$, $R^{25d}$, and $R^{25e}$ are each independently selected from the group consisting of hydrogen, halogen, hydroxy, nitro, amino, cyano, alkoxy, alkyl, or haloalkyl, or a pharmaceutically acceptable salt thereof.

XLII. The compound of any one of particular embodiments XXIX-XL, wherein $R^2$ is optionally substituted pyridyl, or a pharmaceutically acceptable salt thereof.

XLIII. The compound of particular embodiment XXIX having Formula XXVI

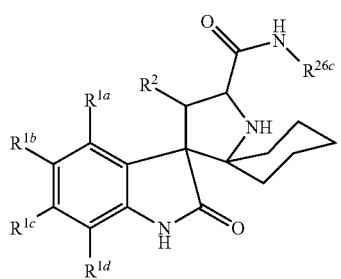

XXVI or a pharmaceutically acceptable salt thereof.

XLIV. The compound of particular embodiment XLIII having Formula XXVII:

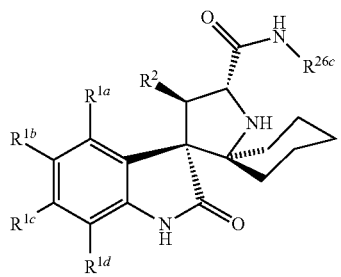

XXVII or a pharmaceutically acceptable salt thereof.

XLV. The compound of particular embodiment XLIII having Formula XXVIII:

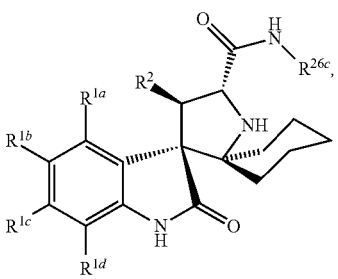

XXVIII or a pharmaceutically acceptable salt thereof.

XLVI. The compound of any one of particular embodiments XXIX-XLV, wherein $R^{26c}$ is optionally substituted alkyl, or a pharmaceutically acceptable salt thereof.

XLVII. The compound of particular embodiment XLVI, wherein the optionally substituted alkyl is substituted with an optionally substituted cycloalkyl, or a pharmaceutically acceptable salt thereof.

XLVIII. The compound of particular embodiment XLVI, wherein the optionally substituted alkyl is substituted with an optionally substituted heteroaryl, or a pharmaceutically acceptable salt thereof.

XLIX. The compound of any one of claims XXIX-XLV, wherein $R^{26c}$ is aralkyl, or a pharmaceutically acceptable salt thereof.

L. The compound of any one of particular embodiments XXIX-XLV, wherein $R^{26c}$ is optionally substituted cycloalkyl, or a pharmaceutically acceptable salt thereof.

LI. The compound particular embodiment L, wherein $R^{26c}$ is hydroxycycloalkyl, or a pharmaceutically acceptable salt thereof.

LII. The compound of particular embodiment L, wherein the optionally substituted cycloalkyl is substituted with at least one —$CO_2H$, or a pharmaceutically acceptable salt thereof.

LIII. The compound of particular embodiment L, wherein $R^{26c}$ is selected from the group consisting of:

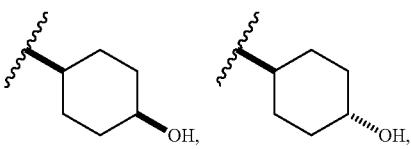

-continued

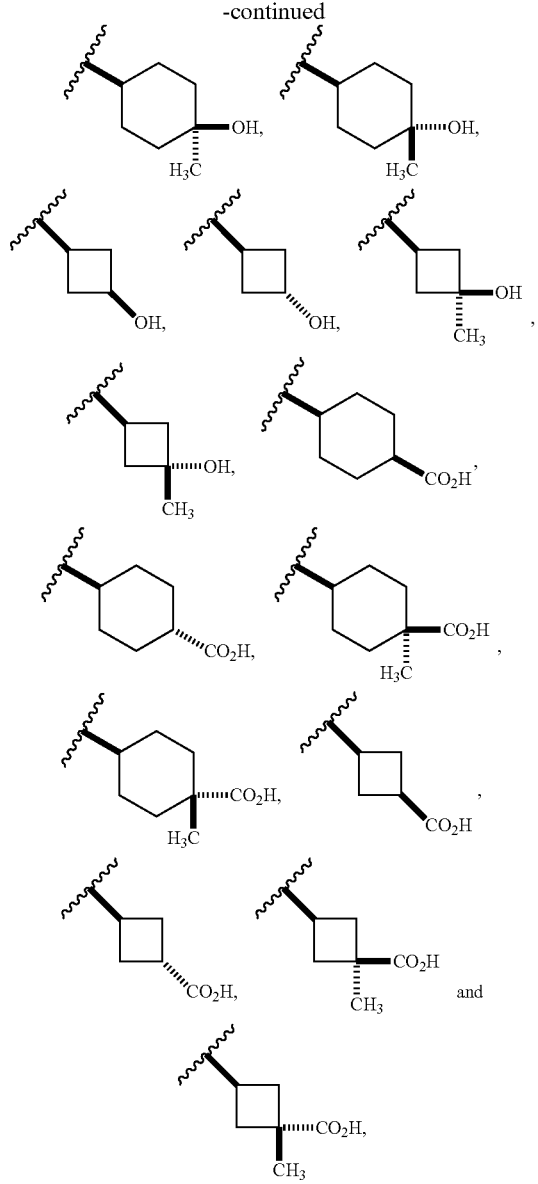

or a pharmaceutically acceptable salt thereof.

LIV. The compound of any one of particular embodiment XXIX-XLV, wherein $R^{26c}$ is optionally substituted heterocyclo, or a pharmaceutically acceptable salt thereof.

LV. The compound of any one of particular embodiment XXIX-XLV, wherein $R^{26c}$ is optionally substituted aryl, or a pharmaceutically acceptable salt thereof.

LVI. The compound of particular embodiment LV, wherein $R^{26c}$ is optionally substituted phenyl, or a pharmaceutically acceptable salt thereof.

LVII. The compound of particular embodiment LVI, wherein the optionally substituted phenyl is substituted with at least one —$CO_2H$, or a pharmaceutically acceptable salt thereof.

LVIII. The compound of any one of particular embodiments XXIX-XLV, wherein $R^{26c}$ is optionally substituted heteroaryl, or a pharmaceutically acceptable salt thereof.

LIX. The compound of particular embodiment LVIII, wherein $R^{26c}$ is optionally substituted pyridyl, or a pharmaceutically acceptable salt thereof.

LX. A compound selected from the group consisting of:

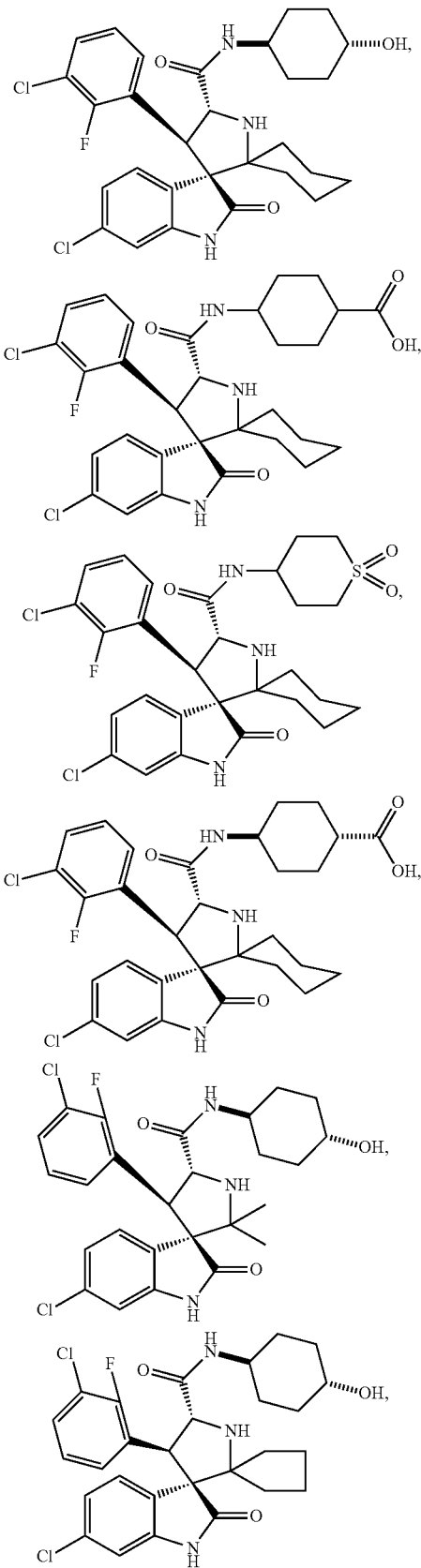

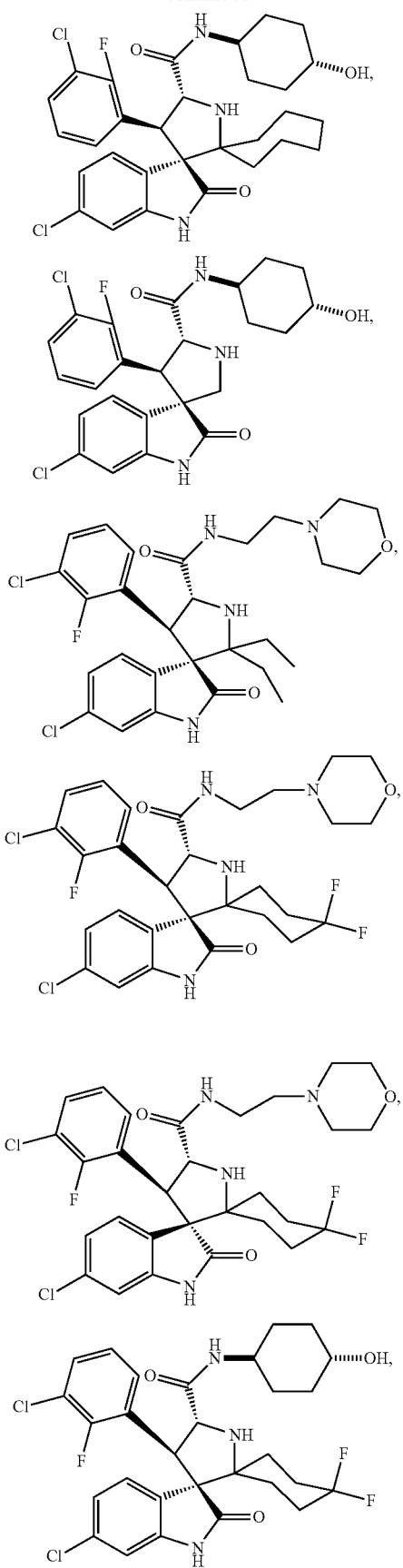
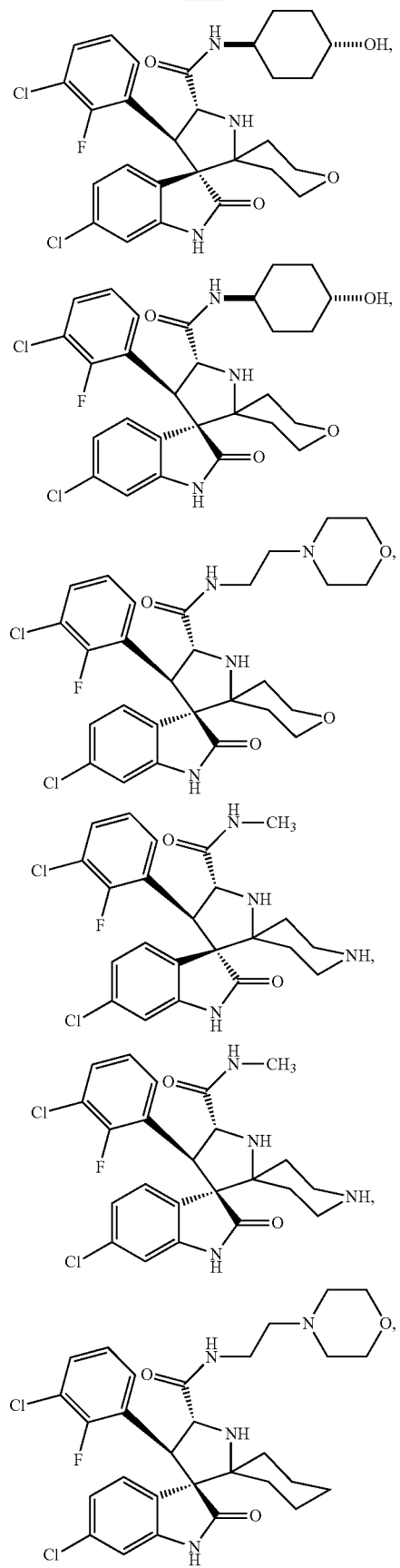

101
-continued
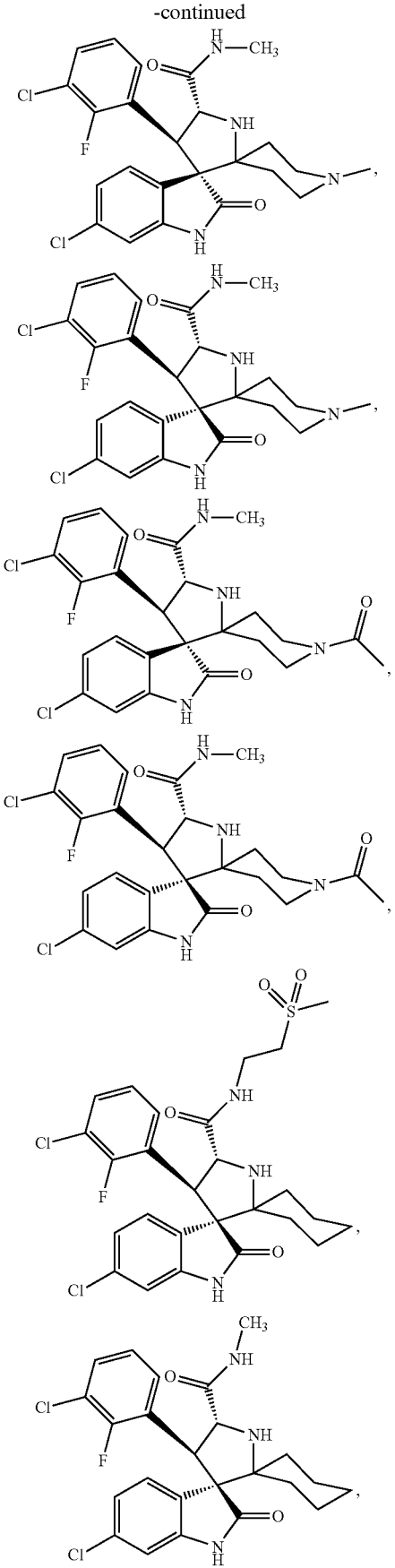
102
-continued
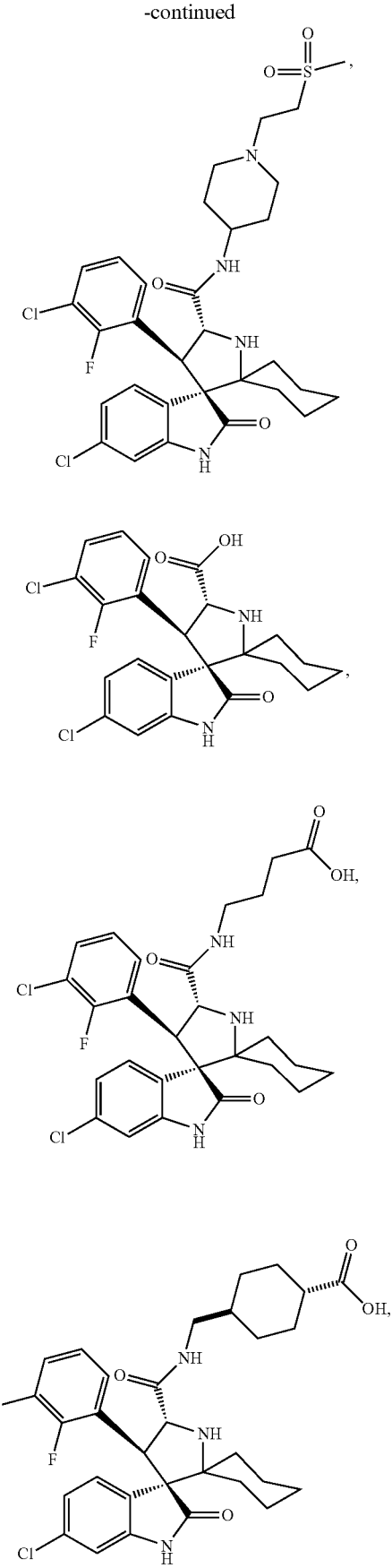

103
-continued
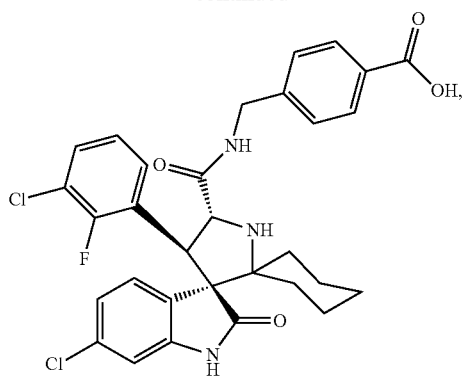
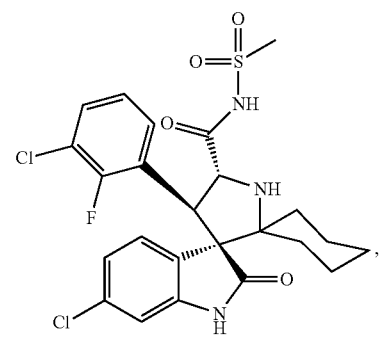
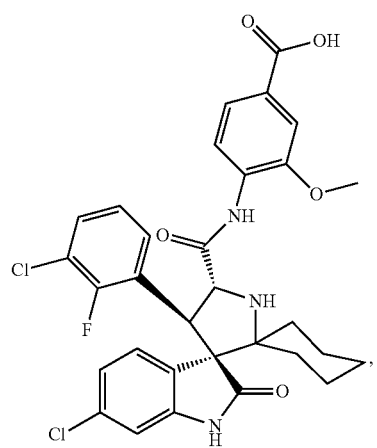
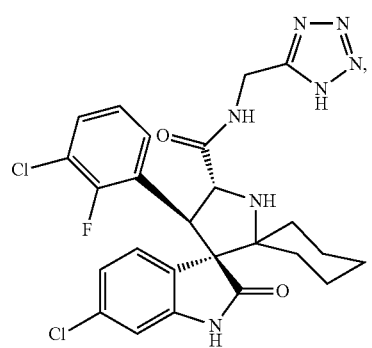
104
-continued
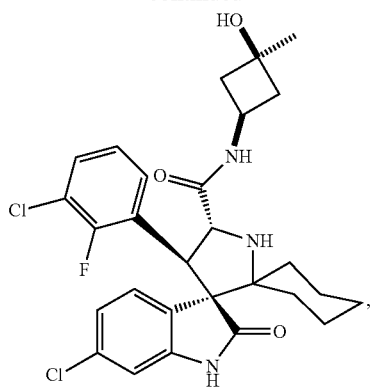
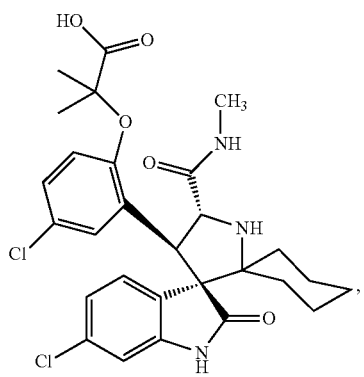
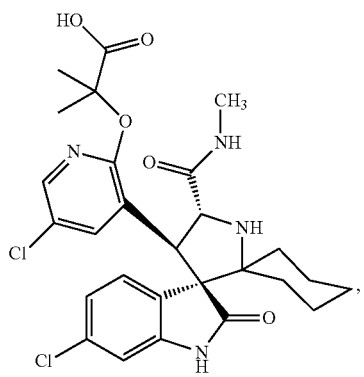
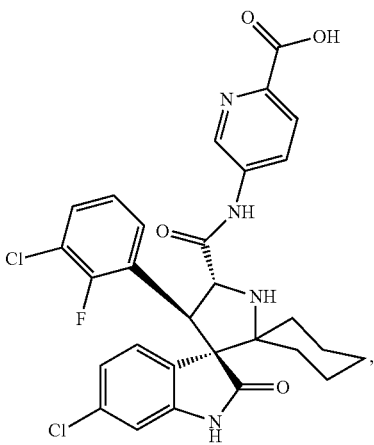

-continued
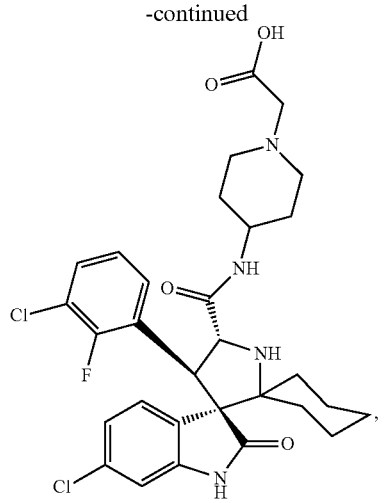
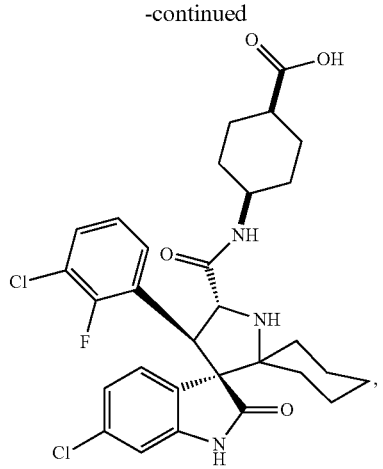
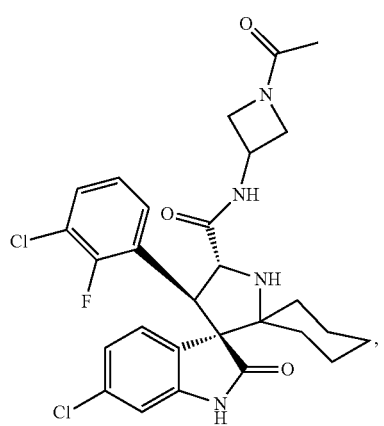
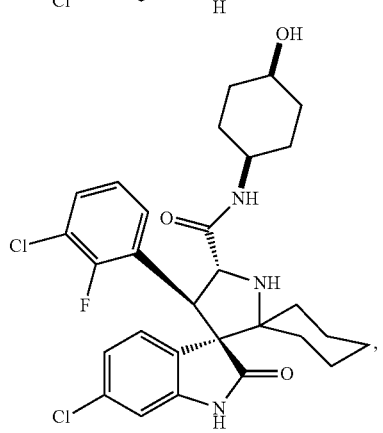
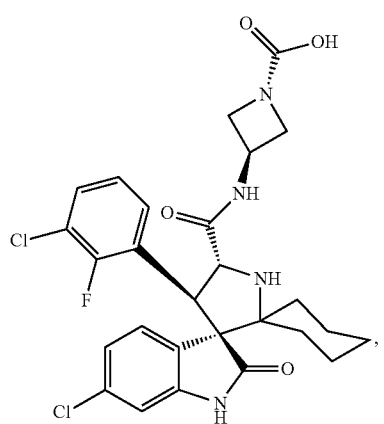
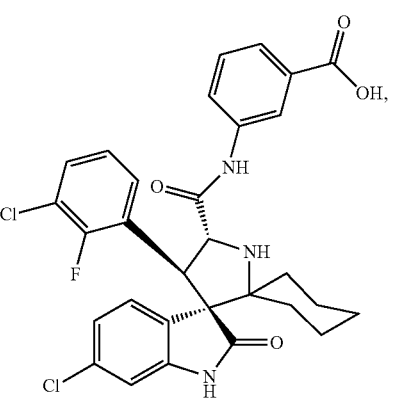

107
-continued
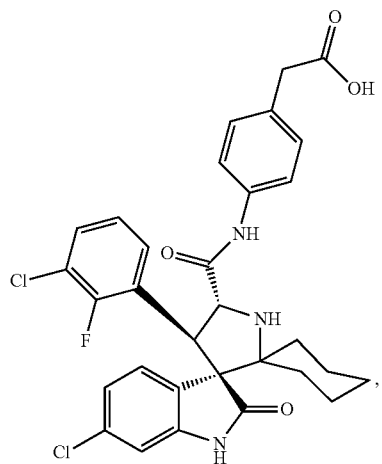
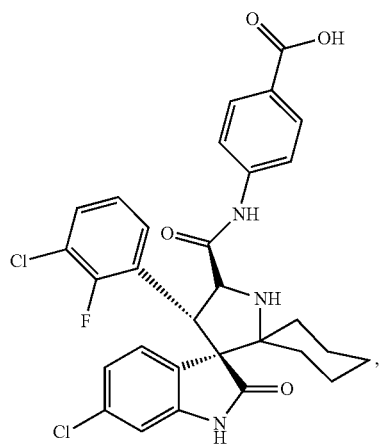
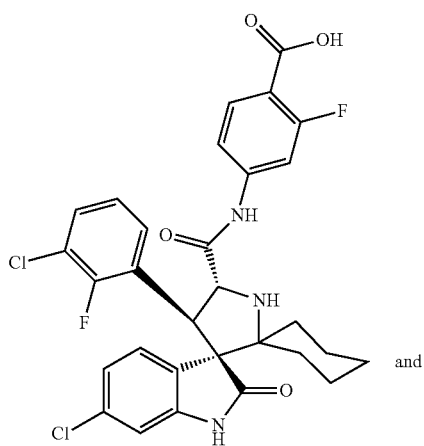
and
108
-continued
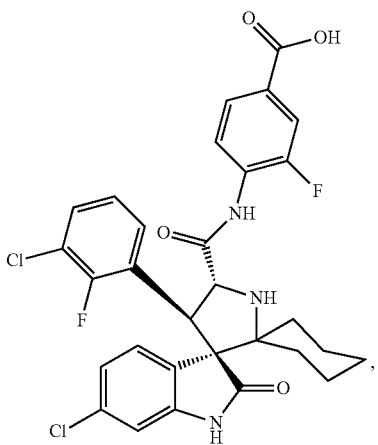
or a pharmaceutically acceptable salt thereof.
LXI. A compound selected from the group consisting of:
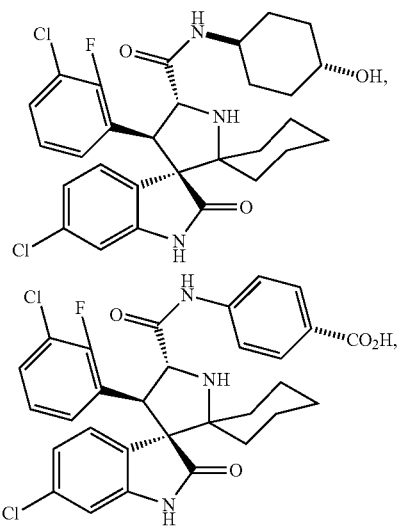
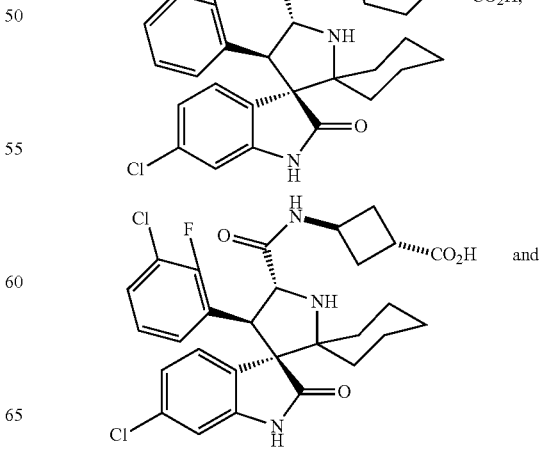
and -continued

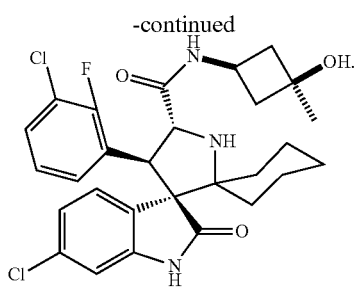

or a pharmaceutically acceptable salt thereof.

LXII. The compound of particular embodiment XXIX, wherein E is —OR$^{26a}$, or a pharmaceutically acceptable salt thereof.

LXIII. The compound of particular embodiment LXII, wherein R$^{26a}$ is hydrogen, or a pharmaceutically acceptable salt thereof.

LXIV. A pharmaceutical composition comprising the compound of any one of particular embodiments XXIX-LXI, or a pharmaceutically acceptable salt thereof, and a pharmaceutically acceptable carrier.

LXV. A method of treating a patient comprising administering to the patient a therapeutically effective amount of the compound of any one of particular embodiments XXIX-LXI, or a pharmaceutically acceptable salt thereof, wherein the patient has a hyperproliferative disease.

LXVI. The method of particular embodiment LXV, wherein the hyperproliferative disease is cancer.

LXVII. The method of particular embodiment LXVI, wherein the cancer is selected from the group consisting of melanoma, lung cancer, sarcoma, colon cancer, prostate cancer, choriocarcinoma, breast cancer, retinoblastoma, stomach carcinoma, acute myeloid leukemia, lymphoma, multiple myeloma, and leukemia.

LXVIII. The method of particular embodiment LXVII, wherein the cancer is selected from the group consisting of liposarcoma and melanoma.

LXIX. A kit comprising a compound of any one of particular embodiments XXIX-LXI, or a pharmaceutically acceptable salt, thereof, and instructions for administering the compound to a patient having a hyperproliferative disease.

LXX. The kit of particular embodiment LXIX, wherein the hyperproliferative disease is cancer.

LXXI. A method of preparing a compound having Formula XVI:

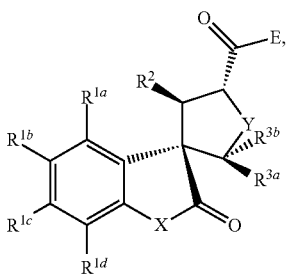

XVI comprising:
a) allowing a compound of particular embodiment XXXI to isomerize; and
b) isolating the compound having Formula XVI substantially free from the compound of claim 3, wherein X and Y are NH.

LXXII. The method of particular embodiment LXXI, wherein E is —OR$^{26a}$.

LXXIII. The method of particular embodiment LXXI, wherein E is —NR$^{26b}$R$^{26c}$.

LXXIV. The method of any one of particular embodiments LXXI-LXXIII, wherein R$^{3a}$ and R$^{3b}$ taken together form a 3- to 9-membered optionally substituted cycloalkyl.

The compounds provided herein will be better understood in connection with the following synthetic schemes which illustrate the methods by which the compounds provided herein may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reagents and agents in the syntheses shown below.

Compounds of Formula III wherein Y is NH and E is —NR$^{26c}$R$^{26c}$ can be synthesized as described in Schemes 2 and 3.

Scheme 2

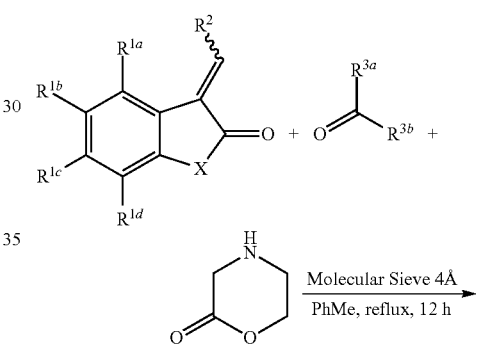

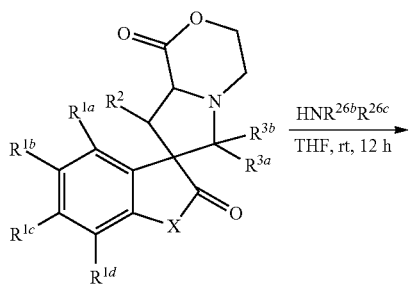

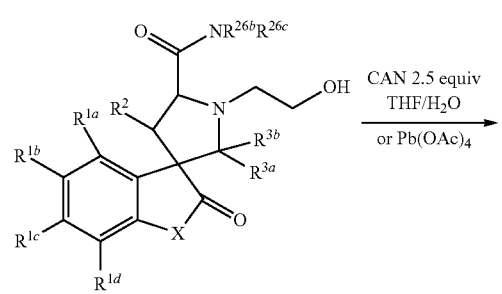

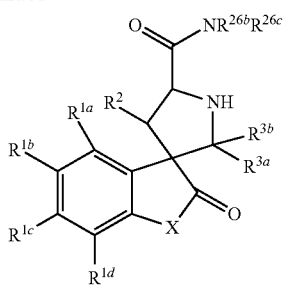

Formula III
(wherein Y is NH and E is NR$^{26b}$R$^{26c}$)

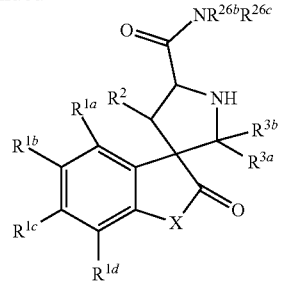

Formula III
(wherein Y is NH and E is NR$^{26b}$R$^{26c}$)

R = hydrogen, p-OMeBn———, Bn———, Me———
or other alkyl group

Compounds of Formula III can be separated by chiral resolution methods well known in the art, e.g., chiral column chromatography, to give compounds of Formulae VI-XXI. Suitable chiral columns for use in chiral resolutions include, for example, Daicel CHIRALCEL® OD-H, Daicel CHIRAKPAK® AD-H and Regis Technologies ULMO chiral columns. Other chiral resolution methods are also possible. Compounds of Formulae VI-XXI can also be prepared by asymmetric synthetic methods. For example, compounds of Formula VI, wherein Y is NH and E is NR$^{26b}$R$^{26c}$, can be synthesized by using a asymmetric 1,3-dipolar cycloaddition as the key step as previously described (See U.S. Pat. Nos. 7,759,383 B2 and 7,737,174 B2, and Ding et al., *J. Am. Chem. Soc.* 127:10130-10131 (2005)). Compounds of Formula VI can undergo isomerization in solution to give compounds of Formula XVI.

Scheme 3

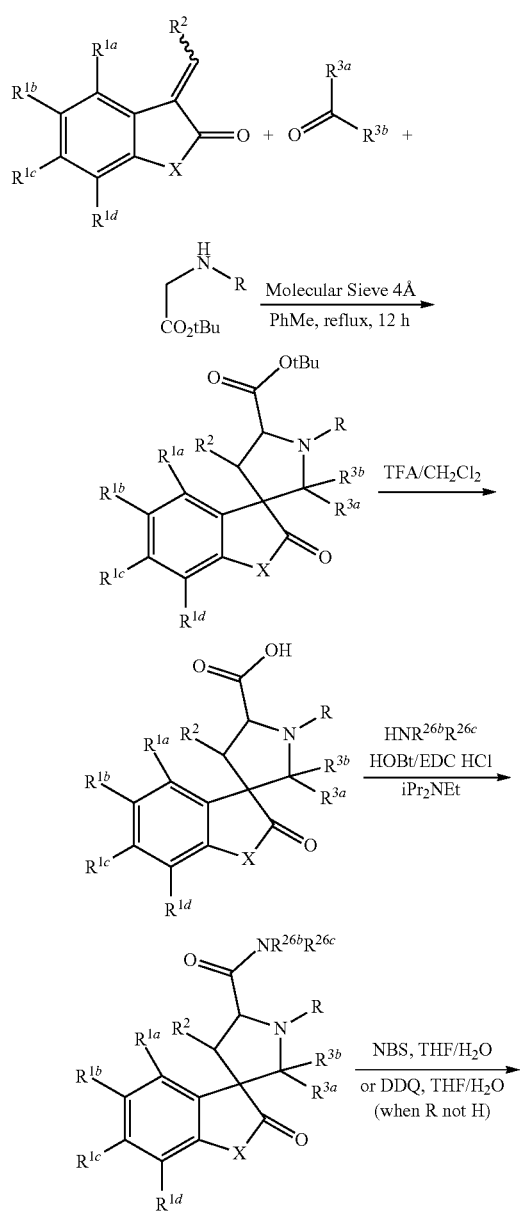

Scheme 4

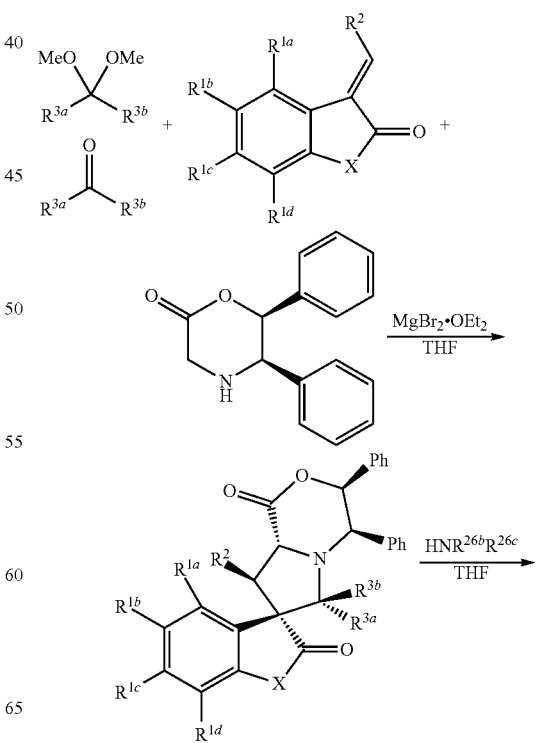

-continued

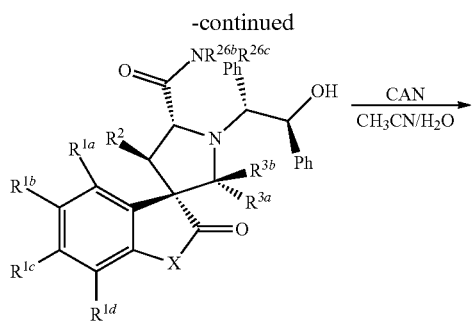

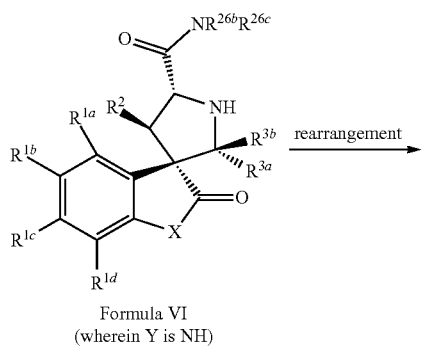

Formula VI
(wherein Y is NH)

-continued

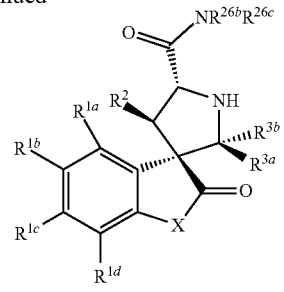

Formula XVI
(wherein Y is NH)

Without intending to be bound by theory, the isomerization of Formula VI to Formula XVI may involve formation of the imine intermediate shown in Scheme 5. Compounds of Formula XVI may be less likely to isomerize, i.e., they may be chemically more stable, than compounds of Formula VI. In addition, isolation and purification of compounds of Formula XVI may be improved when $R^{3a}$ and $R^{3a}$ are the same, e.g., $R^{3a}$ and $R^{3b}$ are methyl, $R^{3a}$ and $R^{3b}$ taken together form a cyclohexyl ring, because the 2' position of the pyrrolidine ring is not an asymmetric center, and the number of possible isomerization products of Formula VI is reduced. General methods to prepare compounds provided in the present disclosure are shown in Schemes 4-8.

Scheme 5

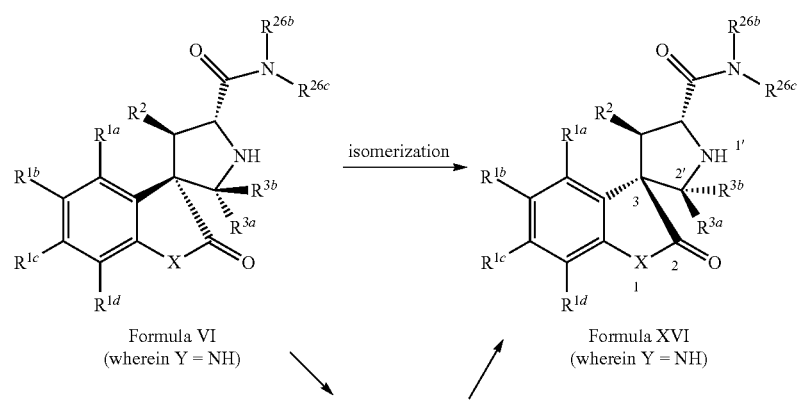

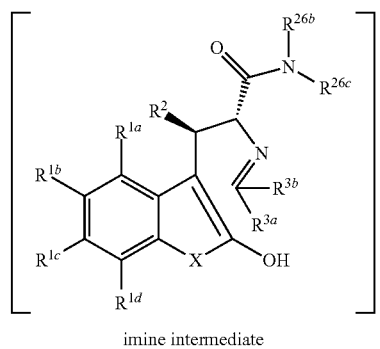

imine intermediate

Scheme 6
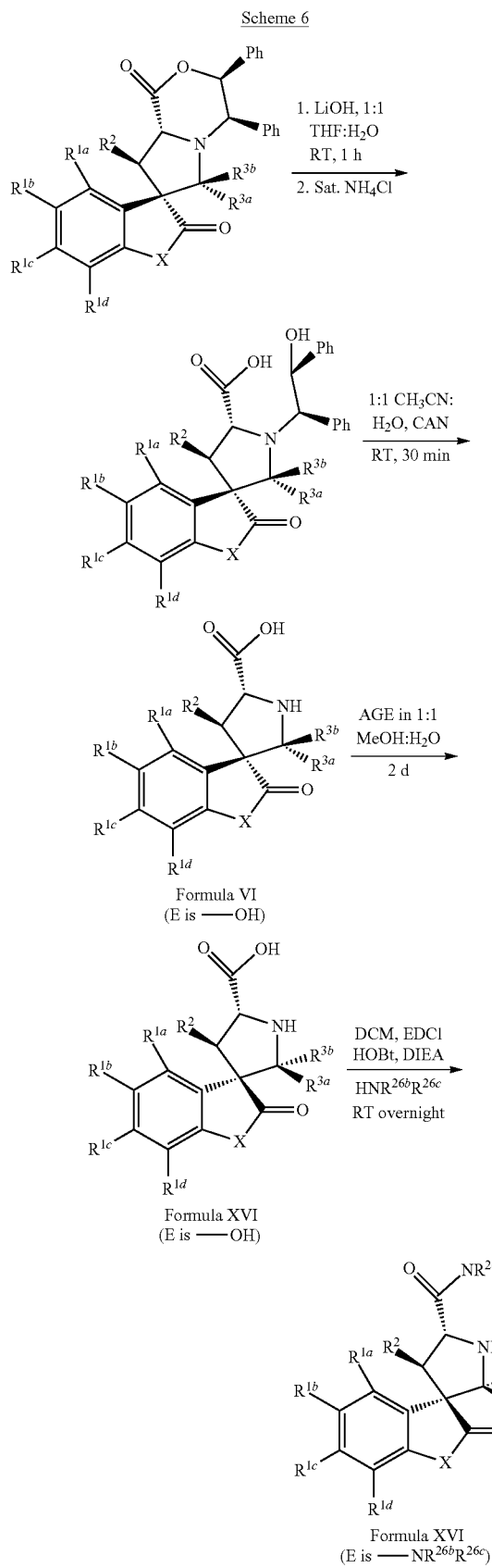
Scheme 7
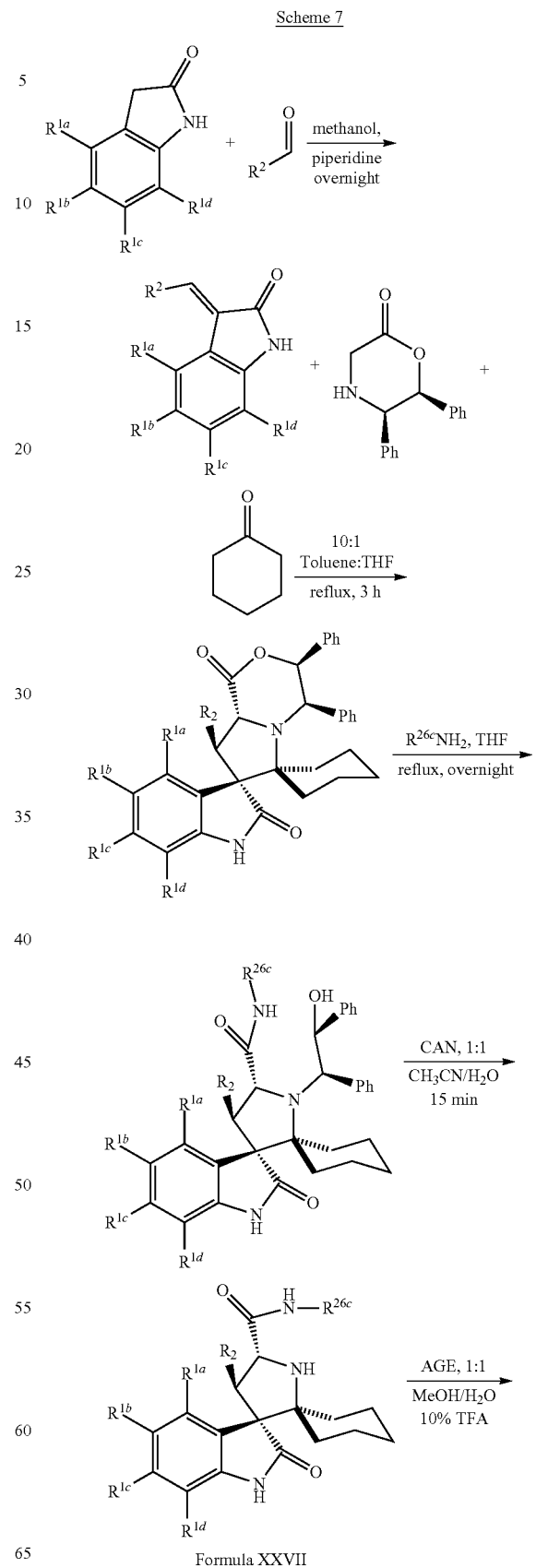

-continued

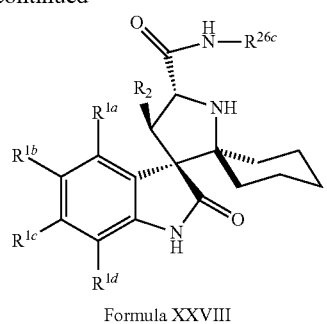

Formula XXVIII

-continued

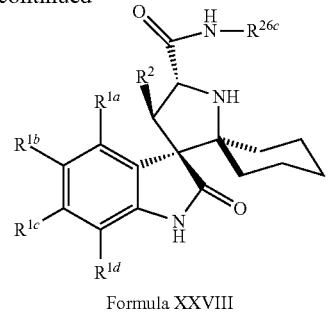

Formula XXVIII

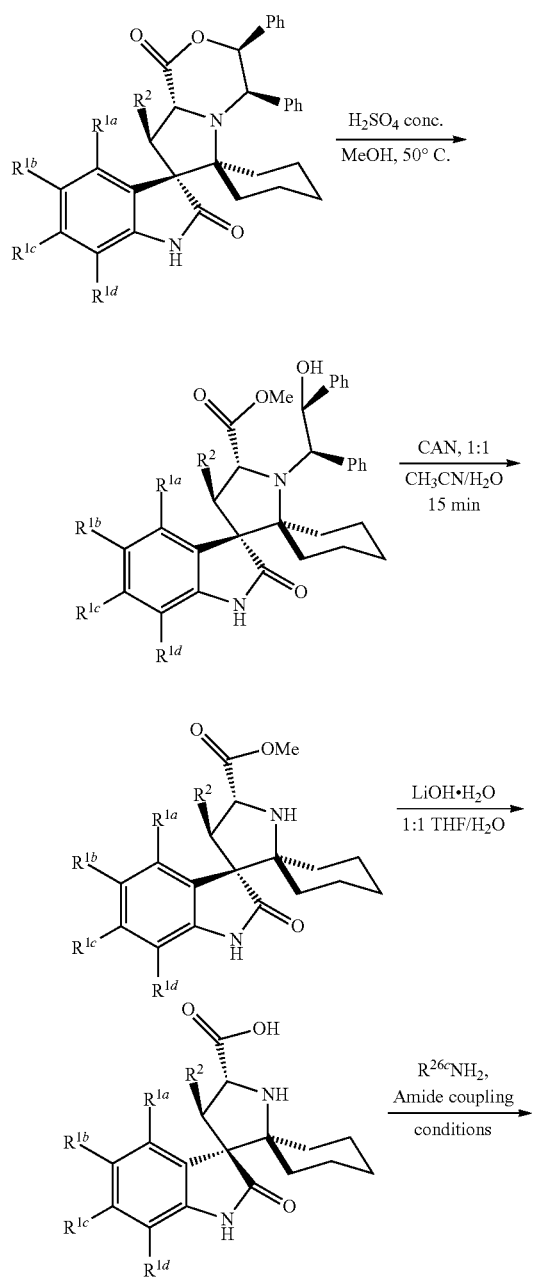

Scheme 8

Methods

The present disclosure contemplates that exposure of animals suffering from cancer to therapeutically effective amounts of drug(s) (e.g., small molecules) that increase the function(s) of p53 and p53-related proteins (e.g., p63, p'73) inhibits the growth of cancer cells or supporting cells. The compounds provided herein inhibit the interaction between p53 or p53-related proteins and MDM2 or MDM2-related proteins (e.g., MDMX). Inhibiting the interaction between p53 or p53-related proteins and MDM2 or MDM2-related proteins inhibits the growth of cancer cells or supporting cells and/or renders such cells as a population more susceptible to the cell death-inducing activity of cancer therapeutic drugs or radiation therapies. In one embodiment, the inhibitors provided herein prolong the half-life of p53 by interfering with the p53-MDM2 interaction that would normally promote degradation of p53. The compounds provided herein satisfy an unmet need for the treatment of multiple cancer types, either when administered as monotherapy to induce senescence, cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In one embodiment, treatment of patients with a therapeutically effective amount of one or more compounds having Formulae I-XXVIII and one or more anticancer agents produces a greater anti-tumor activity and clinical benefit in such patients compared to those treated with the compound or anticancer drugs/radiation alone. Put another way, because the compounds provided herein can lower the apoptotic threshold of cells that express p53 or p53-related protein, the proportion of cells that successfully execute the apoptosis program in response to the apoptosis inducing activity of anticancer drugs/radiation will be increased when used in combination with one or more of the compounds provided herein. Alternatively, compounds having Formulae I-XXVIII can be used to allow administration of a lower, and therefore less toxic and more tolerable, dose of an anticancer drug and/or radiation to produce the same tumor response/clinical benefit as the conventional dose of the anticancer drug/radiation alone. Since the doses for approved anticancer drugs and radiation treatments are known, the compounds, compositions, and methods provided herein can be used with one or more approved anticancer drugs and/or radiation treatment. Also, since compounds having Formulae I-XXVIII may act, at least in part, by stimulating the pro-apoptotic and/or cell cycle-inhibiting activities of p53 and p53-related proteins, the exposure of cancer cells and supporting cells to therapeutically effective amounts of these compounds can be temporally linked to coincide with the attempts of cells to execute the apoptosis program in response to the anticancer drug or radiation therapy. Thus, in one embodiment, administering the compounds or pharmaceutical compositions provided herein in combination with other known anticancer drugs provides especially efficacious therapeutic practices.

In one embodiment, the inhibitors of the interaction between p53 or p53-related proteins and MDM2 and MDM2-related proteins having Formulae I-XXVIII may protect normal (e.g., non-hyperproliferative) cells from the toxic effects of certain chemotherapeutic agents and radiation, possibly through the ability of the inhibitors to induce cell cycle arrest of normal cells. For example, the inhibitors provided herein may cause cell cycle arrest in cells comprising wild-type or functional p53 (and/or wild-type or functional p53-related proteins) while having no or less effect on cancer cells comprising mutated, deleted, or otherwise non- or less functional p53 (and/or mutated, deleted, or otherwise non- or less functional p53-related proteins). This differential protective effect may allow for more effective treatment of cancer by allowing the use of higher doses or longer treatments of chemotherapeutic agents or treatments without increasing the toxic side effects of such treatment when administered in combination with inhibitors provided herein.

Also provided herein are methods of using compounds having Formulae I-XXVIII for sensitizing cells to additional agent(s), such as inducers of senescence, apoptosis and/or cell cycle arrest. Compounds having Formulae I-XXVIII can also be used to provide chemoprotection of normal cells through the induction of cell cycle arrest prior to treatment with chemotherapeutic agents. In one embodiment, methods of rendering a normal cell resistant to chemotherapeutic agents or treatments comprises contacting the cell with one or more compounds having Formulae I-XXVIII are provided. In another embodiment, methods of protecting normal cells in an animal having a hyperproliferative disease from the toxic side effects of chemotherapeutic agents or treatments, comprises administering to the animal a compound having Formulae I-XXVIII are provided. Also provided herein are methods for the treatment, amelioration, or prevention of disorders, side effects, or conditions caused by the administration of chemotherapeutic agents to normal cells comprising administering to an animal undergoing chemotherapy a compound having Formulae I-XXVIII. Examples of such disorders and conditions caused by chemotherapy include, without limitation, mucositis, stomatitis, xerostomia, gastrointestinal disorders, and alopecia.

Compounds having Formulae I-XXVIII are useful for the treatment, amelioration, or prevention of disorders, such as those responsive to induction of apoptotic cell death, e.g., disorders characterized by dysregulation of apoptosis, including hyperproliferative diseases such as cancer. In one embodiment, these compounds can be used to treat, ameliorate, or prevent cancer that is characterized by resistance to cancer therapies (e.g., those cancer cells which are chemoresistant, radiation resistant, hormone resistant, and the like). In another embodiment, these compounds can be used to treat hyperproliferative diseases characterized by expression of functional p53 or p53-related proteins. In another embodiment, these compounds can be used to protect normal (e.g., non-hyperproliferative) cells from the toxic side effects of chemotherapeutic agents and treatments by the induction of cell cycle arrest in those cells.

In one embodiment, compounds having Formulae I-XXVIII induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. By inhibiting the interaction between p53 or p53-related proteins and MDM2 or MDM2-related proteins, these compounds can be used to induce apoptosis in any disorder that can be treated, ameliorated, or prevented by the induction of apoptosis. In one embodiment, compounds having Formulae I-XXVIII can be used to induce apoptosis in cells comprising functional p53 or p53-related proteins.

In another embodiment, the disclosure pertains to modulating apoptosis with compounds having Formulae I-XXVIII in combination with one or more additional apoptosis-modulating agents, e.g., anticancer agents. Examples of apoptosis-modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Akt, CAD, PI3 kinase, PP1, and caspase proteins. Other agents involved in the initiation, decision and degradation phase of apoptosis are also included. Examples of apoptosis-modulating agents include agents, the activity, presence, or change in concentration of which, can modulate apoptosis in a subject. Apoptosis-modulating agents include those which are inducers of apoptosis, such as TNF or a TNF-related ligand, particularly a TRAMP ligand, a Fas/CD95 ligand, a TNFR-1 ligand, or TRAIL.

In one embodiment, the compounds, compositions, and methods provided herein are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia (CLL) including B-CLL, acute myelogenous leukemia, chronic myelogenous leukemia, chronic granulocytic leukemia, acute granulocytic leukemia, hairy cell leukemia, neuroblastoma, sarcoma such as liposarcoma malignant fibrous histiocytoma, osteosarcoma, Ewing's sarcoma, leiomyosarcoma, and rhabdomyosarcoma, Kaposi's sarcoma, polycythemia vera, essential thrombocytosis, Hodgkin's disease, non-Hodgkin's lymphoma, soft-tissue sarcomas such as lipoma, and malignant Schwannoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In one embodiment, the cancer cells being treated are metastatic. In another embodiment, the cancer cells being treated are resistant to other anticancer agents.

In one embodiment, the compounds, compositions, and methods provided herein are used to treat cancers that express functional or wild type p53 or p53-related proteins. In one embodiment, the compounds, compositions, and methods provided herein are used to treat cancers that express elevated levels of MDM2 or MDM2-related proteins.

In one embodiment, the compounds, compositions, and methods provided herein can be used to treat a patient having a sarcoma, including, for example, liposarcoma, malignant fibrous histiocytoma, osteosarcoma, and rhabdomyosarcoma. In another embodiment, the compounds, compositions, and methods provided herein can be used to treat a patient having a soft tissue tumor, including, for example, Ewing's sarcoma, leiomyosarcoma, lipoma, and malignant Schwannomas. In another embodiment, the compounds, compositions, and methods provided herein can be used to treat a patient having lung, breast, liver, or colon cancer. In another embodiment, the compounds, compositions, and methods provided herein can be used to treat a patient having B-cell chronic lymphocytic leukemia and acute myeloid leukemia.

In one embodiment, the compounds, compositions, and methods provided here can be used to treat a patient having melanoma, lung cancer, sarcoma, colon cancer, prostate cancer, choriocarcinoma, breast cancer, retinoblastoma, stomach carcinoma, acute myeloid leukemia, lymphoma, multiple myeloma, or leukemia.

In one embodiment, the compounds, compositions, and methods provided here can be used to treat a patient having liposarcoma or melanoma.

In one embodiment, infections suitable for treatment with the compounds, compositions, and methods provided herein include, but are not limited to, infections caused by viruses, bacteria, fungi, mycoplasma, prions, and the like.

A further aspect of the present disclosure is to provide the use of a compound having any one of Formulae I-XXVIII for the manufacture of a medicament for treating a hyperproliferative disease such as cancer. In one embodiment, the medicament is to be administered with one or more additional agents.

A further aspect of the present disclosure is to provide a compound having any one of Formulae I-XXVIII, or a pharmaceutical composition comprising a compound having any one of Formulae I-XXVIII, for use in treating a hyperproliferative disease such as cancer.

In one embodiment, methods are provided for administering an effective amount of a compound having Formulae I-XXVIII in combination with at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In one embodiment, the additional therapeutic agent(s) is an anticancer agent.

A number of suitable therapeutic or anticancer agents are contemplated for use in the methods provided herein. Indeed, the methods provided herein can include but are not limited to, administration of numerous therapeutic agents such as: agents that induce apoptosis; polynucleotides (e.g., antisense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of therapeutic agents such as chemotherapeutic compounds and anticancer therapies suitable for co-administration with the disclosed compounds are known to those skilled in the art.

In one embodiment, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In one embodiment, the compositions and methods provided herein include one or more compounds provided herein and at least one anti-hyperproliferative or anticancer agent, e.g., alkylating agents, anti metabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethyleniminies and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In one embodiment, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In one embodiment, chemotherapeutic agents suitable for use in the present compositions and methods include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any anticancer agent that is routinely used in a cancer therapy context finds use in the compositions and methods of the present disclosure. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | |
|---|---|
| Aldesleukin | Proleukin |
| (des-alanyl-1, serine-125 human interleukin-2) | |
| Alemtuzumab | Campath |
| (IgG1κ anti CD52 antibody) | |
| Alitretinoin | Panretin |
| (9-cis-retinoic acid) | |
| Allopurinol | Zyloprim |
| (1,5-dihydro-4H-pyrazolo[3,4-d]pyrimidin-4-one monosodium salt) | |
| Altretamine | Hexalen |
| (N,N,N',N',N'',N''-hexamethyl-1,3,5-triazine-2,4,6-triamine) | |
| Amifostine | Ethyol |
| (ethanethiol, 2-[(3-aminopropyl)amino]-, dihydrogen phosphate (ester)) | |
| Anastrozole | Arimidex |
| (1,3-Benzenediacetonitrile, a,a,a',a'-tetramethyl-5-(1H-1,2,4-triazol-1-ylmethyl)) | |
| Arsenic trioxide | Trisenox |
| Asparaginase | Elspar |
| (L-asparagine amidohydrolase, type EC-2) | |
| BCG Live | TICE BCG |
| (lyophilized preparation of an attenuated strain of *Mycobacterium bovis* (*Bacillus Calmette-Gukin* [BCG], substrain Montreal) | |
| bexarotene capsules | Targretin |

TABLE 1-continued

| | |
|---|---|
| (4-[1-(5,6,7,8-tetrahydro-3,5,5,8,8-pentamethyl-2-napthalenyl)ethenyl] benzoic acid) | |
| bexarotene gel | Targretin |
| Bleomycin | Blenoxane |
| (cytotoxic glycopeptide antibiotics produced by *Streptomyces verticillus*; bleomycin $A_2$ and bleomycin $B_2$) | |
| Capecitabine | Xeloda |
| (5'-deoxy-5-fluoro-N-[(pentyloxy)carbonyl]-cytidine) | |
| Carboplatin | Paraplatin |
| (platinum, diammine [1,1-cyclobutane-dicarboxylato(2-)-0,0']-, (SP-4-2)) | |
| Carmustine | BCNU, BiCNU |
| (1,3-bis(2-chloroethyl)-1-nitrosourea) | |
| Carmustine with Polifeprosan 20 Implant | Gliadel Wafer |
| Celecoxib | Celebrex |
| (as 4-[5-(4-methylphenyl)-3-(trifluoromethyl)-1H-pyrazol-1-yl] benzenesulfonamide) | |
| Chlorambucil | Leukeran |
| (4-[bis(2chlorethyl)amino]benzenebutanoic acid) | |
| Cisplatin | Platinol |
| ($PtCl_2H_6N_2$) | |
| Cladribine | Leustatin, 2-CdA |
| (2-chloro-2'-deoxy-b-D-adenosine) | |
| Cyclophosphamide | Cytoxan, Neosar |
| (2-[bis(2-chloroethyl)amino]tetrahydro-2H-13,2-oxazaphosphorine 2-oxide monohydrate) | |
| Cytarabine | Cytosar-U |
| (1-b-D-Arabinofuranosylcytosine, $C_9H_{13}N_3O_5$) | |
| cytarabine liposomal | DepoCyt |
| Dacarbazine | DTIC-Dome |
| (5-(3,3-dimethyl-1-triazeno)-imidazole-4-carboxamide (DTIC)) | |
| Dactinomycin, actinomycin D | Cosmegen |
| (actinomycin produced by *Streptomyces parvullus*, $C_{62}H_{86}N_{12}O_{16}$) | |
| Darbepoetin alfa | Aranesp |
| (recombinant peptide) | |
| daunorubicin liposomal | DanuoXome |
| ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | |
| Daunorubicin HCl, daunomycin | Cerubidine |
| ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | |
| Denileukin diftitox | Ontak |
| (recombinant peptide) | |
| Dexrazoxane | Zinecard |
| ((S)-4,4'-(1-methyl-1,2-ethanediyl)bis-2,6-piperazinedione) | |
| Docetaxel | Taxotere |
| ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | |
| Doxorubicin HCl | Adriamycin, Rubex |
| (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | |
| doxorubicin | Adriamycin PFS Intravenous injection |
| doxorubicin liposomal | Doxil |
| dromostanolone propionate | Dromostanolone |
| (17b-Hydroxy-2a-methyl-5a-androstan-3-one propionate) | |
| dromostanolone propionate | Masterone injection |
| Elliott's B Solution | Elliott's B Solution |
| Epirubicin | Ellence |
| ((8S-cis)-10-[(3-amino-2,3,6-trideoxy-a-L-arabino-hexopyranosyl)oxy]-7,8,9,10-tetrahydro-6,8,11-trihydroxy- | |

TABLE 1-continued

| Drug | Brand |
|---|---|
| 8-(hydroxyacetyl)-1-methoxy-5,12-naphthacenedione hydrochloride) | |
| Epoetin alfa (recombinant peptide) | Epogen |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt |
| Etoposide phosphate (4'-Demethylepipodophyllotoxin 9-[4,6-O-(R)-ethylidene-(beta)-D-glucopyranoside], 4'-(dihydrogen phosphate)) | Etopophos |
| etoposide, VP-16 (4'-demethylepipodophyllotoxin 9-[4,6-0-(R)-ethylidene-(beta)-D-glucopyranoside]) | Vepesid |
| Exemestane (6-methylenandrosta-1,4-diene-3,17-dione) | Aromasin |
| Filgrastim (r-metHuG-CSF) | Neupogen |
| floxuridine (intraarterial) (2'-deoxy-5-fluorouridine) | FUDR |
| Fludarabine (fluorinated nucleotide analog of the antiviral agent vidarabine, 9-b-D-arabinofuranosyladenine (ara-A)) | Fludara |
| Fluorouracil, 5-FU (5-fluoro-2,4(1H,3H)-pyrimidinedione) | Adrucil |
| Fulvestrant (7-alpha-[9-(4,4,5,5,5-penta fluoropentylsulphinyl)-nonyl]estra-1,3,5-(10)-triene-3,17-beta-diol) | Faslodex |
| Gemcitabine (2'-deoxy-2',2'-difluorocytidine monohydrochloride (b-isomer)) | Gemzar |
| Gemtuzumab Ozogamicin (anti-CD33 hP67.6) | Mylotarg |
| Goserelin acetate | Zoladex Implant |
| Hydroxyurea | Hydrea |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)- propyl]-[N-[2-bis(carboxymethyl)amino]-2-(methyl)-ethyl]glycine) | Zevalin |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin |
| Ifosfamide (3-(2-chloroethyl)-2-[(2-chloroethyl]amino]tetrahydro-2H-1,3,2-oxazaphosphorine 2-oxide) | IFEX |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec |
| Interferon alfa-2a (recombinant peptide) | Roferon-A |
| Interferon alfa-2b (recombinant peptide) | Intron A (Lyophilized Betaseron) |
| Irinotecan HCl ((4S)-4,11-diethyl-4-hydroxy-9-[(4-piperi-dinopiperidino)carbonyloxy]-1H-pyrano-[3',4':6,7]indolizino[1,2-b] quinoline-3,14(4H,12H)dione hydrochloride trihydrate) | Camptosar |
| Letrozole (4,4'-(1H-1,2,4-Triazol-1-ylmethylene)dibenzonitrile) | Femara |
| Leucovorin (L-Glutamic acid, N[4[[(2amino-5-formyl1,4,5,6,7,8 hexahydro4oxo-6-pteridinyl)methyl]amino]benzoyl], calcium salt (1:1)) | Wellcovorin, Leucovorin |
| Levamisole HCl ((−)-(S)-2,3,5,6-tetrahydro-6-phenylimidazo[2,1-b]thiazole monohydrochloride $C_{11}H_{12}N_2S \cdot HCl$) | Ergamisol |
| Lomustine (1-(2-chloro-ethyl)-3-cyclohexyl-1-nitrosourea) | CeeNU |
| Meclorethamine, nitrogen mustard (2-chloro-N-(2-chloroethyl)-N-methylethanamine hydrochloride) | Mustargen |
| Megestrol acetate 17α(acetyloxy)-6-methylpregna-4,6-diene-3,20-dione | Megace |
| Melphalan, L-PAM (4-[bis(2-chloroethyl)amino]-L-phenylalanine) | Alkeran |
| Mercaptopurine, 6-MP (1,7-dihydro-6H-purine-6-thione monohydrate) | Purinethol |
| Mesna (sodium 2-mercaptoethane sulfonate) | Mesnex |
| Methotrexate (N-[4-[[(2,4-diamino-6-pteridinyl)methyl]methyl-amino]benzoyl]-L-glutamic acid) | Methotrexate |
| Methoxsalen (9-methoxy-7H-furo[3,2-g][1]-benzopyran-7-one) | Uvadex |
| Mitomycin C | Mutamycin |
| mitomycin C | Mitozytrex |
| Mitotane (1,1-dichloro-2-(o-chlorophenyl)-2-(p-chlorophenyl)ethane) | Lysodren |
| Mitoxantrone (1,4-dihydroxy-5,8-bis[[2-[(2-hydroxyethyl)amino]-ethyl]amino]-9,10-anthracenedione dihydrochloride) | Novantrone |
| Nandrolone phenpropionate | Durabolin-50 |
| Nofetumomab | Verluma |
| Oprelvekin (IL-11) | Neumega |
| Oxaliplatin (cis-[(1R,2R)-1,2-cyclohexanediamine-N,N']-[oxalato(2-)-O,O'] platinum) | Eloxatin |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL |
| Pamidronate (phosphonic acid (3-amino-1-hydroxypropylidene)bis-, disodium salt, pentahydrate, (APD)) | Aredia |
| Pegademase ((monomethoxypolyethylene glycol succinimidyl)11-17-adenosine deaminase) | Adagen (Pegademase Bovine) |
| Pegaspargase (monomethoxypolyethylene glycol succinimidyl L-asparaginase) | Oncaspar |
| Pegfilgrastim (covalent conjugate of recombinant methionyl human G-CSF (Filgrastim) and monomethoxypolyethylene glycol) | Neulasta |
| Pentostatin | Nipent |
| Pipobroman | Vercyte |
| Plicamycin, Mithramycin (antibiotic produced by *Streptomyces plicatus*) | Mithracin |
| Porfimer sodium | Photofrin |
| Procarbazine (N-isopropyl-μ-(2-methylhydrazino)-p-toluamide monohydrochloride) | Matulane |
| Quinacrine (6-chloro-9-(1-methyl-4-diethyl-amine)butylamino-2-methoxyacridine) | Atabrine |
| Rasburicase (recombinant peptide) | Elitek |
| Rituximab (recombinant anti-CD20 antibody) | Rituxan |
| Sargramostim (recombinant peptide) | Prokine |
| Streptozocin (streptozocin 2-deoxy-2-[[(methylnitrosoamino)-carbonyl]amino]-a(and b)-D-glucopyranose and 220 mg citric acid anhydrous) | Zanosar |
| Talc ($Mg_3Si_4O_{10}(OH)_2$) | Sclerosol |
| Tamoxifen ((Z)2-[4-(1,2-diphenyl-1-butenyl)phenoxy]-N,N-dimethylethanamine 2-hydroxy-1,2,3-propanetricarboxylate (1:1)) | Nolvadex |
| Temozolomide (3,4-dihydro-3-methyl-4-oxoimidazo[5,1-d]-as-tetrazine-8-carboxamide) | Temodar |
| teniposide, VM-26 | Vumon |

TABLE 1-continued

| | |
|---|---|
| (4'-demethylepipodophyllotoxin 9-[4,6-0-(R)-2-thenylidene-(beta)-D-glucopyranoside]) | |
| Testolactone (13-hydroxy-3-oxo-13,17-secoandrosta-1,4-dien-17-oic acid [dgr]-lactone) | Teslac |
| Thioguanine, 6-TG (2-amino-1,7-dihydro-6H-purine-6-thione) | Thioguanine |
| Thiotepa (Aziridine, 1,1',1''-phosphinothioylidynetris-, or Tris (1-aziridinyl) phosphine sulfide) | Thioplex |
| Topotecan HCl ((S)-10-[(dimethylamino)methyl]-4-ethyl-4,9-dihydroxy-1H-pyrano[3',4':6,7]indolizino[1,2-b]quinoline-3,14-(4H,12H)-dione monohydrochloride) | Hycamtin |
| Toremifene (2-(p-[(Z)-4-chloro-1,2-diphenyl-1-butenyl]-phenoxy)-N,N-dimethylethylamine citrate (1:1)) | Fareston |
| Tositumomab, I 131 Tositumomab (recombinant murine immunotherapeutic monoclonal IgG$_{2a}$ lambda anti-CD20 antibody (I 131 is a radioimmunotherapeutic antibody)) | Bexxar |
| Trastuzumab (recombinant monoclonal IgG$_1$ kappa anti-HER2 antibody) | Herceptin |
| Tretinoin, ATRA (all-trans retinoic acid) | Vesanoid |
| Uracil Mustard | Uracil Mustard Capsules |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar |
| Vinblastine, Leurocristine ($C_{46}H_{56}N_4O_{10} \cdot H_2SO_4$) | Velban |
| Vincristine ($C_{46}H_{56}N_4O_{10} \cdot H_2SO_4$) | Oncovin |
| Vinorelbine (3',4'-didehydro-4'-deoxy-C'-norvincaleukoblastine [R-(R*,R*)-2,3-dihydroxybutanedioate (1:2)(salt)]) | Navelbine |
| Zoledronate, Zoledronic acid ((1-Hydroxy-2-imidazol-1-yl-phosphonoethyl)-phosphonic acid monohydrate) | Zometa |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In one embodiment, the methods provided herein comprise administering one or more compounds having Formulae I-XXVIII in combination with radiation therapy. The methods provided herein are not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In one embodiment, the radiation is delivered to the animal using a linear accelerator. In another embodiment, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

Antimicrobial therapeutic agents may also be used as therapeutic agents in combination with the compounds having Formulae I-XXVIII. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In one embodiment of the methods provided herein, one or more compounds having Formulae I-XXVIII are administered to an animal in need thereof. In another embodiment of the methods provided herein, one or more compounds having Formulae I-XXVIII and one or more additional therapeutic agents or anticancer agents are administered to an animal in need thereof under one or more of the following conditions: at different periodicities, at different durations, at different concentrations, by different administration routes, etc. In one embodiment, the compound having Formulae I-XXVIII is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In another embodiment, the compound having Formulae I-XXVIII is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In another embodiment, the compound having Formulae I-XXVIII and the therapeutic or anticancer agent are administered concurrently but on different schedules, e.g., the compound is administered daily while the therapeutic or anticancer agent is administered once a week, once every two weeks, once every three weeks, or once every four weeks. In another embodiment, the compound is administered once a week while the therapeutic or anticancer agent is administered daily, once a week, once every two weeks, once every three weeks, or once every four weeks.

In one embodiment, a method of treating, preventing, or ameliorating cancer in a patient is provided, wherein the method comprises pulsatile administration to the patient a therapeutically effective amount of a compound having Formulae I-XXVIII, or a pharmaceutically acceptable salt, solvate, or prodrug thereof.

In one embodiment, the pharmaceutical compositions provided herein comprise one or more compounds having Formulae I-XXVIII in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, compounds having Formulae I-XXVIII may be administered as part of a pharmaceutical preparation or composition. In one embodiment, the pharmaceutical composition comprises one or more pharmaceutically acceptable carriers, excipients, and/or auxiliaries. In another embodiment, the one or more carriers, excipients, and auxiliaries facilitate processing of the compound having Formulae I-XXVIII into a preparation which can be used pharmaceutically. The compositions, particularly those compositions which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the one or more carriers, excipients, and/or auxiliaries.

The pharmaceutical compositions provided herein may be administered to any patient which may experience the beneficial effects of compounds having Formulae I-XXVIII. Foremost among such patients are mammals, e.g., humans, although the methods and compositions provided herein are not intended to be so limited. Other patients include veterinary animals (cows, sheep, pigs, horses, dogs, cats and the like).

Compounds having Formulae I-XXVIII and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical compositions and preparations provided herein are manufactured by means of conventional mixing, granulating, dragee-making, dissolving, or lyophilizing processes. Thus, pharmaceutical compositions for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries can be suitable flow-regulating agents and lubricants. Suitable auxiliaries include, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension including, for example, sodium carboxymethyl cellulose, sorbitol, and/or dextran. Optionally, the suspension may also contain stabilizers.

The topical compositions provided herein are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

The following examples are illustrative, but not limiting, of the compounds, compositions, and methods provided herein. Other suitable modifications and adaptations of the variety of conditions and parameters normally encountered in clinical therapy and which are obvious to those skilled in the art are within the spirit and scope of the methods, compounds, and compositions provided herein.

EXAMPLE 1

Synthesis of Compound Example No. 3

Scheme 7

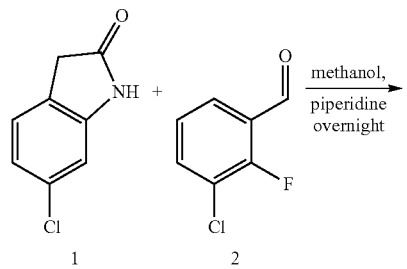

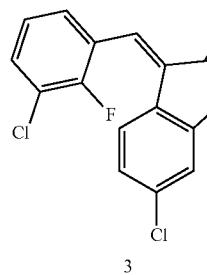

3-Chloro-2-fluorobenzaldehyde (6.24 g, 39.4 mmol) was added to a solution of piperidine (3.88 mL, 39.4 mmol) and 6-chlorooxindole (6.0 g, 35.8 mmol) dissolved in methanol (100 mL). After stirring overnight, the resulting solid was filtered and washed with methanol and hexanes to give 10.6 g of (E)-6-chloro-3-(3-chloro-2-fluorobenzylidene)indolin-2-one (3) as a green solid.

Scheme 8

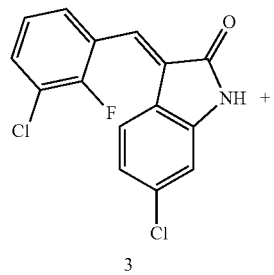

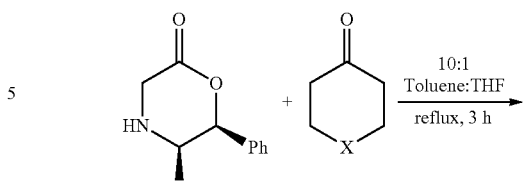

5a = CH$_2$
5b = CF$_2$
5c = O
5d = NBoc
5e = NMe
5f = NAc

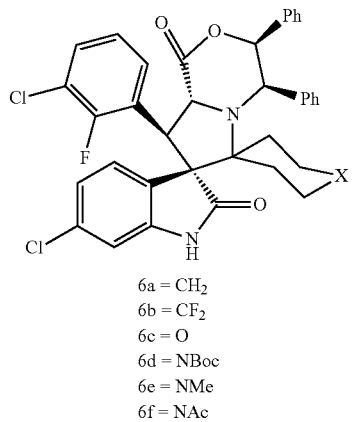

6a = CH$_2$
6b = CF$_2$
6c = O
6d = NBoc
6e = NMe
6f = NAc

Compound 3 (19.5 mmol), (5R,6S)-5,6-diphenylmorpholin-2-one (4) (23.4 mmol), and ketone 5 (39 mmol) were dissolved in THF (7.5 mL) and toluene (75 mL) and refluxed for 3 hours. After cooling to room temperature, the reaction was filtered. The solution was concentrated and purified by column chromatography to give the product (30-50% yield) as a solid.

Scheme 9

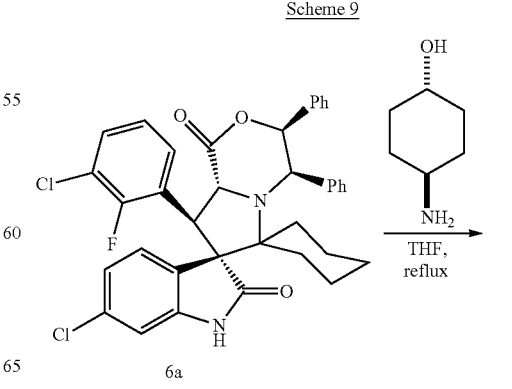

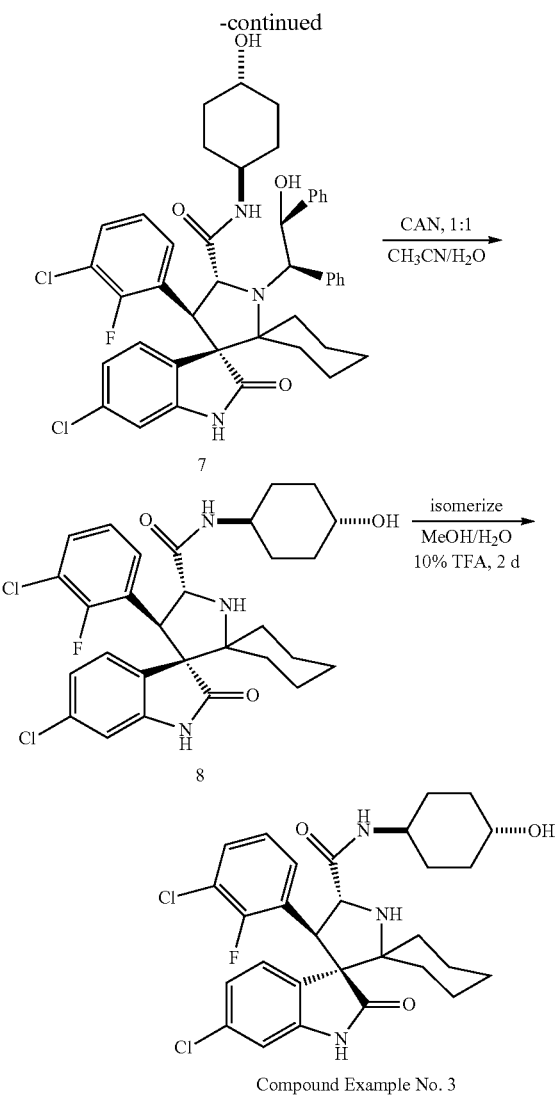

Compound Example No. 3

(d, J=13.4 Hz, 1H), 2.05-1.82 (m, 5H), 1.82-1.65 (m, 3H), 1.64-1.41 (m, 2H), 1.40-1.08 (m, 5H), 1.01-0.83 (m, 1H); ESI-MS m/z 560.9 (M+H)$^+$.

EXAMPLE 2

Synthesis of Compound Example No. 22

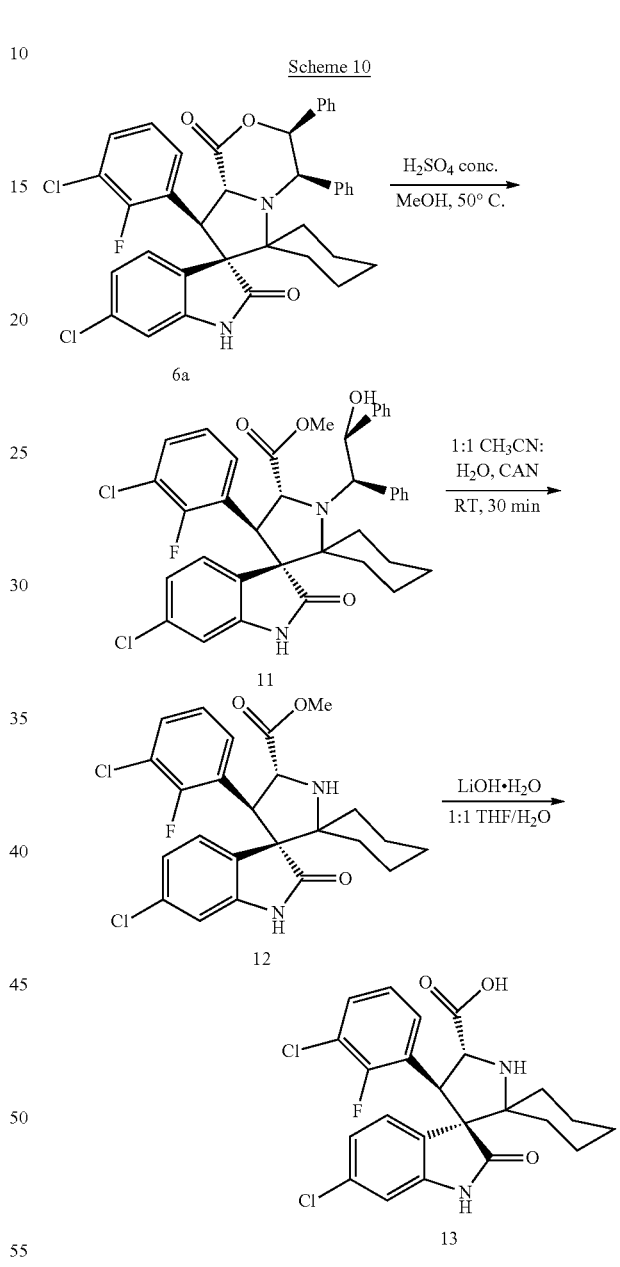

Trans-4-aminocyclohexanol (1.8 g, 15.6 mmol) was added to a solution of intermediate 6a (1.0 g, 1.56 mmol), dissolved in THF (30 mL), and refluxed overnight. The solvent was removed and the crude product was purified by column chromatography to give 0.568 g of intermediate 7 as an off white solid. Intermediate 7 (0.568 g, 0.75 mmol) was dissolved in acetonitrile (5 mL). CAN (823 mg, 1.50 mmol) and water (5 mL) were added. After 15 minutes, the reaction was quenched with saturated sodium bicarbonate, extracted with ethyl acetate, dried over sodium sulfate, and filtered through celite. The solvent was removed and the crude product was purified by column chromatography to give 340 mg of the product 8 as a solid. The solid was dissolved in 1:1 methanol/water with 10% TFA and aged (for isomerization) in this solution for 1-2 days. The solvent was removed. The resulting oil was re-dissolved in 3:1 methanol/water, purified by preparative HPLC, and lyophilized to give Compound Example No. 3 (as the TFA salt) as a white powder. $^1$H NMR (300 MHz, CD$_3$OD) δ ppm 8.19 (d, J=7.5 Hz, 1H), 7.64 (t, J=6.6 Hz, 1H), 7.48 (dd, J=2.1, 8.2 Hz, 1H), 7.39 (t, J=7.6 Hz, 1H), 7.16 (t, J=8.1 Hz, 1H), 7.10 (dd, J=1.9, 8.2 Hz, 1H), 6.79 (d, J=1.8 Hz, 1H), 5.09 (d, J=11.1 Hz, 1H), 4.78 (d, J=11.1 Hz, 1H), 3.70-3.55 (m, 1H), 3.48-3.35 (m, 1H), 2.84 (d, J=8.0 Hz, 1H), 2.19

Concentrated sulfuric acid (2 mL) was added to a solution of intermediate 6a (3.65 g, 5.69 mmol) dissolved in methanol (50 mL), and the resulting solution was heated to 50° C. for 5 hours. The methanol was removed by evaporation, and the resulting concentrate was cooled to 0° C. and slowly neutralized with a solution of saturated sodium bicarbonate. The aqueous solution was extracted with ethyl acetate and the organic layer was dried over sodium sulfate, filtered, and concentrated. The crude product was purified by column chromatography to give 2.20 g (57% yield) of intermediate 11.

Intermediate 11 (2.20 g, 3.25 mmol) was dissolved in acetonitrile (25 mL) and THF (5 mL), CAN (3.56 g, 6.50 mmol), and water (25 mL) were added. After 15 minutes, the reaction was quenched with saturated sodium bicarbonate, extracted with ethyl acetate, dried over sodium sulfate, and filtered through celite. The solvent was removed and the crude product was purified by column chromatography to give 1.43 g (92% yield) of the methyl ester intermediate 12 as a solid.

The methyl ester intermediate 12 (1.43 g, 3.0 mmol) was dissolved in THF (20 mL) and LiOH.H$_2$O (377 mg, 9.0 mmol) was added, followed by water (20 mL). After 2 hours, the reaction was quenched with water and saturated ammonium chloride, and the aqueous layer was extracted with ethyl acetate. The ethyl acetate solution was dried over sodium sulfate, filtered, and concentrated to produce the carboxylic acid intermediate 13 as an off white solid. The acid was used without further purification. ESI-MS m/z 463.17 (M+H)$^+$.

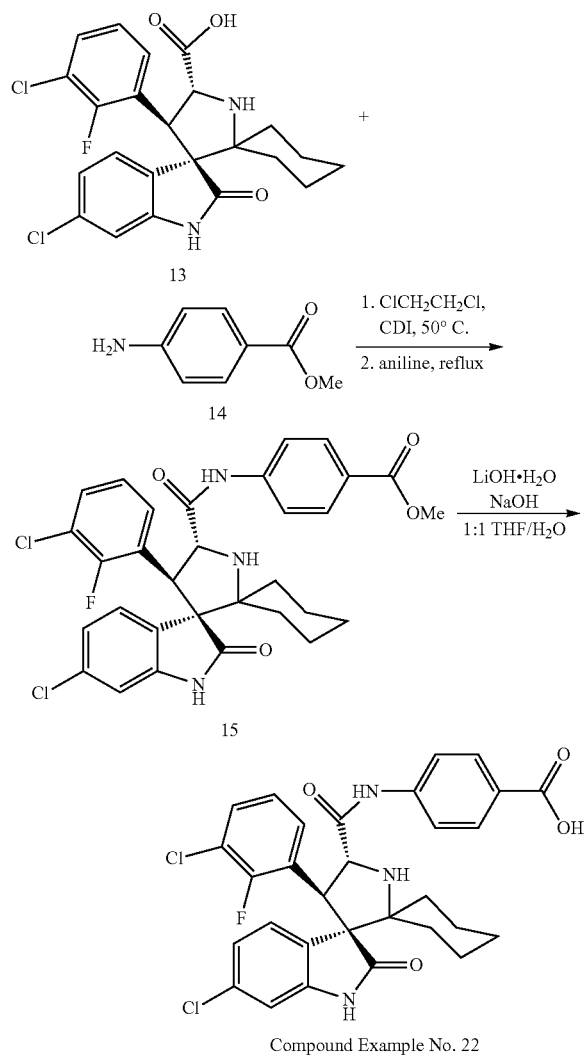

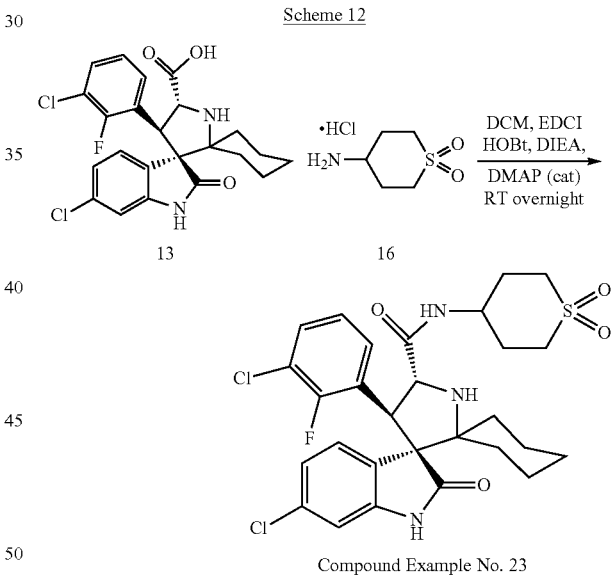

C. After 30 minutes, methyl 4-aminobenzoate 14 (816 mg, 5.4 mmol) was added to the reaction and the reaction was heated to reflux. After heating overnight, the solvent was removed and the crude product was purified by column chromatography to give 265 mg (41% yield) of intermediate 15 as a white solid.

The resulting methyl ester intermediate 15 (265 mg, 0.44 mmol) was dissolved in THF (10 mL) then LiOH.H$_2$O (56 mg, 1.33 mmol), NaOH (53 mg, 1.33 mmol), and H$_2$O were added. After 2 hours, 3 mL of TFA was added, stirred briefly, and the solvent was evaporated. The resulting oil was re-dissolved in methanol and water, purified by preparative HPLC, and lyophilized to give 235 mg of Compound Example No. 22 (as the TFA salt) as a white solid. $^1$H NMR (300 MHz, CD$_3$OD) δ ppm 7.98 (d, J=8.5 Hz, 2H), 7.72 (t, J=7.1 Hz, 1H), 7.65 (d, J=8.5 Hz, 2H), 7.54 (d, J=8.2 Hz, 1H), 7.37 (t, J=7.5 Hz, 1H), 7.18 (t, J=8.0 Hz, 1H), 7.11 (d, J=8.0 Hz, 1H), 6.69 (s, 1H), 5.32 (d, J=10.9 Hz, 1H), 4.97 (d, J=10.9 Hz, 1H), 2.89 (d, J=9.9 Hz, 1H), 2.19 (d, J=14.0 Hz, 1H), 2.08-1.85 (m, 3H), 1.78 (d, J=11.8 Hz, 2H), 1.54 (q, J=14.2 Hz, 1H), 1.32-1.10 (m, 2H); ESI-MS m/z 582.17 (M+H)$^+$.

EXAMPLE 3

Synthesis of Compound Example No. 23

EDCI (19 mg, 0.097 mmol), HOBt (13 mg, 0.097 mmol), and DIEA (0.034 mL, 0.195 mmol) were added to a solution of carboxylic acid intermediate 13 (30 mg, 0.065 mmol) dissolved in DCM. After 10 minutes, 4-aminotetrahydro-2H-thiopyran-1,1-dioxide hydrochloride (24 mg, 0.13 mmol) and a catalytic amount of DMAP were added. After stirring overnight, the solvent was removed and the crude product was purified by column chromatography to give 15 mg of Compound Example No. 23 as a white solid. The solid was further purified by preparative HPLC, and lyophilized to give 10 mg of Compound Example No. 23 (as the TFA salt) as a white powder. $^1$H NMR (300 MHz, CD$_3$OD) δ ppm 7.64 (t, J=7.1 Hz, 1H), 7.49 (dd, J=2.1, 8.1 Hz, 1H), 7.41 (t, J=7.5 Hz, 1H), 7.18 (t, J=9.9 Hz, 1H), 7.11 (dd, J=1.6, 8.2 Hz, 1H), 6.79 (d, J=1.6 Hz, 1H), 5.10 (d, J=11.1 Hz, 1H), 4.80 (d, J=11.2 Hz, CDI (525 mg, 3.24 mmol), DIEA (0.941 mL, 5.4 mmol), and DMAP (catalytic) were added to a solution of carboxylic acid intermediate 13 (500 mg, 1.08 mmol) dissolved in 1,2-dichloroethane, and the resulting solution was heated to 50°

1H), 4.10-3.94 (m, 1H), 3.27-2.91 (m, 3H), 2.88-2.74 (m, 2H), 2.35-1.64 (m, 10H), 1.52 (q, J=13.9 Hz, 1H), 1.31-1.11 (m, 2H); ESI-MS m/z 594.50 (M+H)⁺.

EXAMPLE 4

Synthesis of Compound Example 24

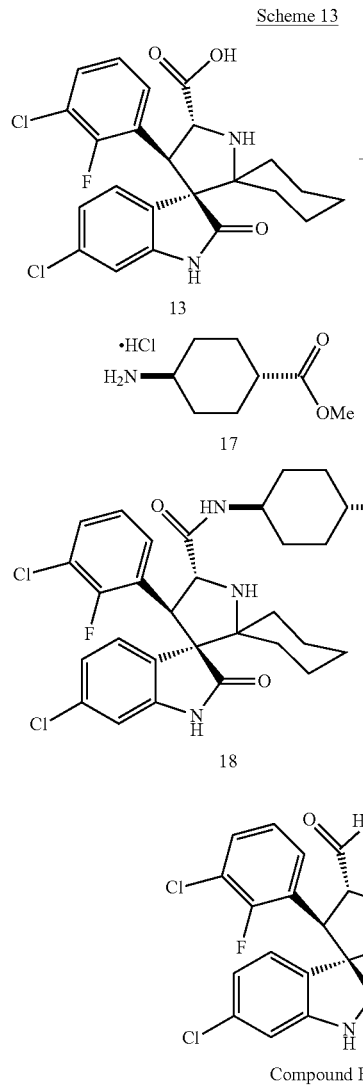

EDCI (19 mg, 0.097 mmol), HOBt (13 mg, 0.097 mmol), and DIEA (0.034 mL, 0.195 mmol) were added to a solution of carboxylic acid intermediate 13 (30 mg, 0.065 mmol) dissolved in DCM. After 10 minutes, methyl trans-4-aminocyclohexanecarboxylate hydrochloride (25 mg, 0.13 mmol) and a catalytic amount of DMAP were added. After stirring overnight, the solvent was removed and the crude product was purified by column chromatography to give the 30 mg of intermediate 18 as a white solid.

Methyl ester intermediate 18 (30 mg, 0.05 mmol) was dissolved in THF (1 mL) then LiOH·H₂O (6.2 mg, 0.15 mmol) and H₂O were added. After 2 hours, 0.5 mL of TFA was added, and the solvent was evaporated. The oil was re-dissolved in 3:1 methanol/water with 10% TFA, purified by preparative HPLC, and lyophilized to give 20 mg of Compound Example No. 24 (as the TFA salt) as a white powder. ¹H NMR (300 MHz, CD₃OD) δ ppm 7.64 (t, J=7.1 Hz, 1H), 7.49 (d, J=8.1 Hz, 1H), 7.39 (t, J=7.5 Hz, 1H), 7.17 (t, J=8.1 Hz, 1H), 7.11 (d, J=8.1 Hz, 1H), 6.79 (s, 1H), 5.08 (d, J=11.1 Hz, 1H), 4.79 (d, J=11.1 Hz, 1H), 3.72-3.54 (m, 1H), 2.84 (d, J=8.4 Hz, 1H), 2.25-2.07 (m, 2H), 2.04-1.84 (m, 6H), 1.77 (d, J=12.0 Hz, 2H), 1.63 (d, J=13.0 Hz, 1H), 1.56-1.34 (m, 3H), 1.32-1.11 (m, 3H), 0.99-0.82 (m, 1H) ESI-MS m/z 588.33 (M+H)⁺.

EXAMPLE 5

The following compounds were prepare using methodology described in Examples 1-4. Unless otherwise indicated, each Compound Example was purified by reverse phase HPLC and isolated as the TFA salt. Unless otherwise indicated, all ¹H NMR chemical shifts reported herein are denoted by the delta (δ) scale.

Compound Example No. 1

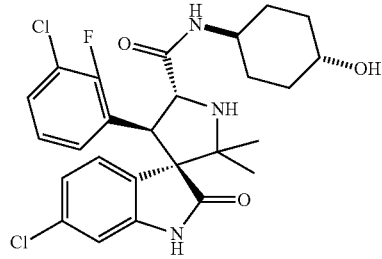

¹H NMR (300 MHz, MeOH-d₄): 8.14 (d, J=7.6 Hz, 1H), 7.62 (t, J=7.6 Hz, 1H), 7.51 (dd, J=1.9, 8.1 Hz, 1H), 7.40 (t, J=7.4 Hz, 1H), 7.17 (dd, J=1.9, 8.2 Hz, 1H), 6.80 (d, J=1.8 Hz, 1H), 5.07 (d, J=11.2 Hz, 1H), 4.70-4.90 (m, 1H), 3.51-3.72 (M, 1H), 3.35-3.48 (m, 1H), 1.93 (s, 3H), 1.85-1.95 (m, 1H), 1.85-1.95 (m, 1H), 1.78 (d, J=12.3 Hz, 1H), 1.59 (d, J=12.3 Hz, 1H), 1.41 (s, 3H), 1.10-1.35 (m, 4H), 0.85-1.05 (m, 1H); ESI-MS m/z 520.3 (M+H)⁺, 542.1 (M+Na)⁺.

Compound Example No. 2

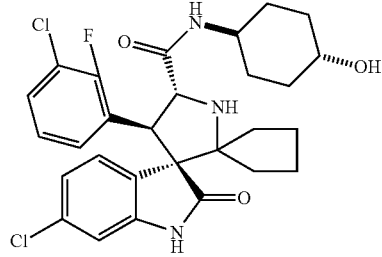

¹H NMR (300 MHz, MeOH-d₄): 8.24 (d, J=7.7 Hz, 1H), 7.45-7.62 (m, 2H), 7.39 (t, J=6.9 Hz, 1H), 7.16 (t, J=8.1 Hz, 1H), 7.10 (dd, J=1.9, 8.2 Hz, 1H), 6.81 (d, J=1.8 Hz, 1H), 5.07 (d, J=11.1 Hz, 1H), 4.69 (d, J=11.1 Hz, 1H), 3.51-3.70 (m, 1H), 3.35-3.48 (m, 1H), 2.65-2.82 (m, 1H), 2.38-2.54 (m, 1H), 2.11-2.24 (m, 1H), 1.95-2.11 (m, 1H), 1.84-1.95 (m, 2H), 1.78-1.74 (m, 2H), 1.43-1.78 (m, 4H), 1.10-1.40 (m, 3H), 0.83-1.05 (m, 1H); ESI-MS m/z 546.7 (M+H)⁺.

Compound Example No. 4

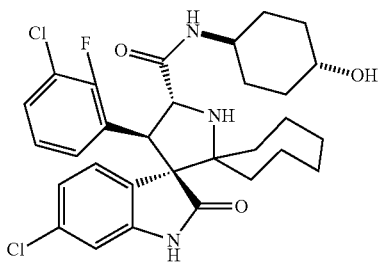

¹H NMR (300 MHz, MeOH-d₄): 8.25 (d, J=7.5 Hz, 1H), 7.50-7.66 (m, 2H), 7.38 (t, J=7.4 Hz, 1H), 7.15 (t, J=8.0 Hz, 1H), 7.08 (d, J=8.2 Hz, 1H), 6.79 (s, 1H), 5.10 (d, J=11.2 Hz, 1H), 4.80-4.88 (m, 1H), 3.53-3.67 (m, 1H), 3.35-3.47 (m, 1H), 3.05 (dd, J=8.3, 15.3 Hz, 1H), 2.41 (dd, J=8.8, 14.4 Hz, 2H), 1.89 (d, J=10.2 Hz, 2H), 1.65-1.84 (m, 4H), 1.40-1.65 (m, 5H), 1.14-1.38 (m, 4H), 1.00-1.12 (m, 1H), 0.82-1.00 (m, 1H); ESI-MS m/z 574.6 (M+H)⁺, 596.1 (M+Na)⁺.

Compound Example No. 5

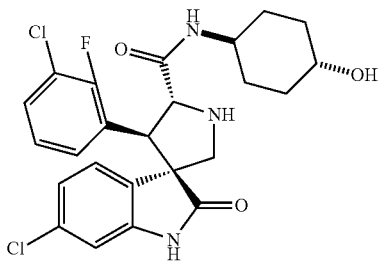

¹H NMR (300 MHz, MeOH-d₄): 8.25 (d, J=7.3 Hz, 1H), 7.28-7.42 (m, 2H), 6.91-7.12 (m, 2H), 6.77 (d, J=1.8 Hz, 1H), 4.80-4.97 (m, 1H), 4.40 (d, J=12.0 Hz, 1H), 4.04 (d, J=12.4 Hz, 1H), 3.84 (d, J=12.6 Hz, 1H), 3.51-3.68 (m, 1H), 3.36-3.51 (m,1H), 1.91 (d, J=9.3 Hz, 2H), 1.74 (d, J=12.7 Hz, 1H), 1.49 (d, J=12.3 Hz, 1H), 1.14-1.36 (m, 3H), 0.86-1.05 (m, 1H); ESI-MS m/z 492.60 (M+H)⁺.

Compound Example No. 6

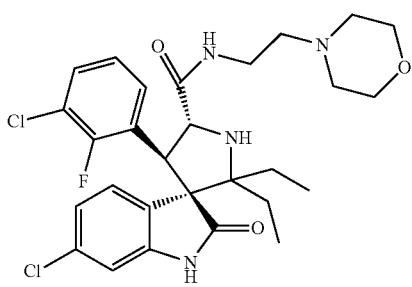 [SMILES: CCC1(CC)N[C@@H](C(=O)NCCN2CCOCC2)[C@H](c2cccc(Cl)c2F)[C@]12C(=O)Nc1cc(Cl)ccc12]

ESI-MS m/z 563.67 (M+H)⁺.

Compound Example No. 7

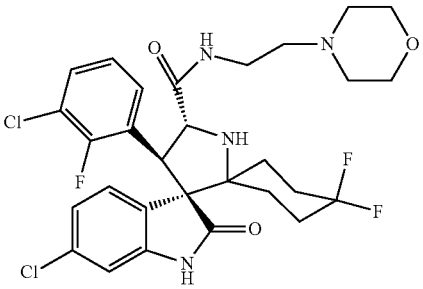 [SMILES: O=C(NCCN1CCOCC1)[C@@H]1NC2(CCC(F)(F)CC2)[C@@]2(C(=O)Nc3cc(Cl)ccc32)[C@H]1c1cccc(Cl)c1F]

The title compound was prepared as described in EXAMPLE 1 using intermediate 6b and 2-morpholinoethanamine (2 equivalents) at room temperature. ¹H NMR (300 MHz, CD₃OD) δ ppm 7.64 (t, J=7.1 Hz, 1H), 7.49 (dd, J=2.2, 8.2 Hz, 1H), 7.33 (t, J=8.0 Hz, 1H), 7.16-7.07 (m, 2H), 6.77 (d, J=1.7 Hz, 1H), 5.02 (d, J=10.2 Hz, 1H), 4.82 (d, J=10.3 Hz, 1H), 4.12-3.38 (m, 11H), 2.75-1.73 (m, 7H), 1.50-1.31 (m, 1H); ESI-MS m/z 611.25 (M+H)⁺.

Compound Example No. 8

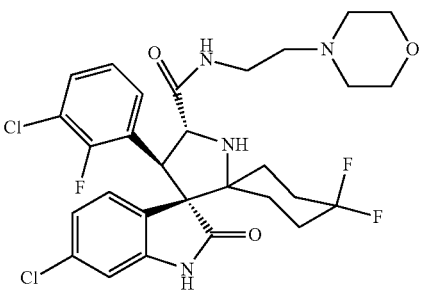 [SMILES: O=C(NCCN1CCOCC1)[C@@H]1NC2(CCC(F)(F)CC2)[C@]2(C(=O)Nc3cc(Cl)ccc32)[C@H]1c1cccc(Cl)c1F]

The title compound was prepared as described in Example 1 using intermediate 6b and 2-morpholinoethanamine (2 equivalents) at room temperature. ¹H NMR (300 MHz, CD₃OD) δ ppm 7.33 (t, J=7.3 Hz, 1H), 7.26 (t, J=7.5 Hz, 1H), 7.05-6.84 (m, 3H), 6.82 (s, 1H), 4.68 (d, J=9.2 Hz, 1H), 4.56 (d, J=9.2 Hz, 1H), 4.16-3.01 (m, 11H), 2.48-1.63 (m, 7H), 1.31 (dt, J=3.8, 14.0 Hz, 1H); ESI-MS m/z 611.25 (M+H)⁺.

Compound Example No. 9

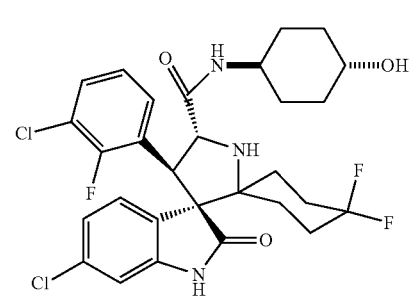

The title compound was prepared as described in EXAMPLE 1 using intermediate 6b. ¹H NMR (300 MHz, CD₃OD) δ ppm 8.12 (d, J=8.1 Hz, 1H), 7.62 (t, J=7.2 Hz, 1H), 7.49 (dd, J=2.3, 8.2 Hz, 1H), 7.33 (t, J=8.3 Hz, 1H), 7.16-7.05 (m, 2H), 6.78 (d, J=1.9 Hz, 1H), 4.77 (d, J=10.3 Hz, 1H), 3.70-3.41 (m, 2H), 2.74-1.64 (m, 11H), 1.48-1.21 (m, 4H), 1.18-1.02 (m, 1H); ESI-MS m/z 596.75 (M+H)⁺.

Compound Example No. 10

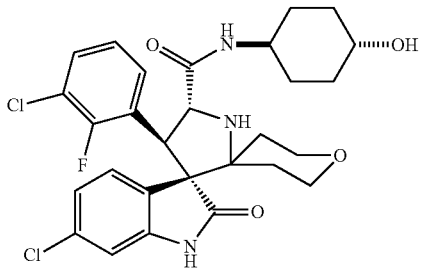

The title compound was prepared as described in Example 1 using intermediate 6c. ¹H NMR (300 MHz, CD₃OD) δ ppm 8.02 (d, J=8.0 Hz, 1H), 7.31-7.15 (m, 3H), 7.01-6.91 (m, 2H), 6.82 (d, J=1.9 Hz, 1H), 4.70 (d, J=10.4 Hz, 1H), 4.59 (d, J=10.4 Hz, 1H), 4.12-3.80 (m, 3H), 3.76-3.48 (m, 3H), 2.25-0.94 (m, 12H); ESI-MS m/z 562.92 (M+H)⁺.

Compound Example No. 11

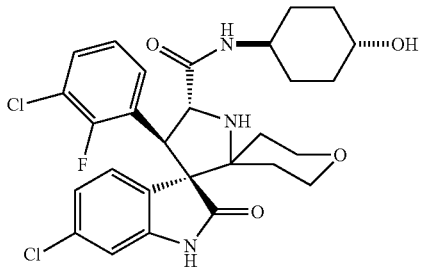

The title compound was prepared as described in EXAMPLE 1 using intermediate 6c. ¹H NMR (300 MHz, CD₃OD) δ ppm 8.19 (d, J=7.9 Hz, 1H), 7.63 (ddd, J=1.5, 6.5, 7.9 Hz, 1H), 7.51 (dd, J=2.3, 8.2 Hz, 1H), 7.37 (t, J=8.3 Hz, 1H), 7.19-7.07 (m, 2H), 6.80 (d, J=1.9 Hz, 1H), 5.02 (d, J=10.8 Hz, 1H), 4.74 (d, J=10.8 Hz, 1H), 4.11-3.93 (m, 2H), 3.87 (dd, J=3.9, 12.4 Hz, 1H), 3.69-3.55 (m, 2H), 3.50-3.38 (m, 1H), 2.62 (d, J=13.2 Hz, 1H), 2.26-2.12 (m, 1H), 2.04-1.73 (m, 4H), 1.70-1.17 (m, 5H), 1.08 (ddd, J=3.5, 12.7, 24.0 Hz, 1H); ESI-MS m/z 562.67 (M+H)⁺.

Compound Example No. 12

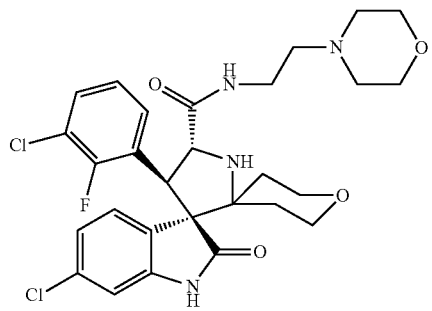 [SMILES: O=C(NCCN1CCOCC1)[C@@H]1NC2(CCOCC2)[C@@]2(C(=O)Nc3cc(Cl)ccc32)[C@H]1c1cccc(Cl)c1F]

The title compound was prepared as described in Example 1 using intermediate 6c, and 2-morpholinoethanamine (2 equivalents) at room temperature. ¹H NMR (300 MHz, CD₃OD) δ ppm 7.64 (t, J=7.9 Hz, 1H), 7.49 (dd, J=2.6, 8.2 Hz, 1H), 7.33 (t, J=8.3 Hz, 1H), 7.15-7.07 (m, 2H), 6.78 (d, J=1.9 Hz, 1H), 5.00 (d, J=10.3 Hz, 1H), 4.77 (d, J=10.3 Hz, 1H), 4.12-3.57 (m, 14H), 3.36-3.19 (m, 2H), 2.37 (d, J=10.3 Hz, 1H), 2.17-2.04 (m, 1H), 1.96-1.80 (m, 1H), 1.50-1.34 (m, 1H); ESI-MS m/z 577.75 (M+H)⁺.

Compound Example No. 13

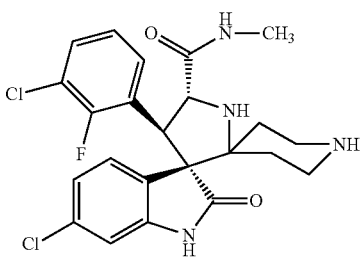 [SMILES: CNC(=O)[C@@H]1NC2(CCNCC2)[C@]2(C(=O)Nc3cc(Cl)ccc32)[C@H]1c1cccc(Cl)c1F]

The title compound was prepared as described in EXAMPLE 1 using intermediate 6d and methyl amine (2 equivalents) at room temperature. ¹H NMR (300 MHz, CD₃OD) δ ppm 8.10 (s, 1H), 7.27-7.15 (m, 3H), 7.00-6.89 (m, 2H), 6.79 (d, J=1.6 Hz, 1H), 4.66 (d, J=10.2 Hz, 1H), 4.60 (d, J=10.1 Hz, 1H), 3.60 (t, J=11.8 Hz, 1H), 3.39-3.15 (m, 3H), 2.76 (s, 3H), 2.33-2.02 (m, 2H), 1.71 (d, J=14.2 Hz, 1H), 1.53-1.33 (m, 1H); ESI-MS m/z 477.17 (M+H)+.

Compound Example No. 14

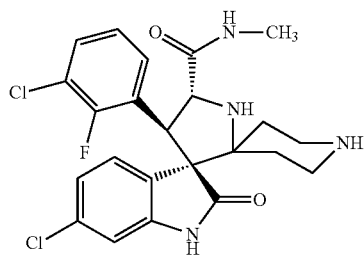 [SMILES: CNC(=O)[C@@H]1NC2(CCNCC2)[C@@]2(C(=O)Nc3cc(Cl)ccc32)[C@H]1c1cccc(Cl)c1F]

The title compound was prepared as described in EXAMPLE 1 using intermediate 6d and methyl amine (2 equivalents) at room temperature. ¹H NMR (300 MHz, CD₃OD) δ ppm 8.24 (s, 1H), 7.64 (t, J=7.2 Hz, 1H), 7.49 (dd, J=2.2, 8.1 Hz, 1H), 7.27 (t, J=7.3 Hz, 1H), 7.13-7.03 (m, 2H), 6.68 (s, 1H), 4.79 (d, J=9.6 Hz, 1H), 4.64 (d, J=9.6 Hz, 1H), 3.70 (t, J=13.1 Hz, 1H), 3.44-3.18 (m, 3H), 2.77 (d, J=4.3 Hz, 3H), 2.39 (d, J=14.5 Hz, 1H), 2.10-1.88 (m, 2H), 1.50-1.26 (m, 1H); ESI-MS m/z 477.17 (M+H)+.

Compound Example No. 15

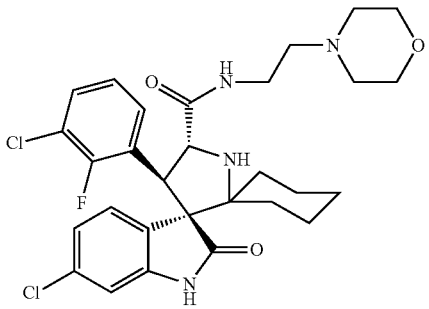 [SMILES: O=C(NCCN1CCOCC1)[C@@H]1NC2(CCCCC2)[C@@]2(C(=O)Nc3cc(Cl)ccc32)[C@H]1c1cccc(Cl)c1F]

The title compound was prepared as described in EXAMPLE 1 using intermediate 6a and 2-morpholinoethanamine (2 equivalents) at room temperature. ¹H NMR (300 MHz, CD₃OD) δ ppm 7.65 (t, J=7.1 Hz, 1H), 7.47 (dd, J=2.3, 8.1 Hz, 1H), 7.35 (t, J=7.5 Hz, 1H), 7.17-7.05 (m, 2H), 6.77 (s, 1H), 5.02 (d, J=10.3 Hz, 1H), 4.80 (d, J=10.5 Hz, 1H), 3.94-3.80 (m, 4H), 3.61 (t, J=6.2 Hz, 2H), 3.29-3.17 (m, 5H), 2.56 (d, J=12.5 Hz, 1H), 2.11-1.48 (m, 7H), 1.29-1.02 (m, 2H); ESI-MS m/z 575.25 (M+H)+.

Compound Example No. 16

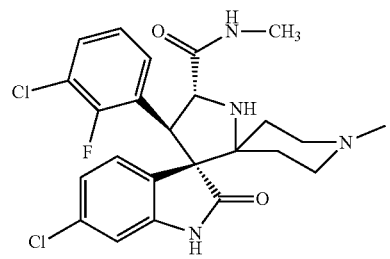 [SMILES: CNC(=O)[C@@H]1NC2(CCN(C)CC2)[C@]2(C(=O)Nc3cc(Cl)ccc32)[C@H]1c1cccc(Cl)c1F]

The title compound was prepared as described in EXAMPLE 1 using intermediate 6e and methyl amine (2 equivalents) at room temperature. NMR (300 MHz, CD₃OD) δ ppm 8.12 (d, J=5.4 Hz, 1H), 7.29 (d, J=8.2 Hz, 1H), 7.26-7.13 (m, 2H), 6.99 (dd, J=1.9, 8.1 Hz, 1H), 6.92 (t, J=7.5 Hz, 1H), 6.79 (d, J=1.9 Hz, 1H), 4.67 (d, J=9.9 Hz, 1H), 4.61 (d, J=9.9 Hz, 1H), 3.67 (dt, J=3.8, 13.0 Hz, 1H), 3.56-3.41 (m, 2H), 3.26-3.13 (m, 1H), 2.87 (s, 3H), 2.77 (d, J=3.7 Hz, 3H), 2.36-2.10 (m, 2H), 1.77-1.63 (m, 1H), 1.54-1.38 (m, 1H); ESI-MS m/z 491.42 (M+H)+.

Compound Example No. 17

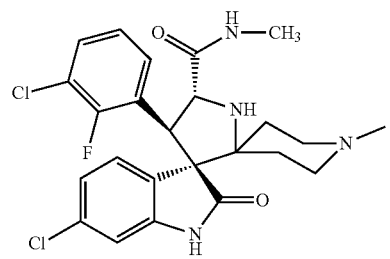 [SMILES: CNC(=O)[C@@H]1NC2(CCN(C)CC2)[C@@]2(C(=O)Nc3cc(Cl)ccc32)[C@H]1c1cccc(Cl)c1F]

The title compound was prepared as described in EXAMPLE 1 using intermediate 6e and methyl amine (2 equivalents) at room temperature. ¹H NMR (300 MHz, CD₃OD) δ ppm 8.25 (d, J=5.8 Hz, 1H), 7.62 (t, J=7.3 Hz, 1H), 7.47 (dd, J=2.1, 8.2 Hz, 1H), 7.25 (t, J=7.5 Hz, 1H), 7.12-7.01 (m, 2H), 6.77 (d, J=1.6 Hz, 1H), 4.76 (d, J=9.5 Hz, 1H), 4.62 (d, J=9.5 Hz, 1H), 3.75 (t, J=12.5 Hz, 1H), 3.52-3.40 (m, 2H), 3.24-3.12 (m, 1H), 2.86 (s, 3H), 2.76 (d, J=4.0 Hz, 3H), 2.40 (d, J=14.4 Hz, 1H), 2.12-1.86 (m, 2H), 1.54-1.34 (m, 1H); ESI-MS m/z 491.08 (M+H)+.

Compound Example No. 18

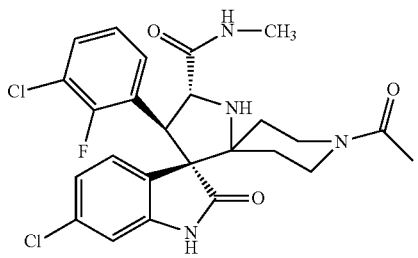 [SMILES: CNC(=O)[C@@H]1NC2(CCN(C(C)=O)CC2)[C@]2(C(=O)Nc3cc(Cl)ccc32)[C@H]1c1cccc(Cl)c1F]

The title compound was prepared as described in EXAMPLE 1 using intermediate 6f and methyl amine (2 equivalents) at room temperature. ESI-MS m/z 519.17 (M+H)+.

Compound Example No. 19

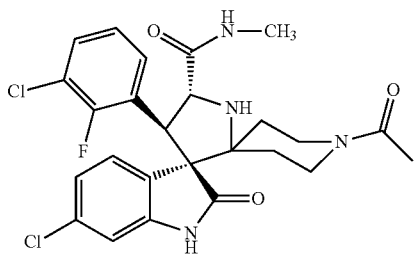 [SMILES: CNC(=O)[C@@H]1NC2(CCN(C(C)=O)CC2)[C@@]2(C(=O)Nc3cc(Cl)ccc32)[C@H]1c1cccc(Cl)c1F]

The title compound was prepared as described in EXAMPLE 1 using intermediate 6f and methyl amine (2 equivalents) at room temperature. ESI-MS m/z 519.17 (M+H)+.

Compound Example No. 20

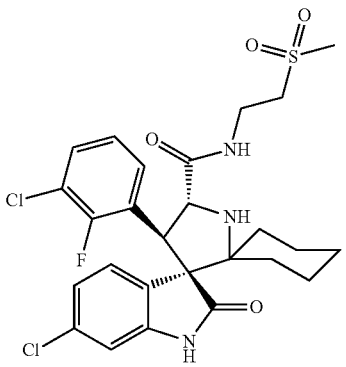 [SMILES: CS(=O)(=O)CCNC(=O)[C@@H]1NC2(CCCCC2)[C@@]2(C(=O)Nc3cc(Cl)ccc32)[C@H]1c1cccc(Cl)c1F]

The title compound was prepared as described in EXAMPLE 1 using intermediate 6a and 2-(methylsulfonyl)ethanamine (2 equivalents) at room temperature. ¹H NMR (300 MHz, CD₃OD) δ ppm 7.63 (t, J=7.9 Hz, 1H), 7.50 (dd, J=2.7, 8.2 Hz, 1H), 7.36 (t, J=8.3 Hz, 1H), 7.19-7.07 (m, 2H), 6.77 (d, J=1.9 Hz, 1H), 5.13 (d, J=10.7 Hz, 1H), 3.84-3.51 (m, 2H), 3.25 (t, J=6.3 Hz, 2H), 2.90 (s, 3H), 2.75 (d, J=10.6 Hz, 1H), 2.13 (d, J=14.6 Hz, 1H), 2.01-1.67 (m, 5H), 1.64-1.42 (m, 1H), 1.31-1.10 (m, 2H); ESI-MS m/z 568.25 (M+H)+

Compound Example No. 21

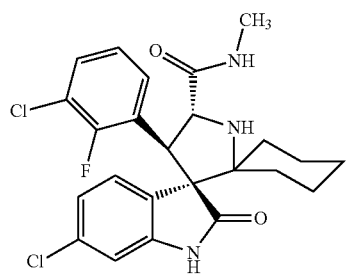 [SMILES: CNC(=O)[C@@H]1NC2(CCCCC2)[C@@]2(C(=O)Nc3cc(Cl)ccc32)[C@H]1c1cccc(Cl)c1F]

The title compound was prepared as described in EXAMPLE 1 using intermediate 6a and methyl amine (2 equivalents) at room temperature. ¹H NMR (300 MHz, CD₃OD) δ ppm 8.29 (s, 1H), 7.63 (t, J=7.2 Hz, 1H), 7.51 (dd, J=2.4, 8.2 Hz, 1H), 7.39 (t, J=7.6 Hz, 1H), 7.21-7.07 (m, 2H), 6.77 (d, J=1.5 Hz, 1H), 5.13 (d, J=10.9 Hz, 1H), 4.83 (d, J=11.0 Hz, 1H), 2.83 (d, J=8.3 Hz, 1H), 2.73 (s, 3H), 2.17 (d, J=15.3 Hz, 1H), 2.04-1.68 (m, 5H), 1.52 (q, J=14.6 Hz, 1H), 1.31-1.09 (m, 2H); ESI-MS m/z 476.25 (M+H)+.

Compound Example No. 25

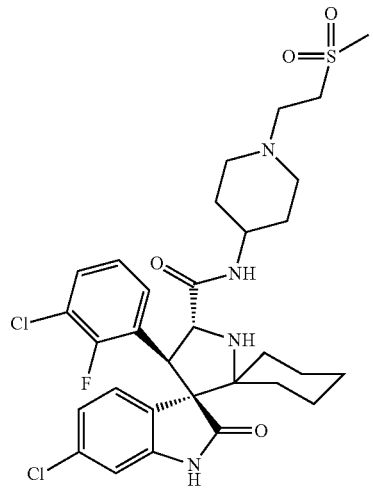 [SMILES: CS(=O)(=O)CCN1CCC(NC(=O)[C@@H]2NC3(CCCCC3)[C@@]3(C(=O)Nc4cc(Cl)ccc43)[C@H]2c2cccc(Cl)c2F)CC1]

The title compound was prepared using 1-(2-(methylsulfonyl)ethyl)piperidin-4-amine hydrochloride. ¹H NMR (300 MHz, CD₃OD) δ ppm 7.64 (t, J=7.1 Hz, 1H), 7.47 (dd, J=1.8, 8.2 Hz, 1H), 7.37 (t, J=7.8 Hz, 1H), 7.15 (t, 8.1 Hz, 1H), 7.09 (dd, J=1.5, 8.3 Hz, 1H), 6.78 (d, J=1.4 Hz, 1H), 5.04 (d, J=10.1 Hz, 1H), 4.79 (d, J=10.8 Hz, 1H), 4.05-3.86 (m, 1H), 3.73-3.41 (m, 6H), 3.25-3.10 (m, 2H), 3.08 (s, 3H), 2.79-2.64

(m, 1H), 2.15 (t, J=15.6 Hz, 2H), 2.01-1.44 (m, 9H), 1.32-1.08 (m, 2H); ESI-MS m/z 651.83 (M+H)+.

Compound Example No. 26

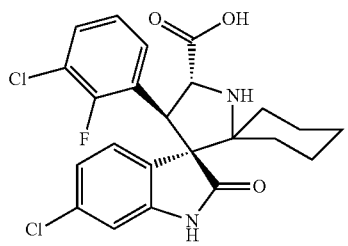 [SMILES: O=C(O)[C@@H]1NC2(CCCCC2)[C@@]2(C(=O)Nc3cc(Cl)ccc32)[C@H]1c1cccc(Cl)c1F]

Intermediate 13 (see EXAMPLE 3) was dissolved in 3:1 methanol/water, treated with 10% TFA, and purified by preparative HPLC to give the title compound as the TFA salt. ¹H NMR (300 MHz, CD₃OD) δ ppm 7.64 (t, J=7.1 Hz, 1H), 7.56 (dd, J=2.1, 8.3 Hz, 1H), 7.35 (t, J=7.4 Hz, 1H), 7.18-7.08 (m, 2H), 6.77 (d, J=1.4 Hz, 1H), 5.17 (d, J=10.6 Hz, 1H), 2.64-2.49 (m, 1H), 2.14 (d, J=13.6 Hz, 1H), 2.02-1.84 (m, 3H), 1.84-1.48 (m, 3H), 1.32-1.10 (m, 2H); ESI-MS m/z 463.17 (M+H)+.

Compound Example No. 27

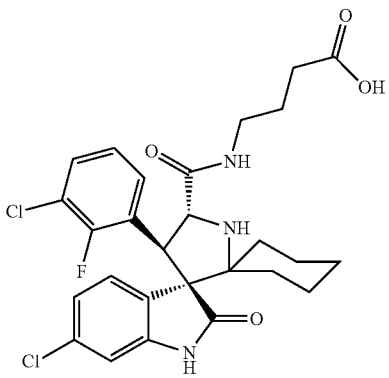 [SMILES: O=C(O)CCCNC(=O)[C@@H]1NC2(CCCCC2)[C@@]2(C(=O)Nc3cc(Cl)ccc32)[C@H]1c1cccc(Cl)c1F]

The title compound was prepared using methyl 4-aminobutanoate hydrochloride. ¹H NMR (300 MHz, CD₃OD) δ ppm 7.64 (t, J=7.1 Hz, 1H), 7.51 (dd, J=2.2, 8.3 Hz, 1H), 7.39 (t, J=7.5 Hz, 1H), 7.17 (t, J=8.1 Hz, 1H), 7.11 (dd, J=1.6, 8.2 Hz, 1H), 6.78 (d, J=1.6 Hz, 1H), 5.12 (d, J=11.0 Hz, 1H), 4.80 (d, J=11.1 Hz, 1H), 3.21-3.04 (m, 1H), 2.81 (d, J=7.4 Hz, 1H), 2.17 (d, J=12.0 Hz, 1H), 2.06 (t, J=7.4 Hz, 2H), 2.01-1.84 (m, 3H), 1.84-1.40 (m, 5H), 1.32-1.12 (m, 2H); ESI-MS m/z 548.42 (M+H)+.

Compound Example No. 28

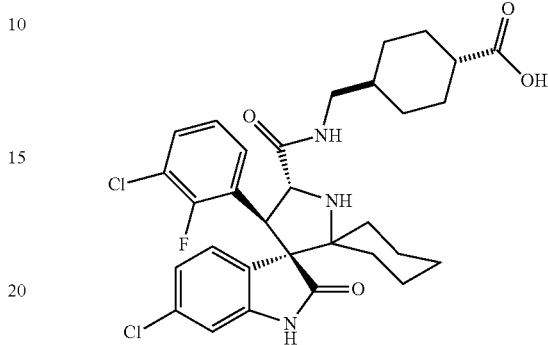

The title compound was prepared using methyl trans-4-(aminomethyl)cyclohexanecarboxylate hydrochloride. ¹H NMR (300 MHz, CD₃OD) δ ppm 8.36-8.26 (m, 1H), 7.67 (t, J=6.8 Hz, 1H), 7.52 (d, J=8.2 Hz, 1H), 7.42 (t, J=7.5 Hz, 1H), 7.20 (t, d=8.0 Hz, 1H), 7.12 (dd, J=1.4, 8.2 Hz, 1H), 6.78 (d, J=1.5 Hz, 1H), 5.14 (d, J=11.1 Hz, 1H), 4.78 (d, J=11.3 Hz, 1H), 3.48-3.34 (m, 1H), 2.90-2.64 (m, 2H), 2.19 (d, J=11.3 Hz, 1H), 2.09-1.70 (m, 8H), 1.61-1.11 (m, 8H), 0.79-0.59 (m, 2H); ESI-MS m/z 602.58 (M+H)+.

Compound Example No. 29

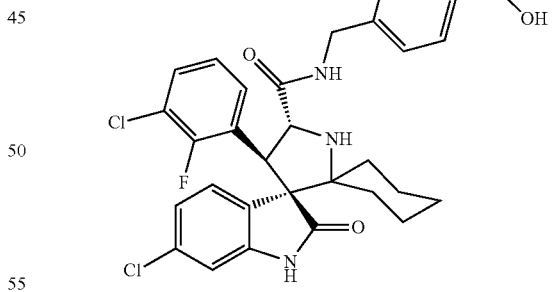

The title compound was prepared using methyl 4-(aminomethyl)benzoate hydrochloride. ¹H NMR (300 MHz, CD₃OD) δ ppm 7.87 (d, J=8.2 Hz, 2H), 7.66 (t, J=7.0 Hz, 1H), 7.50 (dd, J=2.3, 8.3 Hz, 1H), 7.40 (t, J=7.6 Hz, 1H), 7.22-7.08 (m, 2H), 7.04 (d, J=8.2 Hz, 2H), 6.78 (d, J=1.6 Hz, 1H), 5.20 (d, J=11.2 Hz, 1H), 4.80 (d, J=11.1 Hz, 1H), 4.66 (d, J=15.3 Hz, 1H), 4.20 (d, J=15.3 Hz, 1H), 2.83 (d, J=10.0 Hz, 1H), 2.20 (d, J=15.8 Hz, 1H), 2.04-1.85 (m, 3H), 1.77 (d, J=11.9 Hz, 2H), 1.52 (q, J=13.7 Hz, 1H), 1.33-1.10 (m, 2H); ESI-MS m/z 596.33 (M+H)⁺.

Compound Example No. 30

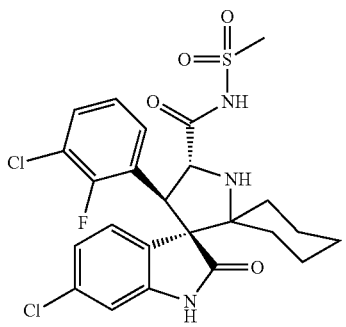 [SMILES: CS(=O)(=O)NC(=O)[C@@H]1NC2(CCCCC2)[C@@]2(C(=O)Nc3cc(Cl)ccc32)[C@H]1c1cccc(Cl)c1F]

The title compound was prepared using methanesulfonamide. ¹H NMR (300 MHz, CD₃OD) δ ppm 7.61 (t, J=7.5 Hz, 1H), 7.53 (dd, J=2.1, 8.2 Hz, 1H), 7.33 (t, J=8.0 Hz, 1H), 7.17-7.06 (m, 2H), 6.76 (d, J=1.7 Hz, 1H), 4.98 (d, J=10.4 Hz, 1H), 3.09 (s, 3H), 2.60 (d, J=13.7 Hz, 1H), 2.09 (d, J=16.1 Hz, 1H), 2.01-1.43 (m, 6H), 1.34-1.06 (m, 2H); ESI-MS m/z 540.08 (M+H)⁺.

Compound Example No. 31

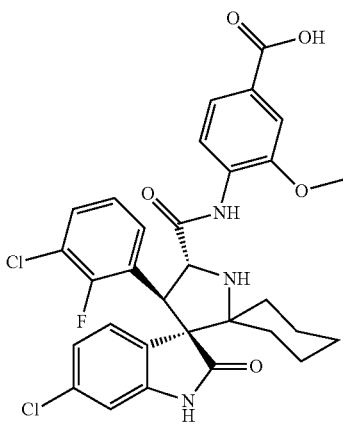 [SMILES: COc1cc(C(=O)O)ccc1NC(=O)[C@@H]1NC2(CCCCC2)[C@@]2(C(=O)Nc3cc(Cl)ccc32)[C@H]1c1cccc(Cl)c1F]

The title compound was prepared using methyl 4-amino-3-methoxybenzoate. NMR (300 MHz, CD₃OD) δ ppm 8.26 (d, J=8.6 Hz, 1H), 7.79 (t, J=7.1 Hz, 1H), 7.66 (dd, J=1.4, 8.4 Hz, 1H), 7.60 (s, 1H), 7.51 (dd, J=2.2, 8.3 Hz, 1H), 7.40 (t, J=8.2 Hz, 1H), 7.21 (t, J=8.6 Hz, 1H), 7.10 (dd, J=1.8, 8.1 Hz, 1H), 6.79 (d, J=1.7 Hz, 1H), 5.49-5.23 (m, 1H), 3.80 (s, 3H), 2.68-2.47 (m, 1H), 2.21-1.52 (m, 7H), 1.35-1.07 (m, 2H); ESI-MS m/z 612.17 (M+H)⁺.

Compound Example No. 32

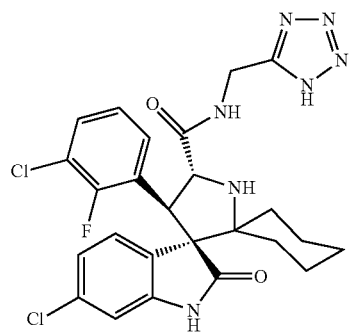 [SMILES: O=C(NCc1nnn[nH]1)[C@@H]1NC2(CCCCC2)[C@@]2(C(=O)Nc3cc(Cl)ccc32)[C@H]1c1cccc(Cl)c1F]

The title compound was prepared using (1H-tetrazol-5-yl)methanamine hydrochloride. NMR (300 MHz, CD₃OD) δ ppm 7.63 (t, J=7.2 Hz, 1H), 7.51 (dd, J=2.3, 8.1 Hz, 1H), 7.36 (t, J=7.6 Hz, 1H), 7.19-7.06 (m, 2H), 6.77 (d, J=1.4 Hz, 1H), 5.19 (d, J=10.7 Hz, 1H), 4.67 (q, J=16.1 Hz, 2H), 2.77 (d, J=11.4 Hz, 1H), 2.15 (d, J=12.5 Hz, 1H), 2.03-1.81 (m, 3H), 1.76 (d, J=13.3 Hz, 2H), 1.67-1.09 (m, 3H); ESI-MS m/z 544.25 (M+H)⁺.

Compound Example No. 33

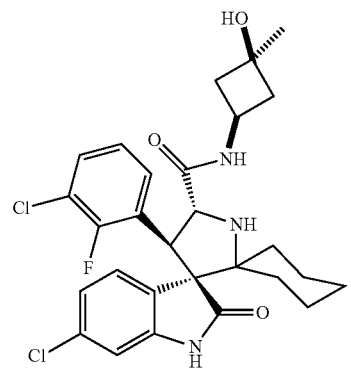

The title compound was prepared using (1s,3s)-3-(tert-butyldimethylsilyloxy)-3-methylcyclobutanamine. ¹H NMR (300 MHz, CD₃OD) δ ppm 8.62 (d, J=6.9 Hz, 1H), 7.64 (t, J=6.8 Hz, 1H), 7.49 (dd, J=2.4, 8.2 Hz, 1H), 7.39 (t, J=7.1 Hz, 1H), 7.17 (t, J=8.0 Hz, 1H), 7.10 (dd, J=1.8, 8.2 Hz, 1H), 6.78 (d, J=1.7 Hz, 1H), 5.10 (d, J=11.0 Hz, 1H), 4.80 (d, J=11.1 Hz, 1H), 3.98-3.76 (m, 1H), 2.84 (d, J=9.8 Hz, 1H), 2.45-2.23 (m, 2H), 2.17 (d, J=13.5 Hz, 1H), 2.05-1.82 (m, 4H), 1.82-

1.61 (m, 3H), 1.61-1.34 (m, 1H), 1.30 (s, 3H), 1.27-1.07 (m, 2H); ESI-MS m/z 546.67 (M+H)+.

Compound Example No. 34

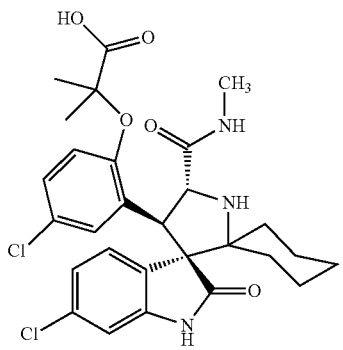 [SMILES: CNC(=O)[C@@H]1NC2(CCCCC2)[C@@]2(C(=O)Nc3cc(Cl)ccc32)[C@H]1c1cc(Cl)ccc1OC(C)(C)C(=O)O]

¹H NMR (300 MHz, CD₃OD) δ ppm 8.15 (d, J=5.3 Hz, 1H), 7.67 (d, J=2.2 Hz, 1H), 7.49 (d, J=8.2 Hz, 1H), 7.13 (dd, J=2.4, 8.9 Hz, 1H), 7.06 (dd, J=1.6, 8.3 Hz, 1H), 6.76 (d, J=1.5 Hz, 1H), 6.68 (d, J=8.9 Hz, 1H), 5.25 (d, J=11.3 Hz, 1H), 4.96 (d, J=11.4 Hz, 1H), 2.85 (d, J=8.5 Hz, 1H), 2.69 (s, 3H), 2.19 (d, J=12.2 Hz, 1H), 2.03-1.83 (m, 3H), 1.77 (d, J=15.3 Hz, 2H), 1.62-1.40 (m, 7H), 1.40-1.08 (m, 2H); ESI-MS m/z 560.58 (M+H)+.

Compound Example No. 35

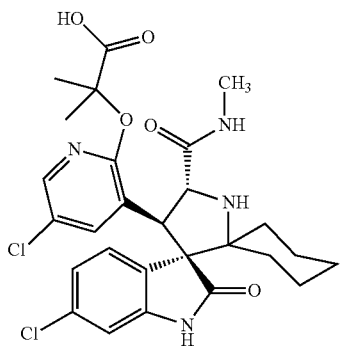 [SMILES: CNC(=O)[C@@H]1NC2(CCCCC2)[C@@]2(C(=O)Nc3cc(Cl)ccc32)[C@H]1c1cc(Cl)cnc1OC(C)(C)C(=O)O]

¹H NMR (300 MHz, CD₃OD) δ ppm 7.93 (dd, J=2.2, 18.7 Hz, 2H), 7.47 (d, J=8.2 Hz, 1H), 7.12 (d, J=8.1 Hz, 1H), 6.80 (d, J=1.3 Hz, 1H), 4.91 (s, 1H), 2.79-2.62 (m, 4H), 2.13 (d, J=14.4 Hz, 1H), 2.01-1.83 (m, 3H), 1.83-1.68 (m, 2H), 1.66-1.40 (m, 7H), 1.32-1.08 (m, 2H); ESI-MS m/z 561.33 (M+H)+.

Compound Example No. 36

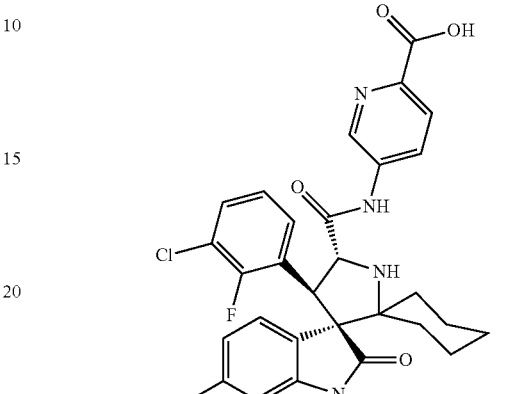

The title compound was prepared using methyl 5-aminopicolinate. ¹H NMR (300 MHz, CD₃OD) δ ppm 8.80 (s, 1H), 8.27 (d, J=8.8 Hz, 1H), 8.15 (d, J=8.7 Hz, 1H), 7.71 (t, J=7.2 Hz, 1H), 7.55 (d, J=8.7 Hz, 1H), 7.37 (t, J=7.1 Hz, 1H), 7.18 (t, J=7.9 Hz, 1H), 7.12 (d, J=8.1 Hz, 1H), 6.80 (s, 1H), 5.30 (d, J=11.1 Hz, 1H), 5.00 (d, J=10.8 Hz, 1H), 2.90-2.75 (m, 1H), 2.16 (d, J=16.9 Hz, 1H), 2.06-1.84 (m, 3H), 1.78 (d, J=13.2 Hz, 2H), 1.66-1.42 (m, 1H), 1.32-1.11 (m, 2H); ESI-MS m/z 583.96 (M+H)+.

Compound Example No. 37

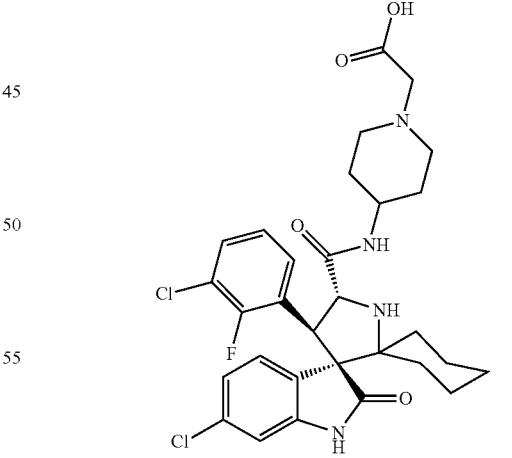

The title compound was prepared using methyl 2-(4-aminopiperidin-1-yl)acetate hydrochloride. ¹H NMR (300 MHz, CD₃OD) δ ppm 7.66 (t, J=7.1 Hz, 1H), 7.48 (dd, J=2.1, 8.2 Hz, 1H), 7.39 (t, J=7.3 Hz, 1H), 7.17 (t, J=8.0 Hz, 1H), 7.10 (dd, J=1.6, 8.1 Hz, 1H), 6.79 (d, J=1.7 Hz, 1H), 5.12 (d, J=11.0 Hz, 1H), 4.80 (d, J=10.9 Hz, 1H), 4.05-3.89 (m, 3H), 3.79-3.39 (m, 2H), 3.29-3.04 (m, 2H), 2.79 (d, J=9.4 Hz, 1H), 2.17 (d, J=9.4 Hz, 2H), 2.03-1.42 (m, 8H), 1.42-1.33 (m, 2H), 1.31-1.10 (m, 2H); ESI-MS m/z 603.67 (M+H)+.

Compound Example No. 38

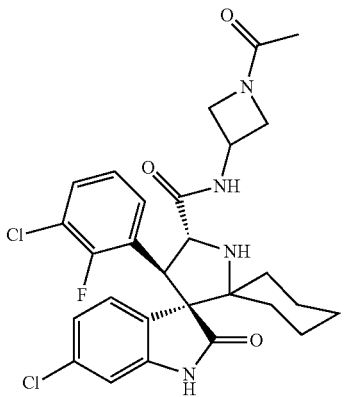 [SMILES: CC(=O)N1CC(NC(=O)[C@@H]2NC3(CCCCC3)[C@@]3(C(=O)Nc4cc(Cl)ccc43)[C@H]2c2cccc(Cl)c2F)C1]

The title compound was prepared using tert-butyl 3-aminoazetidine-1-carboxylate. The Boc protecting group was removed by treating the compound with TFA in DCM. The free amine was then treated with AcOH, EDCI, HOBt, DIEA, and DMAP(catalytic) in DCM. After stirring overnight, the solvent was removed and the product was purified by column chromatography then preparative HPLC to give Compound Example No. 38 (as the TFA salt) as a white powder. $^1$H NMR (300 MHz, CD$_3$OD) δ ppm 7.64 (t, J=7.2 Hz, 1H), 7.50 (dd, J=1.8, 8.2 Hz, 1H), 7.40 (t, J=7.7 Hz, 1H), 7.17 (t, J=8.1 Hz, 1H), 7.11 (dd, J=1.7, 8.2 Hz, 1H), 6.79 (s, 1H), 5.10 (d, J=10.6 Hz, 1H), 4.64-4.36 (m, 2H), 4.29-4.11 (m, 1H), 4.09-3.56 (m, 2H), 2.79 (d, J=9.8 Hz, 1H), 2.16 (d, J=14.9 Hz, 1H), 2.01-1.68 (m, 8H), 1.64-1.37 (m, 1H), 1.34-1.11 (m, 2H); ESI-MS m/z 560.08 (M+H)+.

Compound Example No. 39

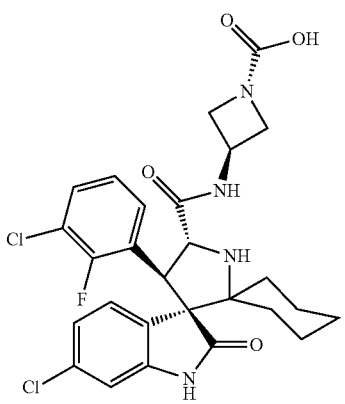

The title compound was prepared using methyl trans-3-aminocyclobutanecarboxylate hydrochloride. $^1$H NMR (300 MHz, CD$_3$OD) δ ppm 7.65 (t, J=7.0 Hz, 1H), 7.49 (dd, J=1.7, 8.0 Hz, 1H), 7.40 (t, J=7.3 Hz, 1H), 7.18 (t, J=8.0 Hz, 1H), 7.11 (d, J=8.3 Hz, 1H), 6.79 (s, 1H), 5.06 (d, J=10.8 Hz, 1H), 4.79 (d, J=10.8 Hz, 1H), 4.47 (p, J=8.1 Hz, 1H), 2.96-2.71 (m, 2H), 2.63-2.38 (m, 2H), 2.29-2.08 (m, 2H), 2.05-1.83 (m, 4H), 1.76 (d, J=16.2 Hz, 2H), 1.62-1.39 (m, 1H), 1.33-1.11 (m, 2H); ESI-MS m/z 560.50 (M+H)+.

Compound Example No. 40

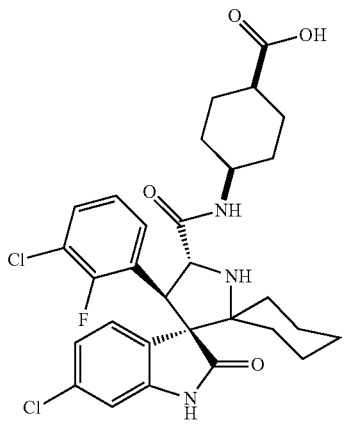

$^1$H NMR (300 MHz, CD$_3$OD) δ ppm 7.67 (t, J=6.61 Hz, 1H), 7.49 (dd, J=2.0, 8.1 Hz, 1H), 7.37 (t, J=7.5 Hz, 1H), 7.16 (t, J=7.9 Hz, 1H), 7.10 (dd, J=1.7, 8.3 Hz, 1H), 6.79 (d, J=1.7 Hz, 1H), 5.20 (d, J=11.3 Hz, 1H), 4.76 (d, J=11.2 Hz, 1H), 3.89-3.75 (m, 1H), 2.84 (d, J=9.1 Hz, 1H), 2.41-2.29 (m, 1H), 2.20 (d, J=15.3 Hz, 1H), 2.03-1.12 (m, 16H); ESI-MS m/z 588.50 (M+H)+.

Compound Example No. 41

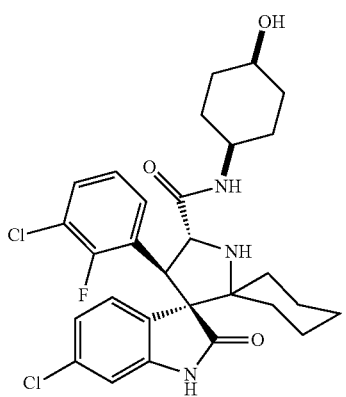

$^1$H NMR (300 MHz, CD$_3$OD) δ ppm 8.18 (d, J=7.9 Hz, 1H), 7.66 (t, J=6.8 Hz, 1H), 7.48 (dd, J=2.3, 8.2 Hz, 1H), 7.38 (t, J=7.7 Hz, 1H), 7.17 (t, J=8.1 Hz, 1H), 7.10 (dd, J=1.8, 8.2 Hz, 1H), 6.79 (d, J=1.8 Hz, 1H), 5.14 (d, J=10.9 Hz, 1H), 4.78

(d, J=11.1 Hz, 1H), 3.83-3.65 (m, 2H), 2.83 (d, J=9.9 Hz, 1H), 2.18 (d, J=13.0 Hz, 1H), 2.03-1.10 (m, 17H); ESI-MS m/z 560.83 (M+H)⁺.

Compound Example No. 42

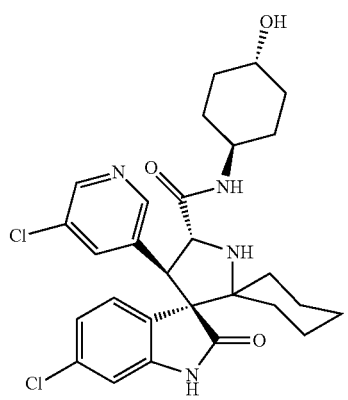 [SMILES: O=C(N[C@H]1CC[C@H](O)CC1)[C@@H]1NC2(CCCCC2)[C@@]2(C(=O)Nc3cc(Cl)ccc32)[C@H]1c1cncc(Cl)c1]

¹H NMR (300 MHz, CD₃OD) δ ppm 8.45 (d, J=2.1 Hz, 1H), 8.24 (d, J=1.7 Hz, 1H), 7.89 (s, 1H), 7.60 (d, J=8.2 Hz, 1H), 7.14 (dd, J=1.8, 8.2 Hz, 1H), 6.78 (d, J=1.8 Hz, 1H), 5.10 (d, J=10.9 Hz, 1H), 4.47 (d, J=10.9 Hz, 1H), 3.73-3.57 (m, 1H), 3.50-3.36 (m, 1H), 2.83 (d, J=12.5 Hz, 1H), 2.17 (d, J=14.3 Hz, 1H), 2.03-1.70 (m, 8H), 1.70-1.13 (m, 7H), 1.08-0.88 (m, 1H); ESI-MS m/z 543.75 (M+H)⁺.

Compound Example No. 43

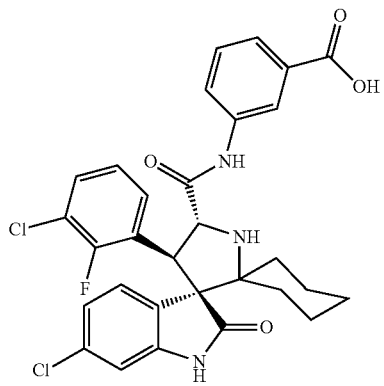 [SMILES: O=C(O)c1cccc(NC(=O)[C@@H]2NC3(CCCCC3)[C@@]3(C(=O)Nc4cc(Cl)ccc43)[C@H]2c2cccc(Cl)c2F)c1]

¹H NMR (300 MHz, CD₃OD) δ ppm 8.14 (s, 1H), 7.84-7.67 (m, 3H), 7.55 (dd, J=1.9, 8.2 Hz, 1H), 7.48-7.34 (m, 2H), 7.19 (t, J=8.0 Hz, 1H), 7.12 (dd, J=1.6, 8.2 Hz, 1H), 6.79 (d, J=1.6 Hz, 1H), 5.29 (d, J=11.0 Hz, 1H), 4.97 (d, J=10.7 Hz, 1H), 2.96-2.84 (m, 1H), 2.18 (d, J=14.0 Hz, 1H), 2.08-1.85 (m, 3H), 1.78 (d, J=12.2 Hz, 2H), 1.63-1.42 (m, 1H), 1.35-1.13 (m, 3H); ESI-MS m/z 582.58 (M+H)⁺.

Compound Example 44

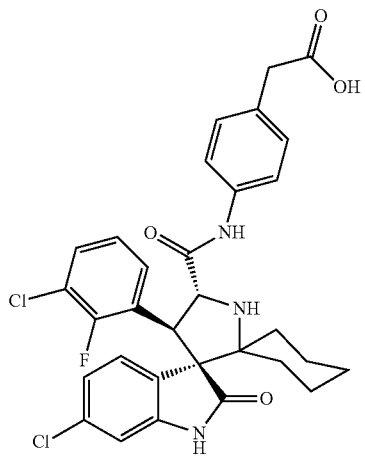 [SMILES: O=C(O)Cc1ccc(NC(=O)[C@@H]2NC3(CCCCC3)[C@@]3(C(=O)Nc4cc(Cl)ccc43)[C@H]2c2cccc(Cl)c2F)cc1]

ESI-MS m/z 596.42 (M+H)⁺.

Compound Example No. 45

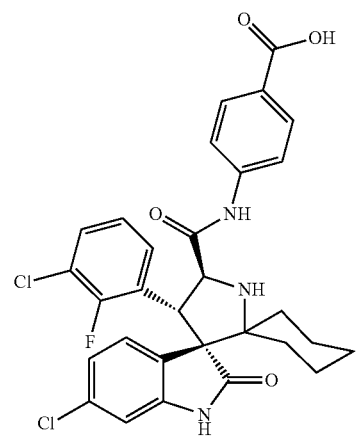 [SMILES: O=C(O)c1ccc(NC(=O)[C@H]2NC3(CCCCC3)[C@]3(C(=O)Nc4cc(Cl)ccc43)[C@@H]2c2cccc(Cl)c2F)cc1]

¹H NMR (300 MHz, CD₃OD) δ ppm 7.98 (d, J=8.6 Hz, 2H), 7.72 (t, J=7.2 Hz, 1H), 7.64 (d, J=8.7 Hz, 2H), 7.54 (dd, J=2.4, 8.1 Hz, 1H), 7.38 (t, J=7.6 Hz, 1H), 7.19 (t, J=8.0 Hz, 1H), 7.12 (dd, J=1.6, 8.2 Hz, 1H), 6.80 (d, J=1.7 Hz, 1H), 5.34 (d, J=10.7 Hz, 1H), 4.97 (d, J=10.9 Hz, 1H), 2.91 (d, J=7.1

Hz, 1H), 2.20 (d, J=14.8 Hz, 1H), 2.06-1.86 (m, 3H), 1.78 (d, J=12.3 Hz, 2H), 1.64-1.42 (m, 1H), 1.34-1.14 (m, 2H); ESI-MS m/z 582.50 (M+H)+.

Compound Example No. 46

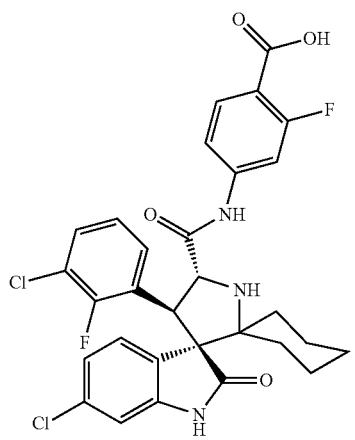 [SMILES: O=C(O)c1ccc(NC(=O)[C@@H]2NC3(CCCCC3)[C@@]3(C(=O)Nc4cc(Cl)ccc43)[C@H]2c2cccc(Cl)c2F)cc1F]

¹H NMR (300 MHz, CD₃OD) δ ppm 7.90 (t, J=8.4 Hz, 1H), 7.74-7.61 (m, 2H), 7.55 (dd, J=2.5, 8.2 Hz, 1H), 7.38 (t, J=7.2 Hz, 1H), 7.26 (dd, J=1.7, 8.6 Hz, 1H), 7.19 (t, J=8.2 Hz, 1H), 7.12 (dd, J=1.8, 8.2 Hz, 1H), 6.80 (d, J=1.7 Hz, 1H), 5.31 (d, J=10.8 Hz, 1H), 4.97 (d, J=10.8 Hz, 1H), 2.94-2.84 (m, 1H), 2.20 (d, J=15.7 Hz, 1H), 2.06-1.85 (m, 3H), 1.79 (d, J=10.9 Hz, 2H), 1.65-1.43 (m, 1H), 1.34-1.11 (m, 2H); ESI-MS m/z 600.42 (M+H)+.

Compound Example No. 47

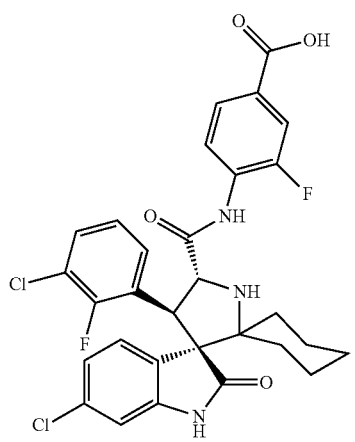 [SMILES: O=C(O)c1ccc(NC(=O)[C@@H]2NC3(CCCCC3)[C@@]3(C(=O)Nc4cc(Cl)ccc43)[C@H]2c2cccc(Cl)c2F)c(F)c1]

¹H NMR (300 MHz, CD₃OD) δ ppm 8.42-8.31 (m, 1H), 8.21 (t, J=8.0 Hz, 1H), 7.91-7.79 (m, 1H), 7.79-7.67 (m, 2H), 7.52 (dd, J=2.4, 8.2 Hz, 1H), 7.37 (t, J=7.3 Hz, 1H), 7.25-7.06 (m, 2H), 6.79 (d, J=1.7 Hz, 1H), 5.41 (d, J=9.4 Hz, 1H), 2.81-2.67 (m, 1H), 2.14 (d, J=14.7 Hz, 1H), 2.00-1.84 (m, 3H), 1.84-1.70 (m, 2H), 1.68-1.47 (m, 1H), 1.41-1.09 (m, 2H); ESI-MS m/z 600.83 (M+H)+.

EXAMPLE 6

Fluorescence-Polarization MDM2 Binding Assay

The binding affinity of the MDM2 inhibitors disclosed herein was determined using a fluorescence polarization-based (FP-based) binding assay using a recombinant human His-tagged MDM2 protein (residues 1-118) and a fluorescently tagged p53-based peptide.

The design of the fluorescence probe was based upon a previously reported high-affinity p53-based peptidomimetic compound called PMDM6-F (García-Echeverria et al., *J. Med. Chem.* 43: 3205-3208 (2000)). The $K_d$ value of PMDM6-F with the recombinant MDM2 protein was determined from the saturation curve. MDM2 protein was serially double diluted in a Dynex 96-well, black, round-bottom plate, and the PMDM6-F peptide was added at 1 nM concentration. The assay was performed in the buffer: 100 mM potassium phosphate, pH 7.5; 100 µg/mL bovine gamma globulin; 0.02% sodium azide, 0.01% Triton X-100) and the polarization values were measured after 3 h of incubation using an ULTRA READER (Tecan U.S. Inc., Research Triangle Park, N.C.). The $IC_{50}$ value was obtained by fitting the mP values in a sigmoidal dose-response curve (variable slope) with a non-linear regression, and was determined to be 1.40 nM f 0.25. The $K_d$ value was calculated using the equation: $K_d$ value=$IC_{50}$–L0/2. L0/2 is the concentration of the free ligand (PMDM6-F). Since PMDM6-F was used at a final concentration of 1 nM, L0/2 was 0.5 nM.

Dose-dependent, competitive binding experiments were performed with serial dilutions of a tested compound in DMSO. A 5 µL sample of the tested compound and pre-incubated MDM2 protein (10 nM) and PMDM6-F peptide (1 nM) in the assay buffer (100 mM potassium phosphate, pH 7.5; 100 µg/mL bovine gamma globulin; 0.02% sodium azide, 0.01% Triton X-100), were added in a Dynex 96-well, black, round-bottom plate to produce a final volume of 125 µL. For each assay, the controls included the MDM2 protein and PMDM6-F (equivalent to 0% inhibition), PMDM6-F peptide alone (equivalent to 100% inhibition). The polarization values were measured after 3 h of incubation. The $IC_{50}$ values, i.e., the inhibitor concentration at which 50% of bound peptide is displaced, were determined from a plot using nonlinear least-squares analysis. Curve fitting was performed using GRAPHPAD PRISM software (GraphPad Software, Inc., San Diego, Calif.). The results of this assay are present in Table 2.

EXAMPLE 7

Cell Growth Assay

Isogenic HCT-116 colon cancer cell lines were a kind gift from Prof. Bert Vogelstein (Johns Hopkins, Baltimore, Md.) and were maintained in McCoy's 5A medium containing 10% FBS. The SJSA-1 cell lines were obtained from ATCC, (Manassas, Va.) and were maintained in RPMI-1640 medium containing 10% FBS.

Figure 2:
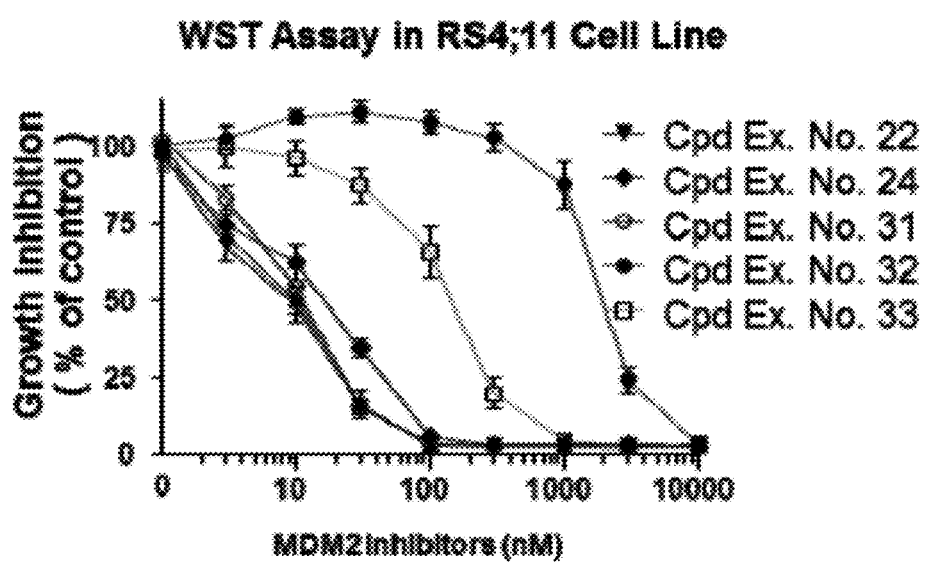
FIG. 2 is a line graph showing cell growth inhibition of MDM2 inhibitors in the RS4;11 leukemia cell line as determined using the WST-based assay. RS4;11 cells were treated with each compound for 4 days.

Cells were seeded in 96-well flat bottom cell culture plates at a density of 2-3×10³ cells/well with compounds and incubated for 4 days. The rate of cell growth inhibition after treatment with increasing concentrations of the tested compounds was determined by WST-8 (2-(2-methoxy-4-nitrophenyl)-3-(4-nitrophenyl)-5-(2,4-disulfophenyl)-2H-tetrazolium monosodium salt (Dojindo Molecular Technologies Inc., Gaithersburg, Md.). WST-8 was added at a final concentration of 10% to each well, and then the plates were incubated at 37° C. for 2-3 hrs. The absorbance of the samples was measured at 450 nm using a TECAN ULTRA Reader. The concentration of the compounds that inhibited cell growth by 50% ($IC_{50}$) was calculated by comparing absorbance in the untreated cells and the cells treated with the compounds using the GraphPad Prism software (GraphPad Software, La Jolla, Calif. 92037, USA). The results of this assay are presented in Table 2 and FIG. 1 and FIG. 2.

TABLE 2

| Compound Number | Binding affinities to MDM2 (1-118) | | | | |
| --- | --- | --- | --- | --- | --- |
| | $IC_{50}$ (nM) | Ki (nM) | HCT116 p53 WT | HCT116 p53 KO | SJSA-1 |
| 1 | 201 | 26.4 | 1.8 | >30 | 2.3 |
| 2 | 41.8 | 4.6 | 0.4 | >30 | 0.5 |
| 3 | 19.3 ± 5.2 | 1.5 ± 0.7 | 0.12 | 24 | 0.33 |
| 4 | 15.6 ± 2.2 | 1.0 ± 0.3 | 7.3 | 48 | 1.9 |
| 5 | >10,000 | | | | |
| 6 | <1,000 | | | | |
| 7 | <1,000 | | | | <5 |
| 8 | <5,000 | | | | <5 |
| 9 | <100 | | | | <1 |
| 10 | <5,000 | | | | <5 |
| 11 | <5,000 | | | | <5 |
| 12 | <5,000 | | | | <10 |
| 13 | >10,000 | | | | >10 |
| 14 | >10,000 | | | | >10 |
| 15 | <100 | | | | <3 |
| 16 | >5,000 | | | | |
| 17 | >5,000 | | | | |
| 18 | >5,000 | | | | |
| 19 | >1,000 | | | | |
| 20 | <100 | | | | |
| 21 | <100 | | | | <5 |
| 22 | <100 | | | | <1 |
| 23 | <100 | | | | <3 |
| 24 | <100 | | | | <1 |
| 25 | <100 | | | | <1 |
| 26 | <500 | | | | <30 |
| 27 | <100 | | | | <5 |
| 28 | <100 | | | | <5 |
| 29 | <100 | | | | |
| 30 | <500 | | | | <10 |
| 31 | <100 | | | | <1 |
| 32 | <100 | | | | |
| 33 | <100 | | | | <1 |
| 34 | >10,000 | | | | |
| 35 | >10,000 | | | | |
| 36 | <100 | | | | <1 |
| 37 | <100 | | | | |
| 38 | <100 | | | | <1 |
| 39 | <100 | | | | <1 |
| 40 | <100 | | | | |
| 41 | <100 | | | | |
| 42 | <1,000 | | | | |
| 43 | <100 | | | | |

EXAMPLE 8

In Vivo Efficacy Studies Using SJSA-Xenograft Models

SJSA-1 (osteosarcoma) tumor cells were harvested with Trypsin (0.05%)-EDTA (0.53 mM) (GIBCO™, Invitrogen Corp.), growth medium was added, and the cells were placed on ice. A cell sample was mixed 1:1 with Trypan Blue (GIBCO™, Invitrogen Corp.) and counted on a hemocytometer to determine the number of live/dead cells. Cells were washed once with 1×PBS (GIBCO™ Invitrogen Corp.) and resuspended in PBS. For Matrigel injections, after washing in PBS, cells are resuspended in an ice cold mixture of 1:1 PBS and Matrigel (BD Biosciences, Invitrogen Corp.) for a final Matrigel protein concentration of 5 mg/ml. SJSA-1 tumors were inoculated into C.B-17 SCID mice at $5 \times 10^6$ cells in 0.1 ml with Matrigel. Cells were injected s.c. into the flank region of each mouse using a 27 gauge needle.

Figure 3:
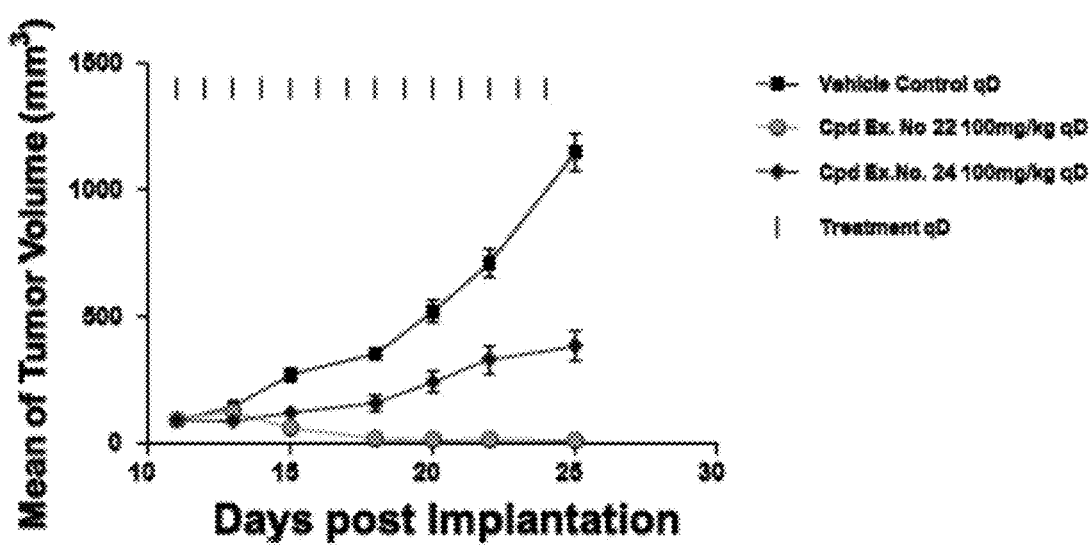
FIG. 3 is a line graph showing the antitumor activity of Compound Example Nos. 22 and 24 in the SJSA-1 xenograft tumor model. Mice bearing SJSA-1 tumors (one tumor per mouse) were treated with Compound Example Nos. 22 and 24 daily for 2 weeks via oral gavage at 100 mg/kg qD.

The size of tumors growing in the mice was measured in two dimensions using calipers. Tumor volume ($mm^3$)=(A× $B^2$)/2 where A and B are the tumor length and width (in mm), respectively. During treatment, tumor volume and body weight was measured three times a week. After the treatment was stopped, tumor volume and body weight was measured at least once a week. Mice were kept for an additional 60 days for further observation of tumor growth and toxicity. The anti-tumor activity of Compound Example Nos. 22 and 24 are shown in FIG. 3.

Suitable vehicles for in vivo administration of the compounds provided herein include, without limitation, 10% PEG 400:3% Cremophor:87% PBS; 98% PEG 200:2% polysorbate 80; 98% PEG 200:2% TPGS; and 0.5% polysorbate 80:0.6% methyl cellulose:98.9% water.

EXAMPLE 9

Stability of Compounds in Solution

Figure 4:
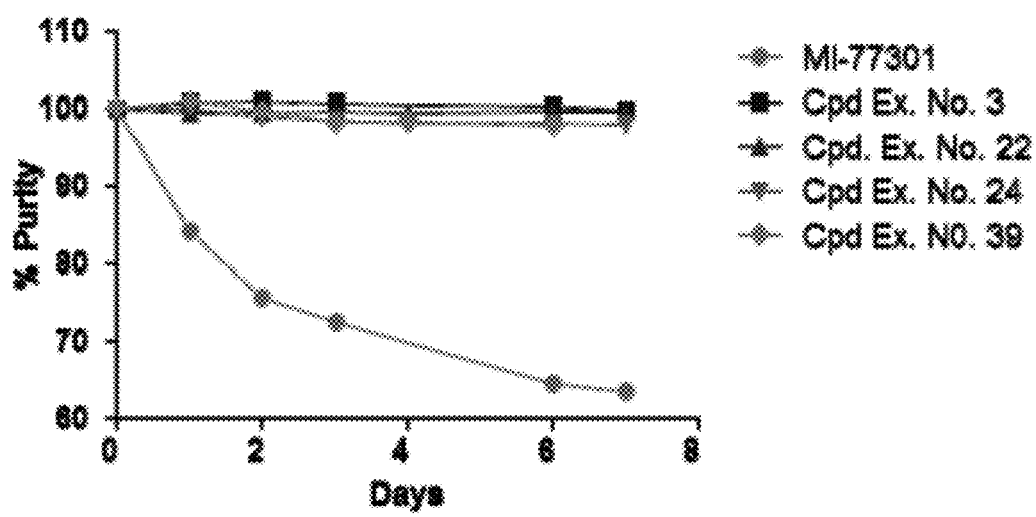
FIG. 4 is a line graph showing the stability of MDM2 inhibitors in a 1:1 methanol/water solution. The Y-axis represents the percent amount of the compound measured by HPLC. The X-axis represents the number of days the sample has been in the methanol/water solution.
Figure 5:
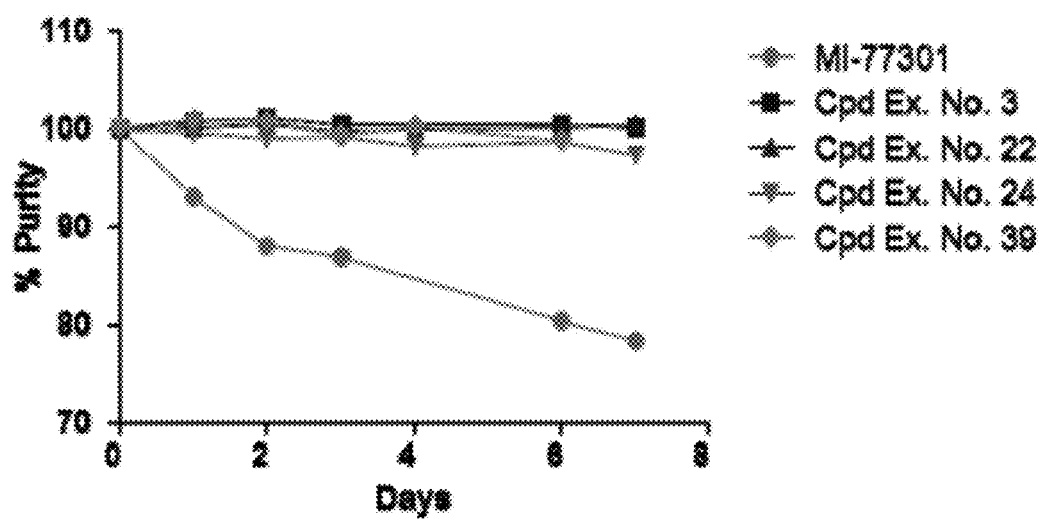
FIG. 5 is a line graph showing the stability of MDM2 inhibitors in a 1:1 acetonitrile/water solution. The Y-axis represents the percent amount of the stable isomer measured by HPLC. The X-axis represents the number of days the sample has been in the acetonitrile/water solution.

The stability of Compound Example Nos. 3, 22, 24, and 39, and MI-77301 (See U.S. Patent Appl. Pub. No. 2011/0112052 A2) were determined in 1:1 MeOH:$H_2O$ (FIG. 4) and 1:1 $CH_3CN$:$H_2O$ (FIG. 5) using ultra performance liquid chromatography. In both solvent systems, Compound Example Nos. 3, 22, 24, and 39 were more stable than MI-77301.

Figure 6:
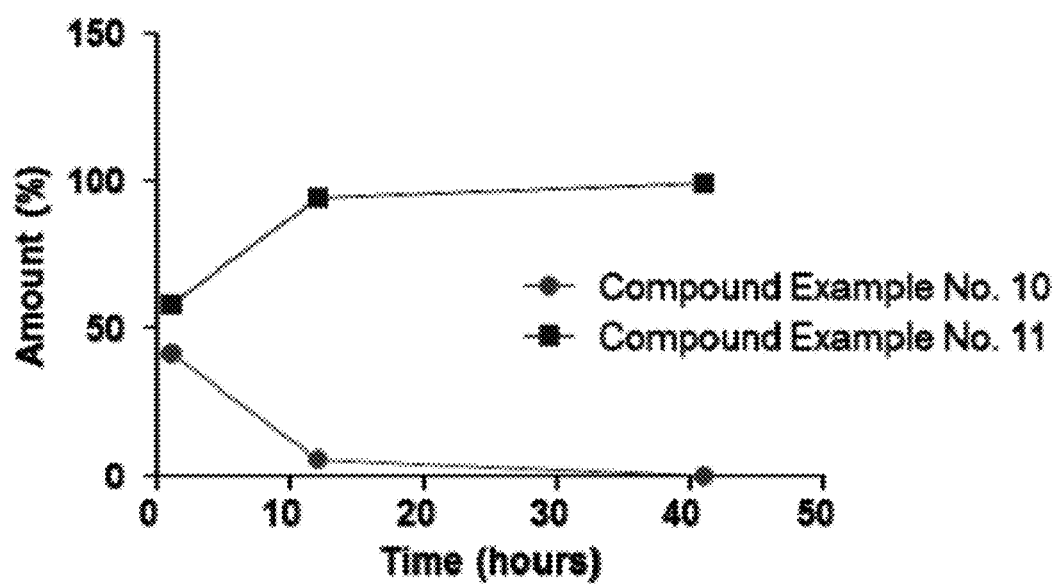
FIG. 6 is a line graph showing the stability of Compound Example Nos. 10 and 11 in a 1:1 methanol/water solution with 10% TFA added. The Y-axis represents the percent amount of the compound measured by HPLC. The X-axis represents the number of hours the sample has been in solution.

The stability of Compound Example Nos. 10 and 11 were determined in 1:1 MeOH:$H_2O$ with 10% TFA added using ultra performance liquid chromatography (FIG. 6). Compound Example No. 10 is converted into Compound Example No. 11 under these conditions.

Having now fully described the compounds, compositions, and methods provided herein, it will be understood by those of skill in the art that the same can be performed within a wide and equivalent range of conditions, formulations, and other parameters without affecting the scope of the compounds, methods, and compositions provided herein or any embodiment thereof. All patents, patent applications, and publications cited herein are fully incorporated by reference herein in their entirety.

What is claimed is:

1. A compound having Formula I:

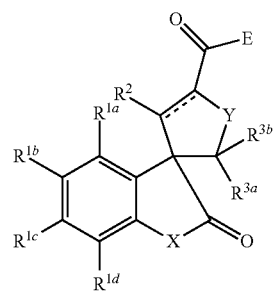

wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;
$R^2$ is selected from the group consisting of optionally substituted aryl and optionally substituted heteroaryl;
$R^{3a}$ is halo;
$R^{3b}$ is halo; or
$R^{3a}$ and $R^{3b}$ taken together form a 3- to 9-membered optionally substituted cycloalkyl or a 3- to 9-membered optionally substituted heterocyclo;
E is selected from the group consisting of —$OR^{26a}$ and —$NR^{26b}R^{26c}$;
$R^{26a}$ is selected from the group consisting of hydrogen, optionally substituted alkyl, optionally substituted cycloalkyl, and optionally substituted aryl;
$R^{26b}$ is selected from the group consisting of hydrogen and optionally substituted $C_1$-$C_6$ alkyl;
$R^{26c}$ is selected from the group consisting of hydrogen, optionally substituted alkyl, optionally substituted cycloalkyl, optionally substituted heterocyclo, optionally substituted aryl, optionally substituted heteroaryl, aralkyl, and —$SO_2R^{5b}$; or
$R^{26b}$ and $R^{26c}$ taken together form a 4- to 9-membered optionally substituted heterocyclo;
X is selected from the group consisting of O, S, and NR';
Y is selected from the group consisting of O, S, and NR";
R' is selected from the group consisting of hydrogen, optionally substituted alkyl, aralkyl, and optionally substituted cycloalkyl;
R" is selected from the group consisting of hydrogen, optionally substituted alkyl, aralkyl, and optionally substituted cycloalkyl; and
⎓ represents a single or a double bond,
or a pharmaceutically acceptable salt thereof.

2. The compound of claim 1 having Formula III:

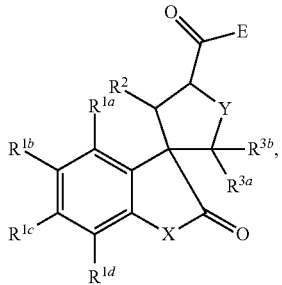

III or a pharmaceutically acceptable salt thereof.

3. The compound of claim 2 having Formula VI:

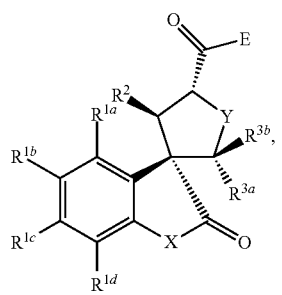

VI or a pharmaceutically acceptable salt thereof.

4. The compound of claim 2 having Formula XVI:

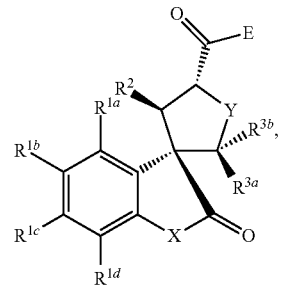

XVI or a pharmaceutically acceptable salt thereof.

5. The compound of claim 1, wherein:
E is —$NR^{26b}R^{26c}$;
$R^2$ is optionally substituted aryl;
$R^{26b}$ is hydrogen; and
X and Y are NH,
or a pharmaceutically acceptable salt thereof.

6. The compound of claim 5, wherein $R^{3a}$ and $R^{3b}$ taken together form a 4- to 8-membered optionally substituted cycloalkyl, or a pharmaceutically acceptable salt thereof.

7. The compound of claim 1, wherein $R^2$ is optionally substituted aryl having Formula $R^2$-1:

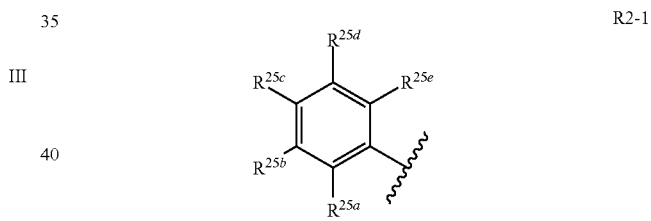

R2-1 wherein $R^{25a}$, $R^{25b}$, $R^{25c}$, $R^{25d}$, and $R^{25e}$ are each independently selected from the group consisting of hydrogen, halogen, hydroxy, nitro, amino, cyano, alkoxy, alkyl, or haloalkyl,
or a pharmaceutically acceptable salt thereof.

8. The compound of claim 1 having Formula XXVII:

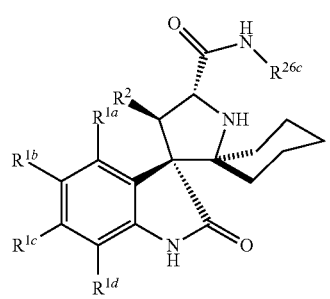

XXVII or a pharmaceutically acceptable salt thereof.

9. The compound of claim 1 having Formula XXVIII:

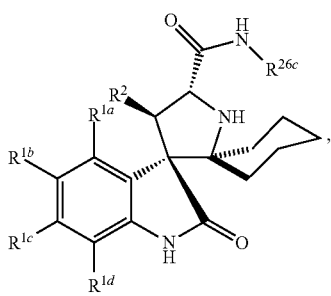

XXVIII or a pharmaceutically acceptable salt thereof.

10. The compound of claim 9, wherein $R^{26c}$ is optionally substituted cycloalkyl, or a pharmaceutically acceptable salt thereof.

11. The compound of claim 10, wherein $R^{26c}$ is selected from the group consisting of:

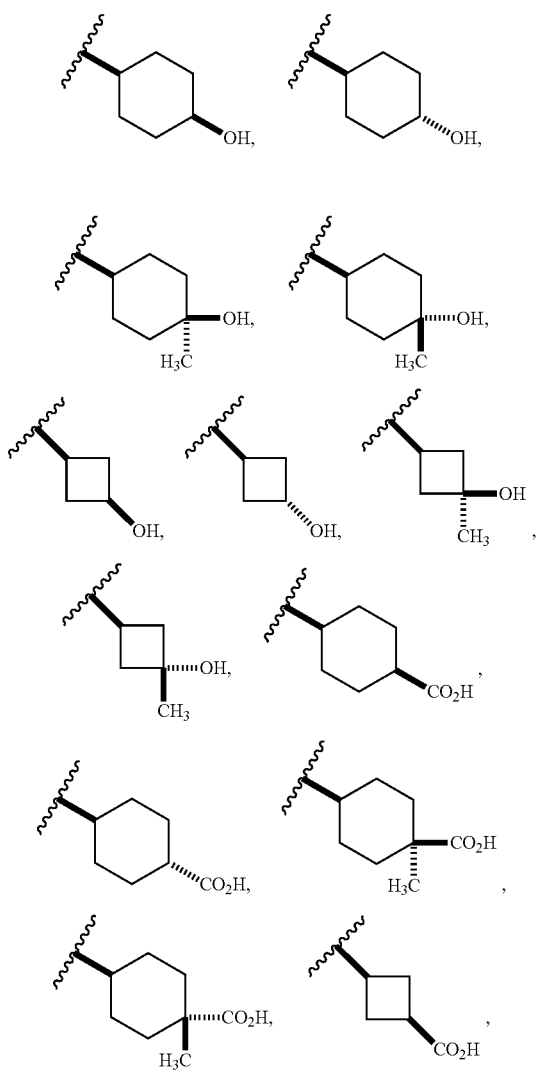

-continued

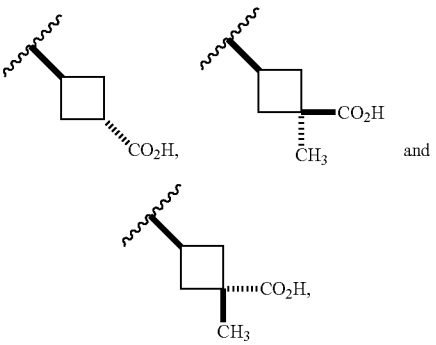

or a pharmaceutically acceptable salt thereof.

12. The compound of claim 9, wherein $R^{26c}$ is optionally substituted phenyl, or a pharmaceutically acceptable salt thereof.

13. A compound selected from the group consisting of:

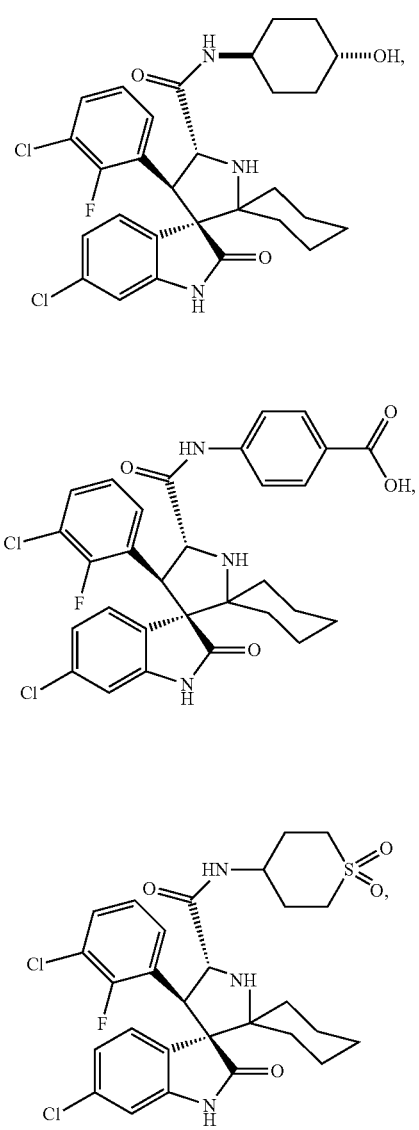

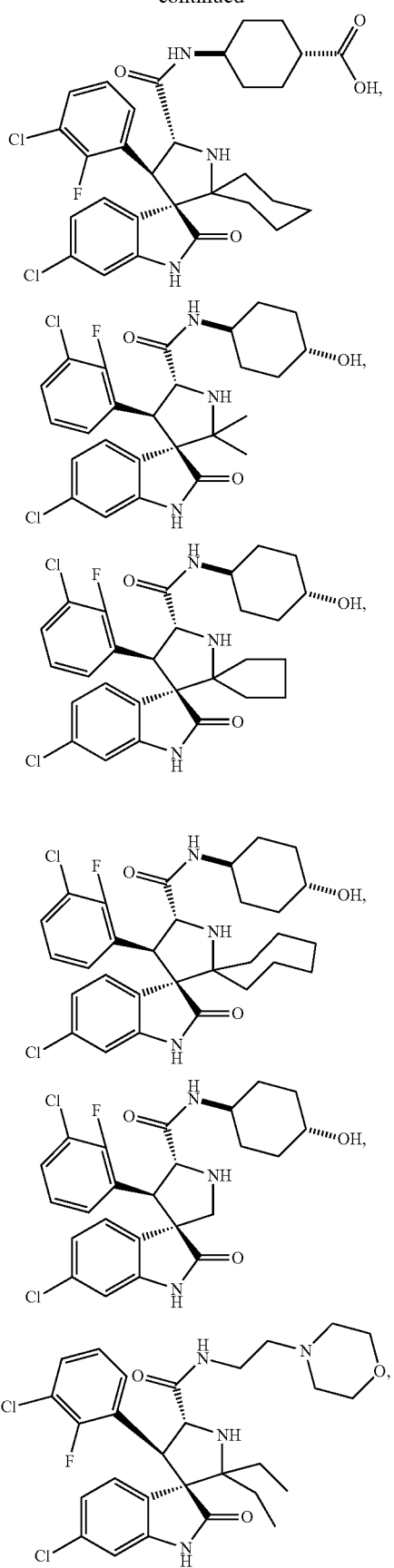
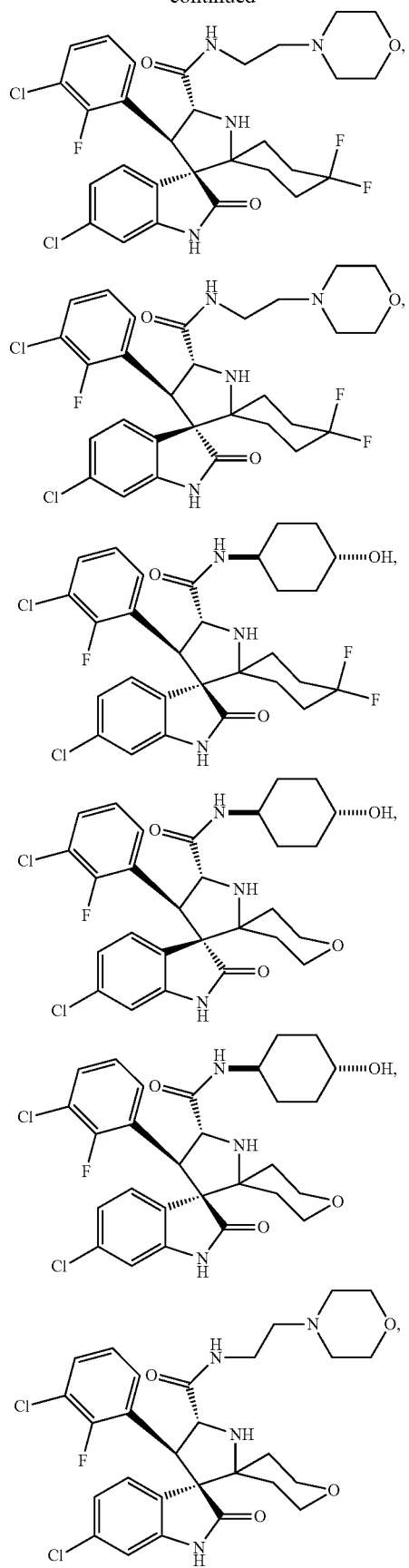

169
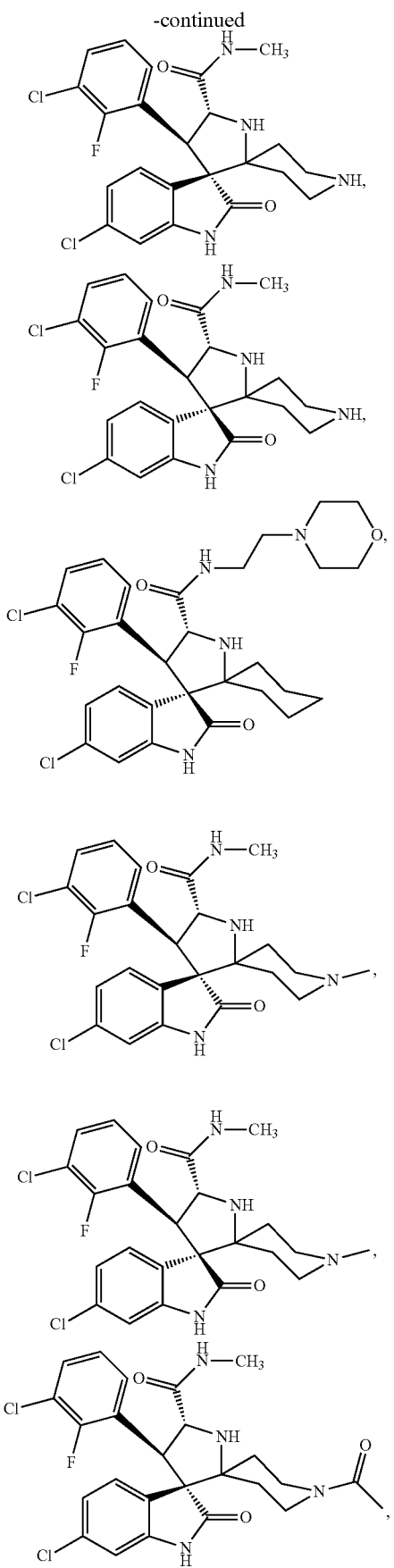
170
-continued
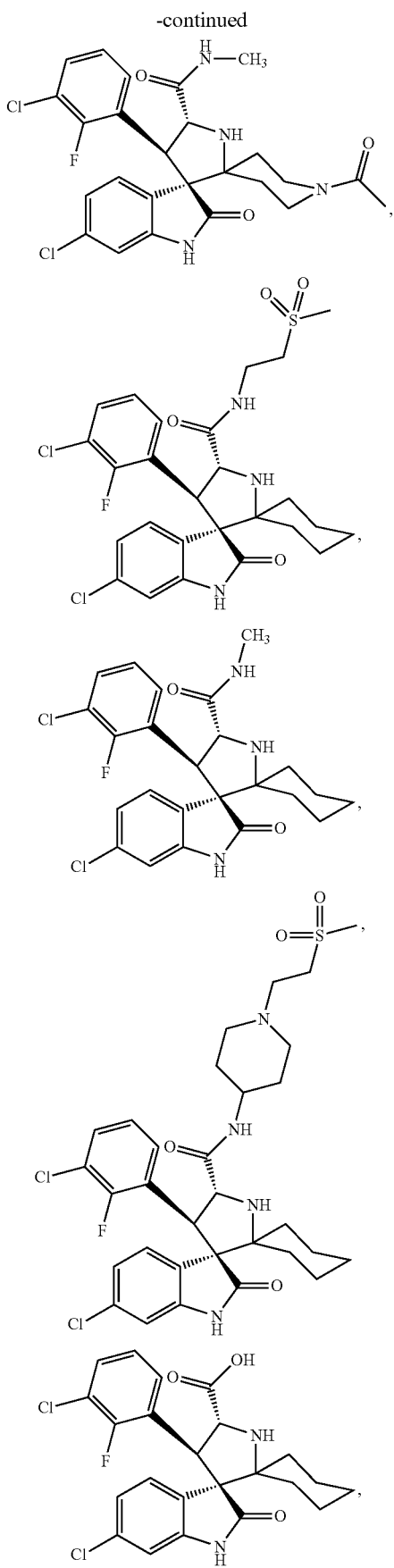

171
-continued
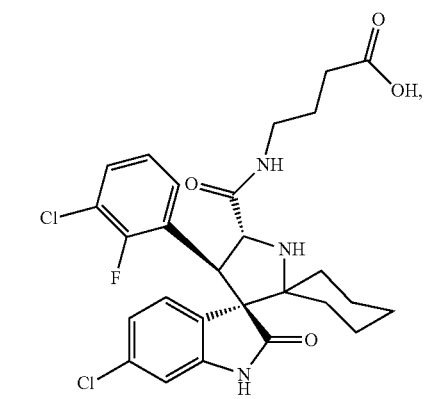
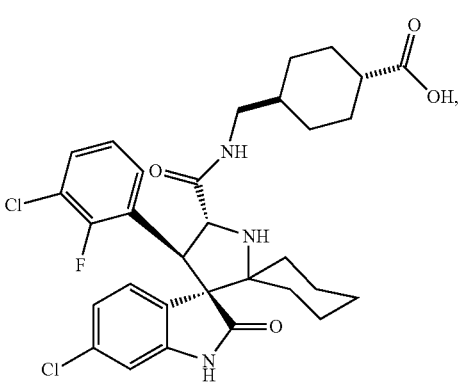
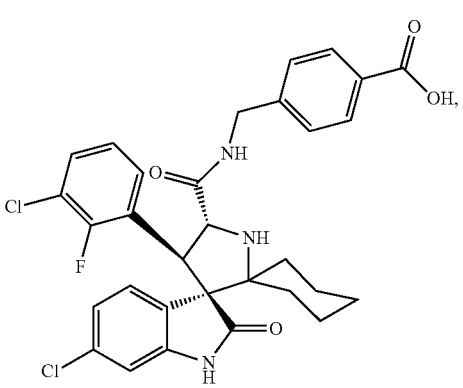
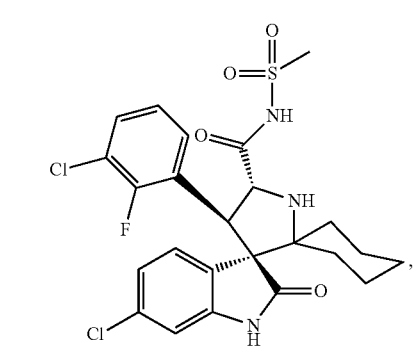
172
-continued
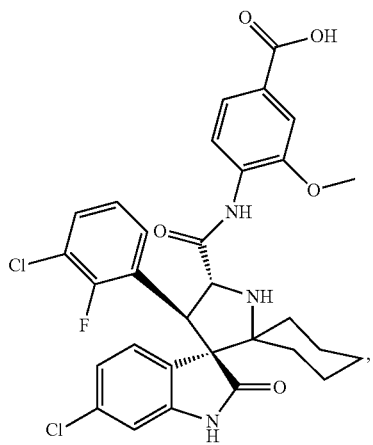
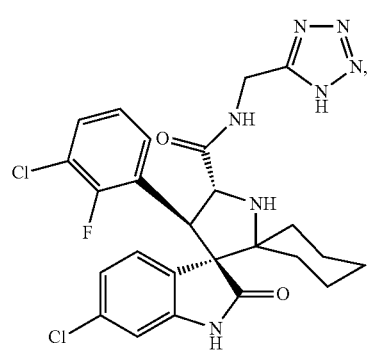
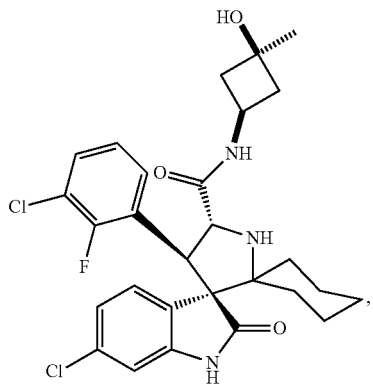
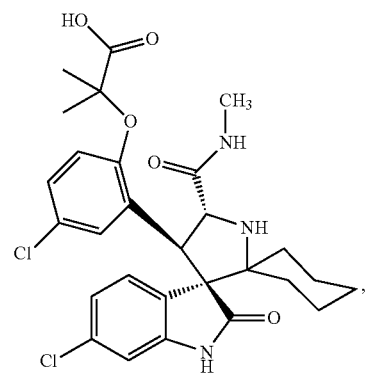

173
-continued
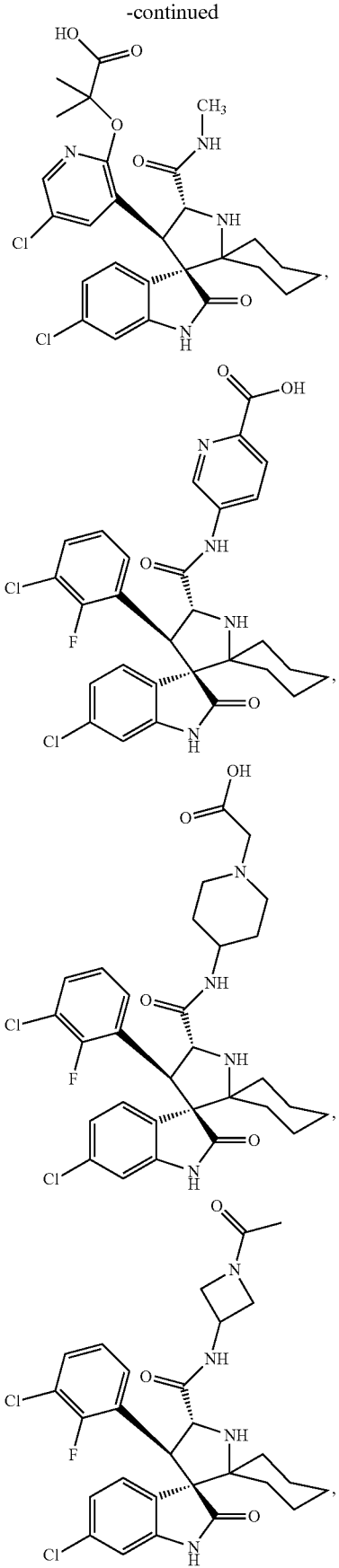
174
-continued
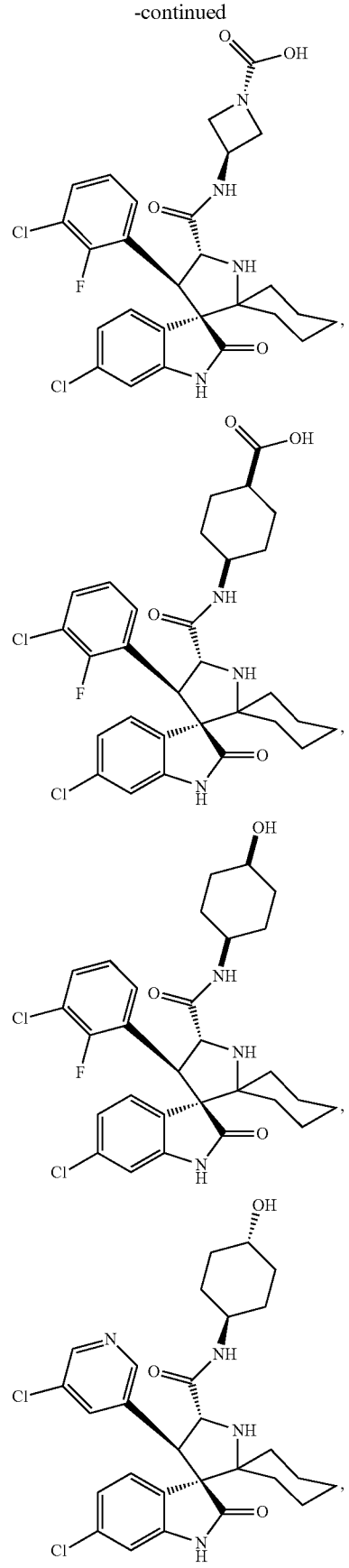

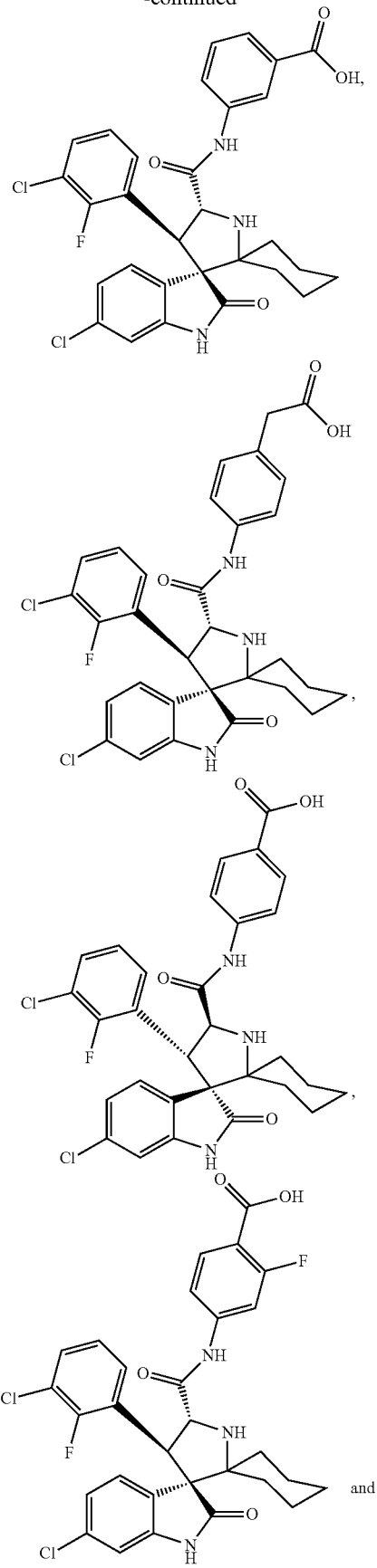
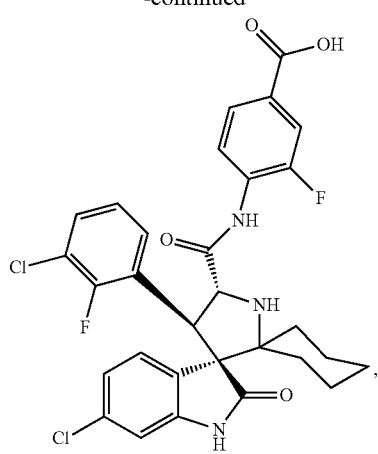
or a pharmaceutically acceptable salt thereof.
14. A compound selected from the group consisting of:
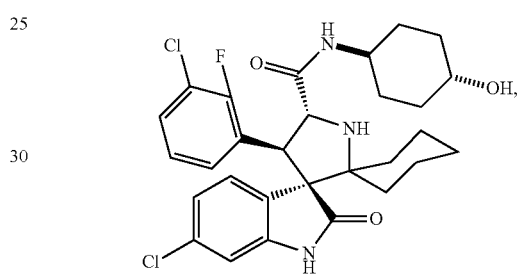

-continued

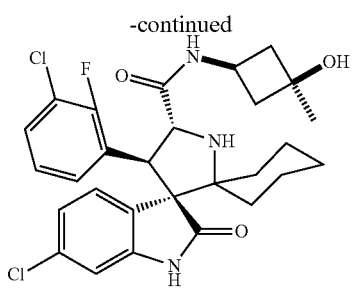

or a pharmaceutically acceptable salt thereof.

15. The compound of claim 1, wherein E is —OR$^{26a}$, or a pharmaceutically acceptable salt thereof.

16. A pharmaceutical composition comprising the compound of claim 1, or a pharmaceutically acceptable salt thereof, and a pharmaceutically acceptable carrier.

17. A method of treating a patient comprising administering to the patient a therapeutically effective amount of the compound of claim 1, or a pharmaceutically acceptable salt thereof, wherein the patient has colon cancer or osteosarcoma.

18. A kit comprising a compound of claim 1, or a pharmaceutically acceptable salt, thereof, and instructions for administering the compound to a patient having colon cancer or osteosarcoma.

19. A method of preparing a compound having Formula XVI:

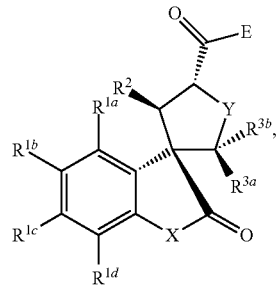

XVI comprising:

a) allowing a compound of claim 3 to isomerize; and b) isolating the compound having Formula XVI substantially free from the compound of claim 3, wherein X and Y are NH.

* * * * *